United States Patent
Fujihara

(10) Patent No.: US 8,889,843 B2
(45) Date of Patent: Nov. 18, 2014

(54) NUCLEIC ACID SYNTHESIZING DIMER AMIDITE AND NUCLEIC ACID SYNTHESIZING METHOD

(75) Inventor: Tsuyoshi Fujihara, Kawasaki (JP)

(73) Assignee: Apta Biosciences Ltd., Ledbury (GB)

(*) Notice: Subject to any disclaimer, the term of this patent is extended or adjusted under 35 U.S.C. 154(b) by 47 days.

(21) Appl. No.: 12/713,857

(22) Filed: Feb. 26, 2010

(65) Prior Publication Data

US 2010/0197902 A1 Aug. 5, 2010

Related U.S. Application Data

(63) Continuation of application No. PCT/JP2008/064701, filed on Aug. 18, 2008.

(30) Foreign Application Priority Data

Aug. 31, 2007 (JP) .................................. 2007-225507

(51) Int. Cl.
C07H 19/167 (2006.01)
C07H 19/173 (2006.01)
C07H 21/00 (2006.01)

(52) U.S. Cl.
USPC ..................... 536/23.1; 536/25.32; 536/25.34; 536/25.6

(58) Field of Classification Search
None
See application file for complete search history.

(56) References Cited

U.S. PATENT DOCUMENTS

| | | | |
|---|---|---|---|
| 4,973,679 A * | 11/1990 | Caruthers et al. | 536/26.71 |
| 7,101,992 B1 * | 9/2006 | Hirao et al. | 536/25.3 |
| 7,517,646 B2 * | 4/2009 | Fujihara et al. | 435/6.16 |
| 7,667,031 B2 * | 2/2010 | Hirao et al. | 536/25.3 |
| 7,723,495 B2 * | 5/2010 | Fujihara et al. | 536/22.1 |
| 7,759,473 B2 * | 7/2010 | Fujihara et al. | 536/23.1 |
| 7,851,157 B1 | 12/2010 | Sekine et al. | |
| 7,910,726 B2 * | 3/2011 | Fujihara | 536/26.7 |
| 2003/0229218 A1 | 12/2003 | Sinha | |
| 2005/0130195 A1 | 6/2005 | Fujihara et al. | |

FOREIGN PATENT DOCUMENTS

| | | |
|---|---|---|
| JP | 2004-508379 A | 3/2004 |
| JP | 3978187 B2 | 9/2007 |
| JP | 2008-162992 A | 7/2008 |
| WO | 02/20543 A2 | 3/2002 |
| WO | 03/078623 A1 | 9/2003 |
| WO | 2006/093157 A1 | 9/2006 |

OTHER PUBLICATIONS

A. M. Avino et al, "Use of NPE-Protecting Groups for the Preparation of Oligonucleotides without Using Nucleophiles During the Final Deprotection," Nucleosides & Nucleotides, 1994, vol. 13, pp. 2059-2069.

R. Eritja et al, "A Synthetic Procedure for the Preparation of Oligonucleotides Without Using Ammonia and Its Application for the Synthesis of Oligonucleotides Containing O-4-alkyl Thymidines," Tetrahedron, 1992, vol. 48, No. 20, (U.K.), pp. 4171-4182.

J. Heikkila et al, "The 9-Fluorenylmethoxycarbonyl (Fmoc) Group for the Protection of Amino Functions of Cytidine, Adenosine, Guanosine, and Their 2'-Deoxysugar Derivatives," Acta. Chemica Scandanavica, 1983, B37, No. 3, Sweden, pp. 263-265.

L. H. Koole et al, "Synthesis of Phosphate-Methylated DNA Fragments Using 9-Fluorenylmethoxycarbonyl as Transient Base Protecting Group," Journal of Organic Chemistry, 1989, vol. 54, No. 7, pp. 1657-1664.

W. H. A. Kuijpers et al, "The 2-(Acetoxymethyl) Benzoyl (AMB) Group as a New Base-Protecting Group, Designed for the Protection of (Phosphate) Modified Oligonucleotides," Tetrahedron Letters, 1990, vol. 31, No. 46, The Netherlands, pp. 6729-6732.

W. H. A. Kuijpers, "The Application of the AMB Protective Group in the Solid-Phase Synthesis of Methylphosphonate DNA Analogues," Nucleic Acids Research, 1993, vol. 21, No. 15, The Netherlands, pp. 3493-3500.

International Search Report of PCT/JP2008/064701, mailing date of Sep. 30, 2008.

Japanese Office Action dated Oct. 16, 2012, issued in corresponding Japanese Patent Application No. 2009-530051, (3 pages).

* cited by examiner

*Primary Examiner* — Lawrence E Crane

(74) *Attorney, Agent, or Firm* — Westerman, Hattori, Daniels & Adrian, LLP

(57) ABSTRACT

To provide an excellent dimer amidite which can be subjected to purification, preferably, whose protective groups can be removed under mild conditions, and a method for synthesizing a nucleic acid using the dimer amidite, a dimer amidite having a structure represented by the following General Formula (1) and a method for synthesizing a nucleic acid including performing condensation reaction of the dimer amidite are provided:

General Formula (1)

wherein in General Formula (1), $R_1$ and $R_2$ each independently represent any one of groups selected from General formulas (2) to (4) and Structural Formulas (12) to (15) with a compound where $R_1$ and $R_2$ are each represent Structural Formulas (12) being excluded:

General Formula (2)

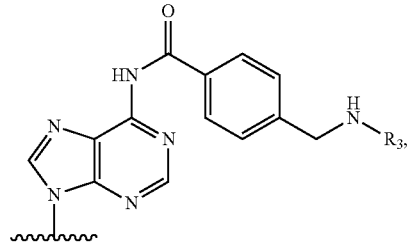

General Formula (3)

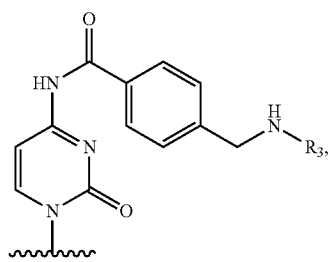

General Formula (4)

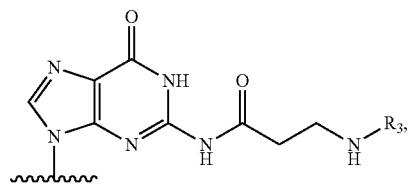

Structural Formula (12)

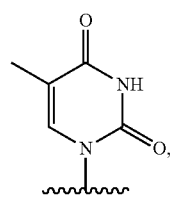

Structural Formula (13)

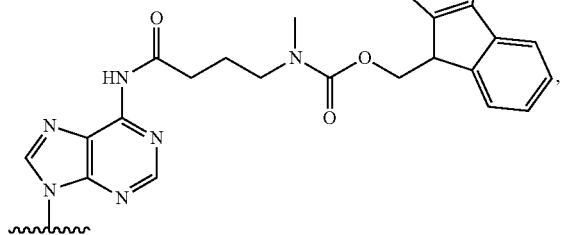

Structural Formula (14)

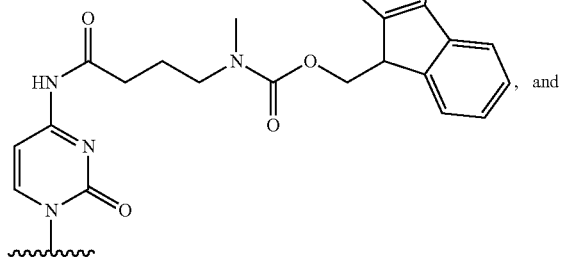

, and

Structural Formula (15)

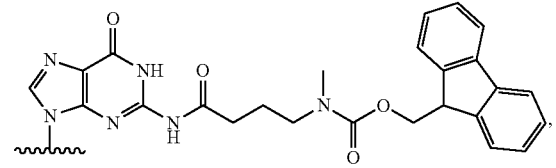

and wherein in the General Formulas (2) to (4), $R_3$ represents any one group represented by the following Structural Formulas (16) to (25):

Structural Formula (16)

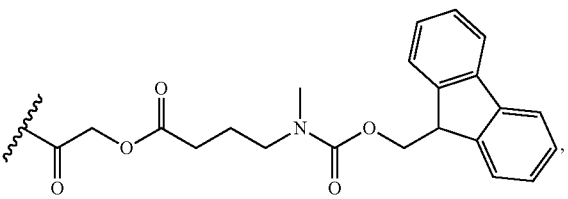

Structural Formula (17)

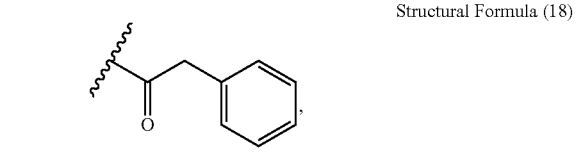

Structural Formula (18)

Structural Formula (19)

-continued
Structural Formula (20)
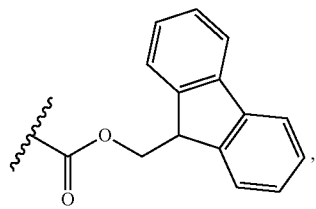
Structural Formula (21)
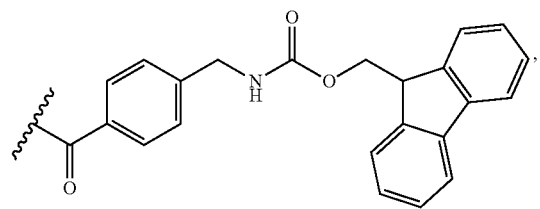
Structural Formula (22)
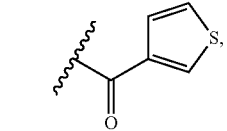
Structural Formula (23)
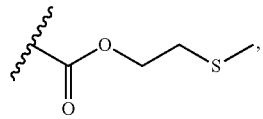
Structural Formula (24)
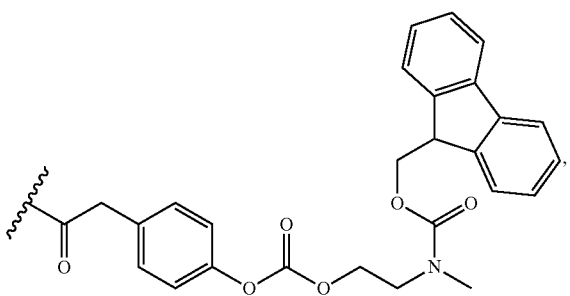
and
Structural Formula (25)
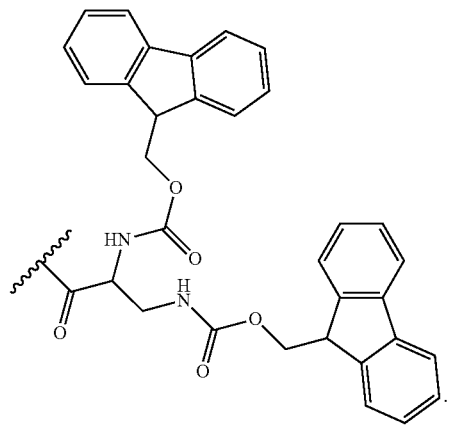
14 Claims, 100 Drawing Sheets

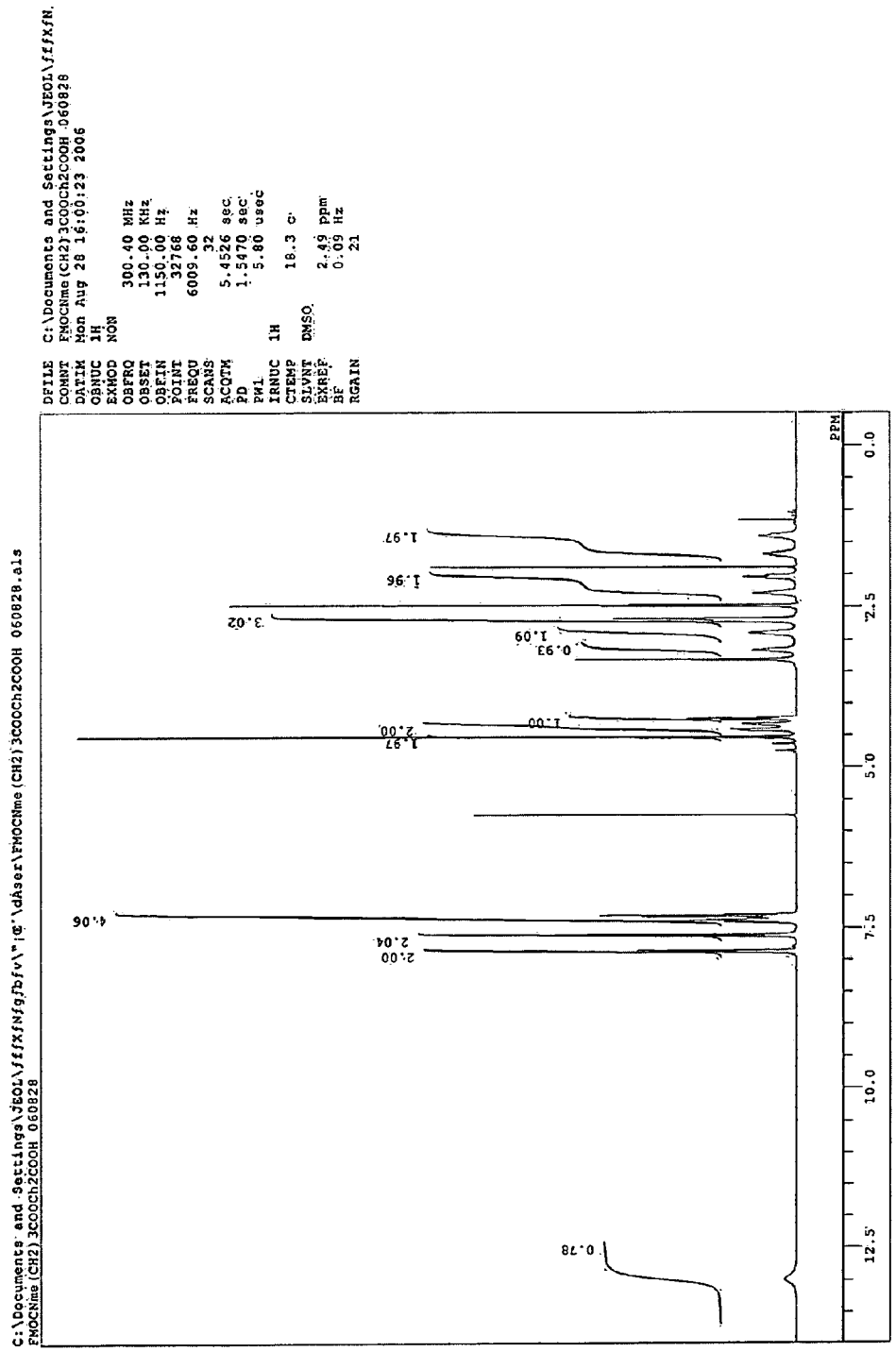
FIG. 2-A

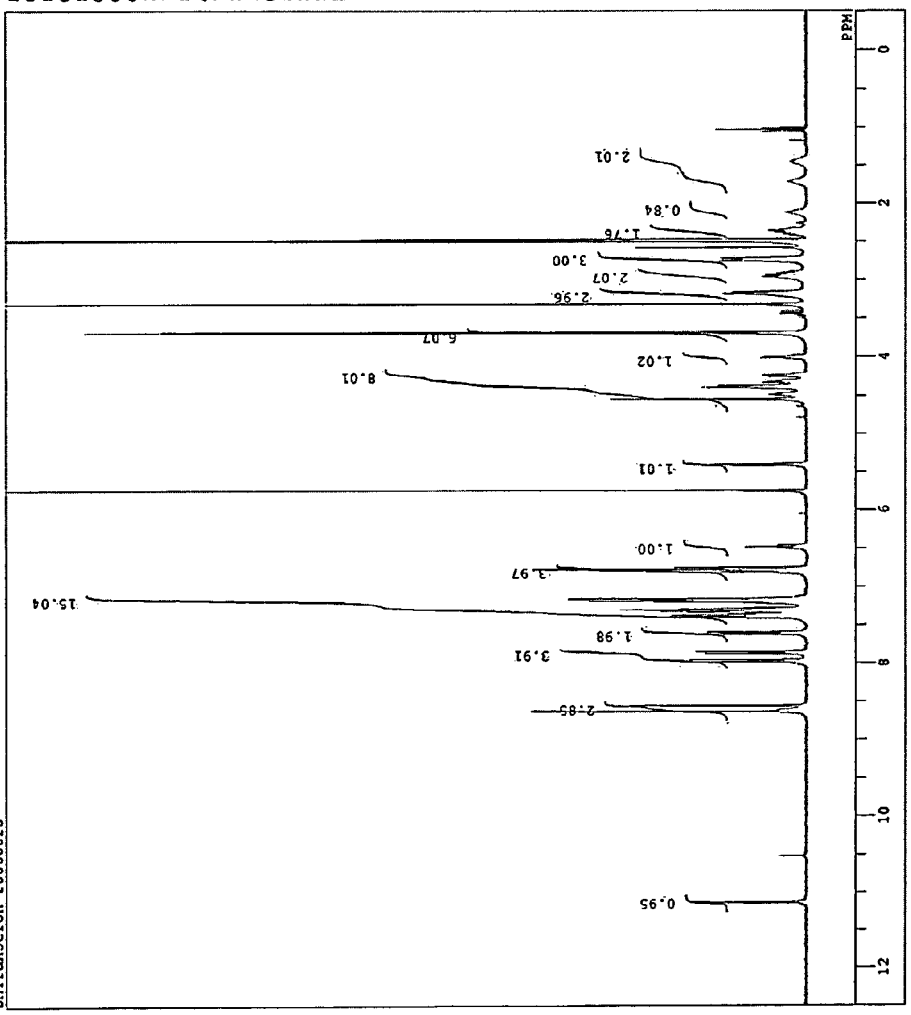
FIG. 2-B

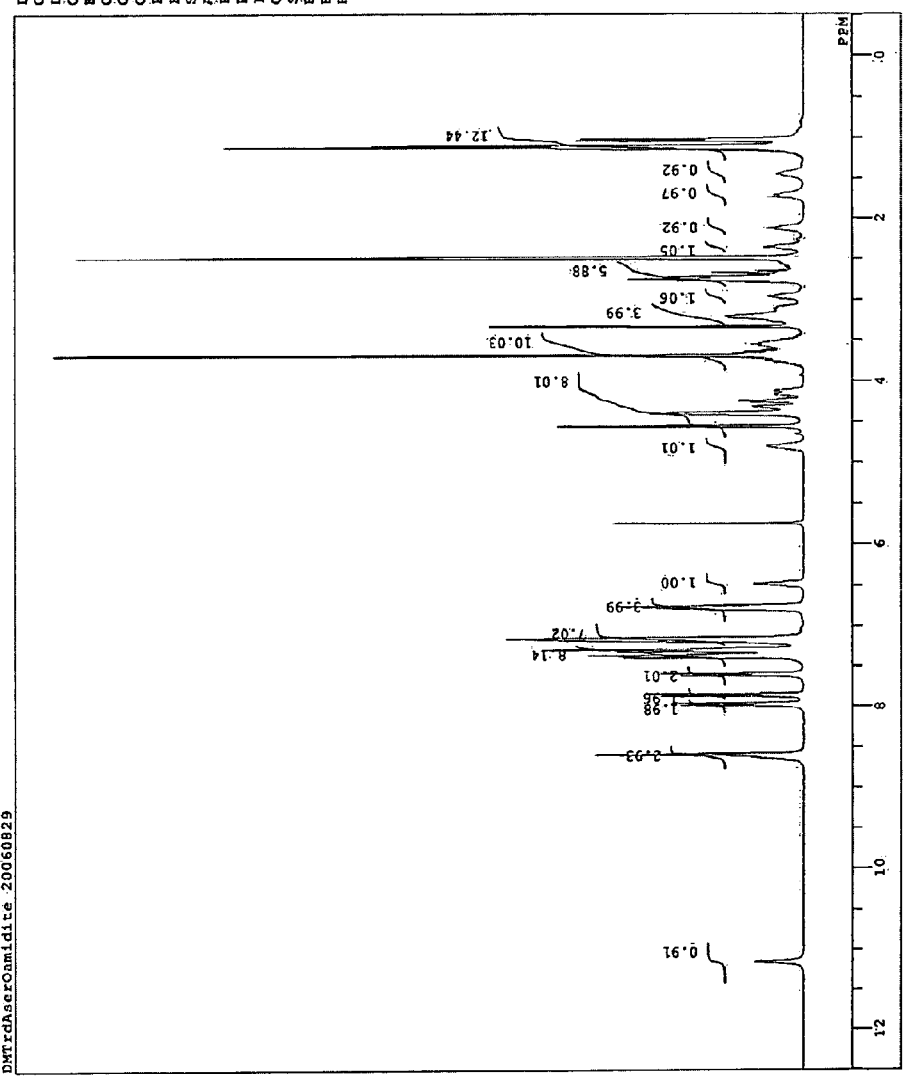
FIG. 2-C

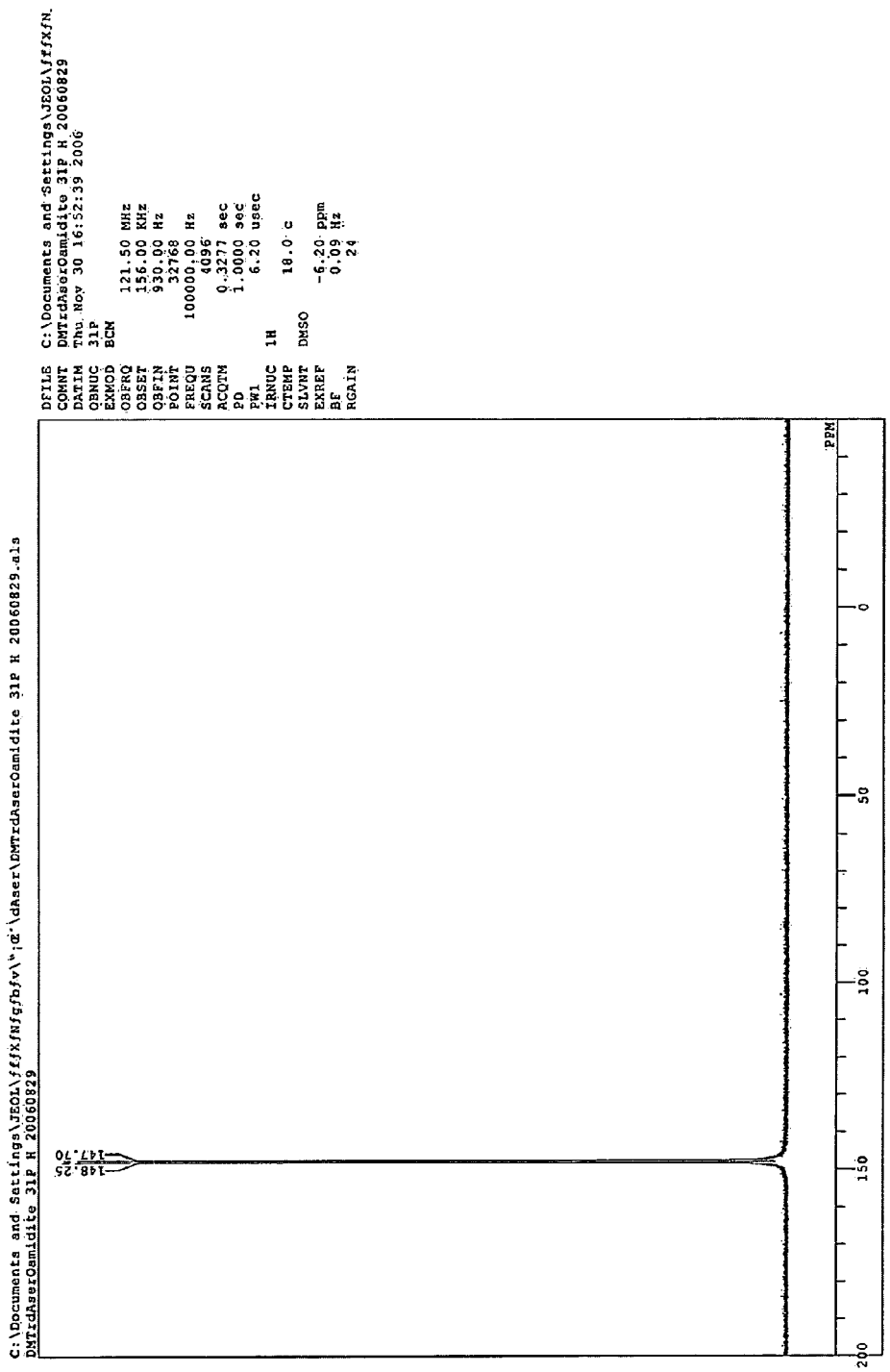
FIG. 2-D

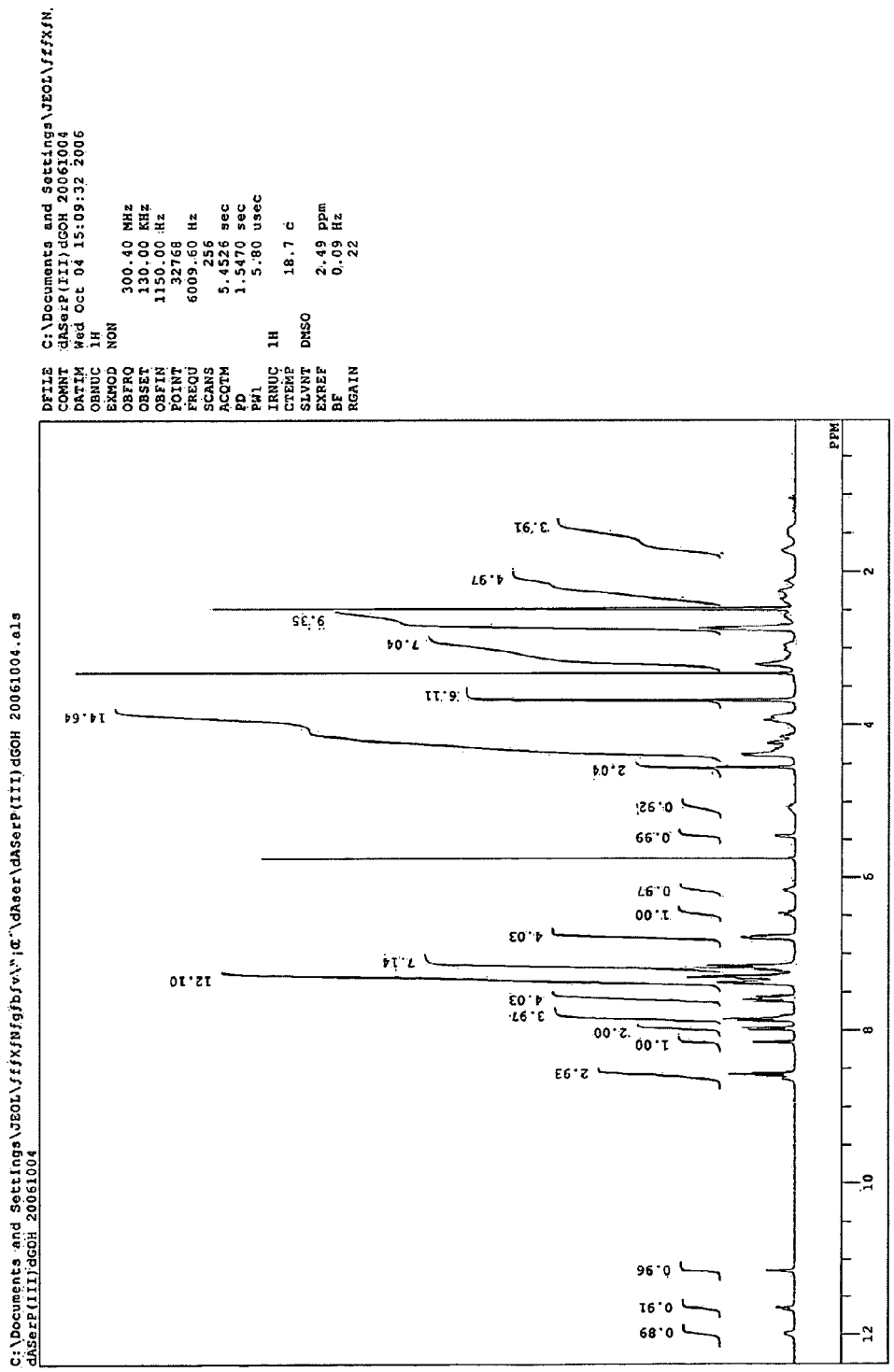
FIG. 2-E

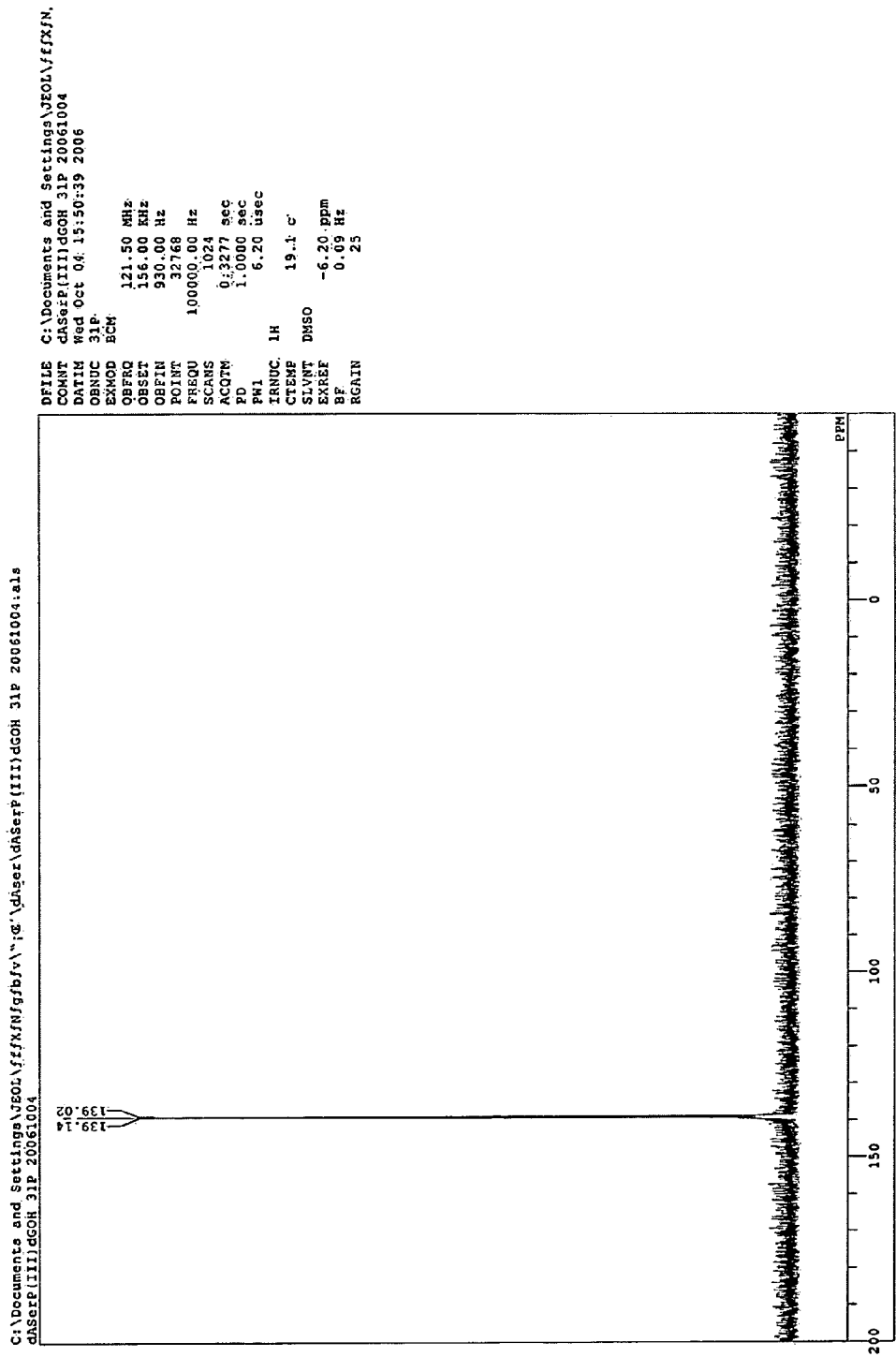
FIG. 2-F

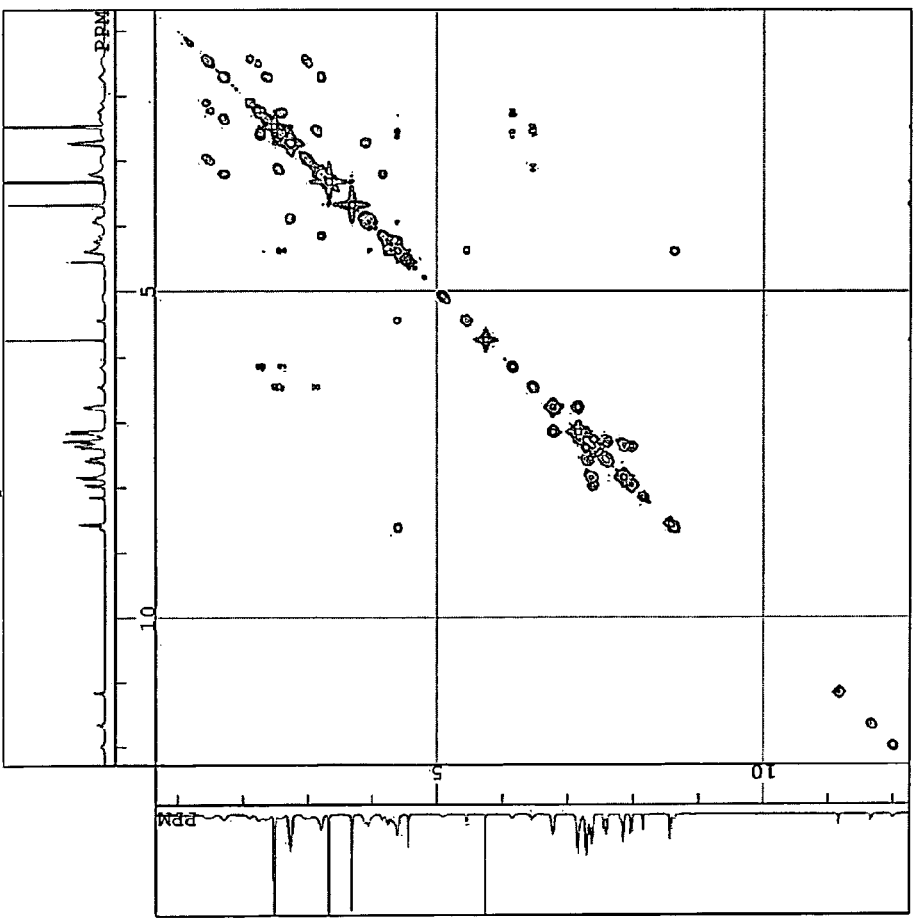
FIG. 2-G

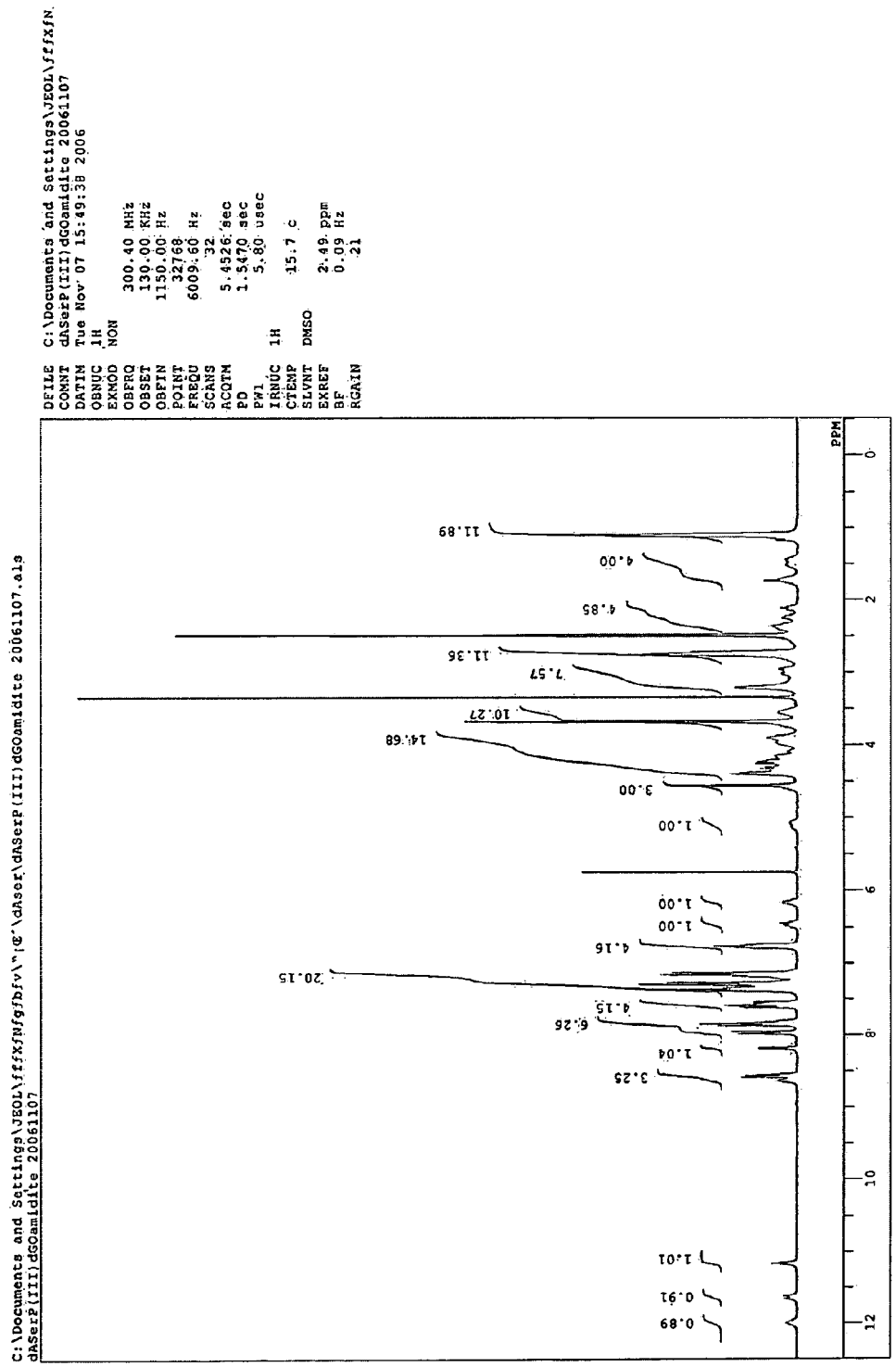
FIG. 2-H

FIG. 2-I
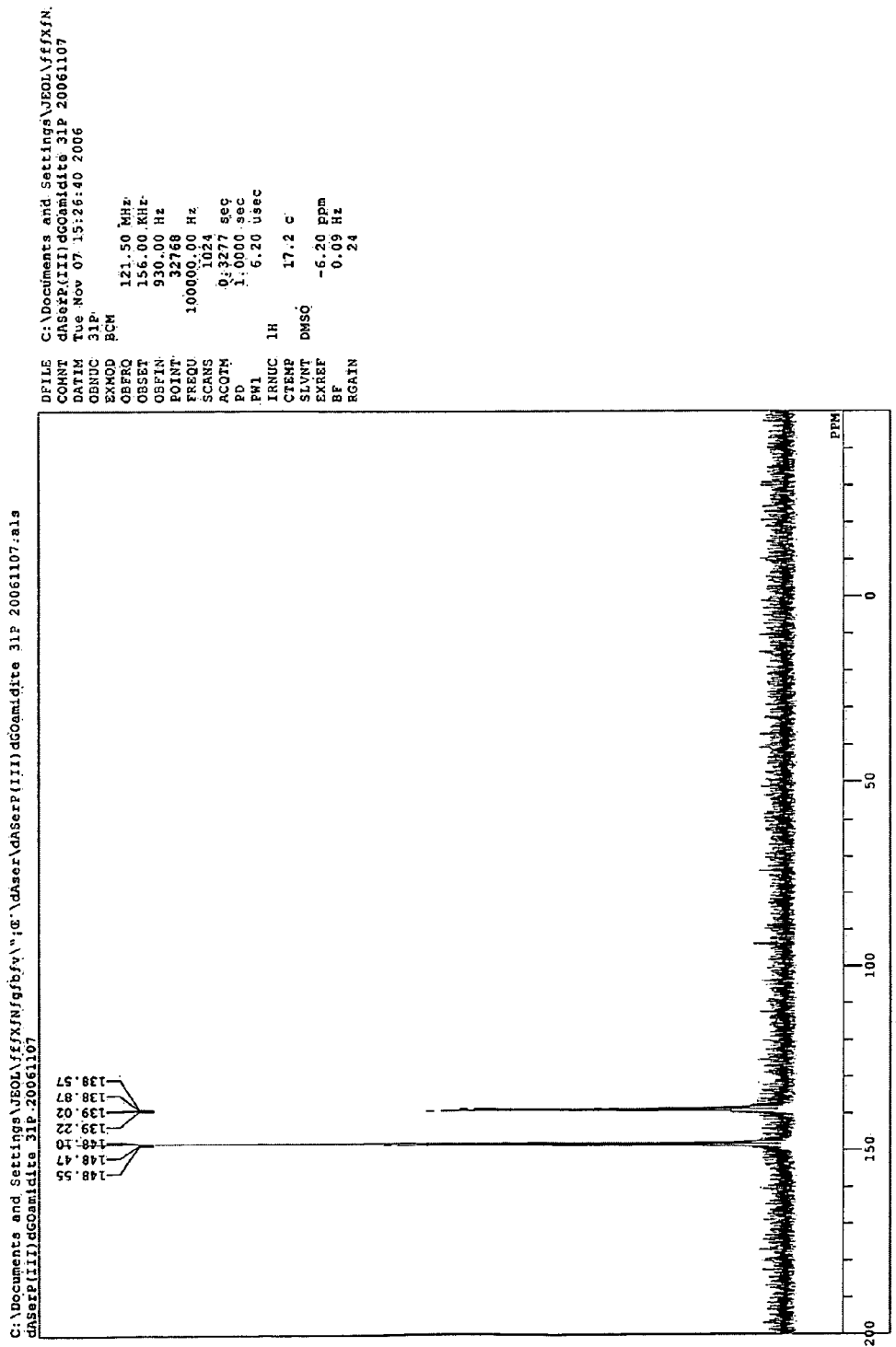

FIG. 2-J
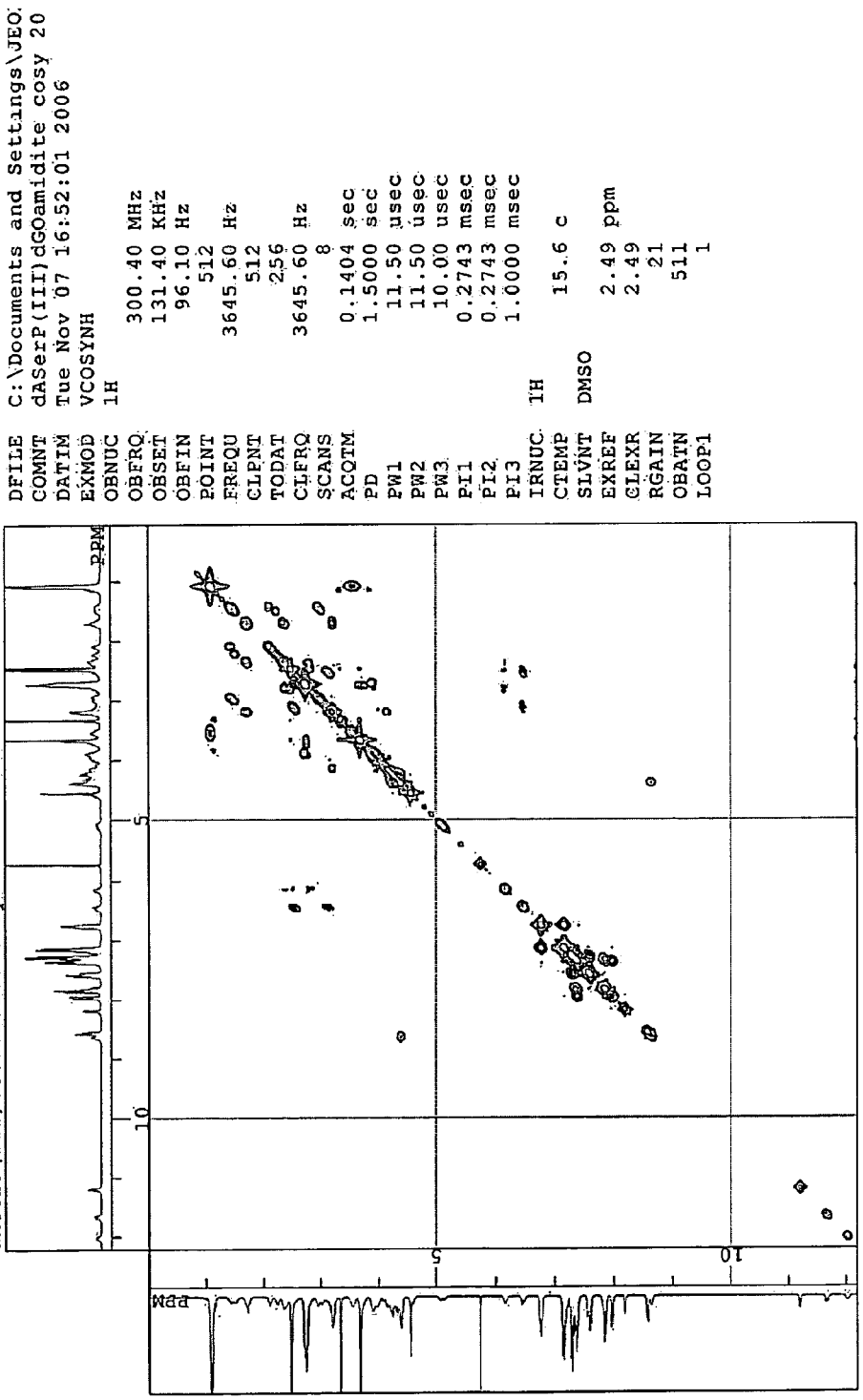

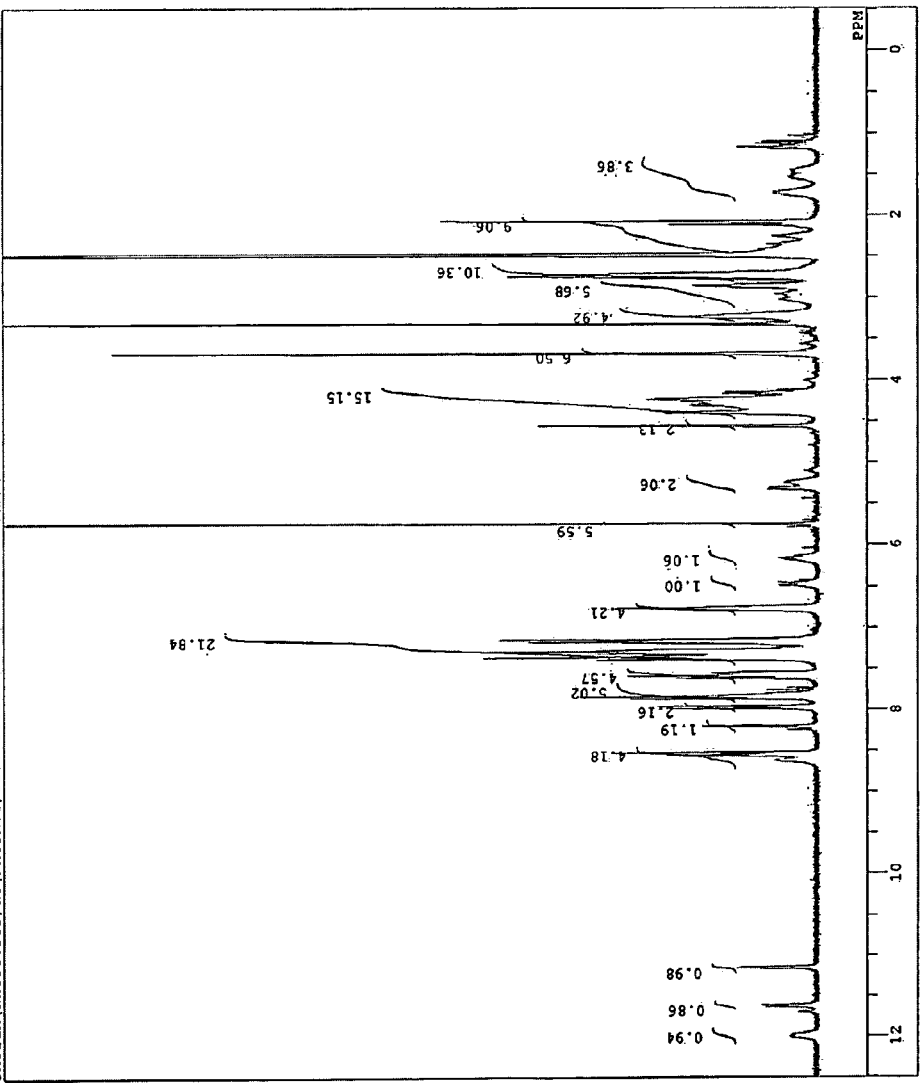
FIG. 2-K

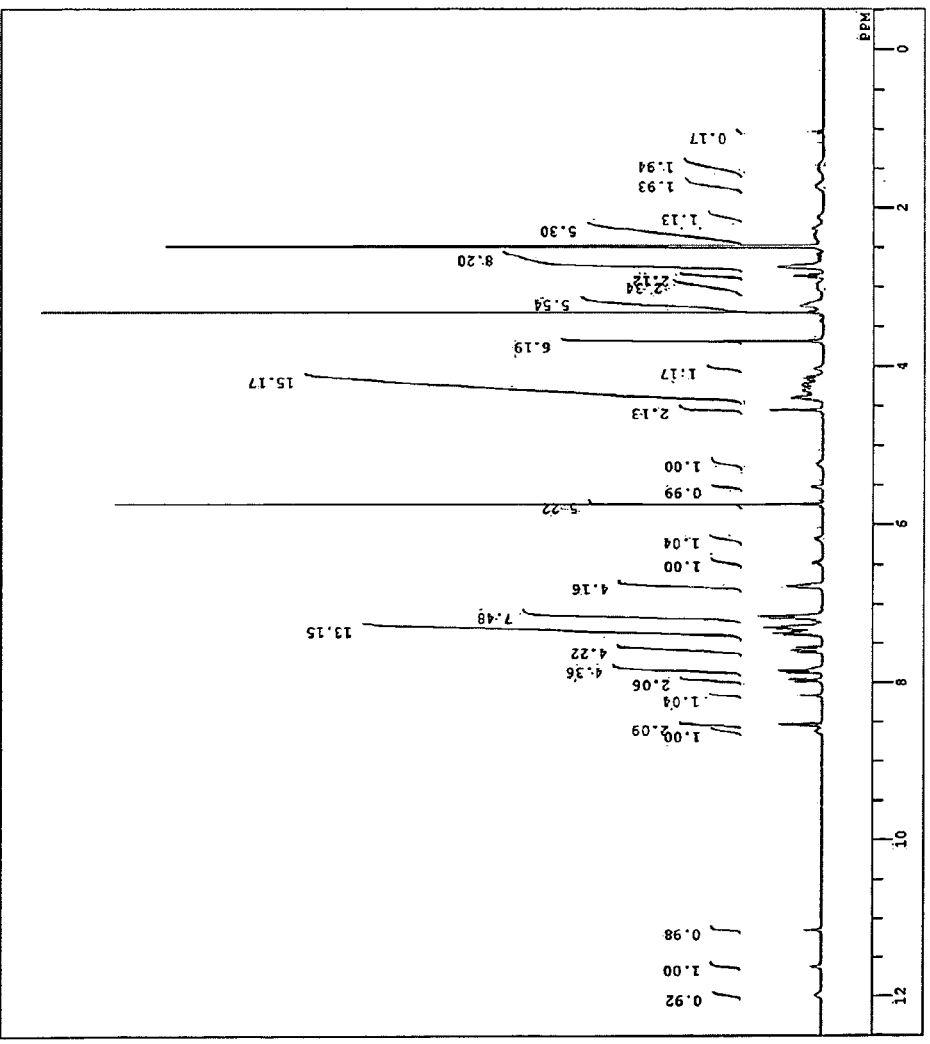
FIG. 2-L

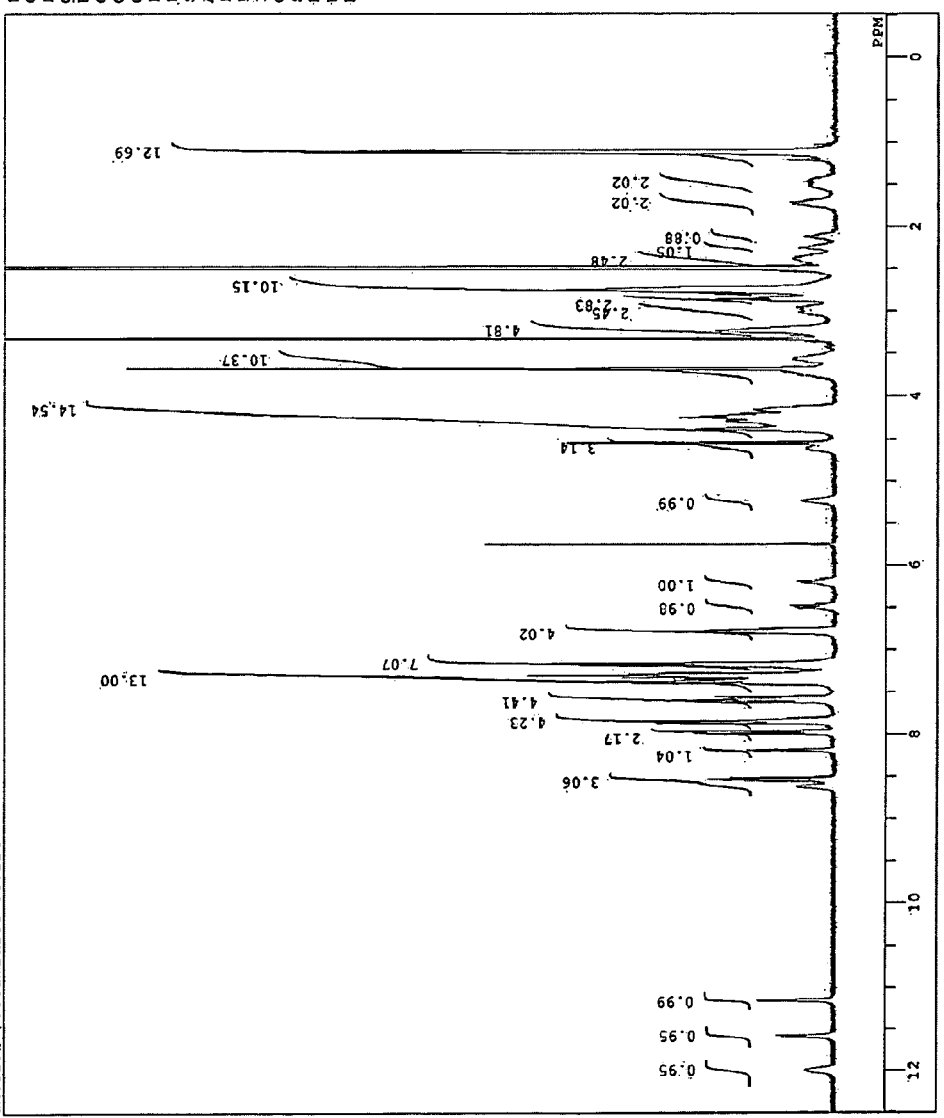
FIG. 2-M

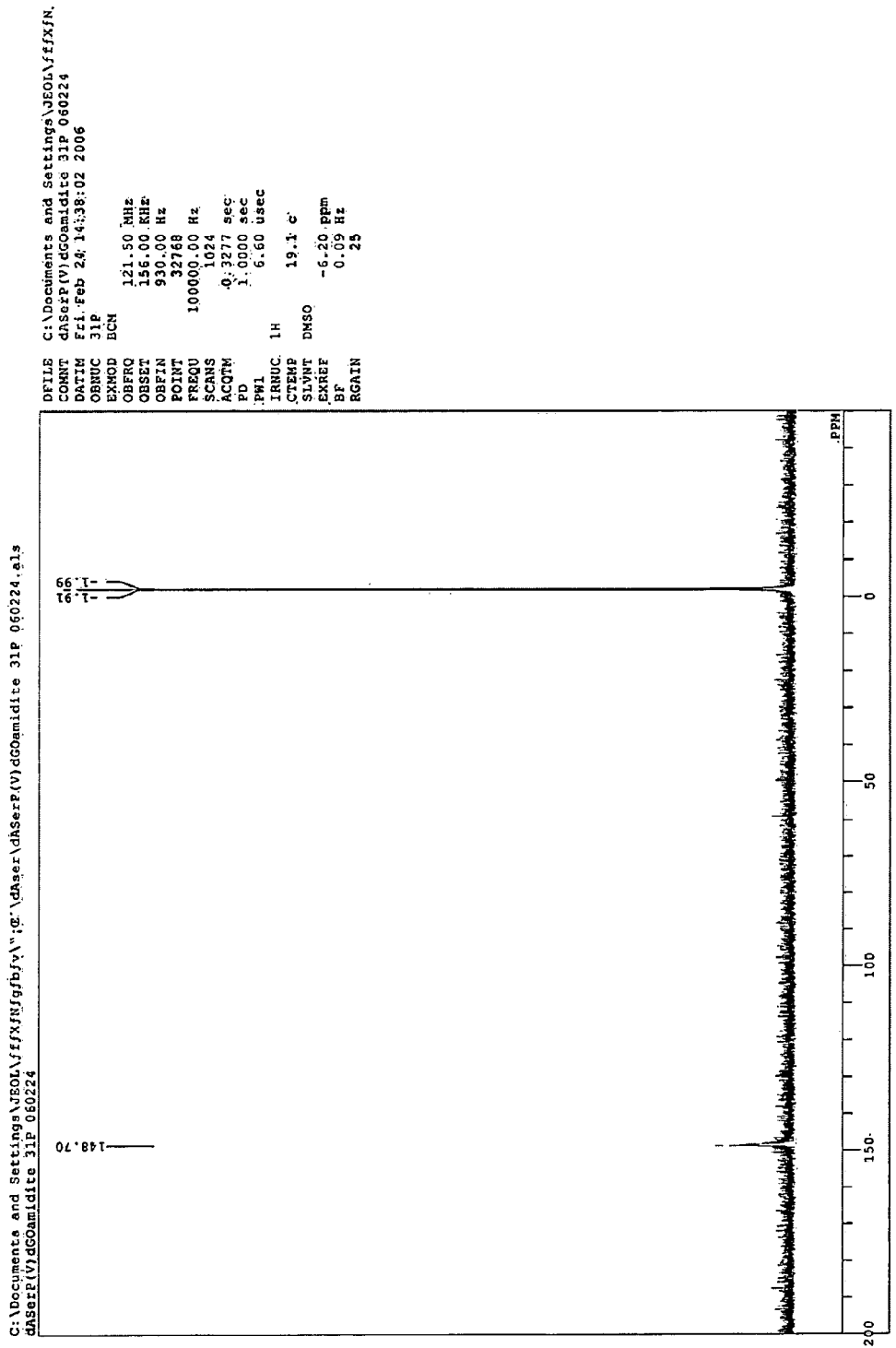
FIG. 2-N

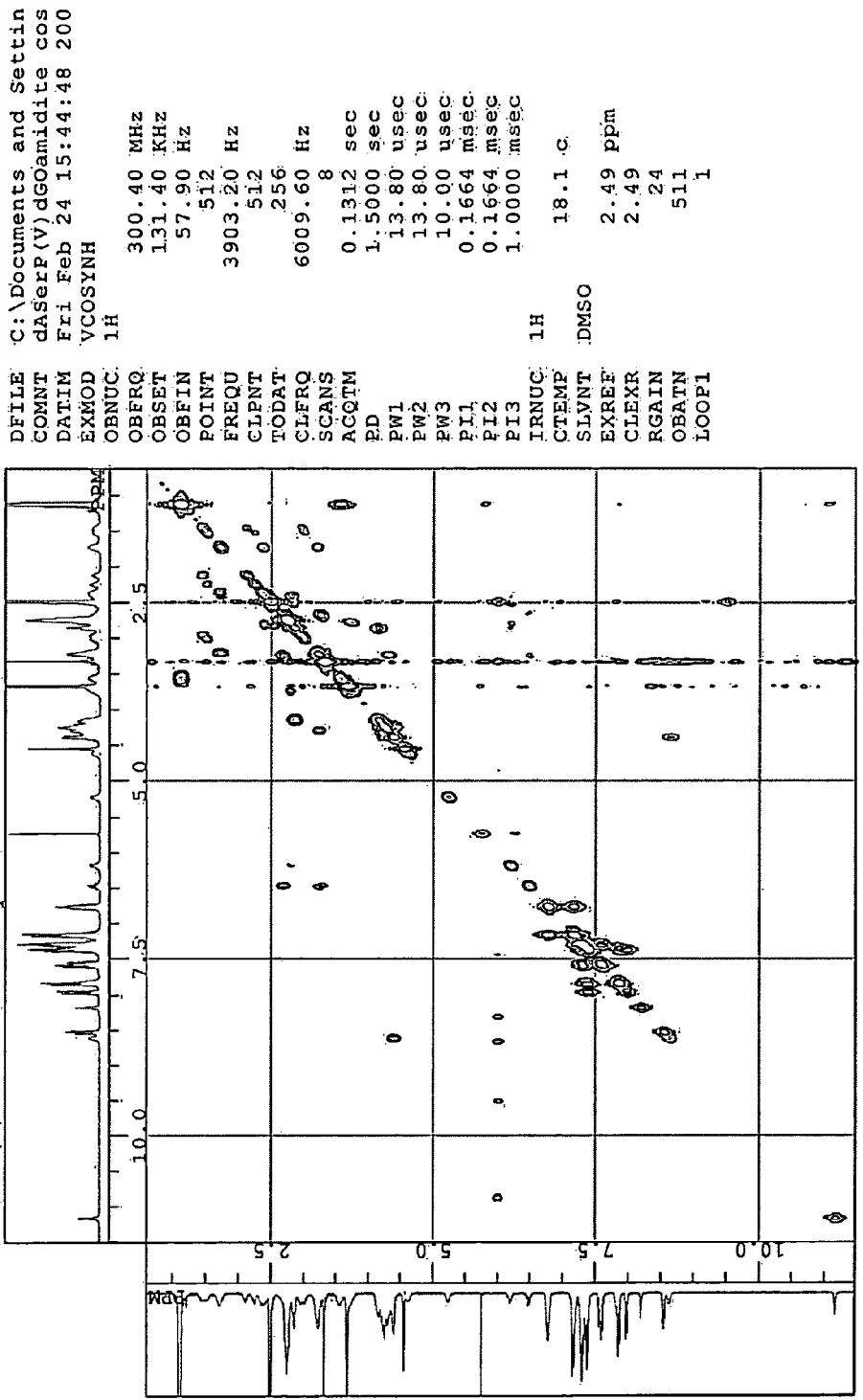
FIG. 2-O

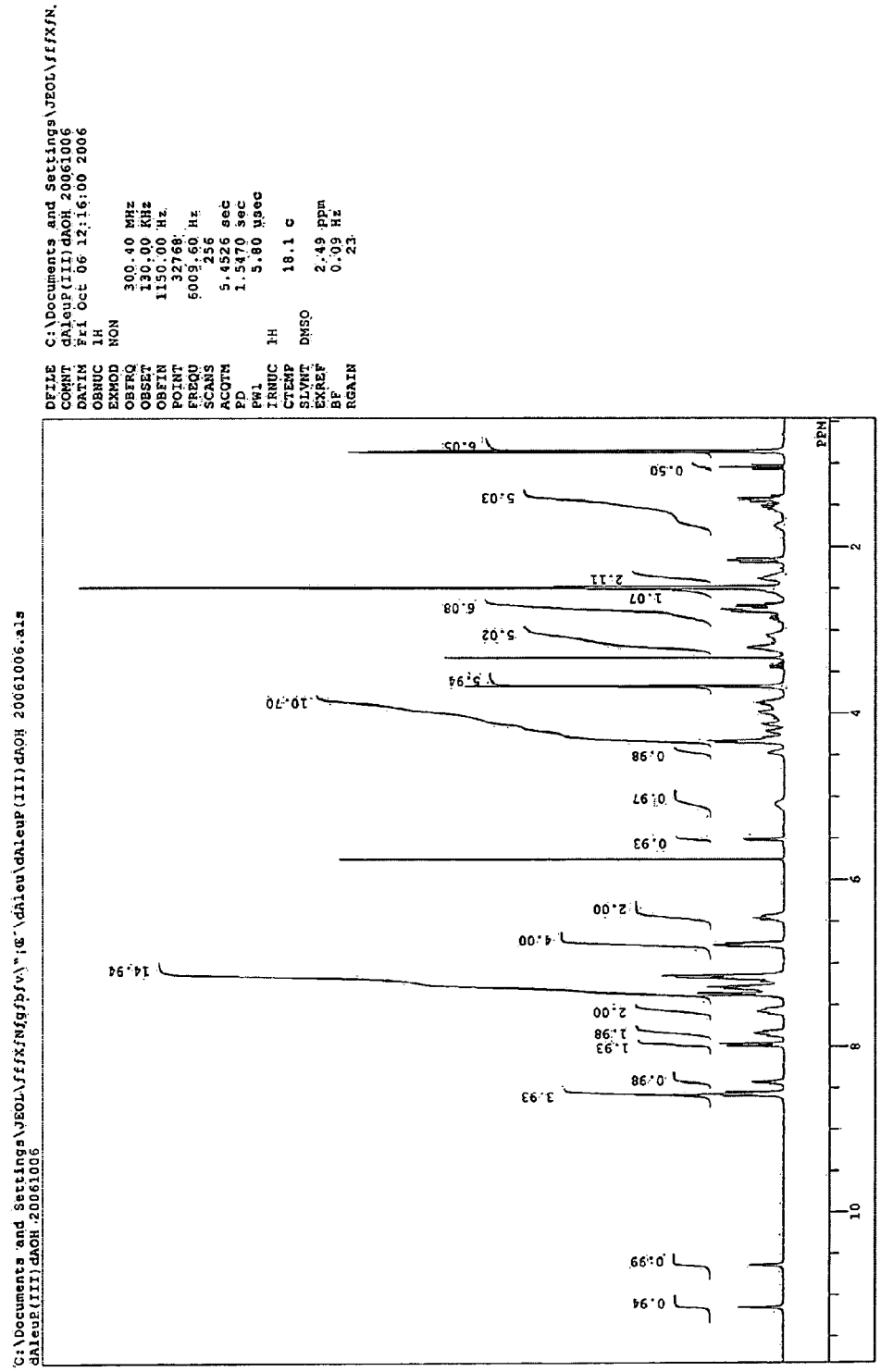
FIG. 3-A

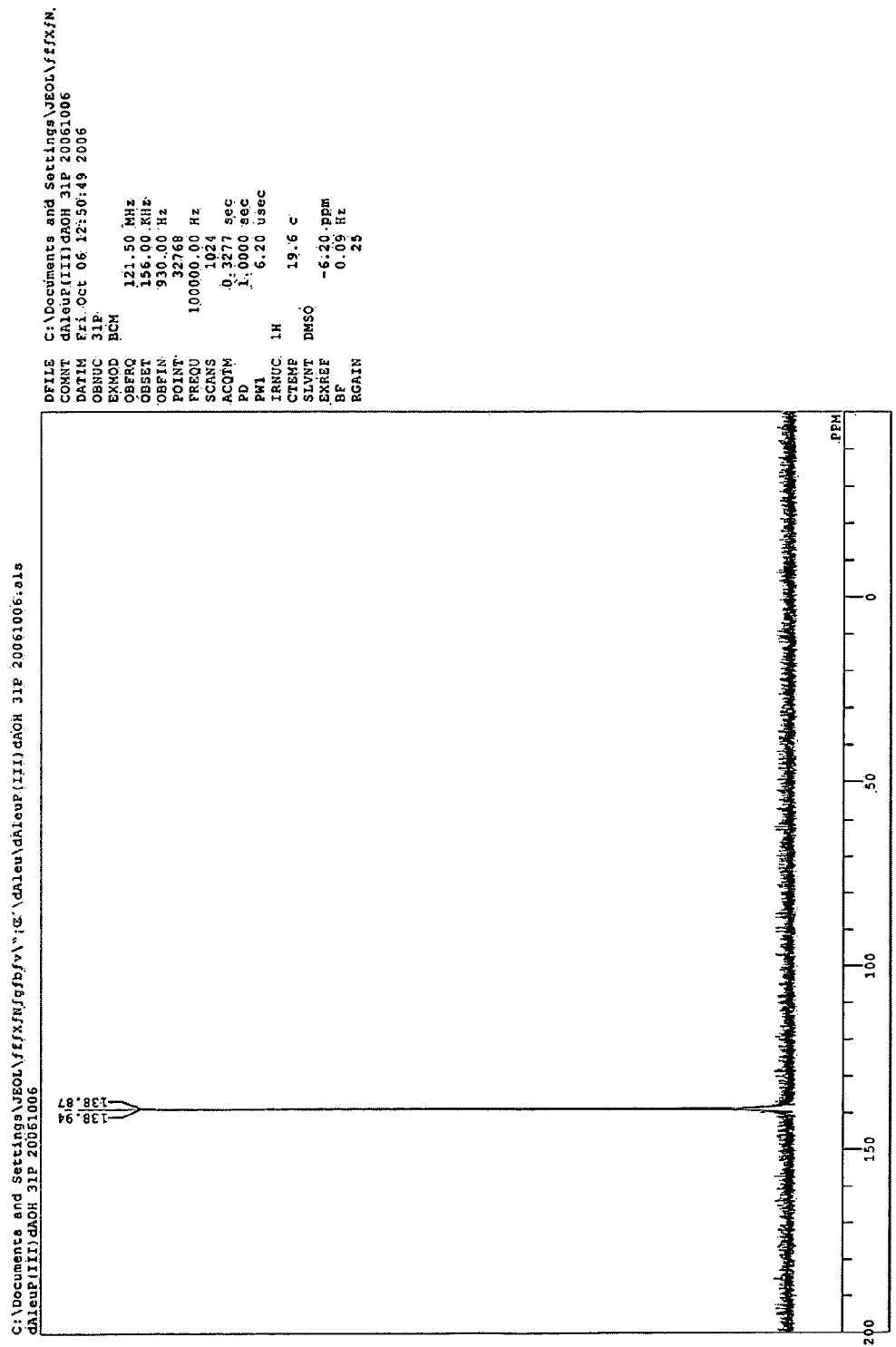
FIG. 3-B

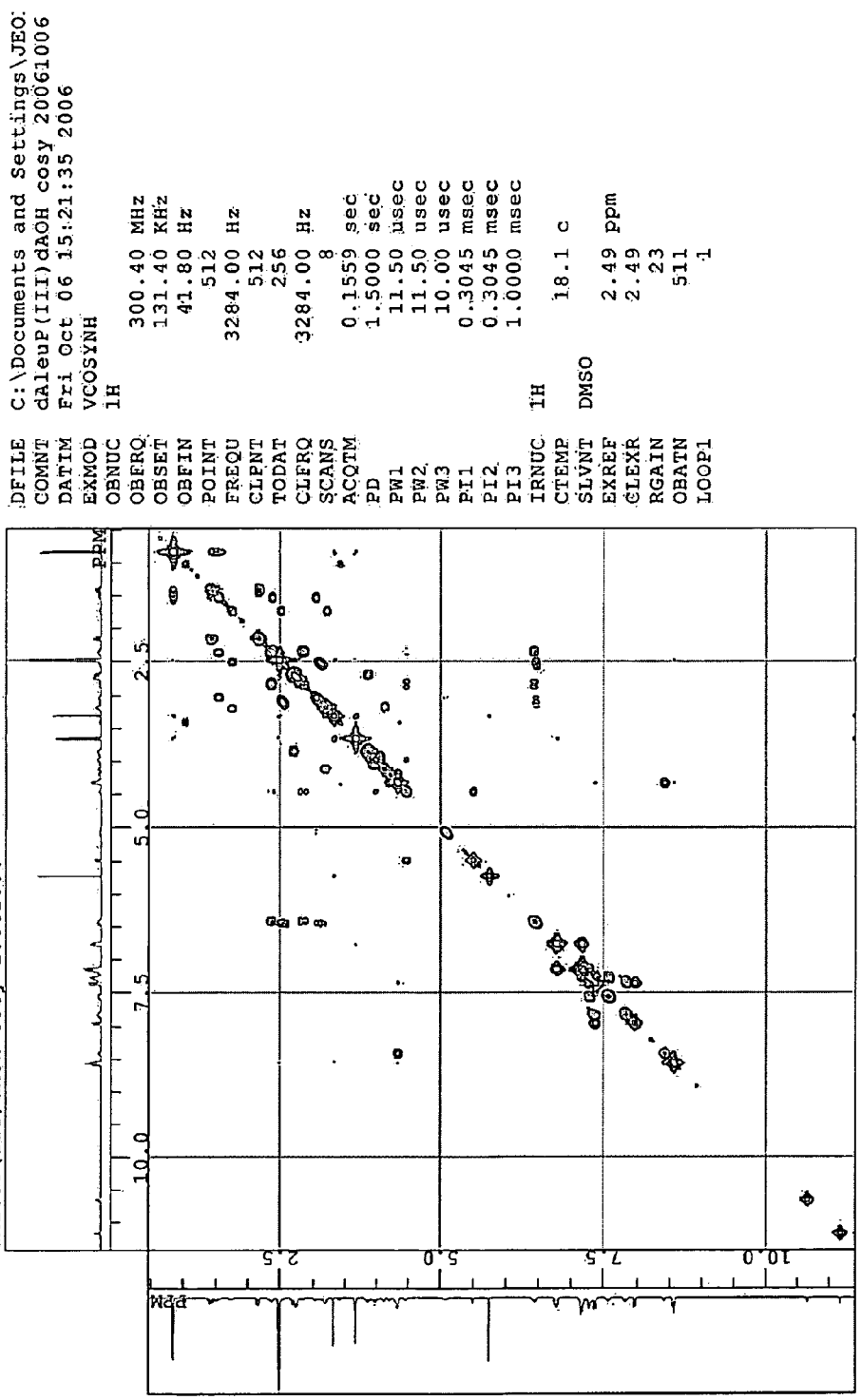
FIG. 3-C

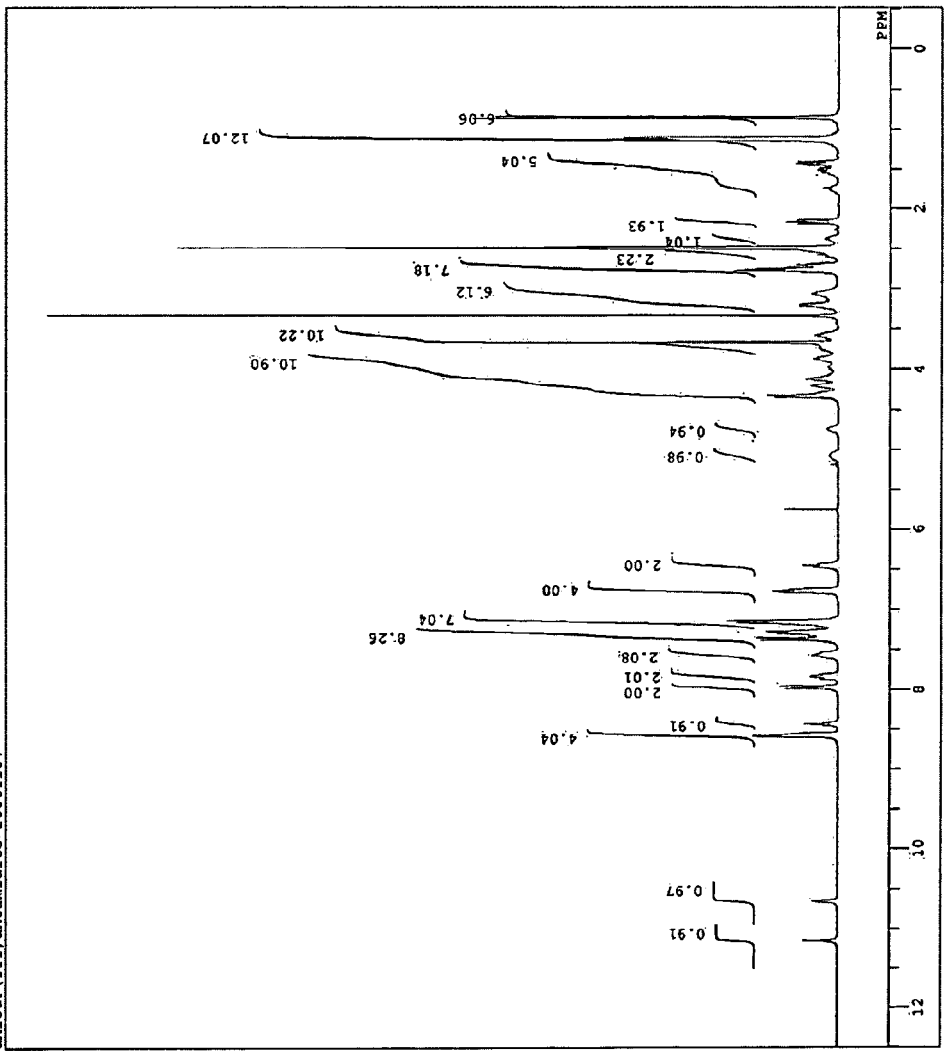
FIG. 3-D

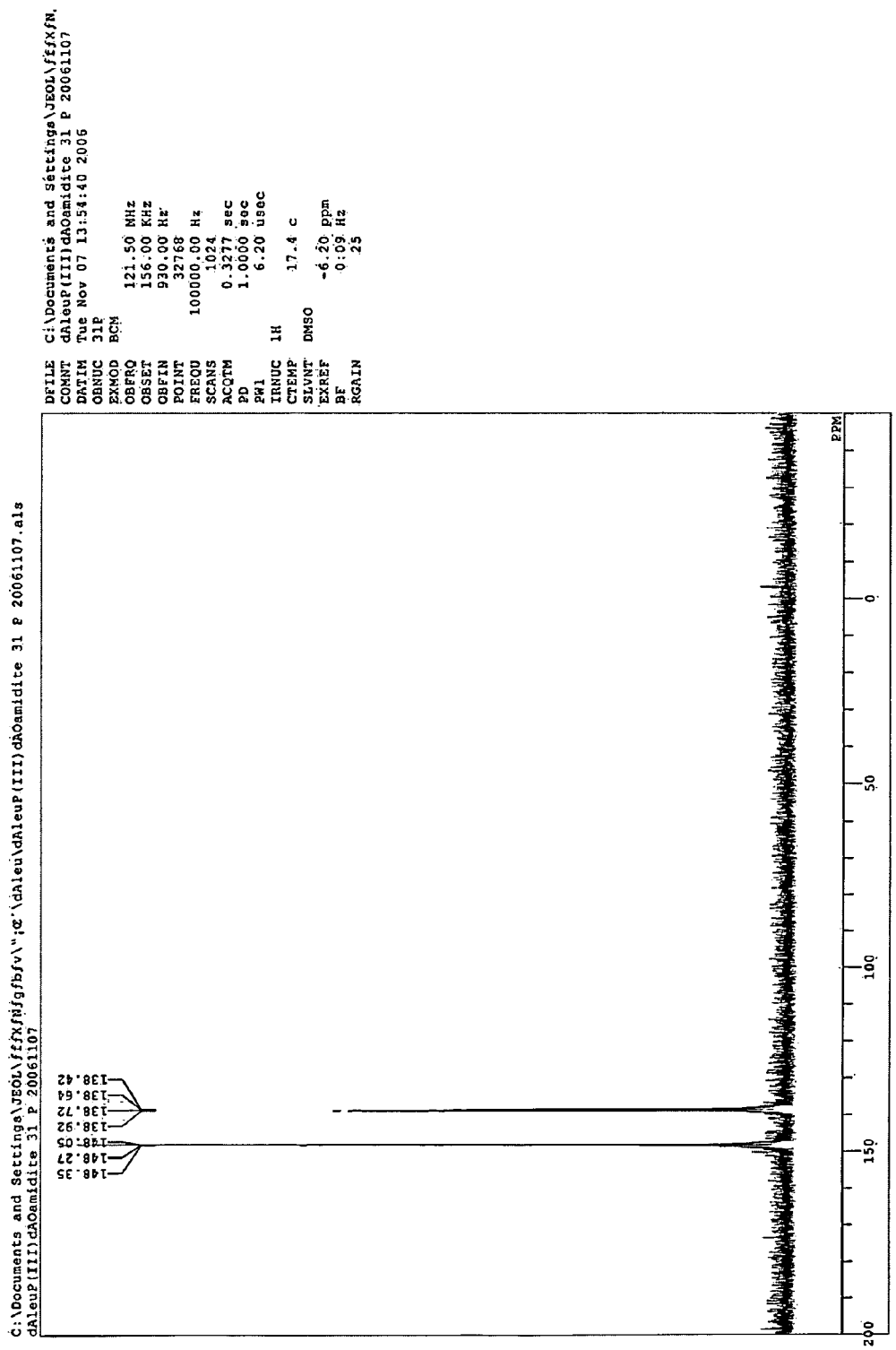
FIG. 3-E

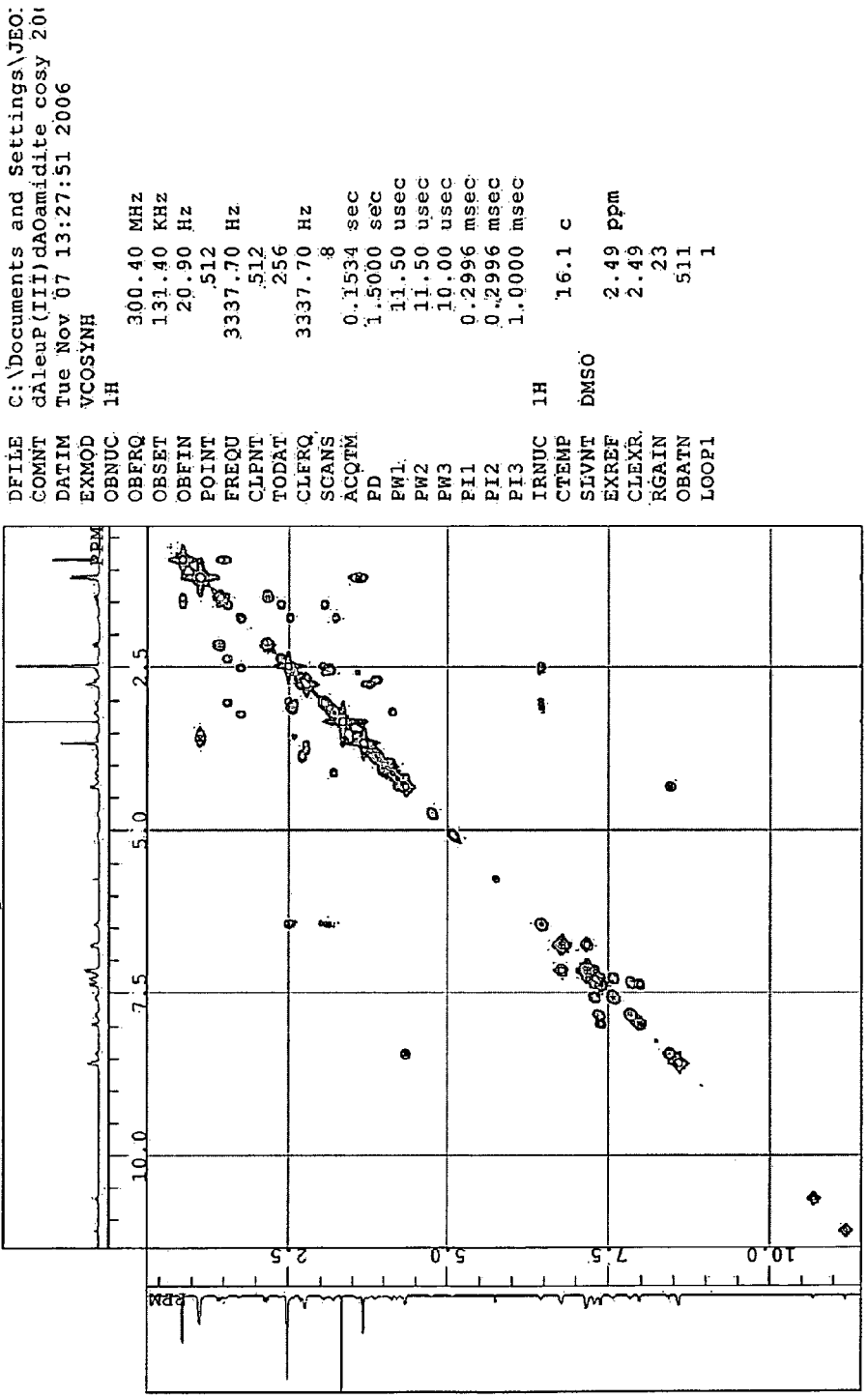
FIG. 3-F

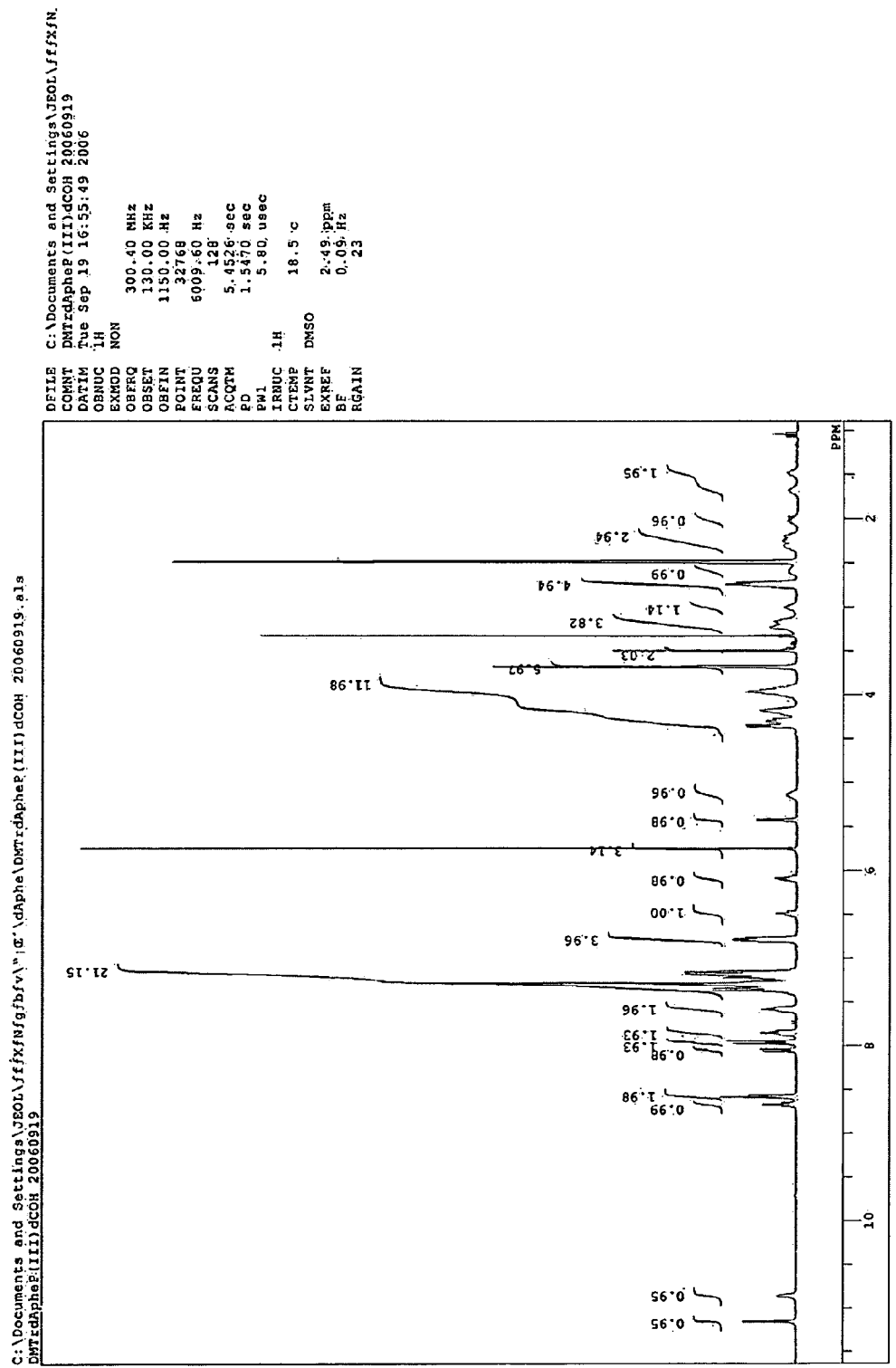
FIG. 4-A

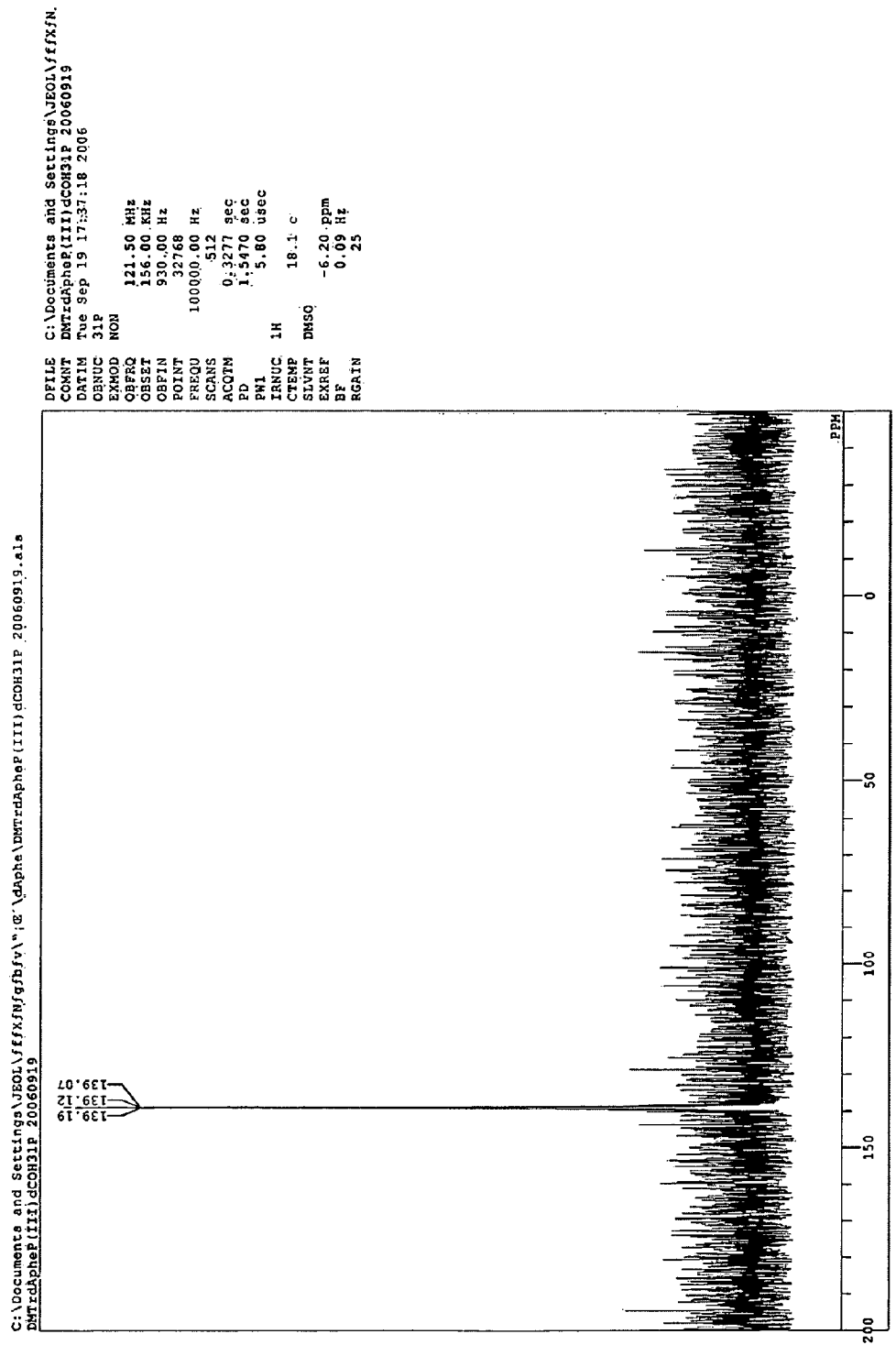
FIG. 4-B

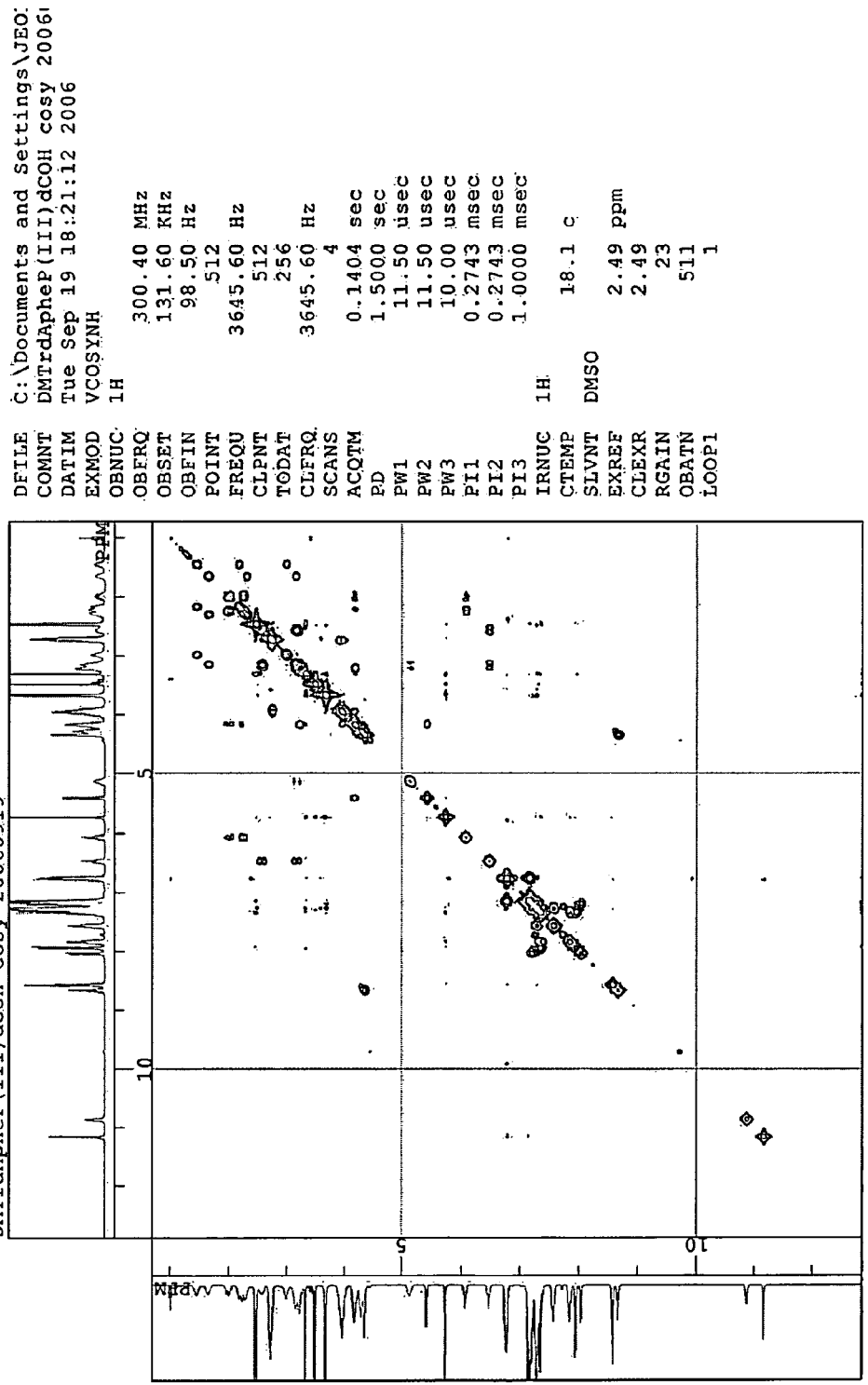
FIG. 4-C

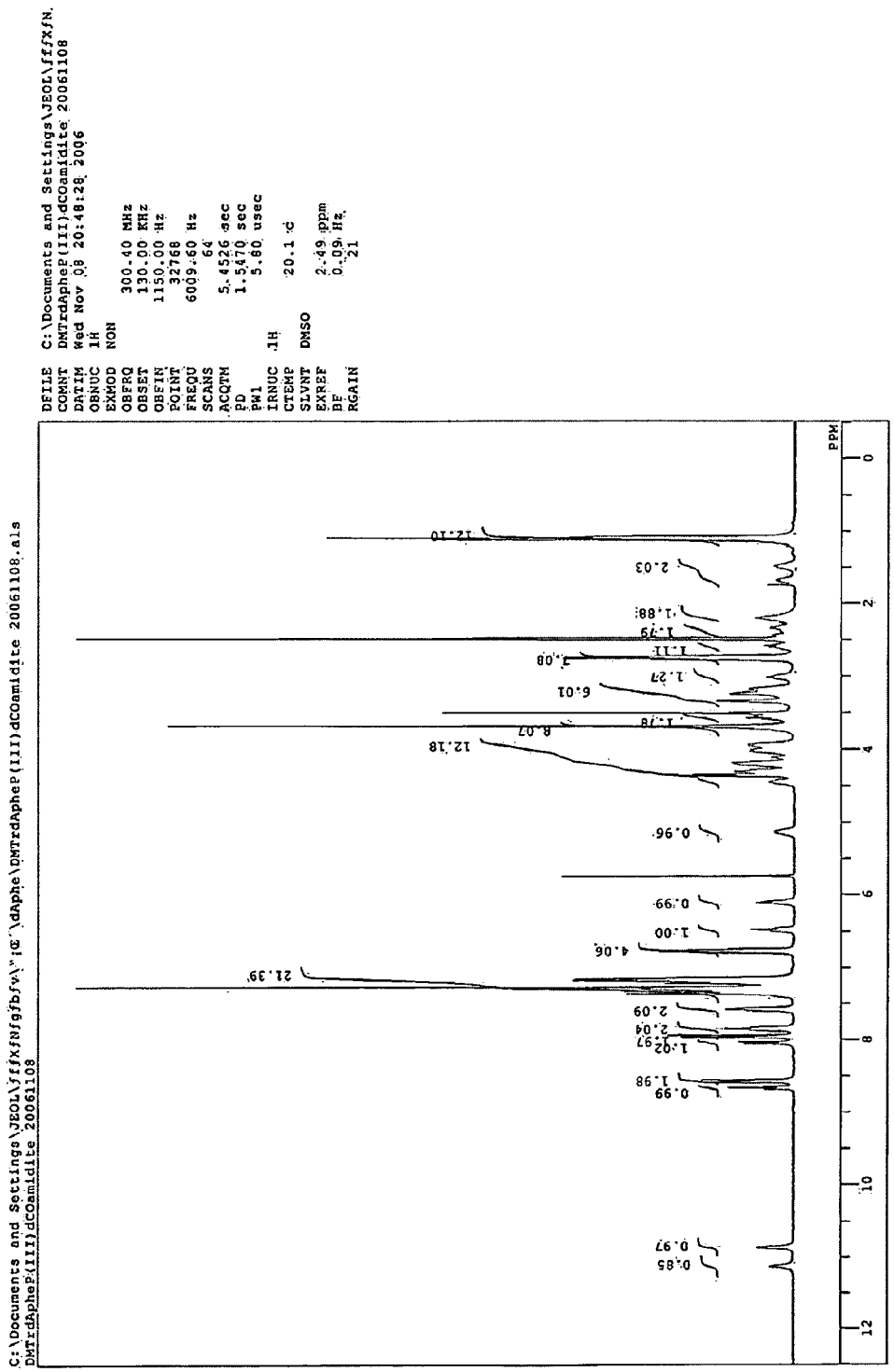
FIG. 4-D

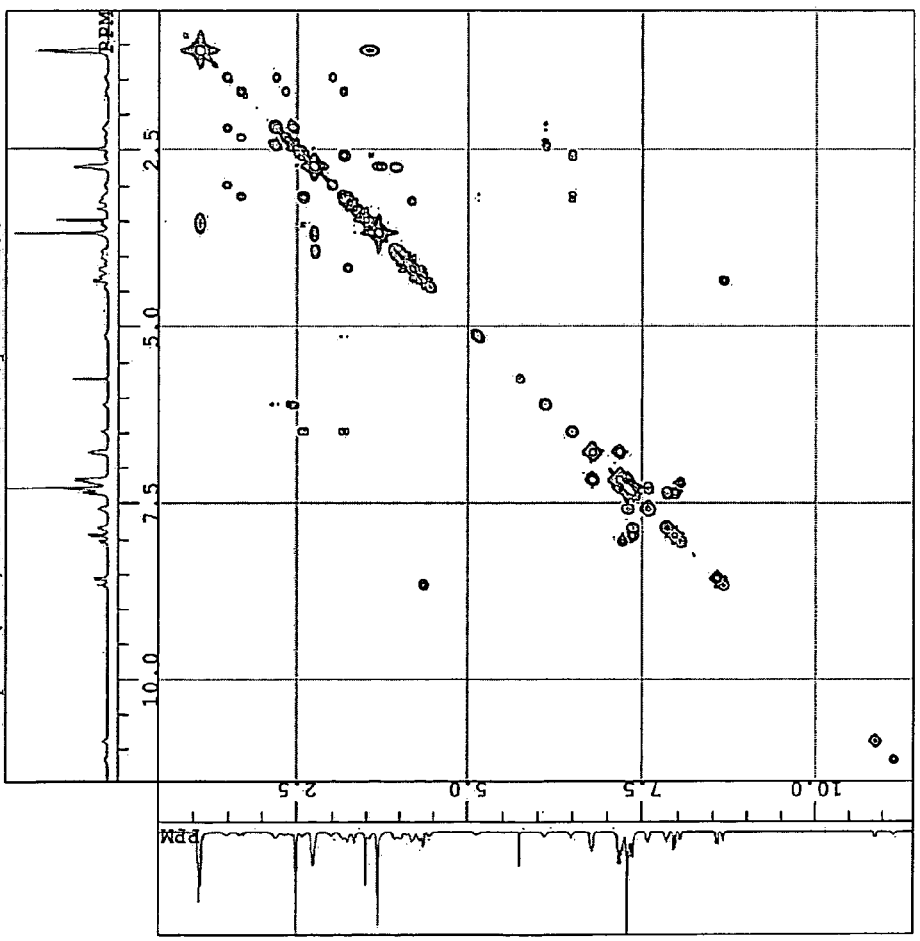
FIG. 4-E

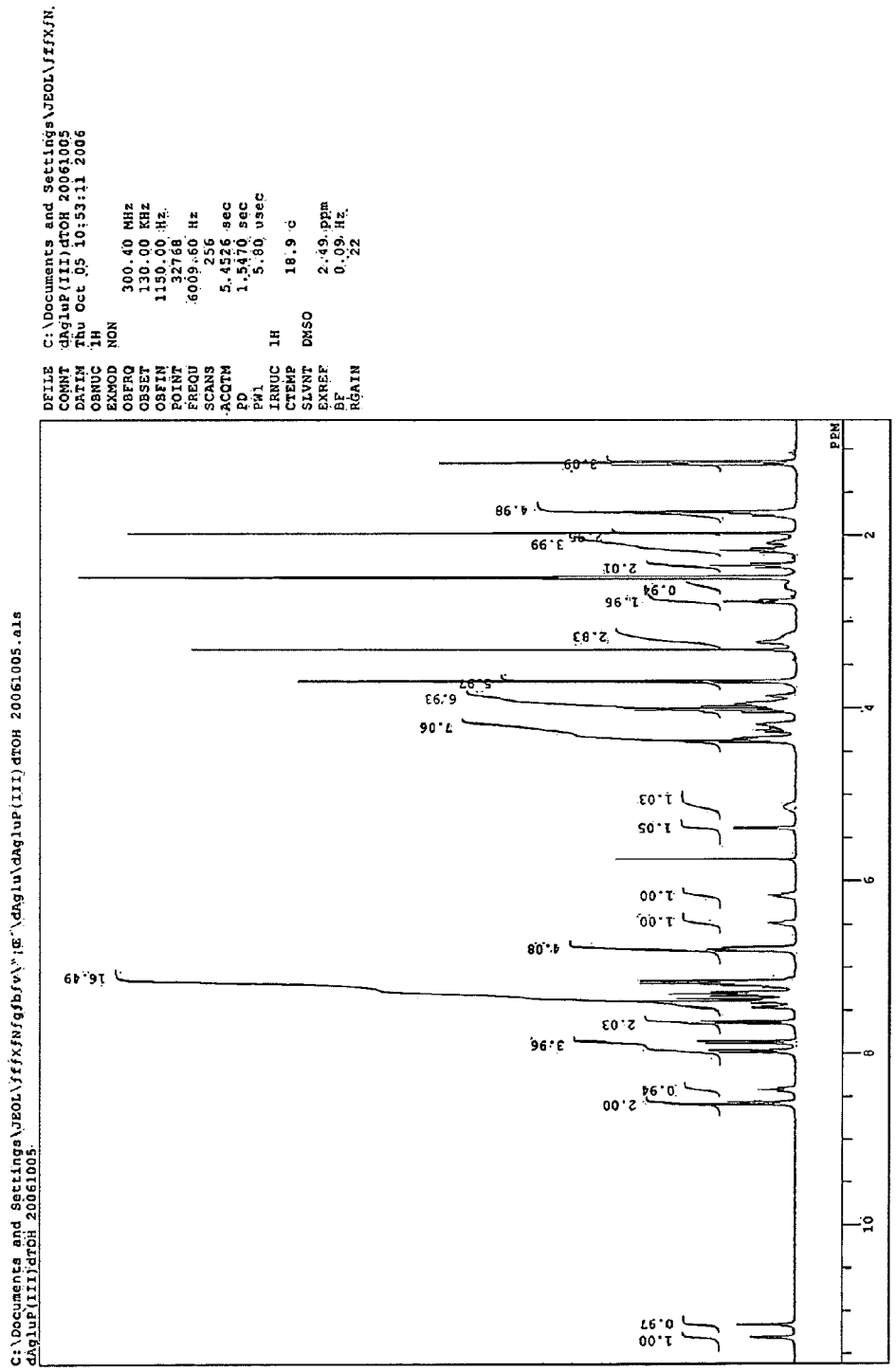
FIG. 5-A

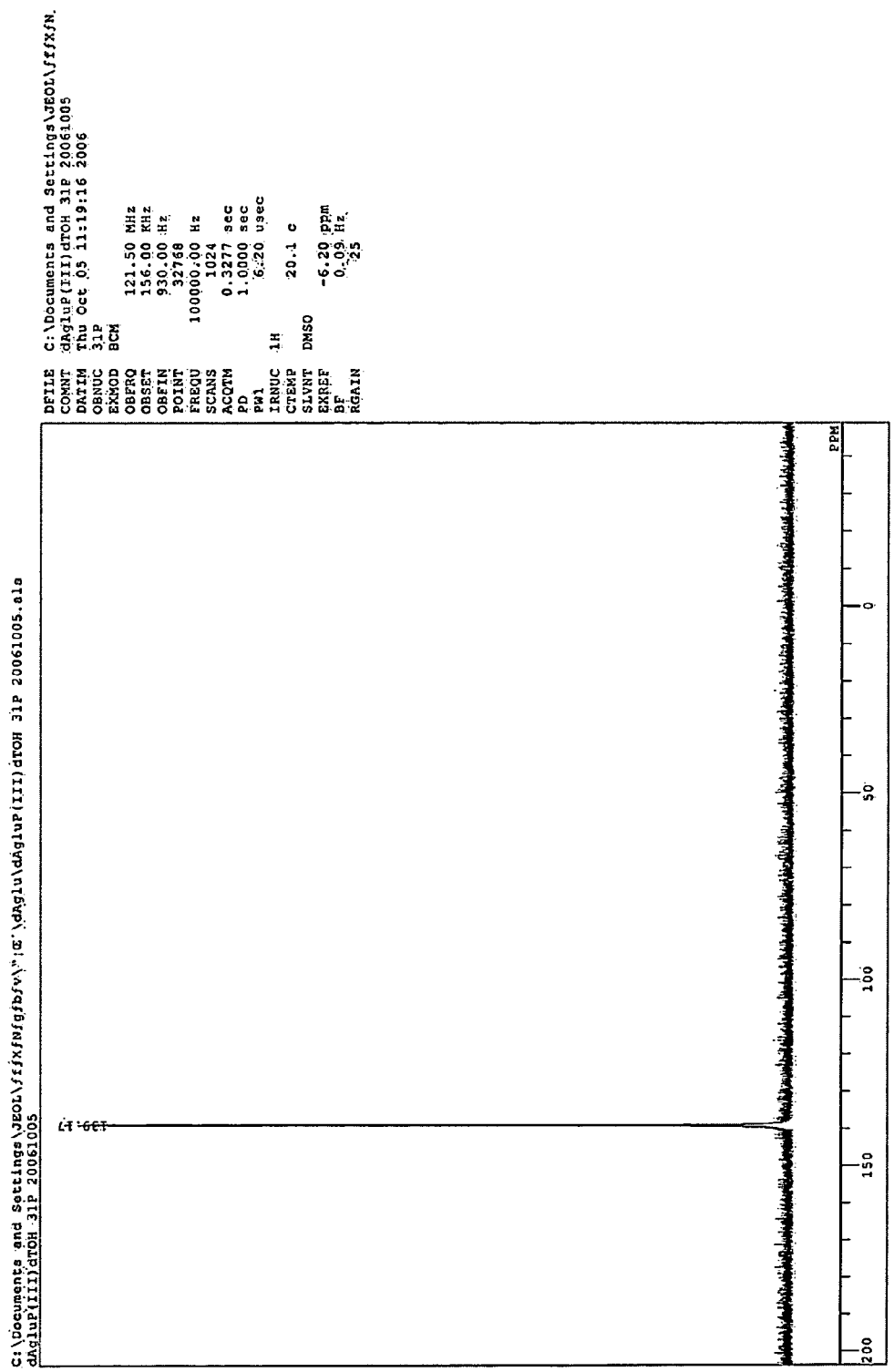
FIG. 5-B

FIG. 5-C
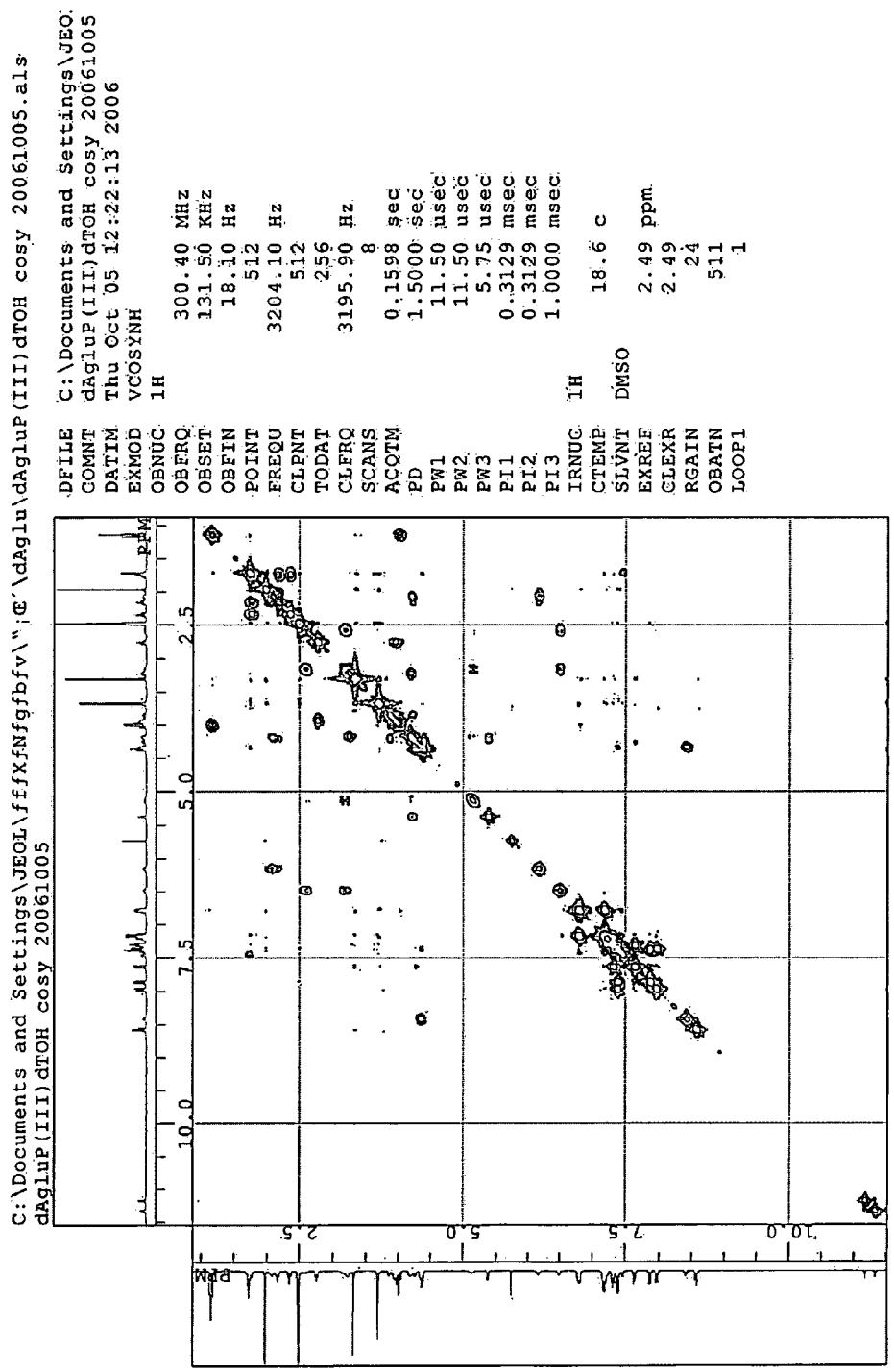

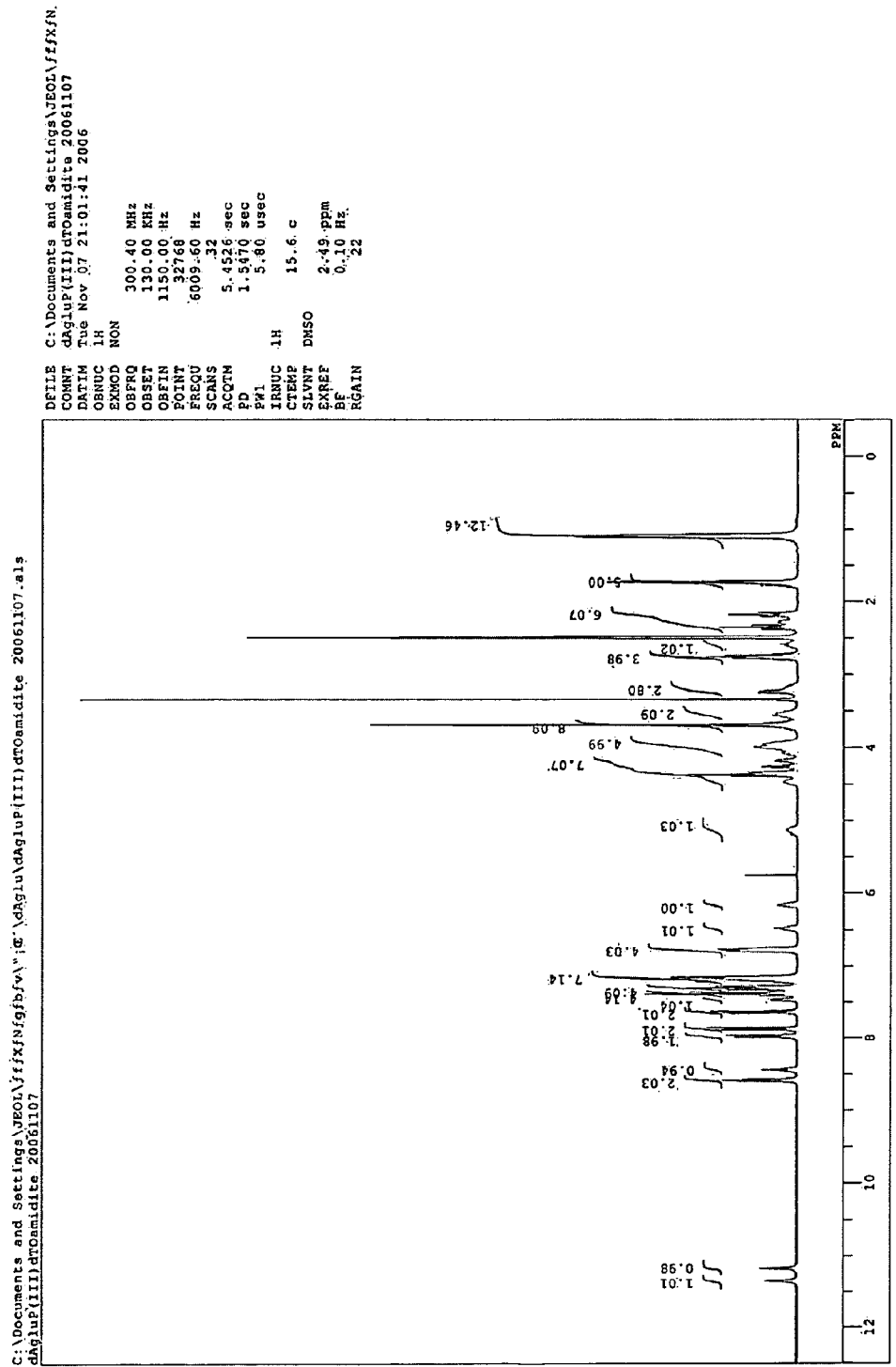
FIG. 5-D

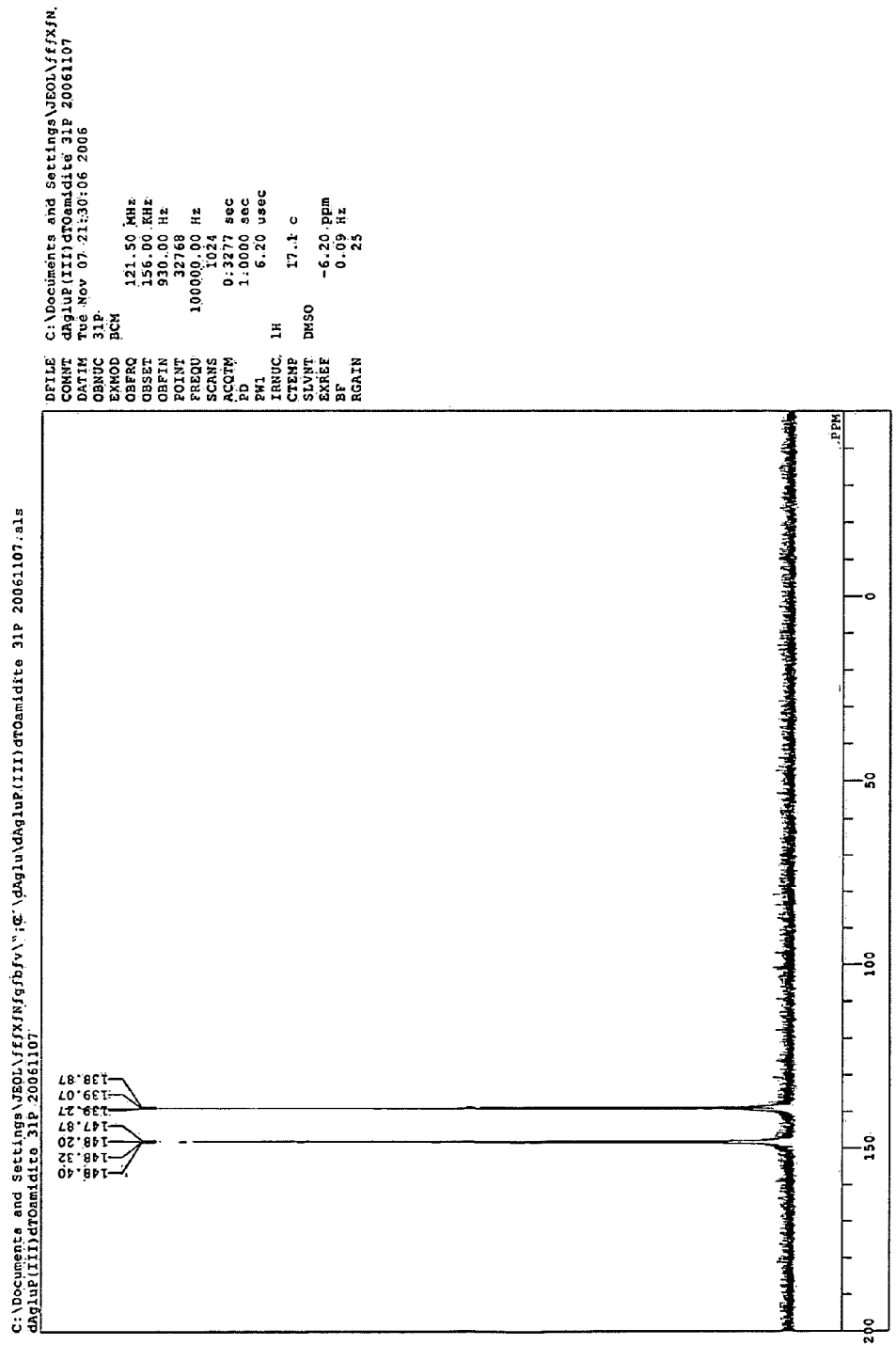
FIG. 5-E

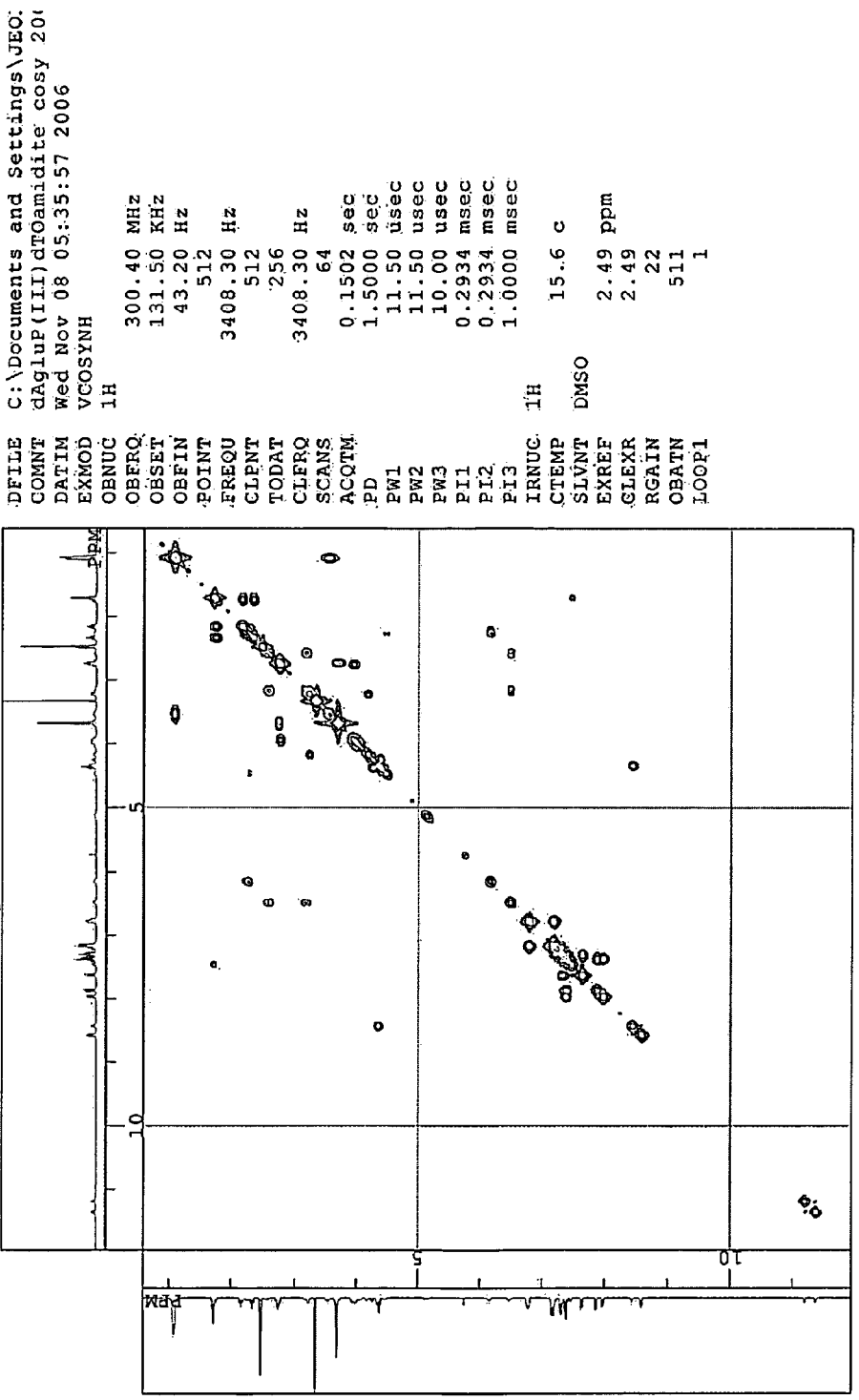
FIG. 5-F

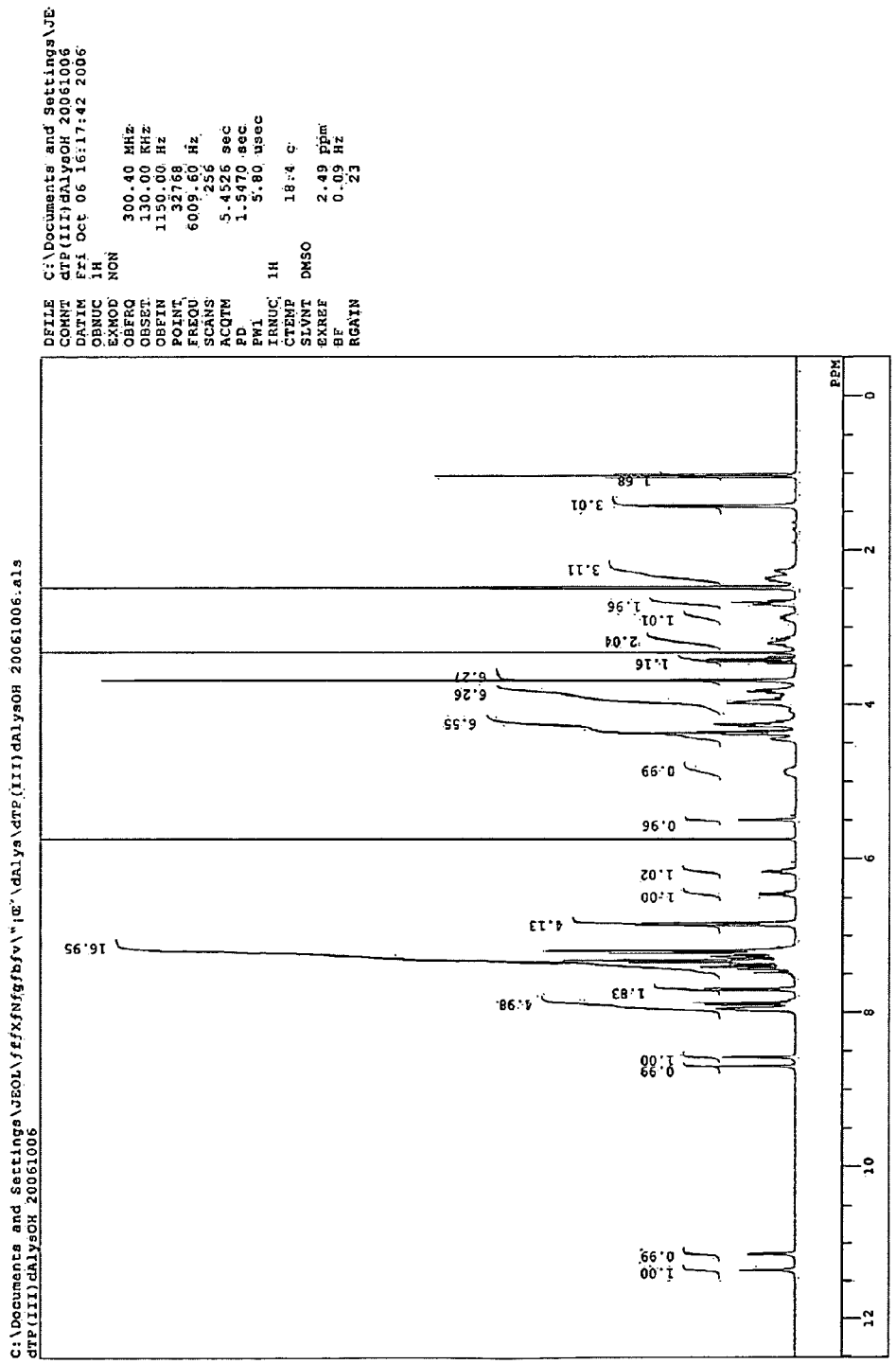
FIG. 6-A

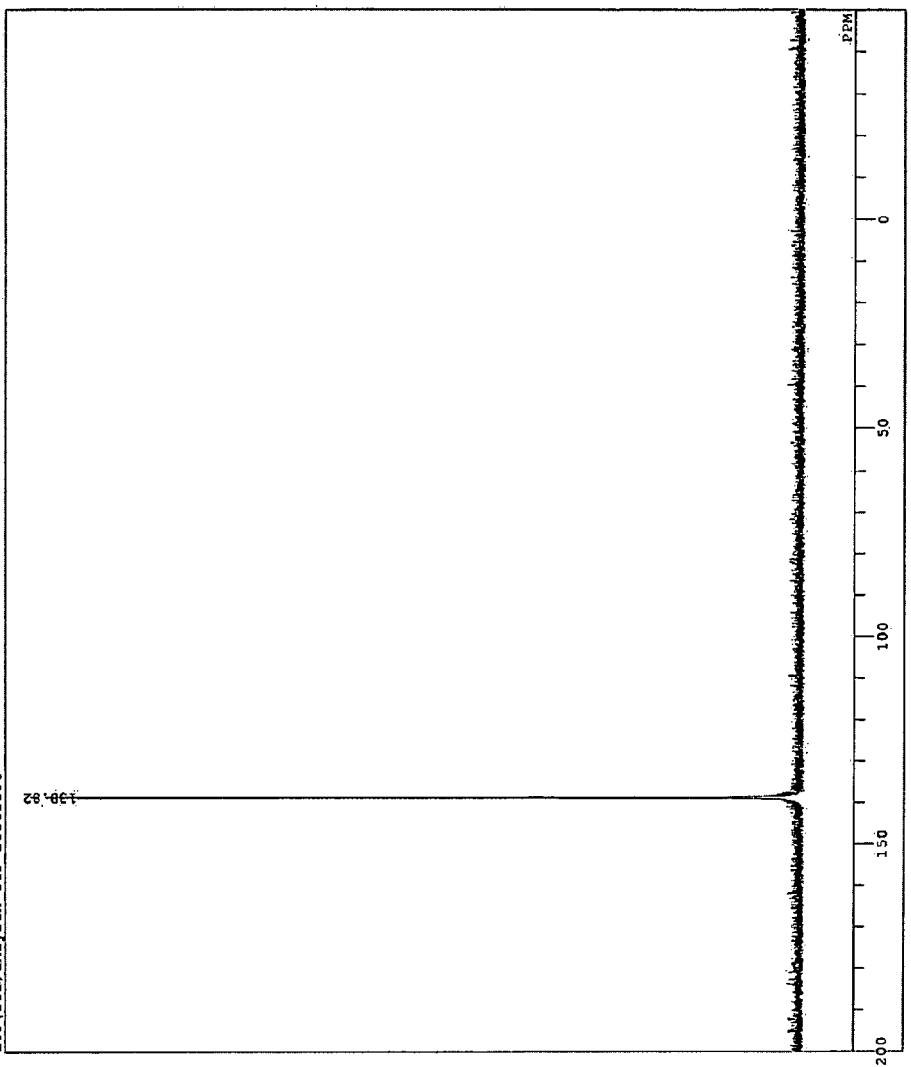
FIG. 6-B

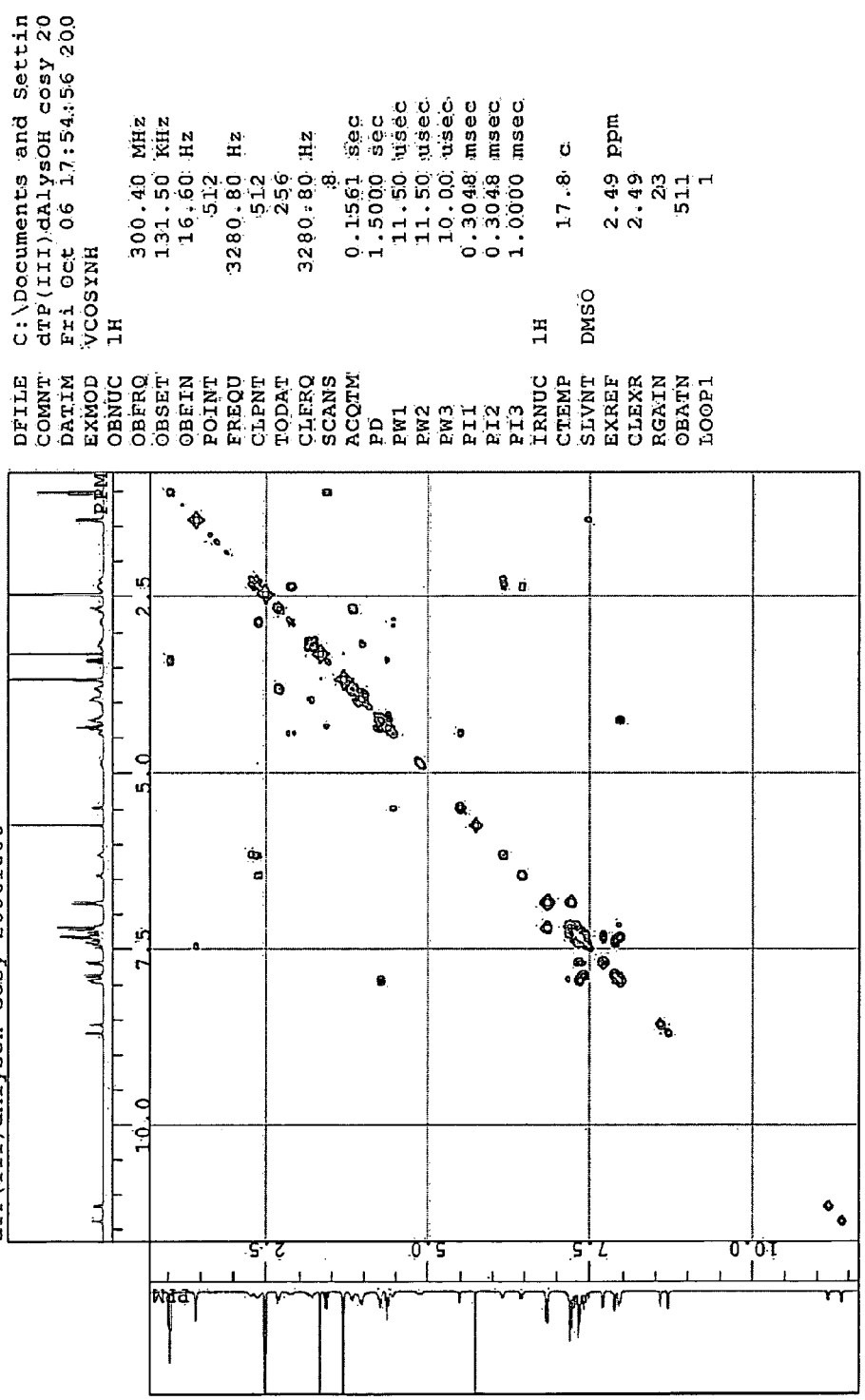
FIG. 6-C

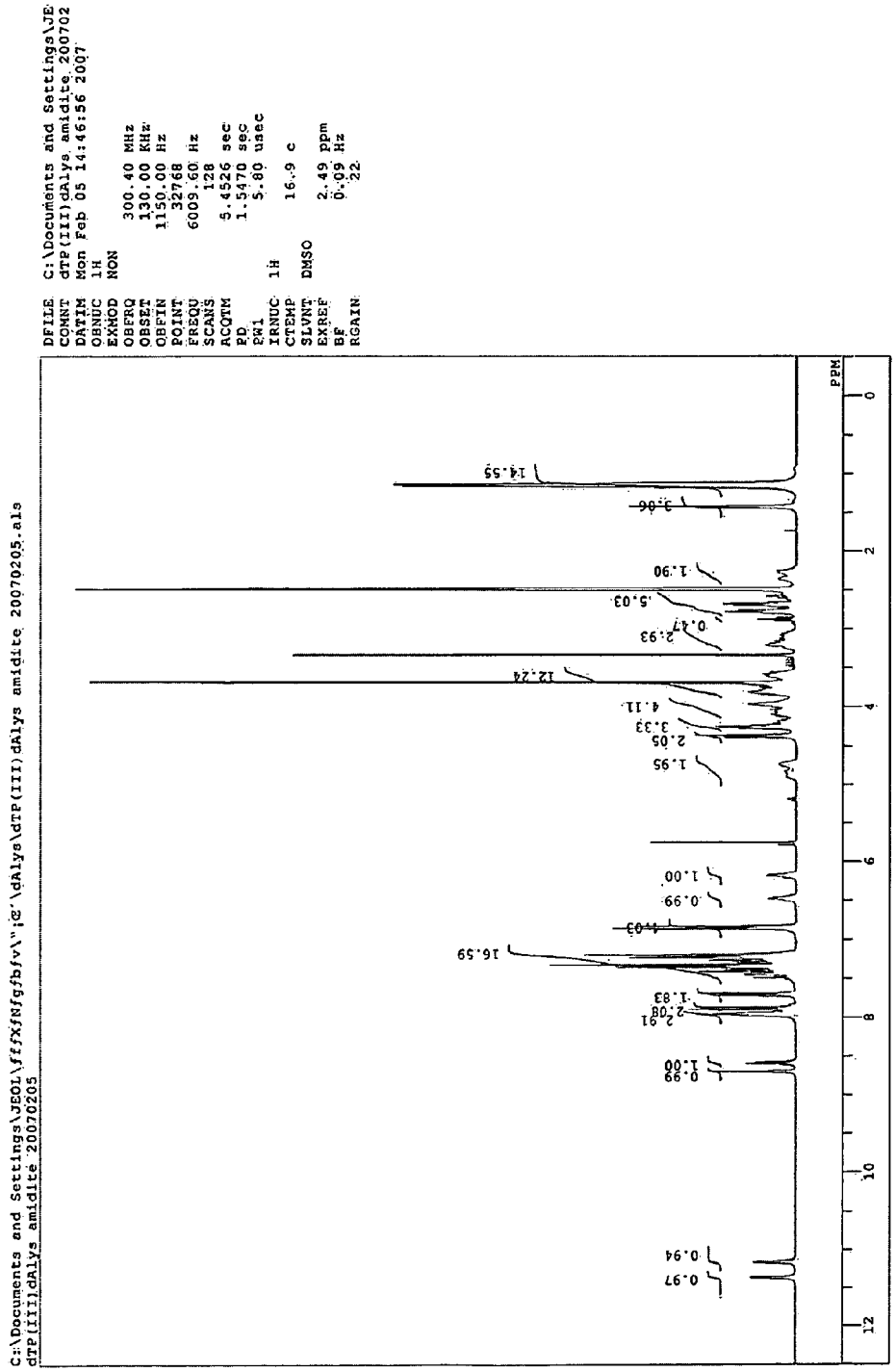
FIG. 6-D

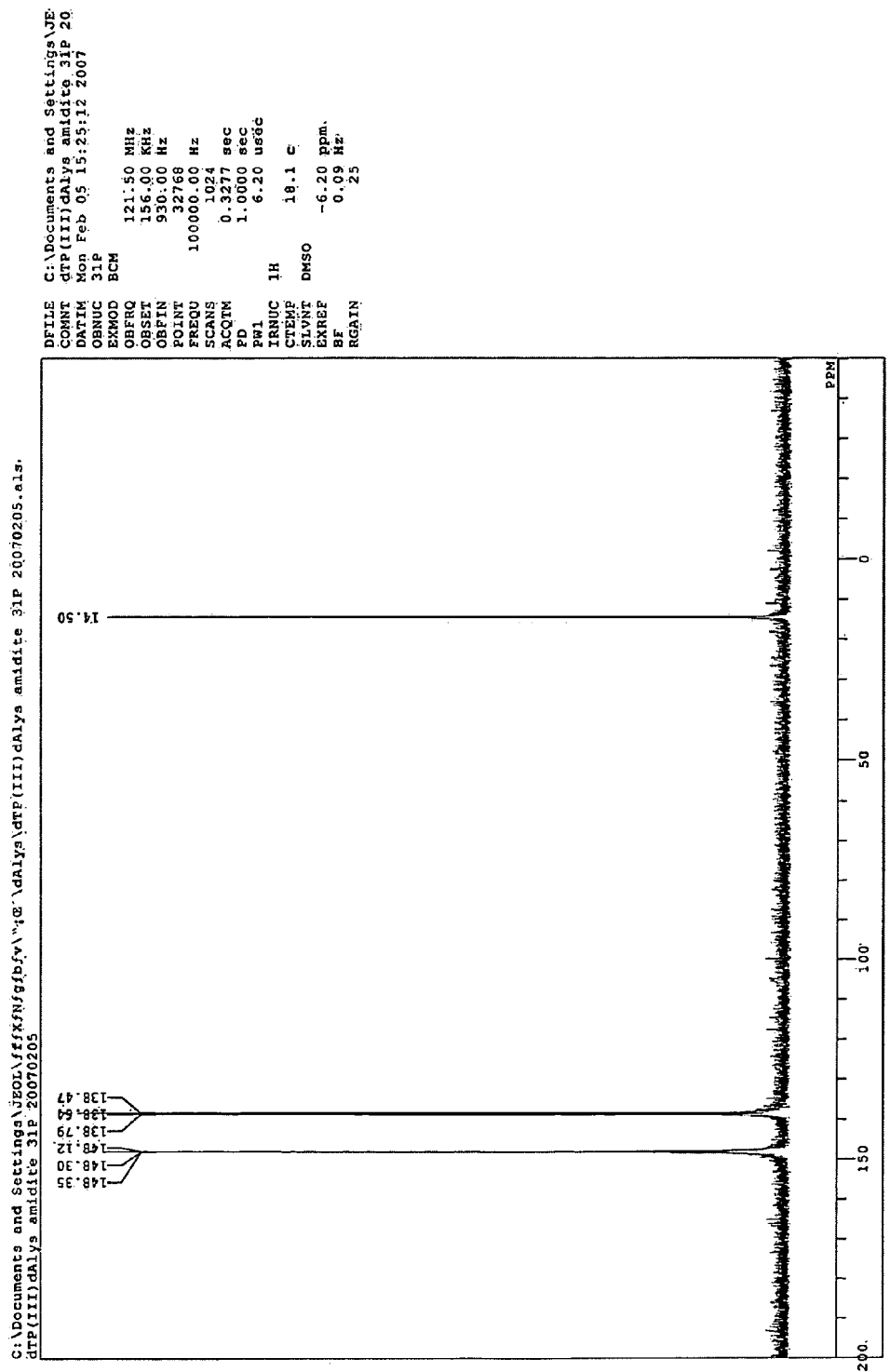
FIG. 6-E

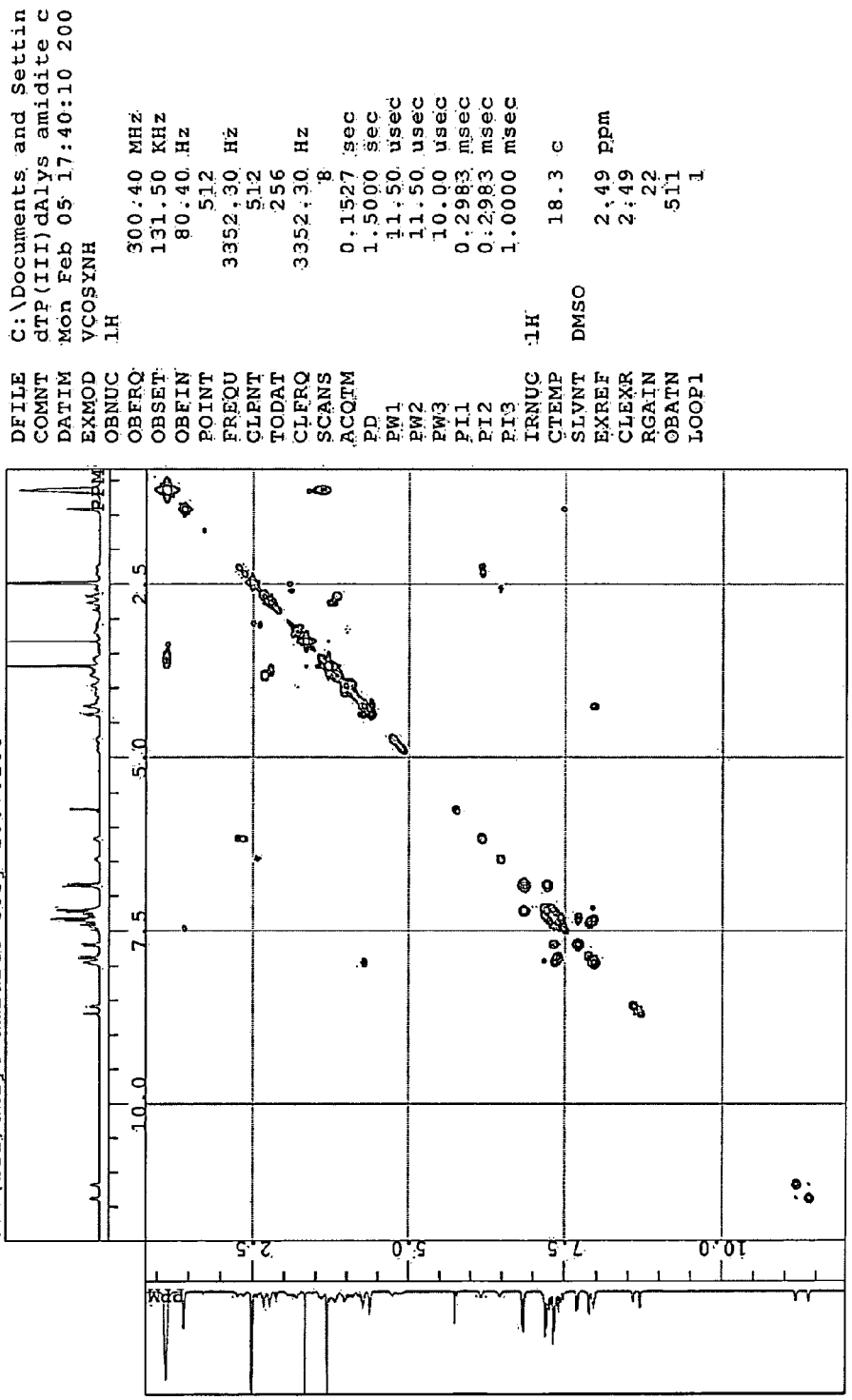
FIG. 6-F

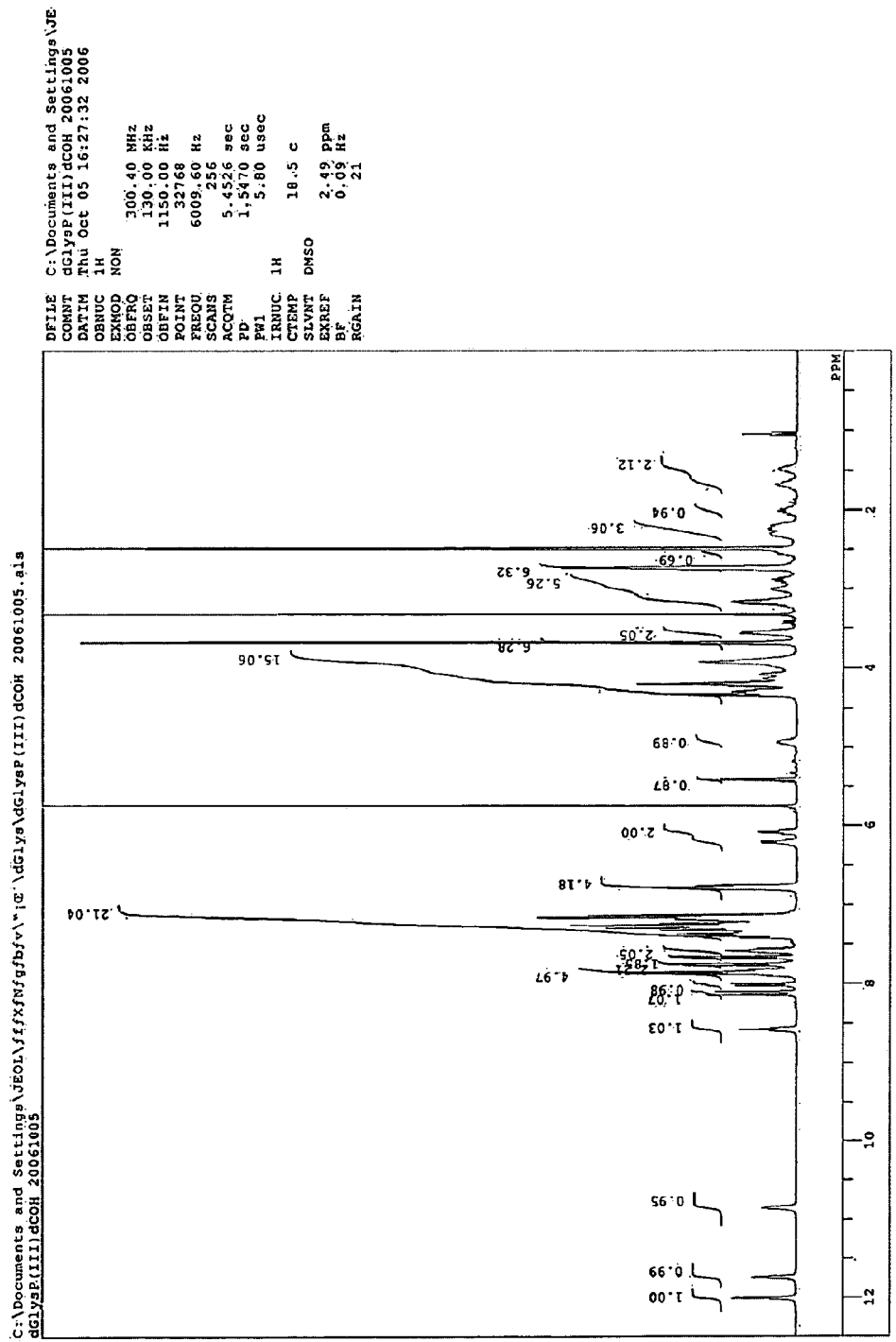
FIG. 7-A

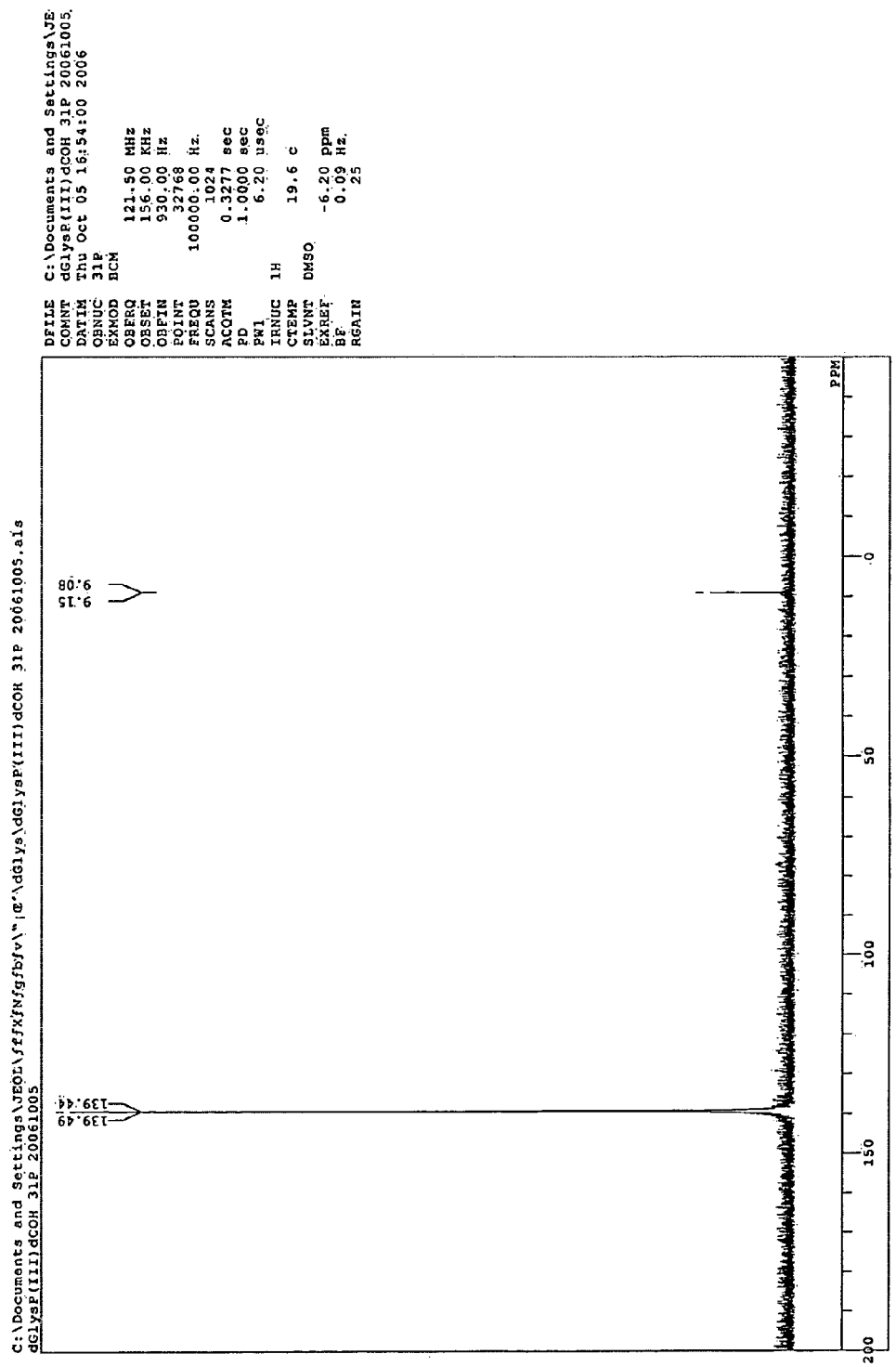
FIG. 7-B

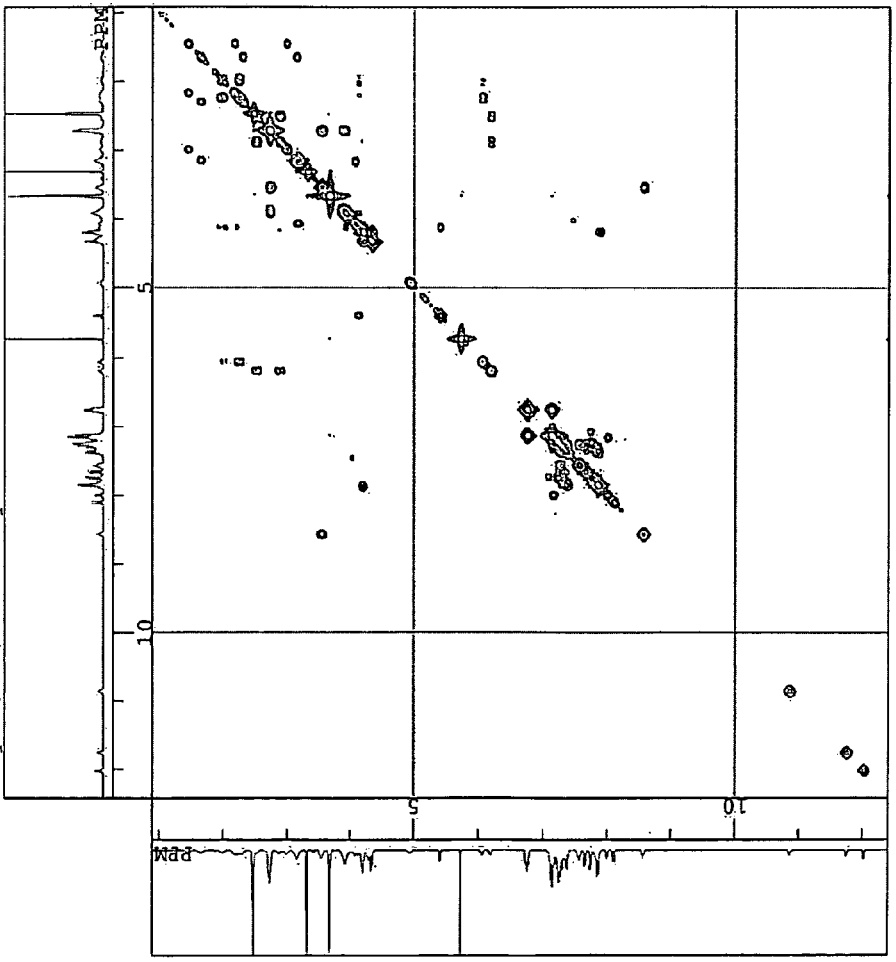
FIG. 7-C

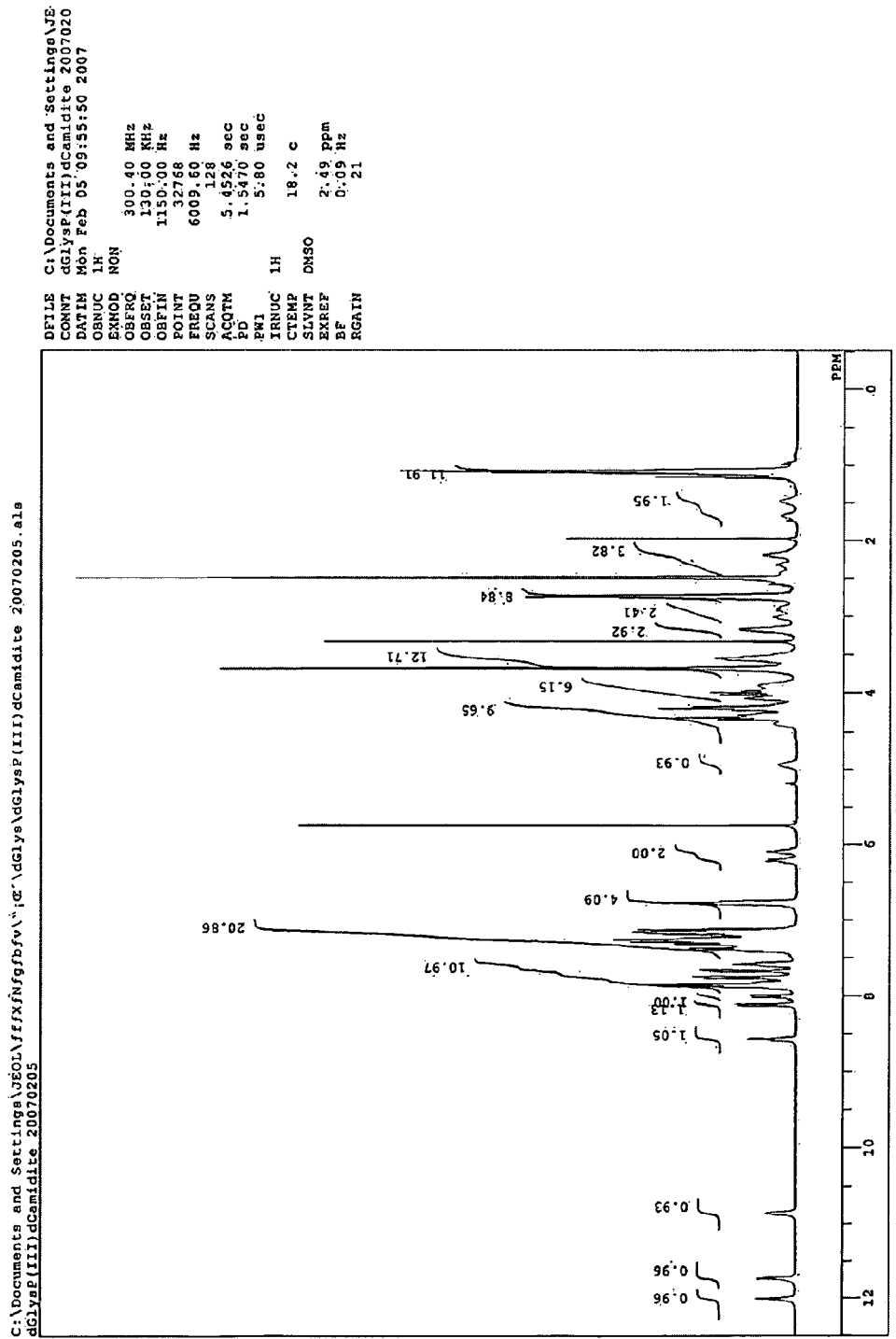
FIG. 7-D

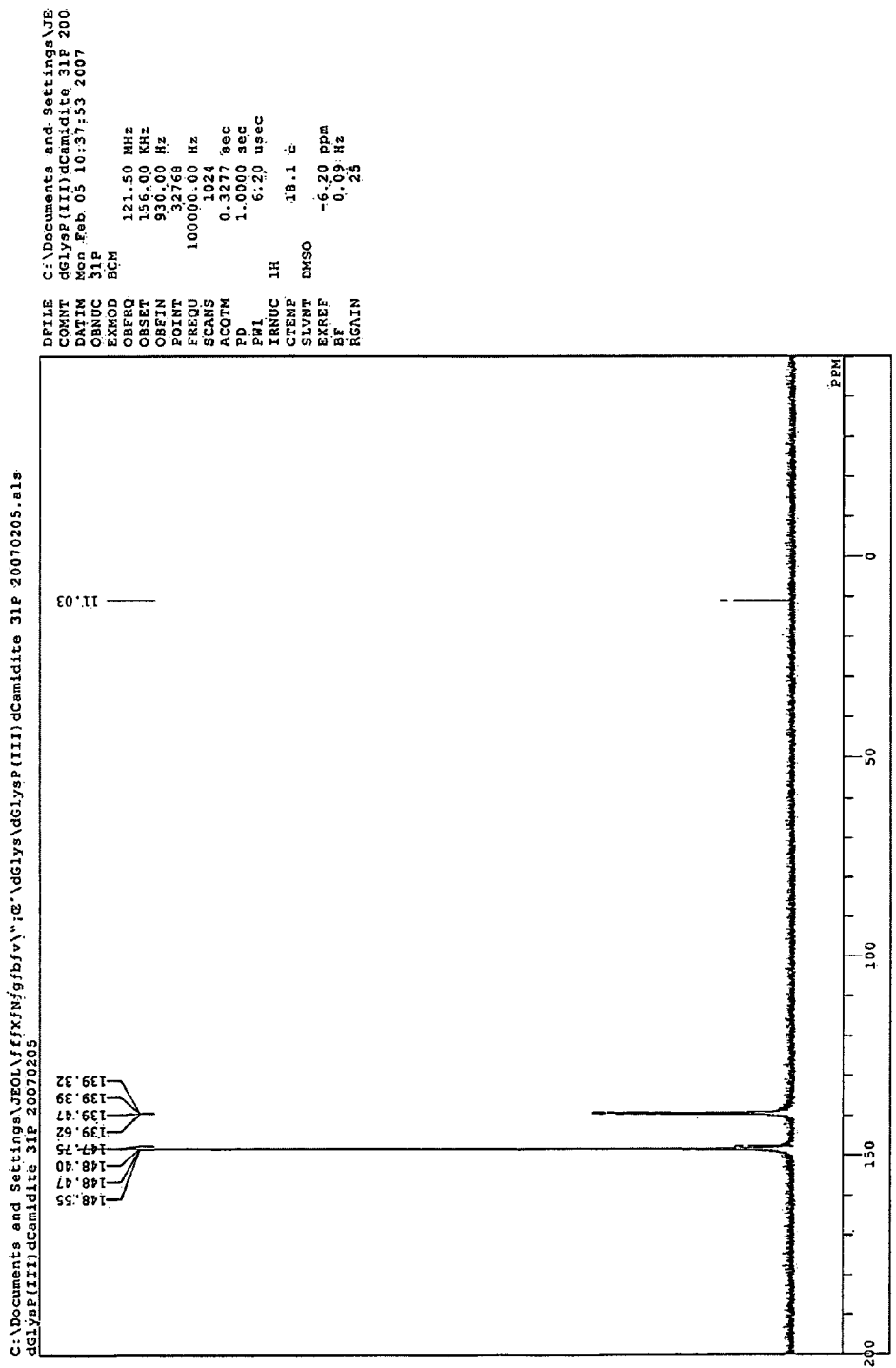
FIG. 7-E

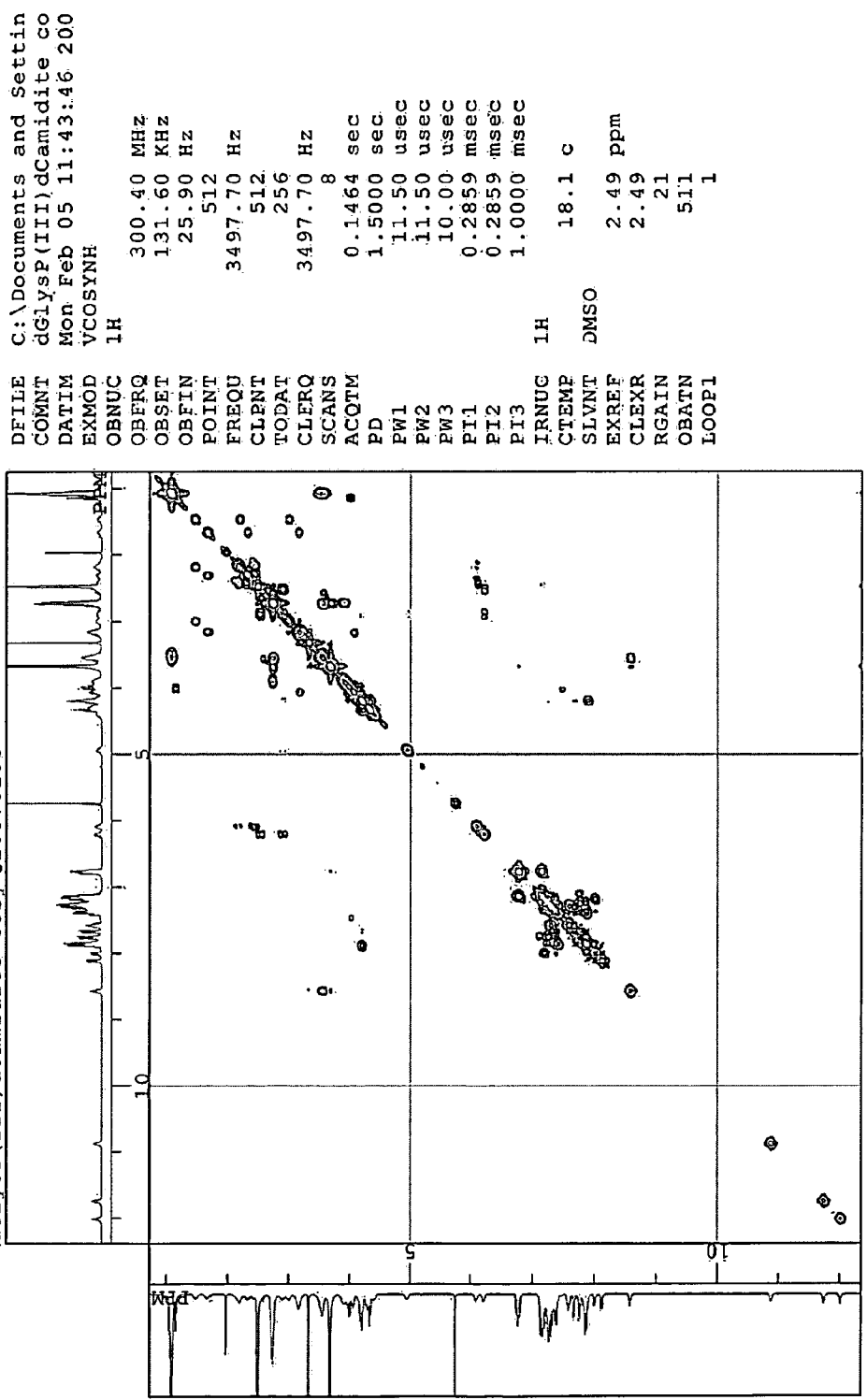
FIG. 7-F

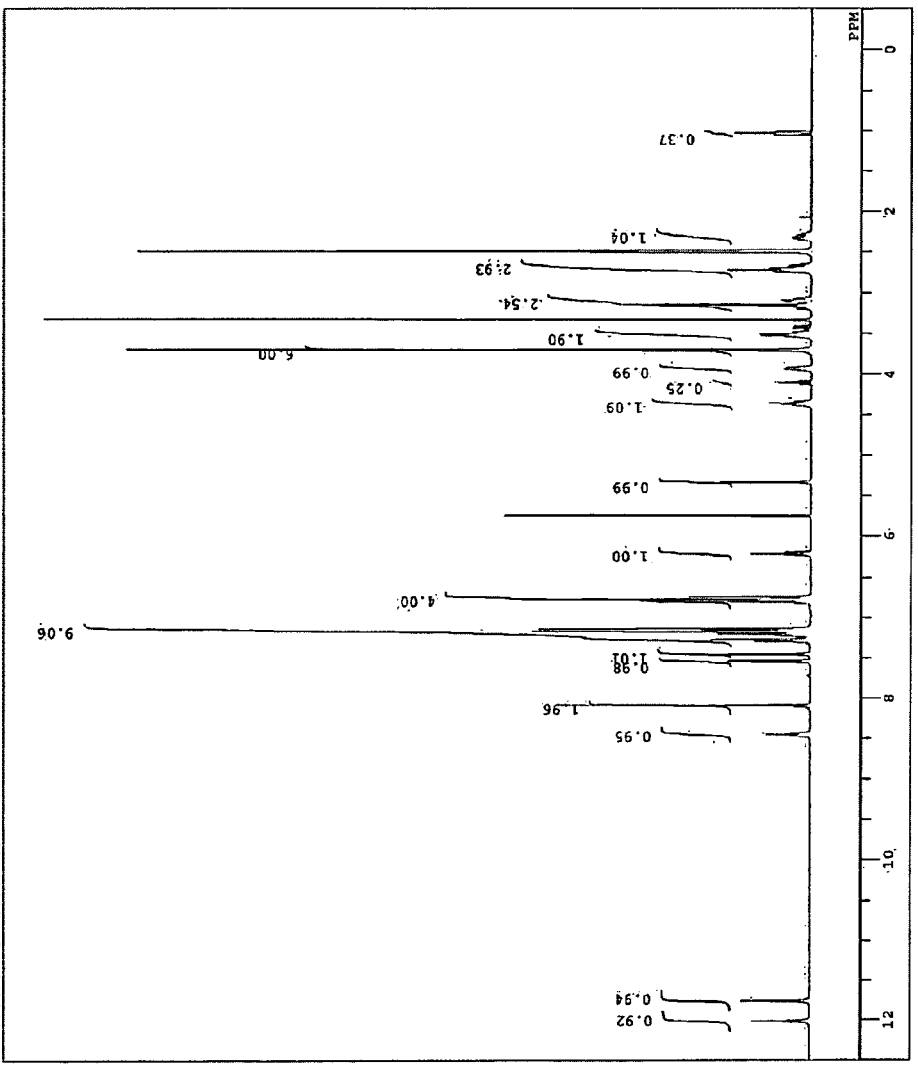
FIG. 8-A

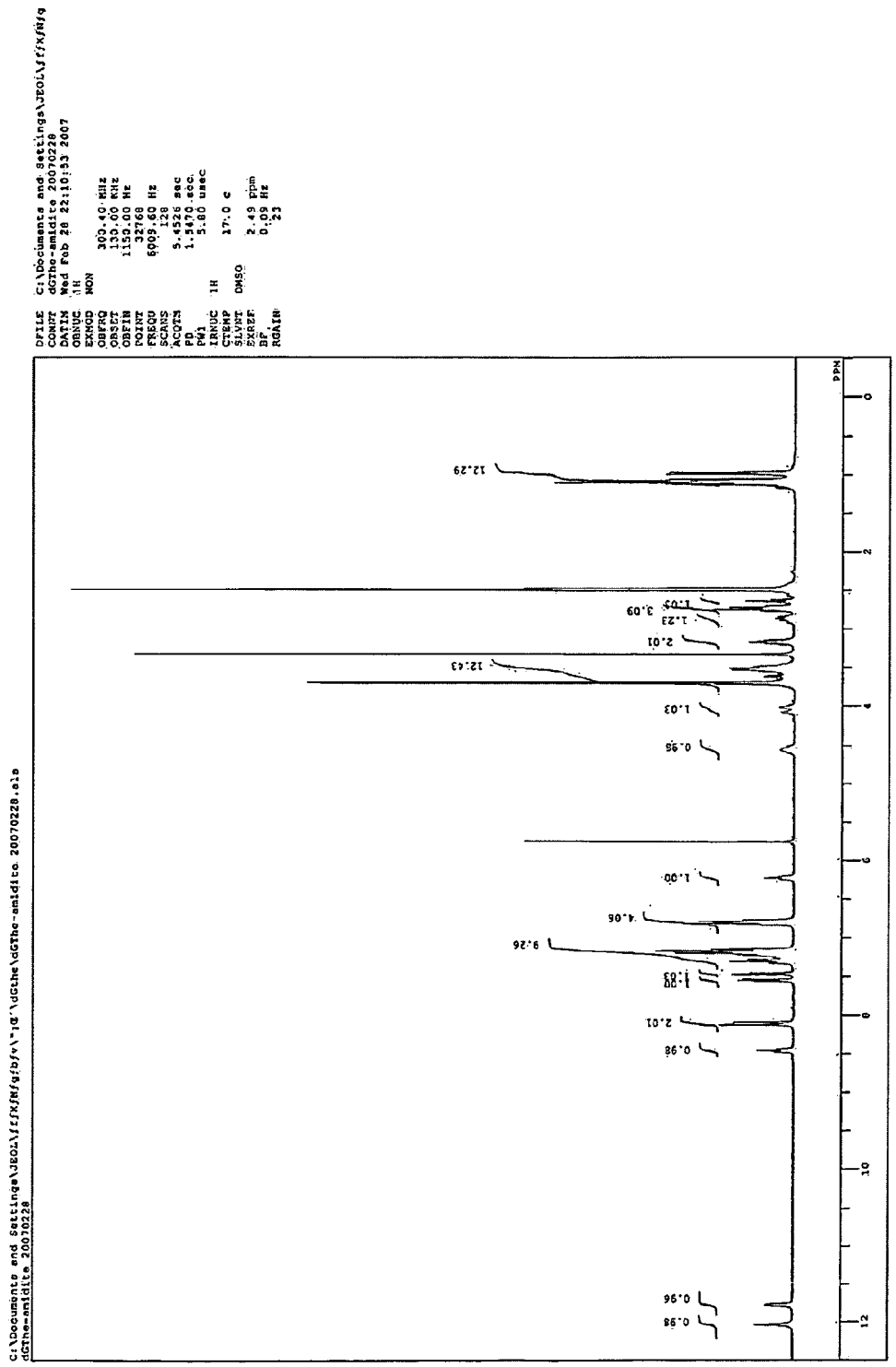
FIG. 8-B

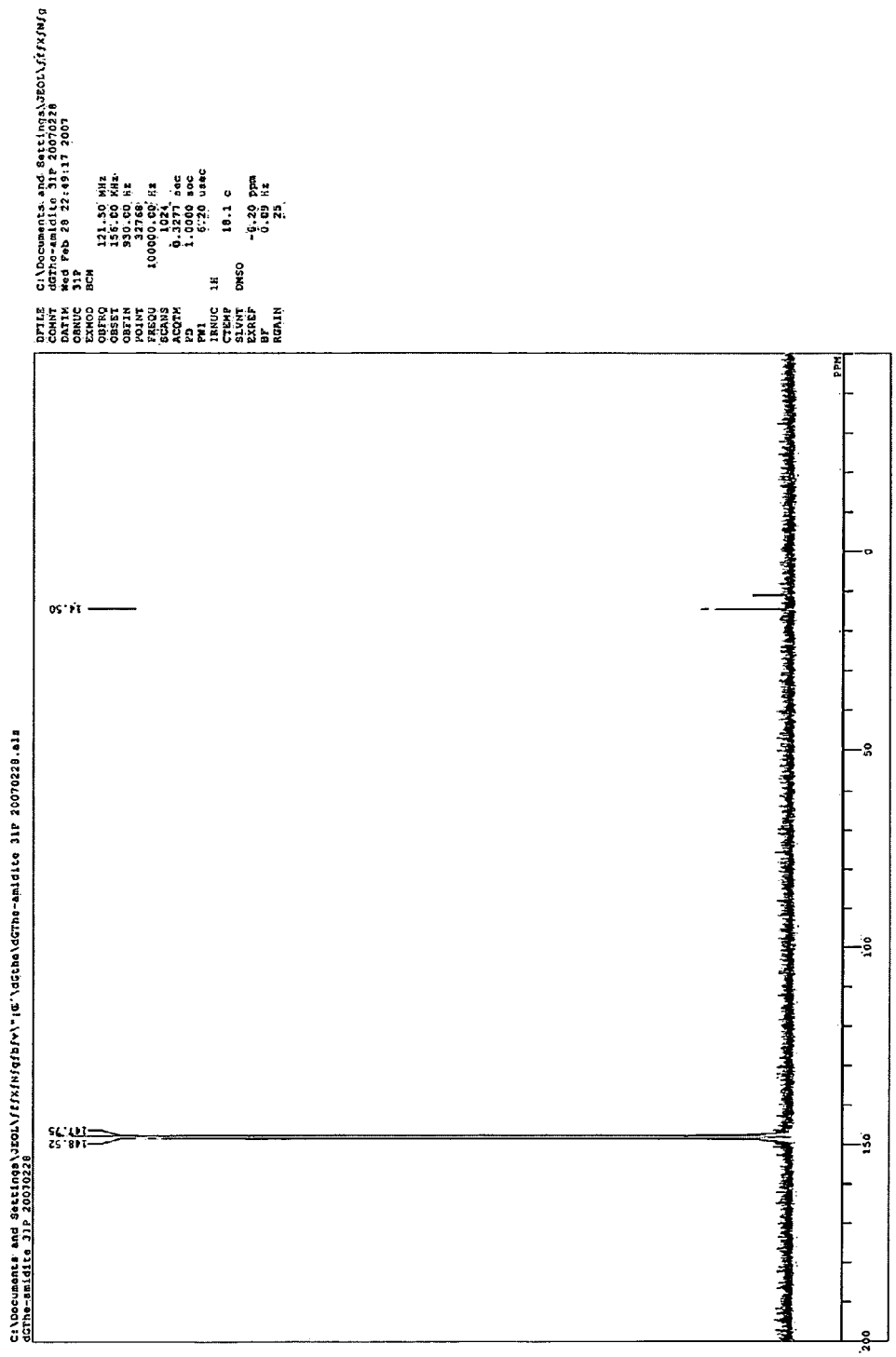
FIG. 8-C

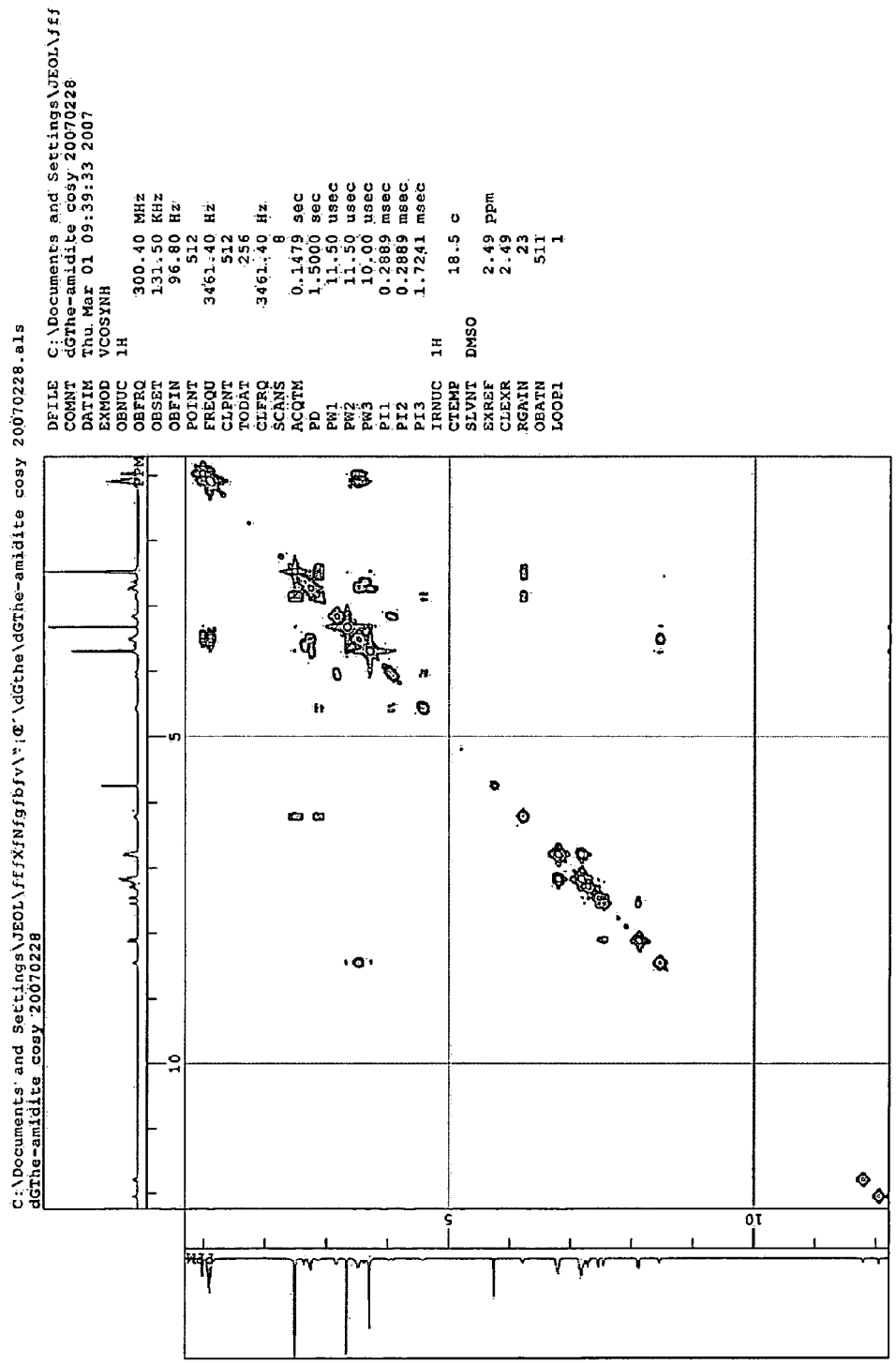
FIG. 8-D

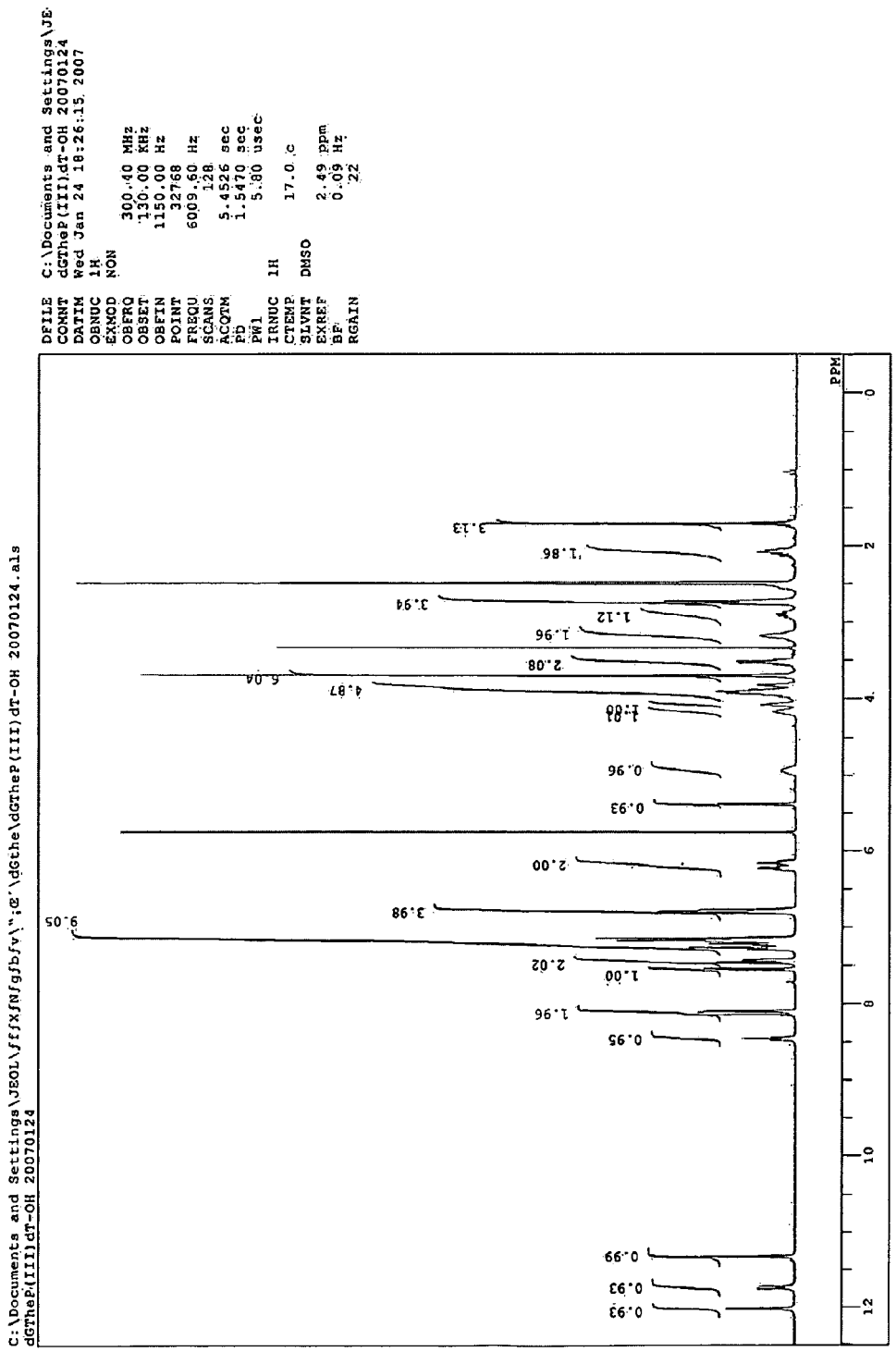
FIG. 8-E

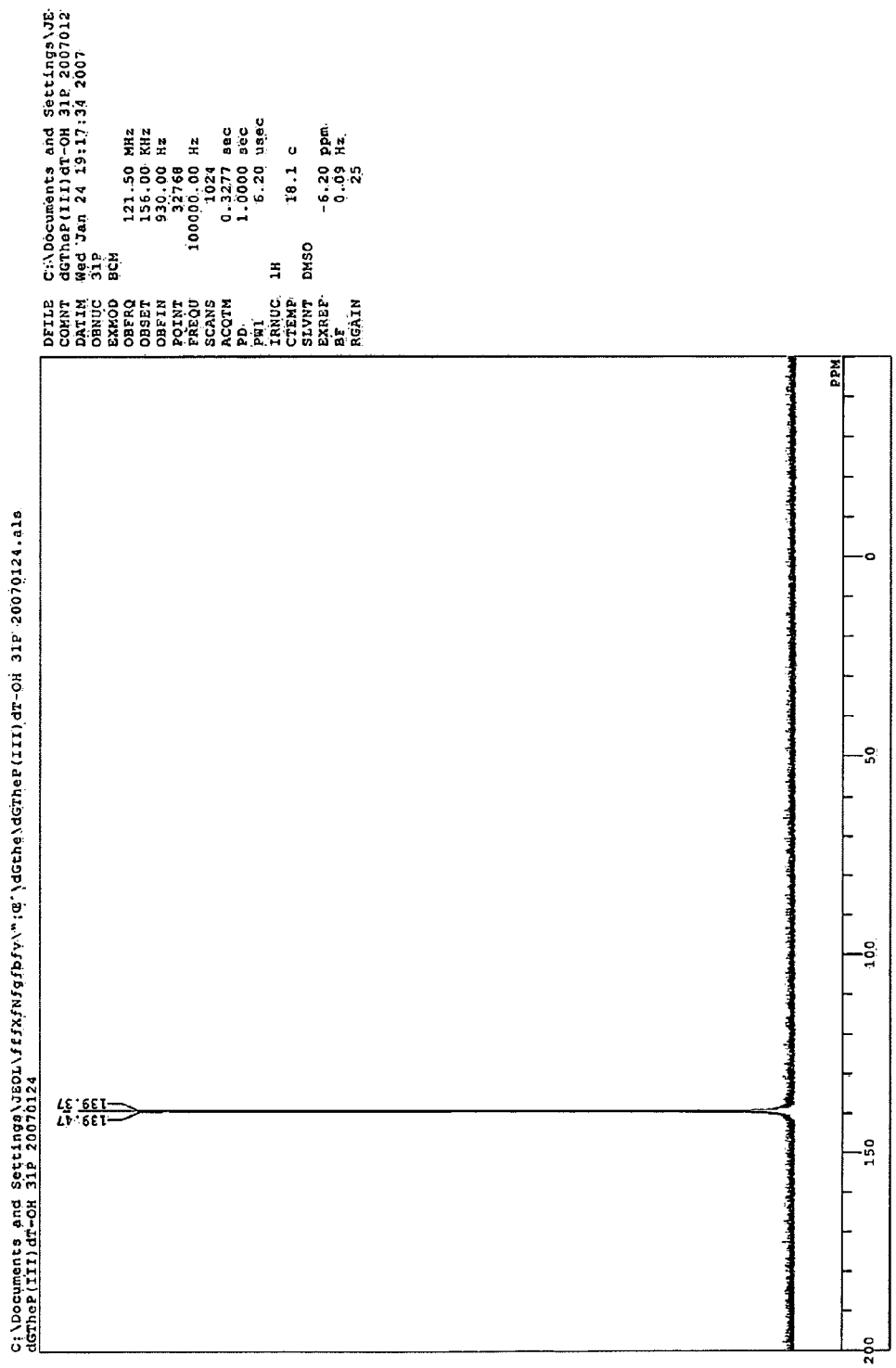
FIG. 8-F

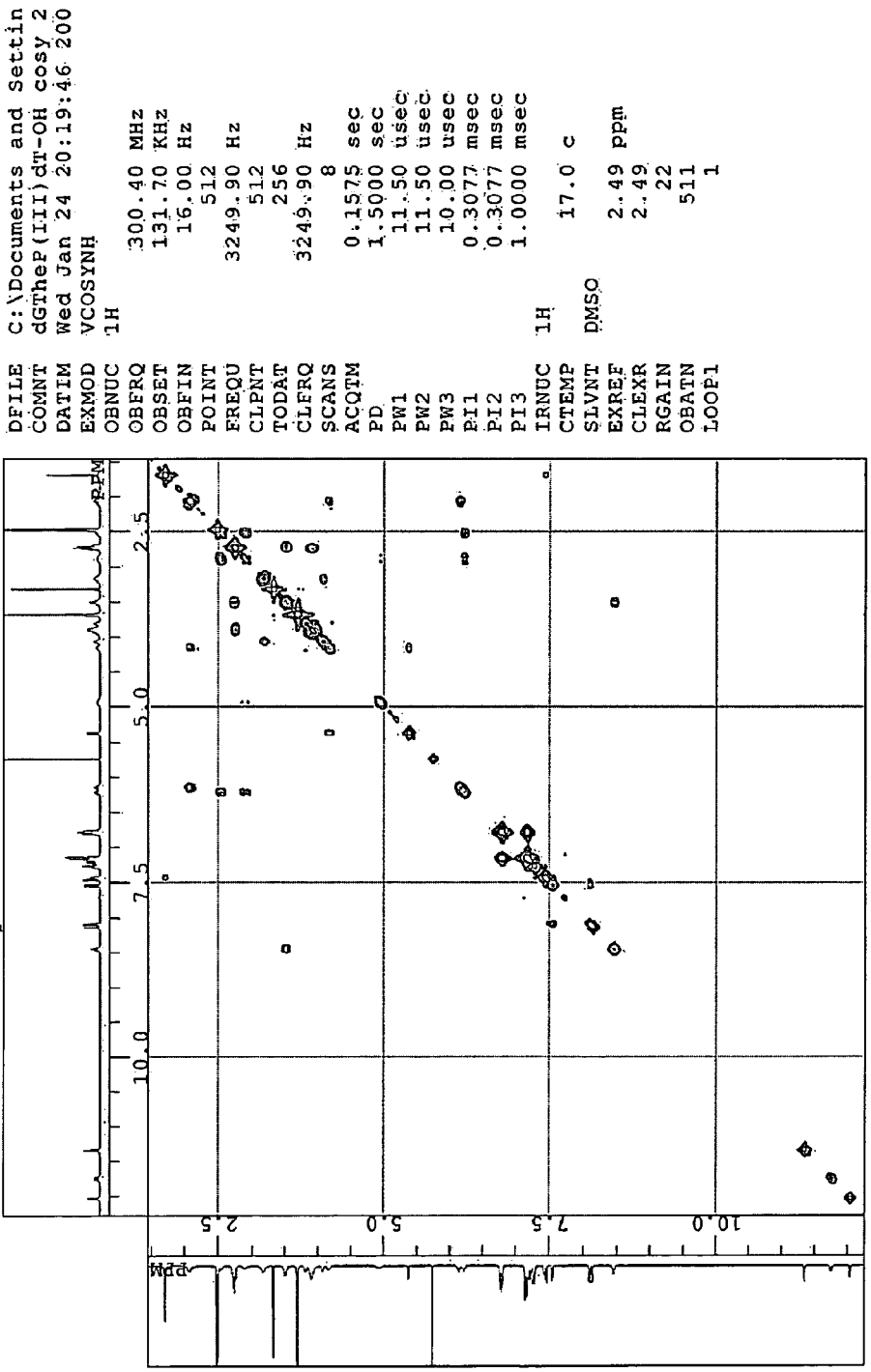
FIG. 8-G

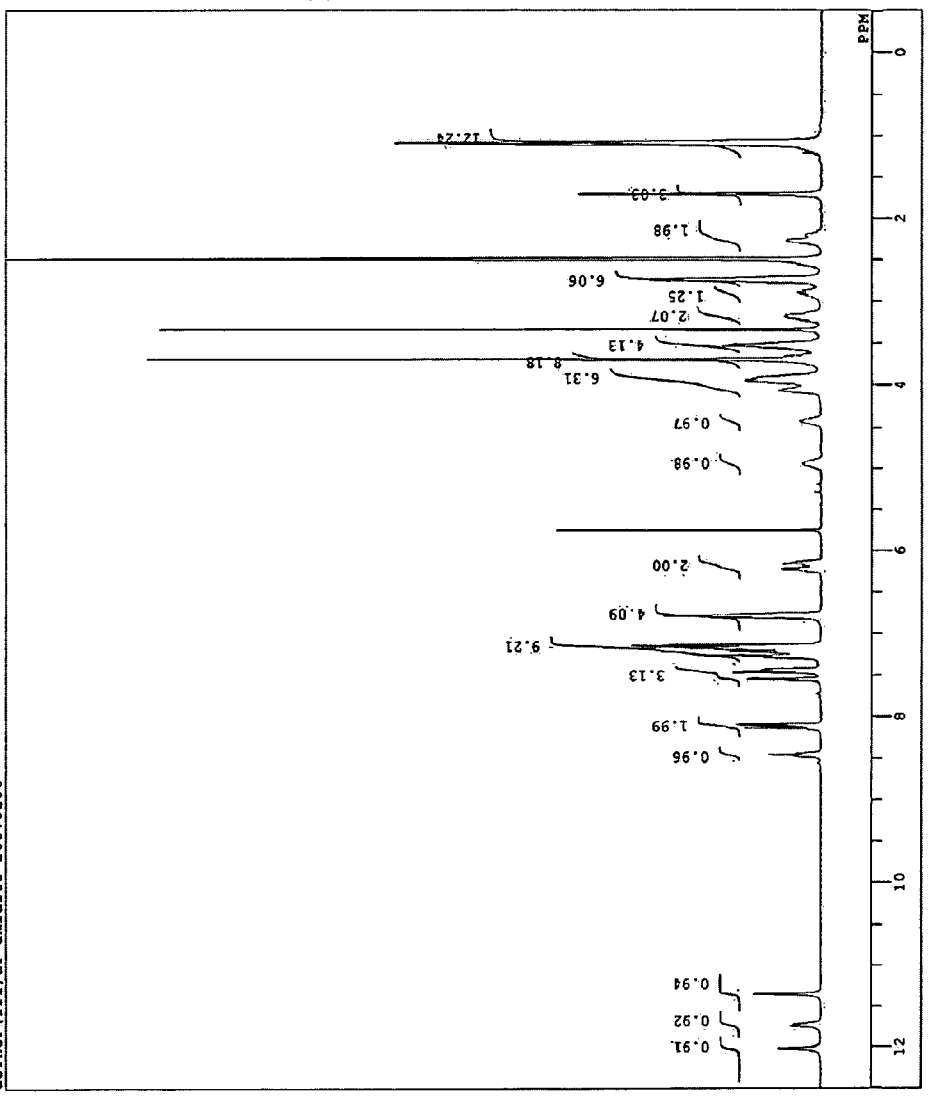
FIG. 8-H

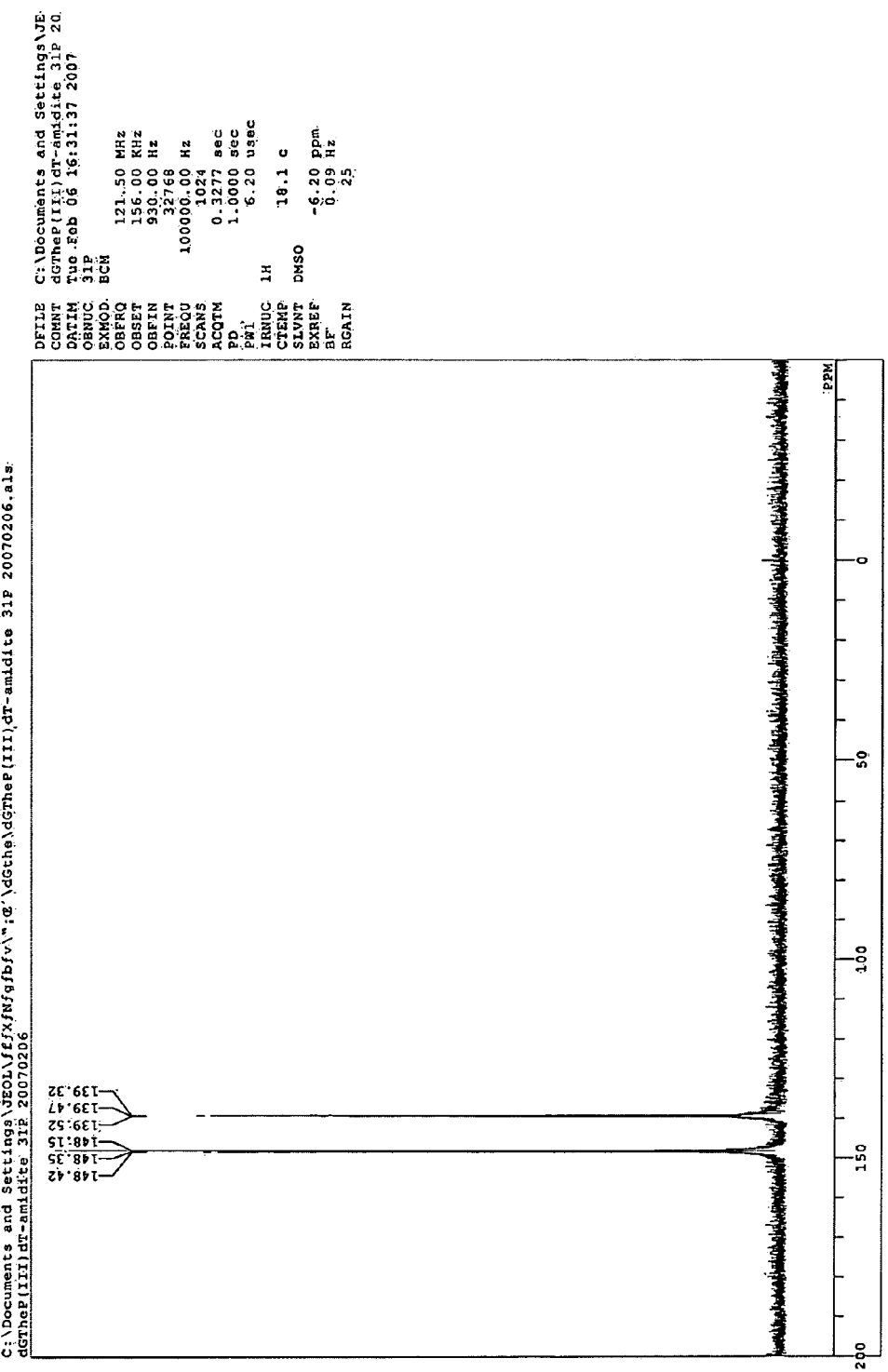
FIG. 8-I

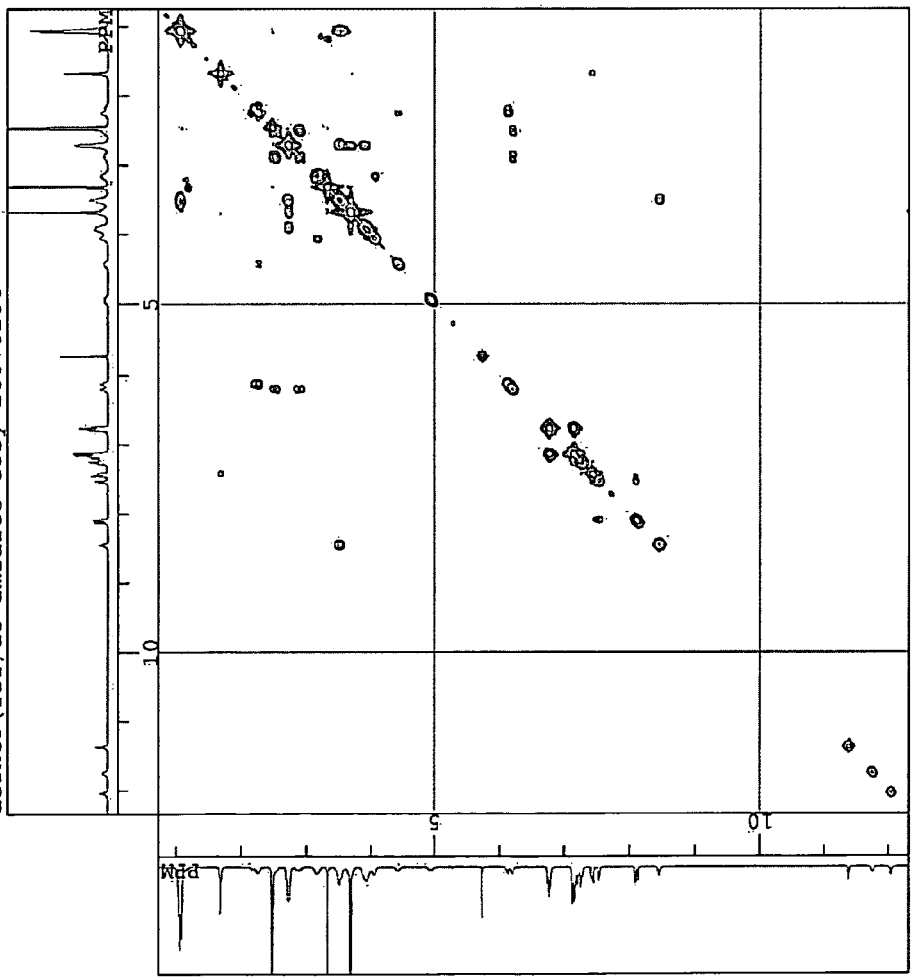
FIG. 8-J

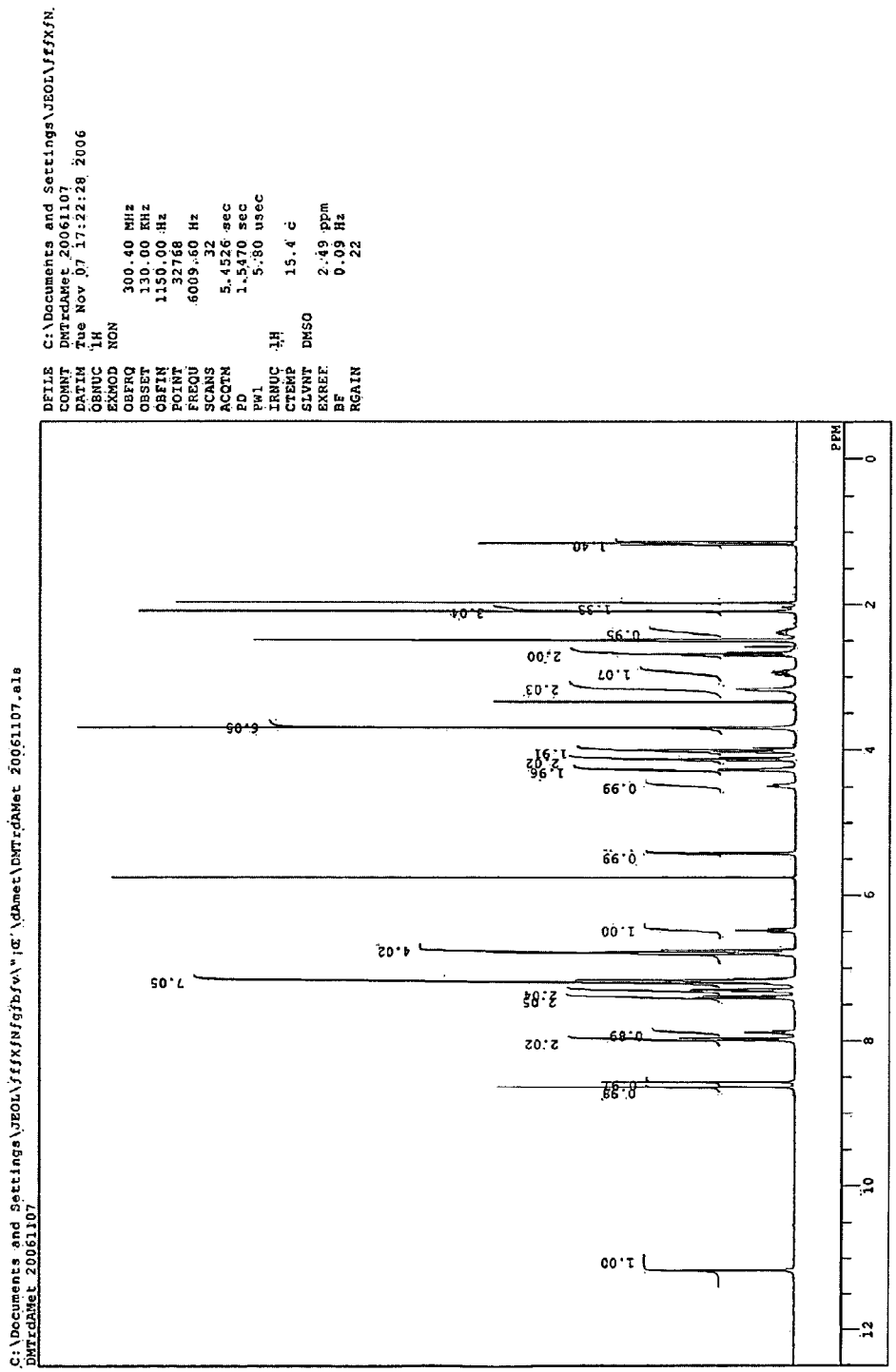
FIG. 9-A

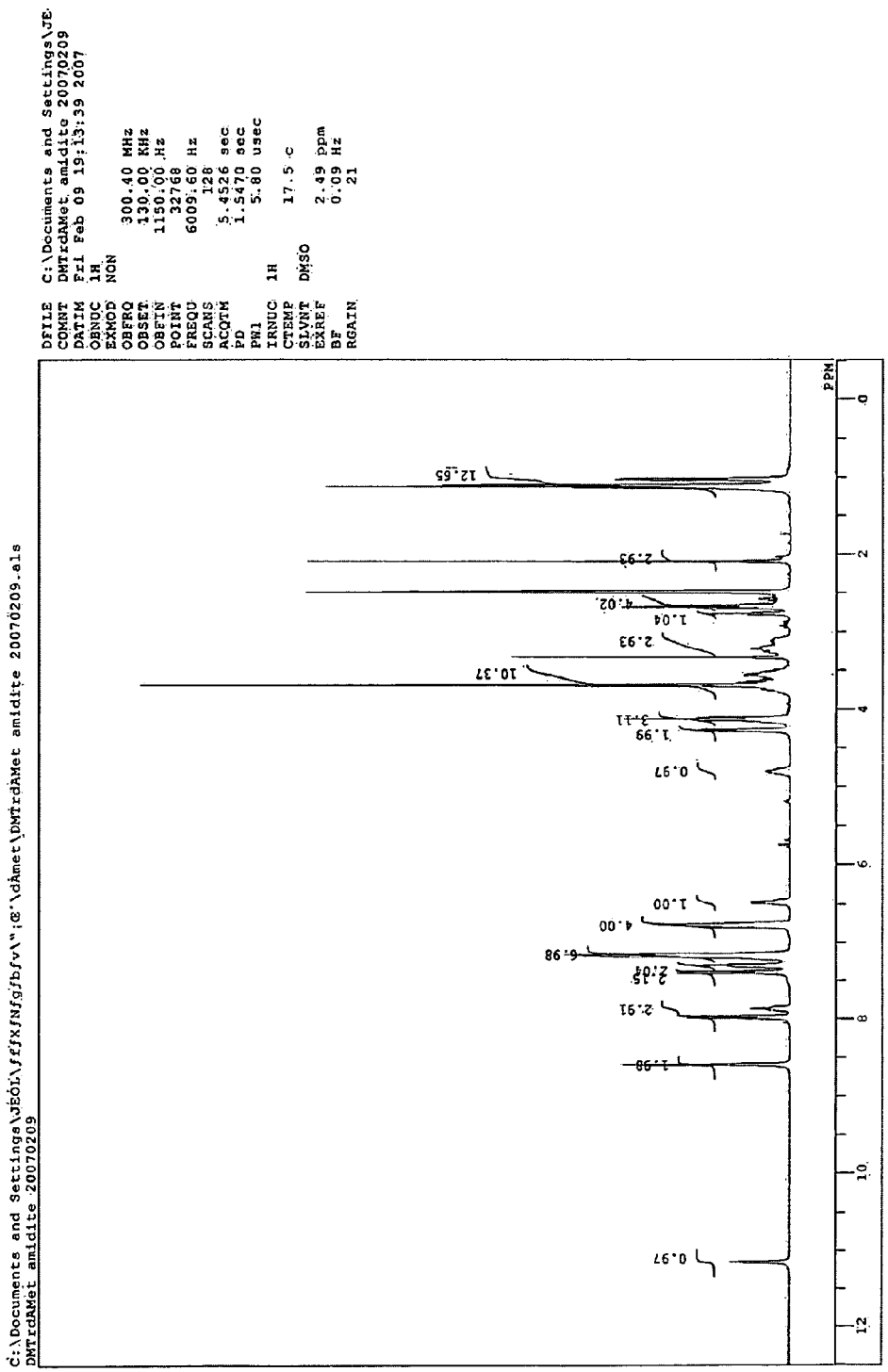
FIG. 9-B

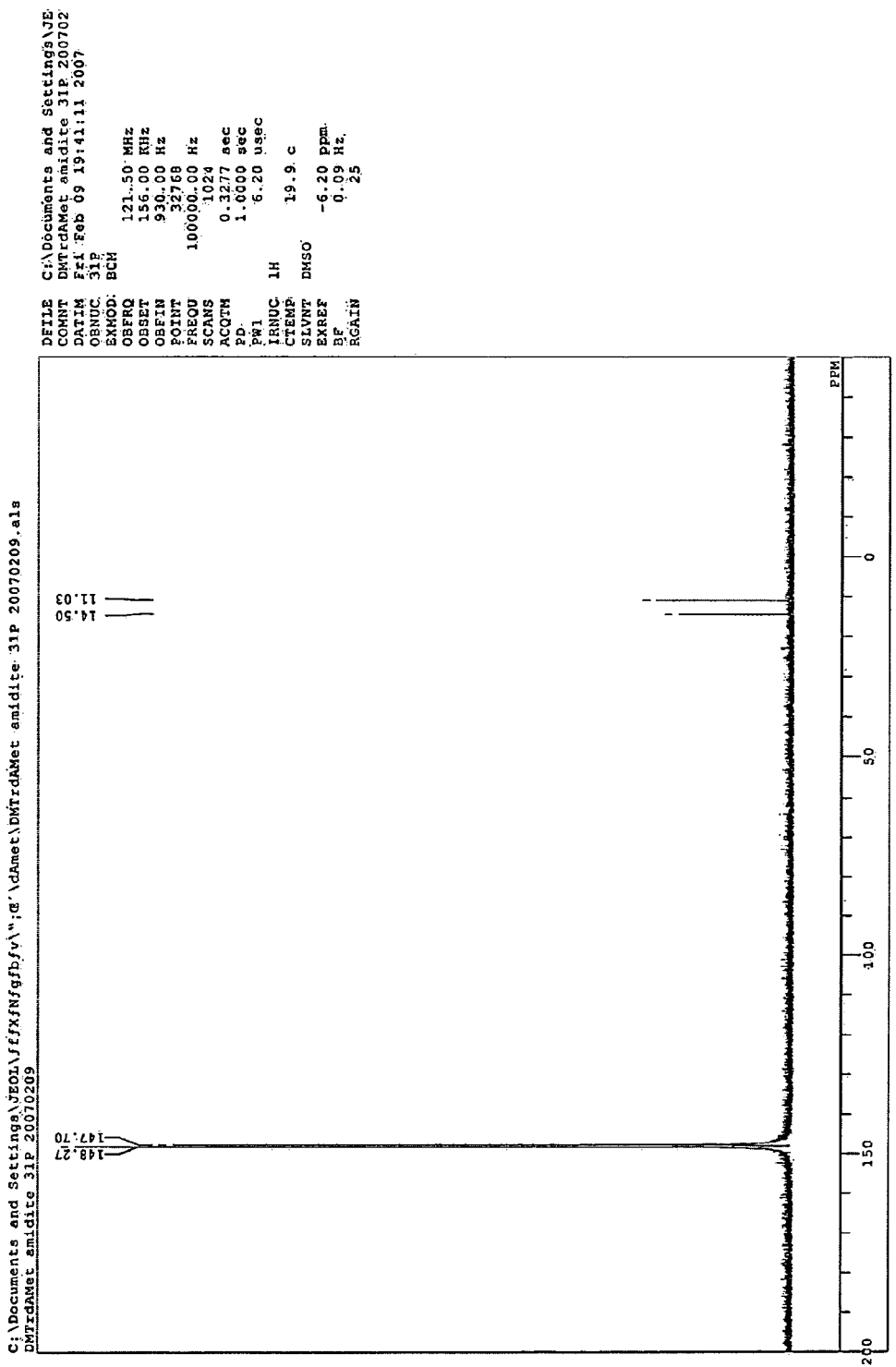
FIG. 9-C

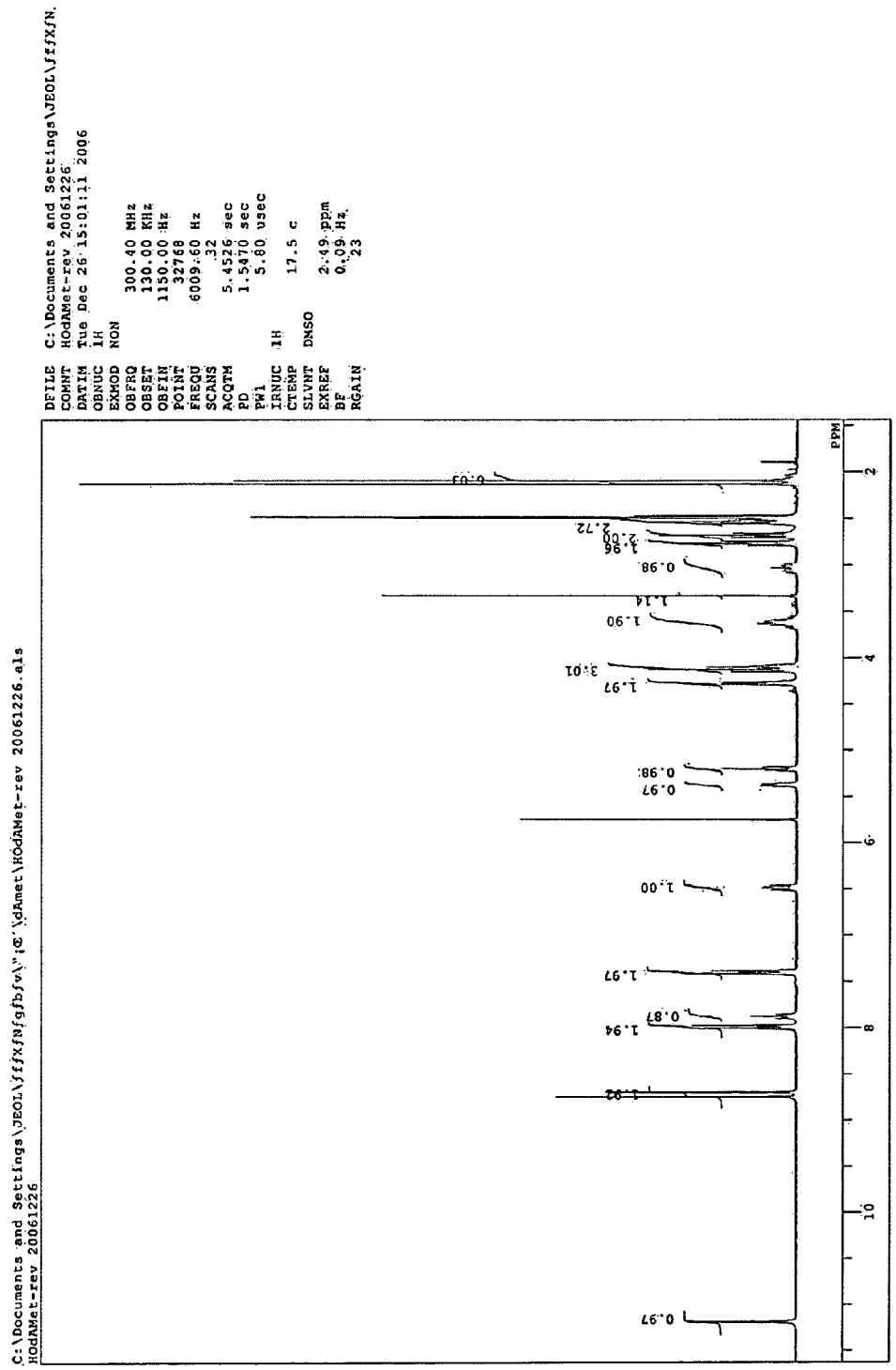
FIG. 9-D

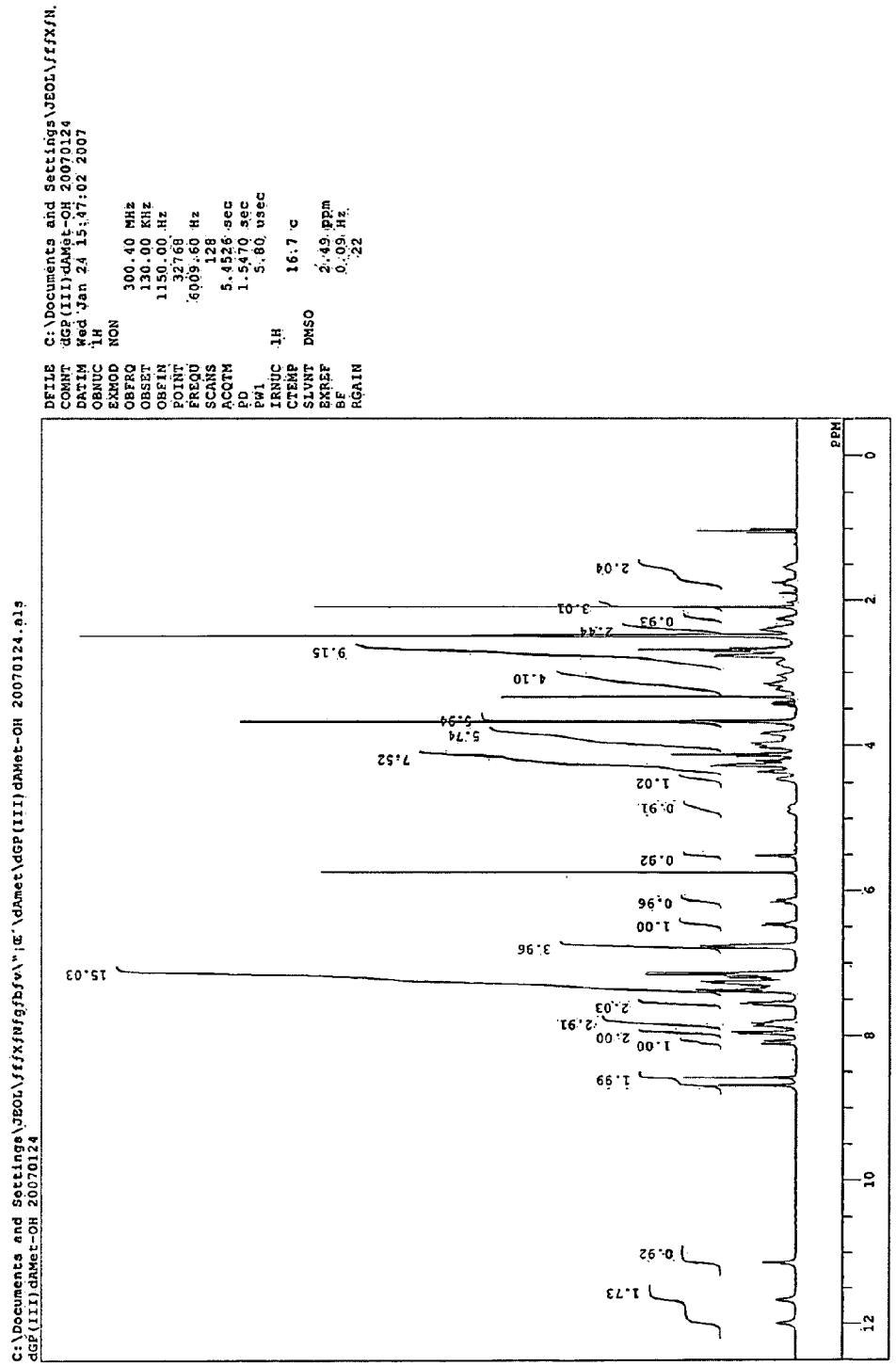
FIG. 9-E

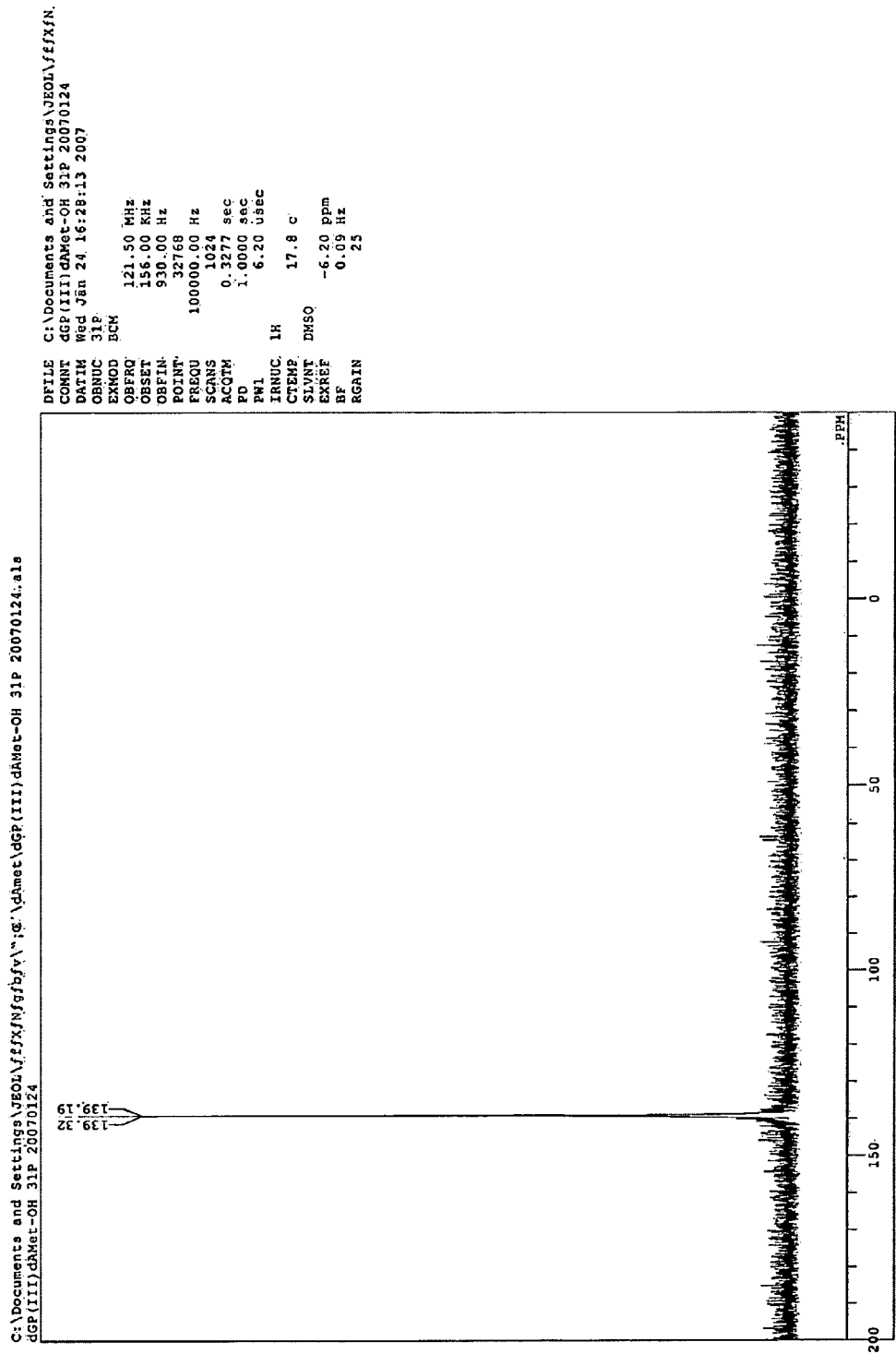
FIG. 9-F

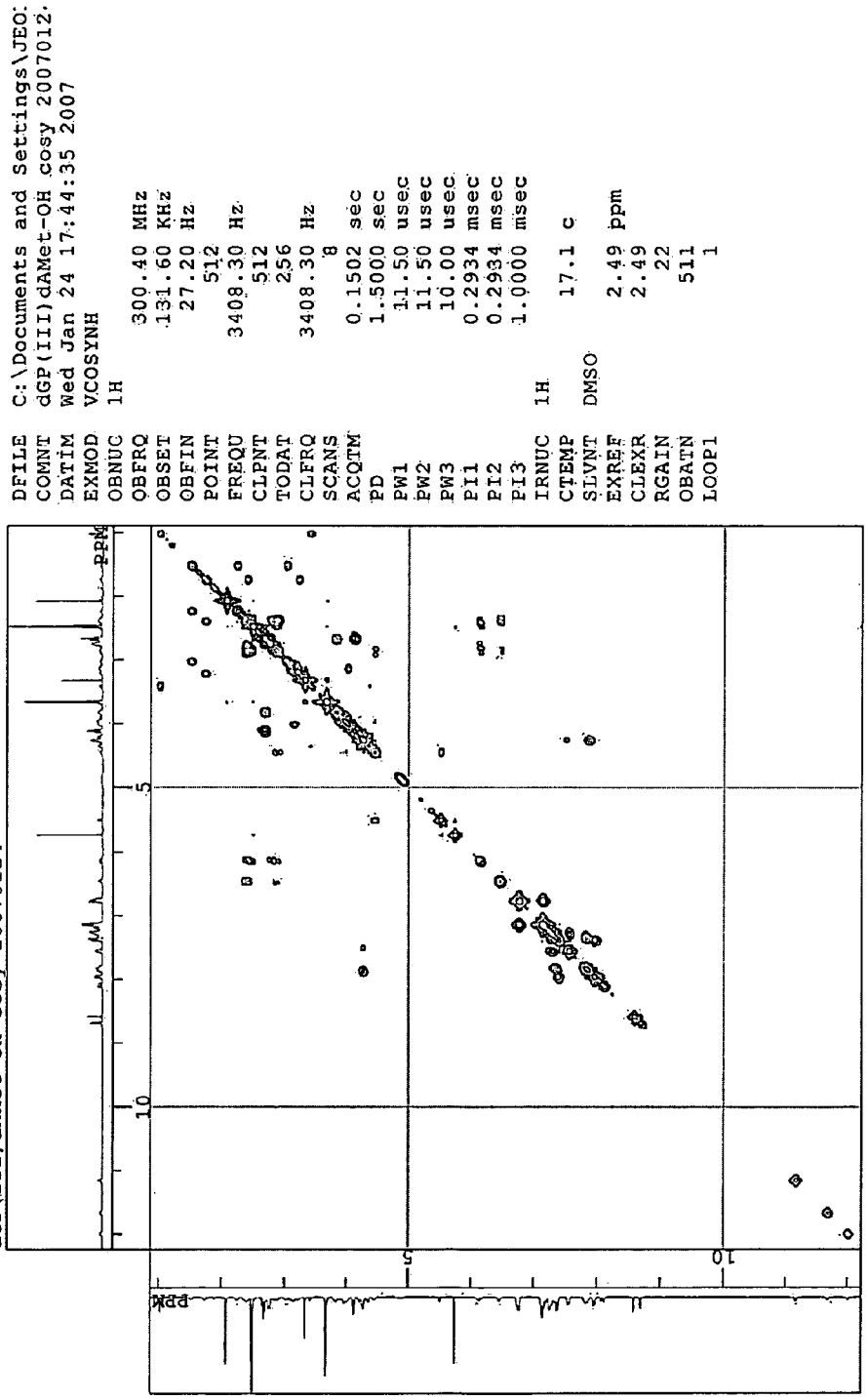
FIG. 9-G

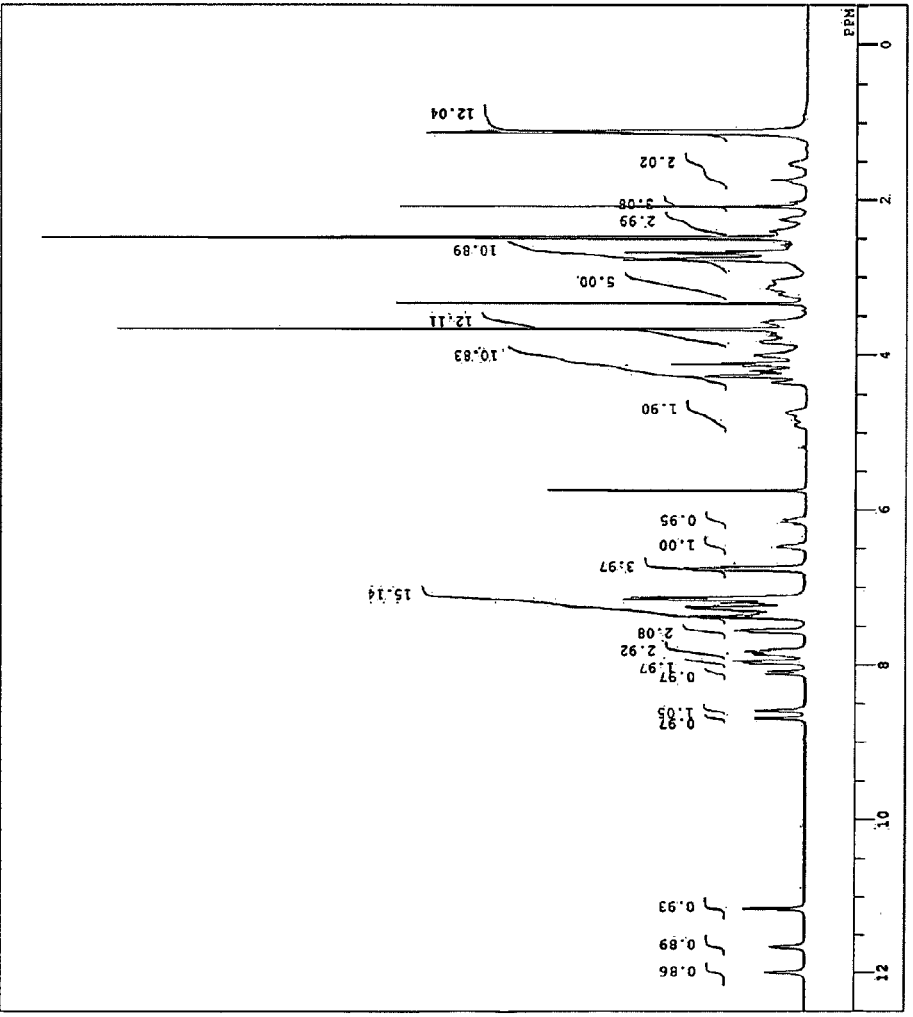
FIG. 9-H

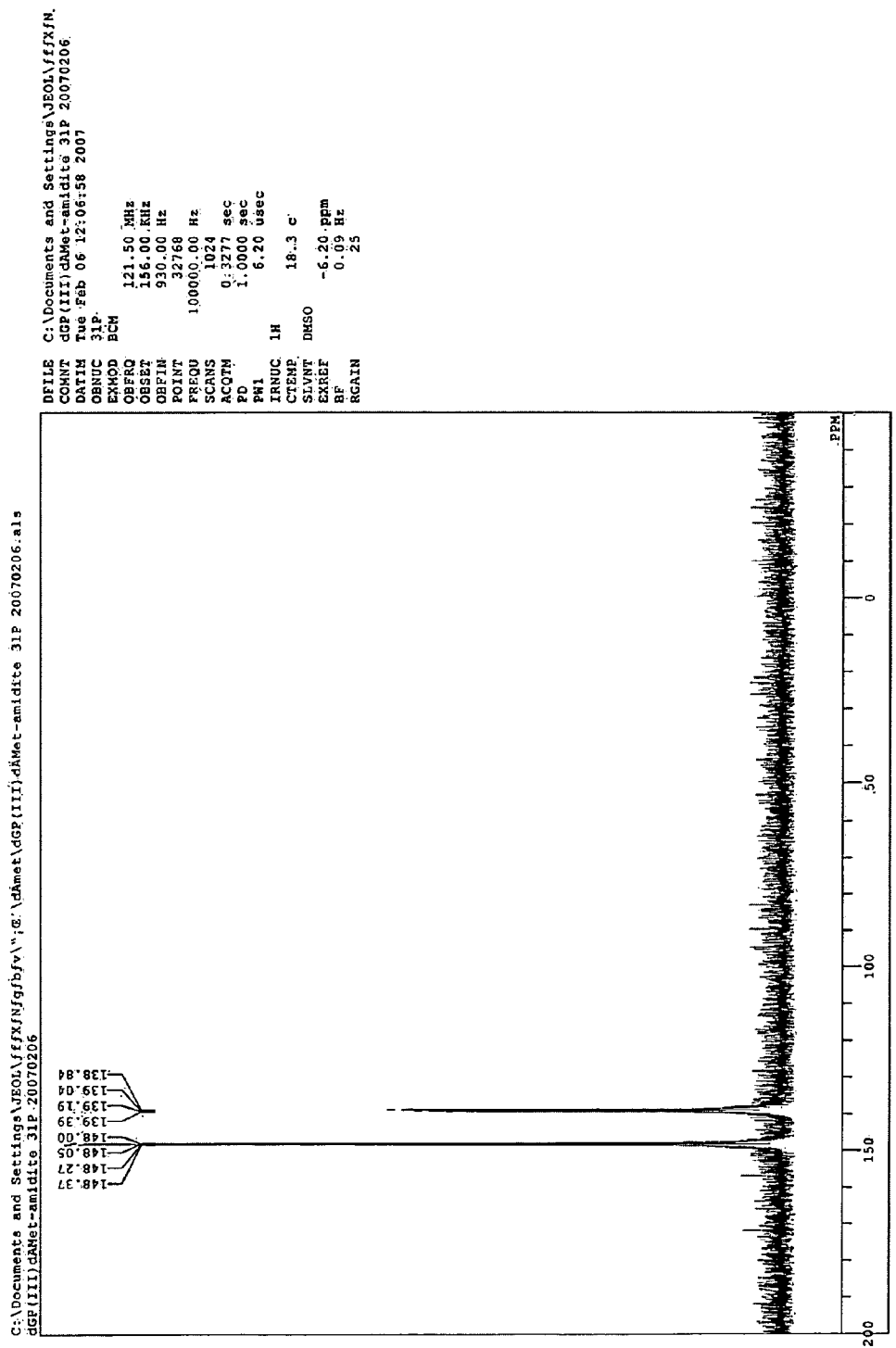
FIG. 9-I

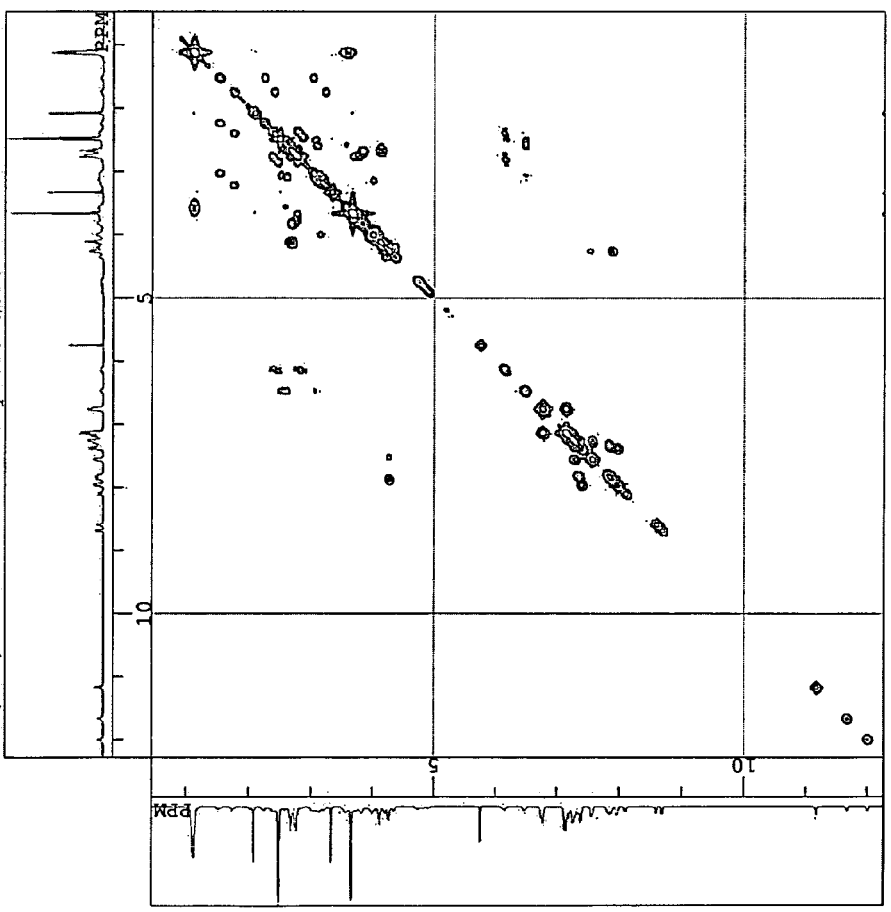
FIG. 9-J

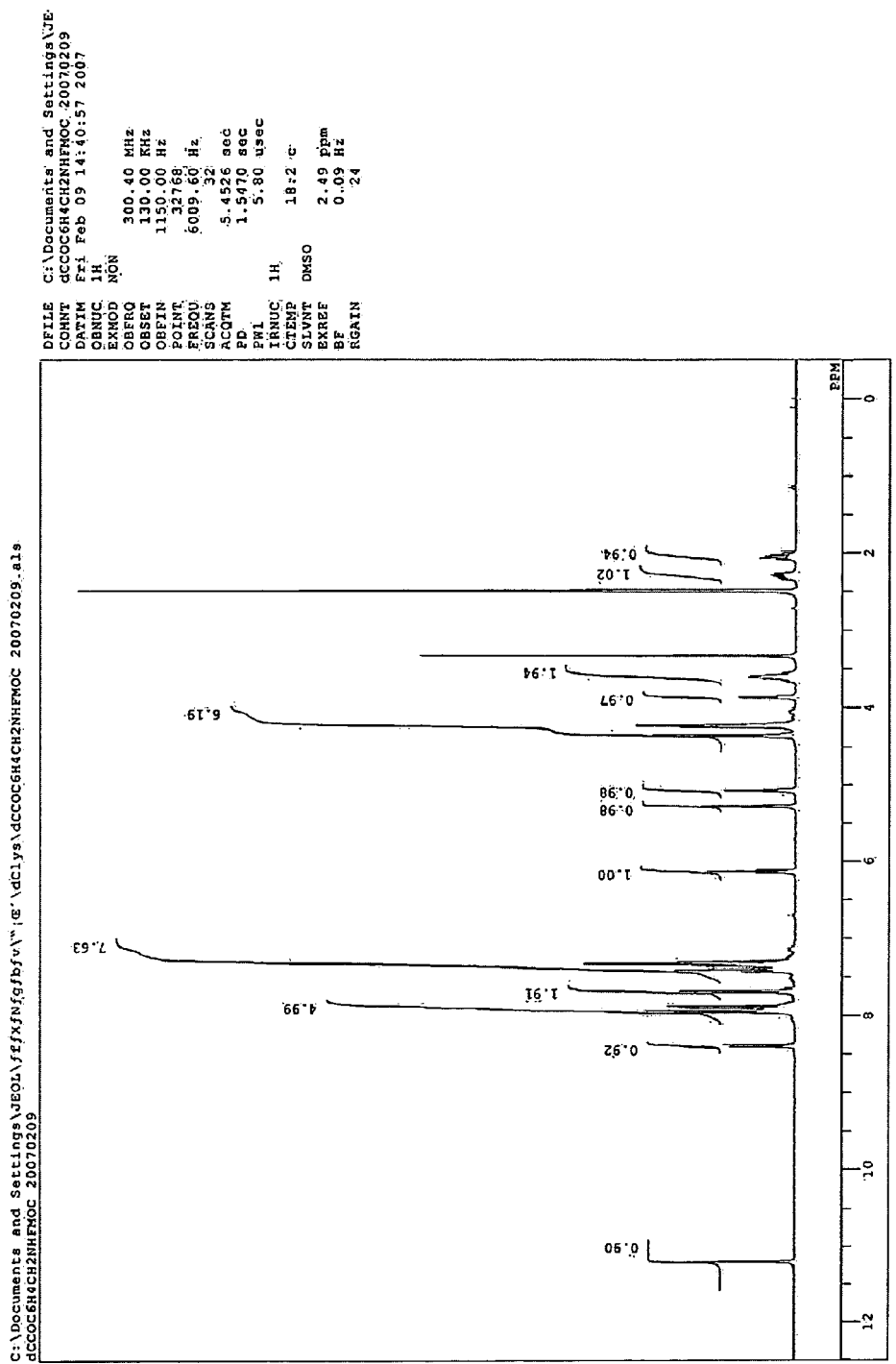
FIG. 10-A

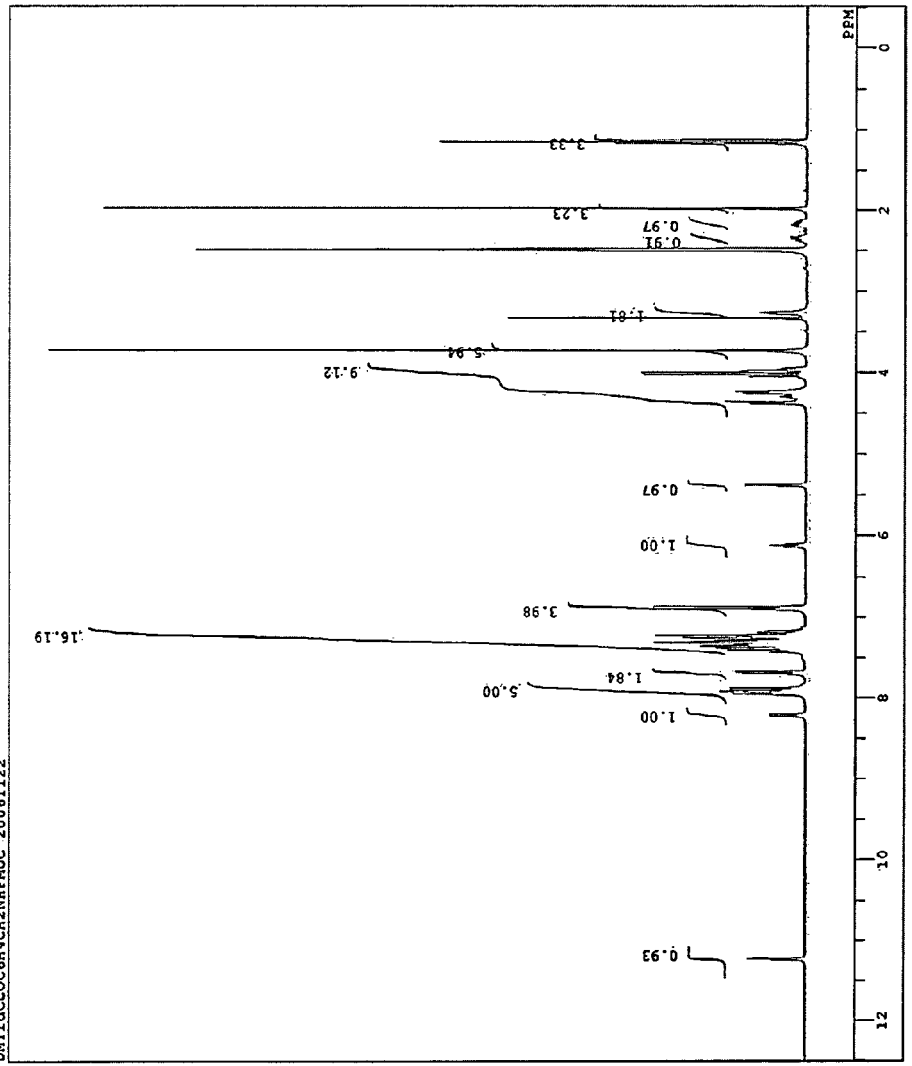
FIG. 10-B

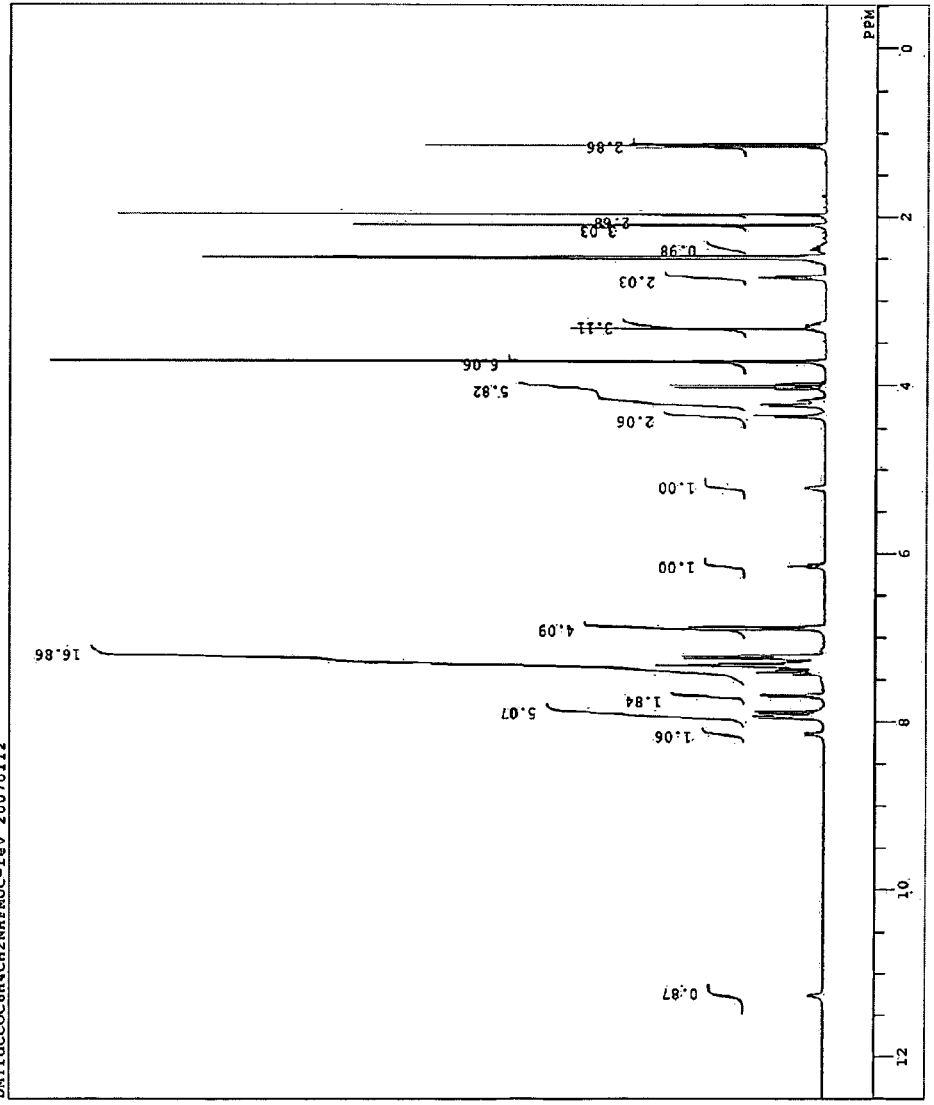
FIG. 10-C

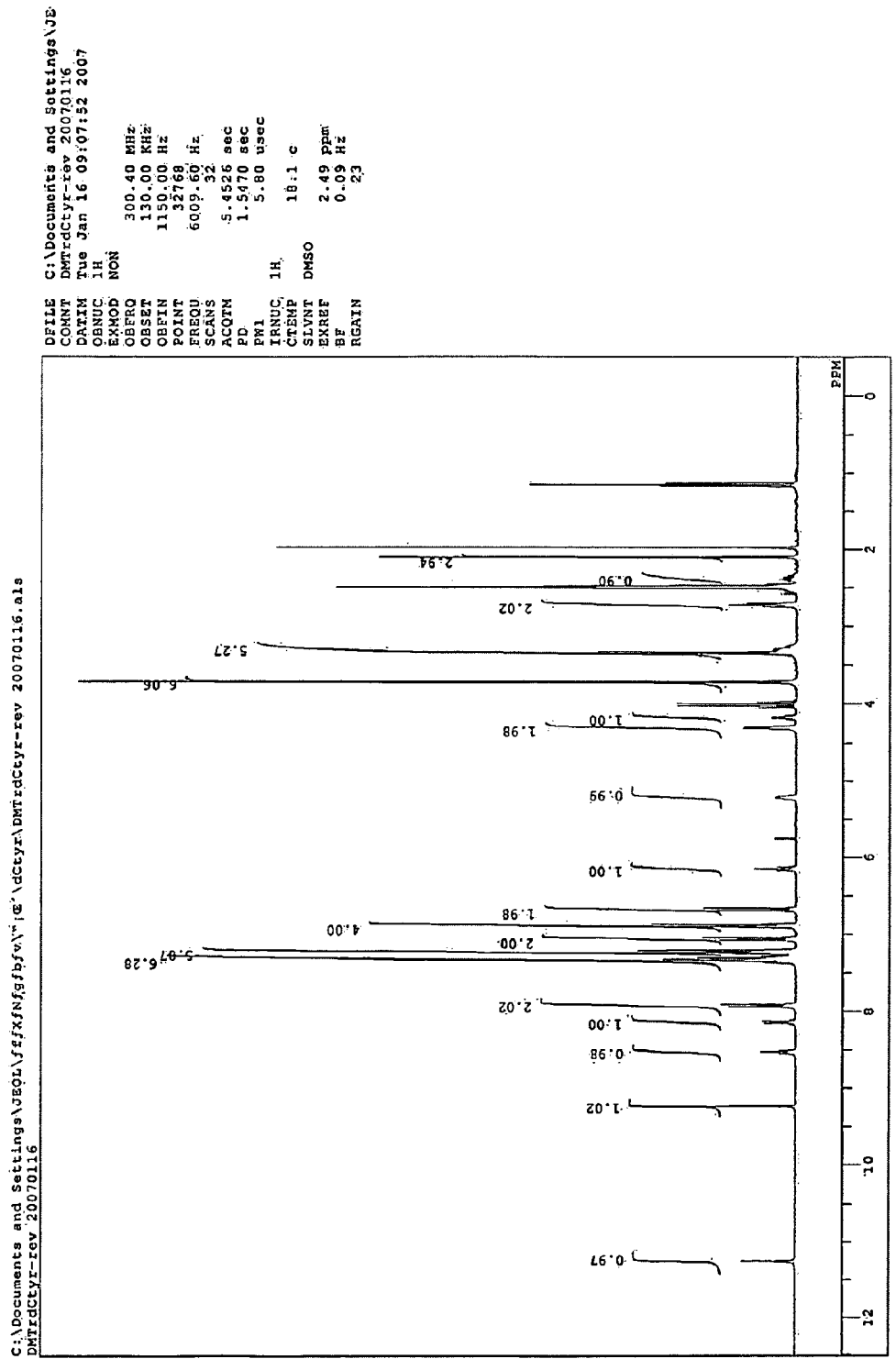
FIG. 10-D

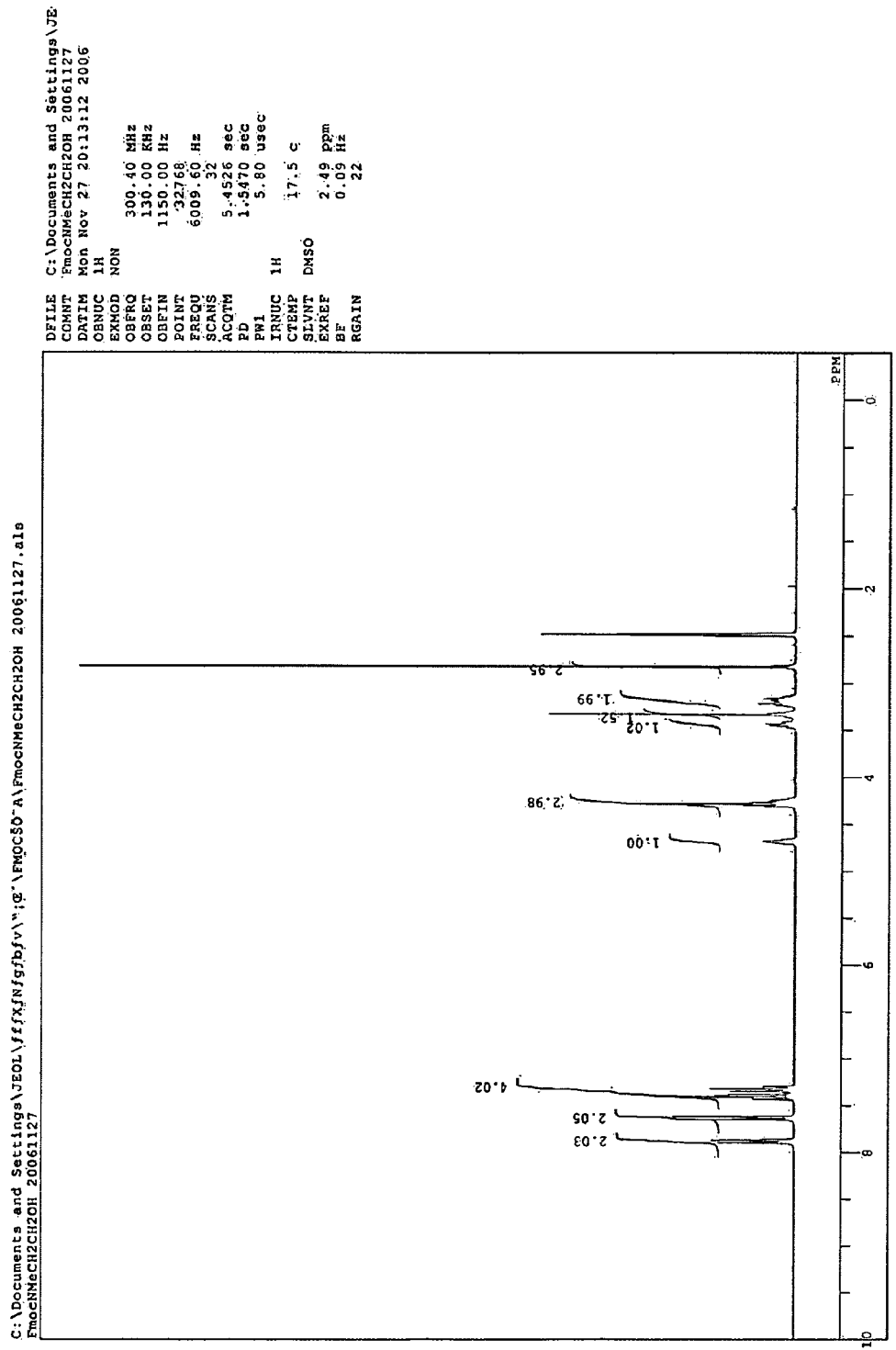
FIG. 10-E

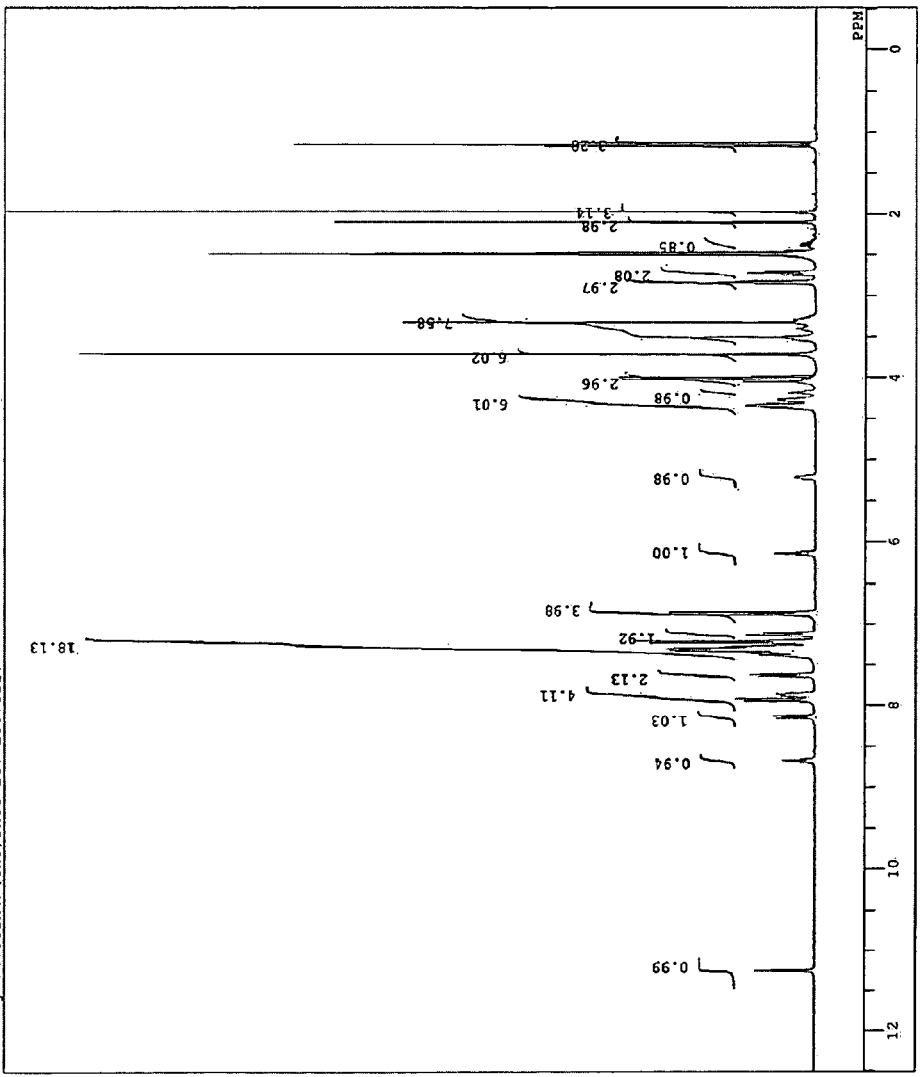
FIG. 10-F

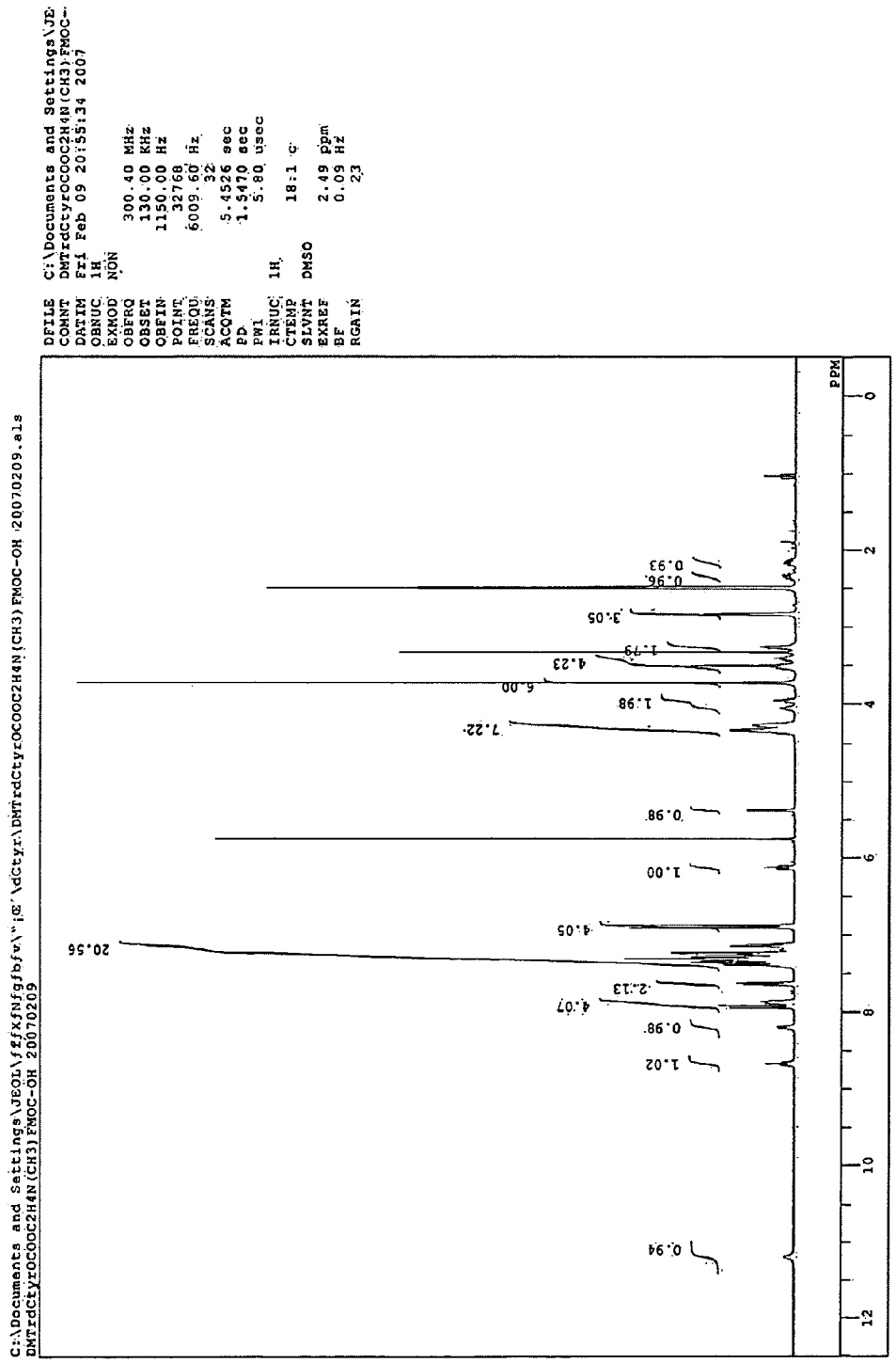
FIG. 10-G

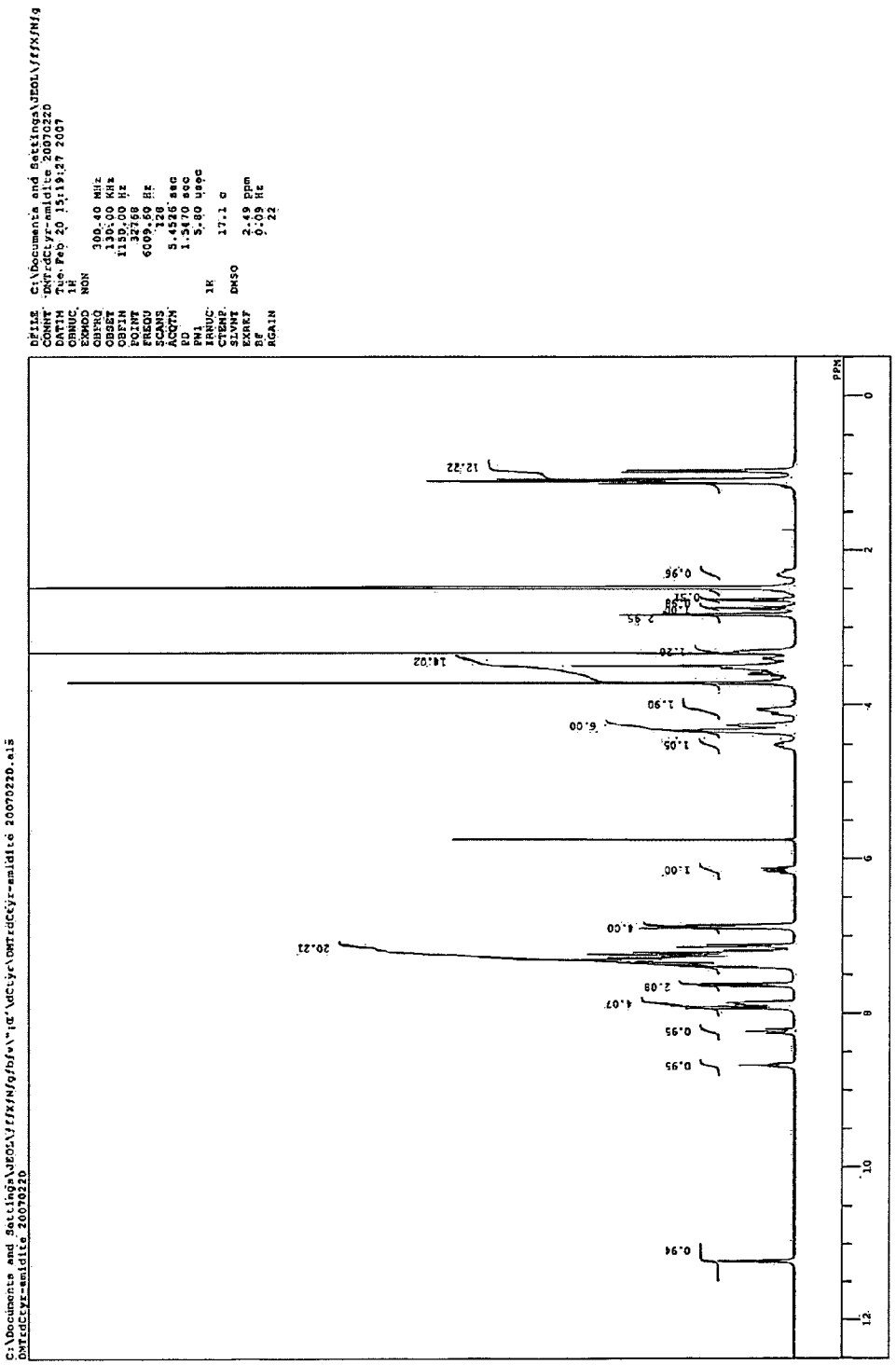
FIG. 10-H

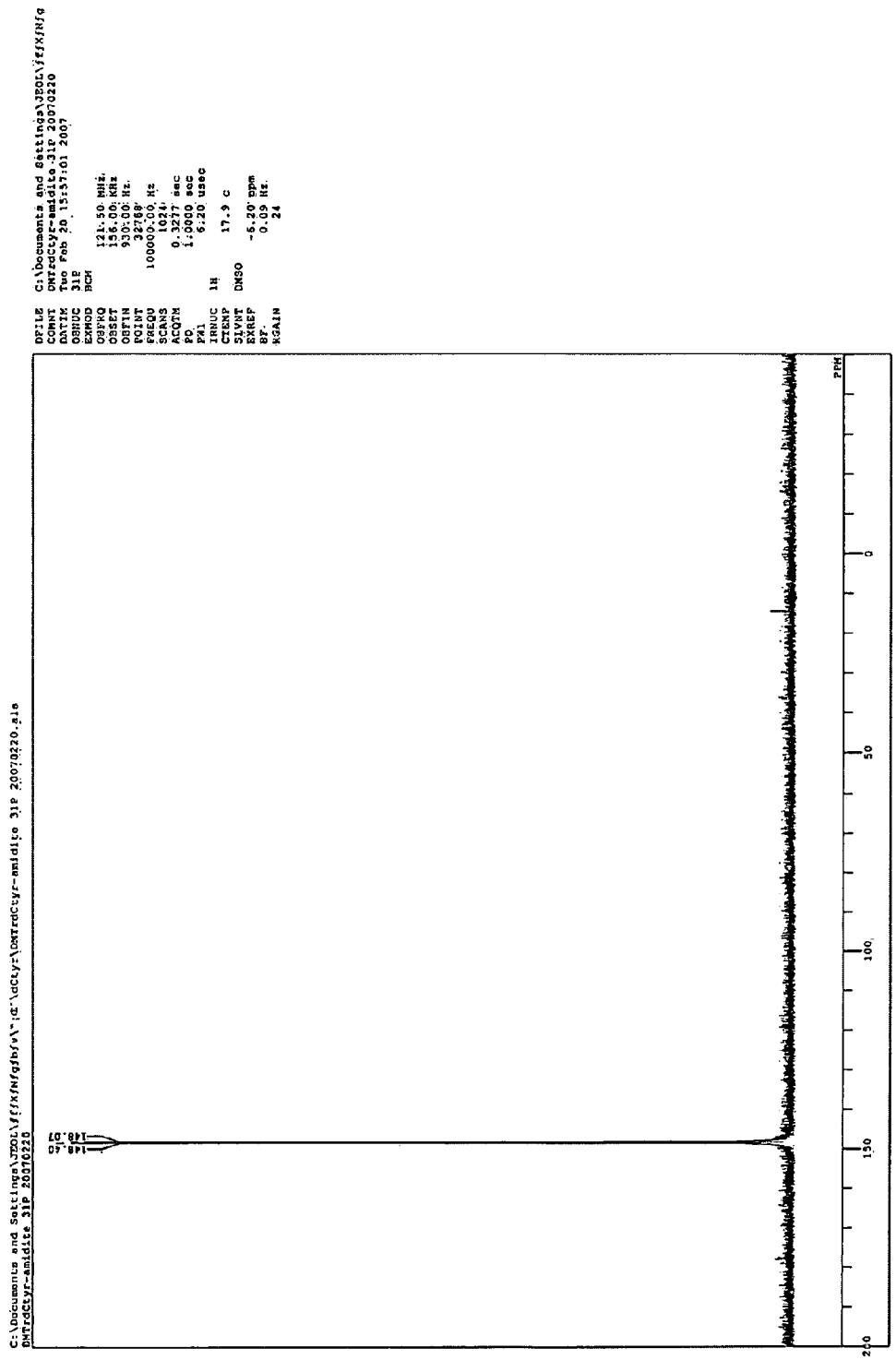
FIG. 10-I

FIG. 10-J
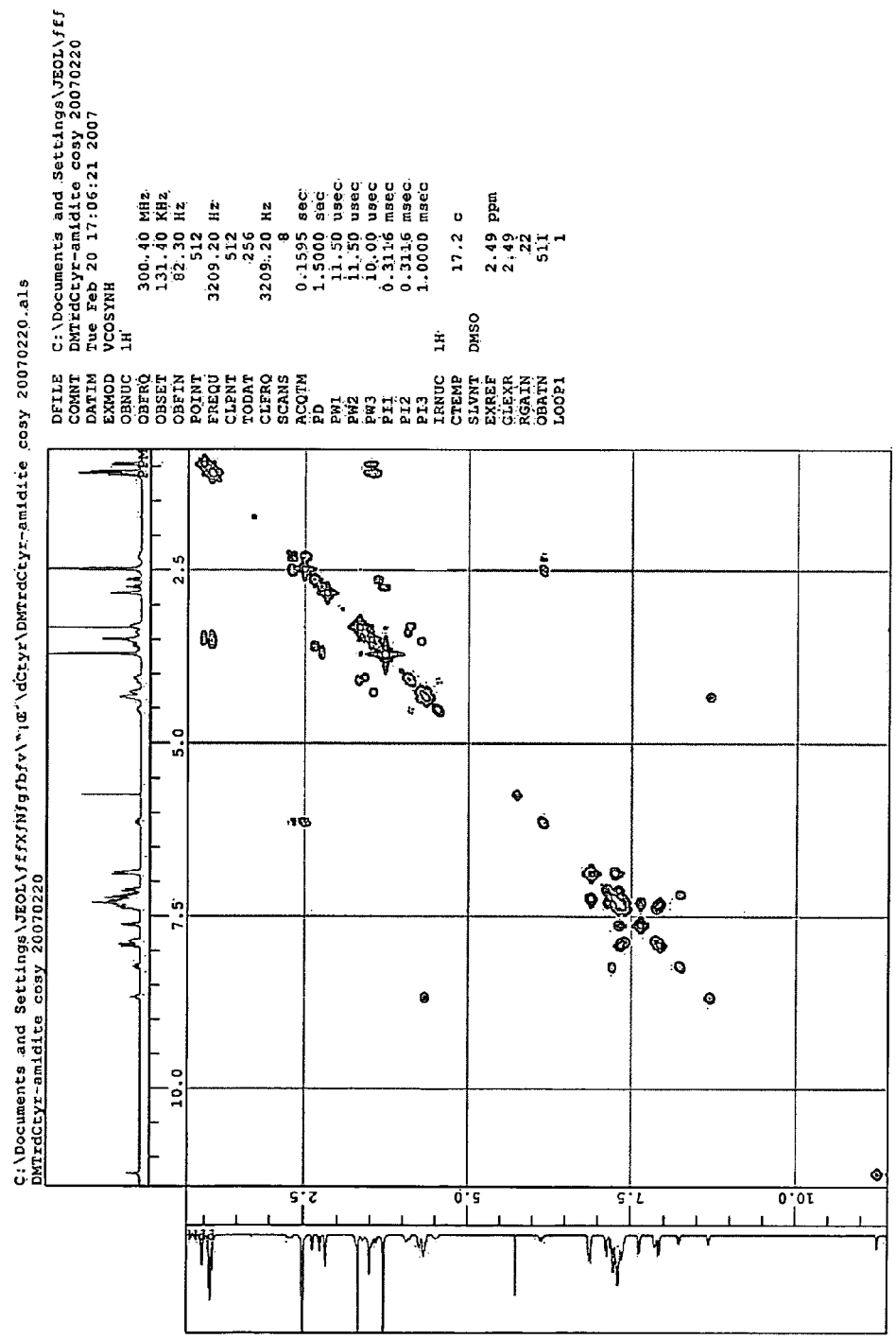

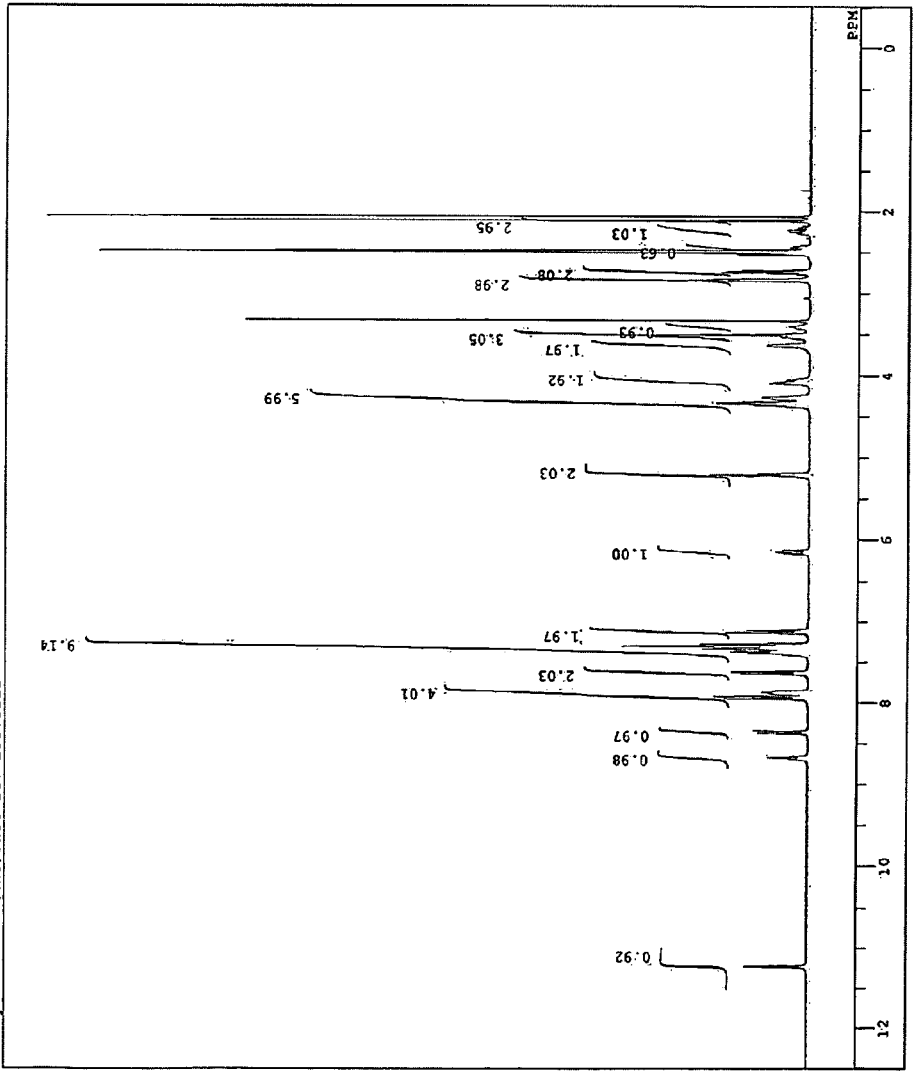
FIG. 10-K

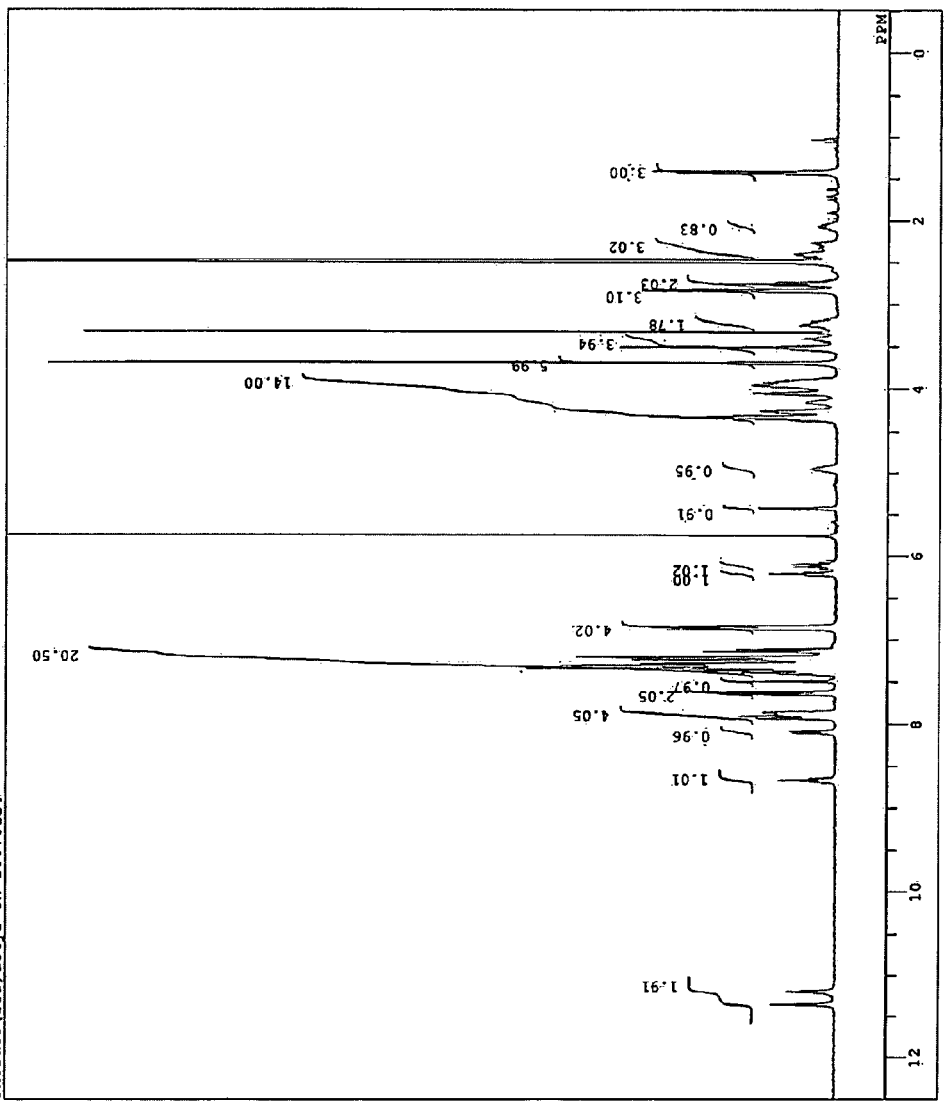
FIG. 10-L

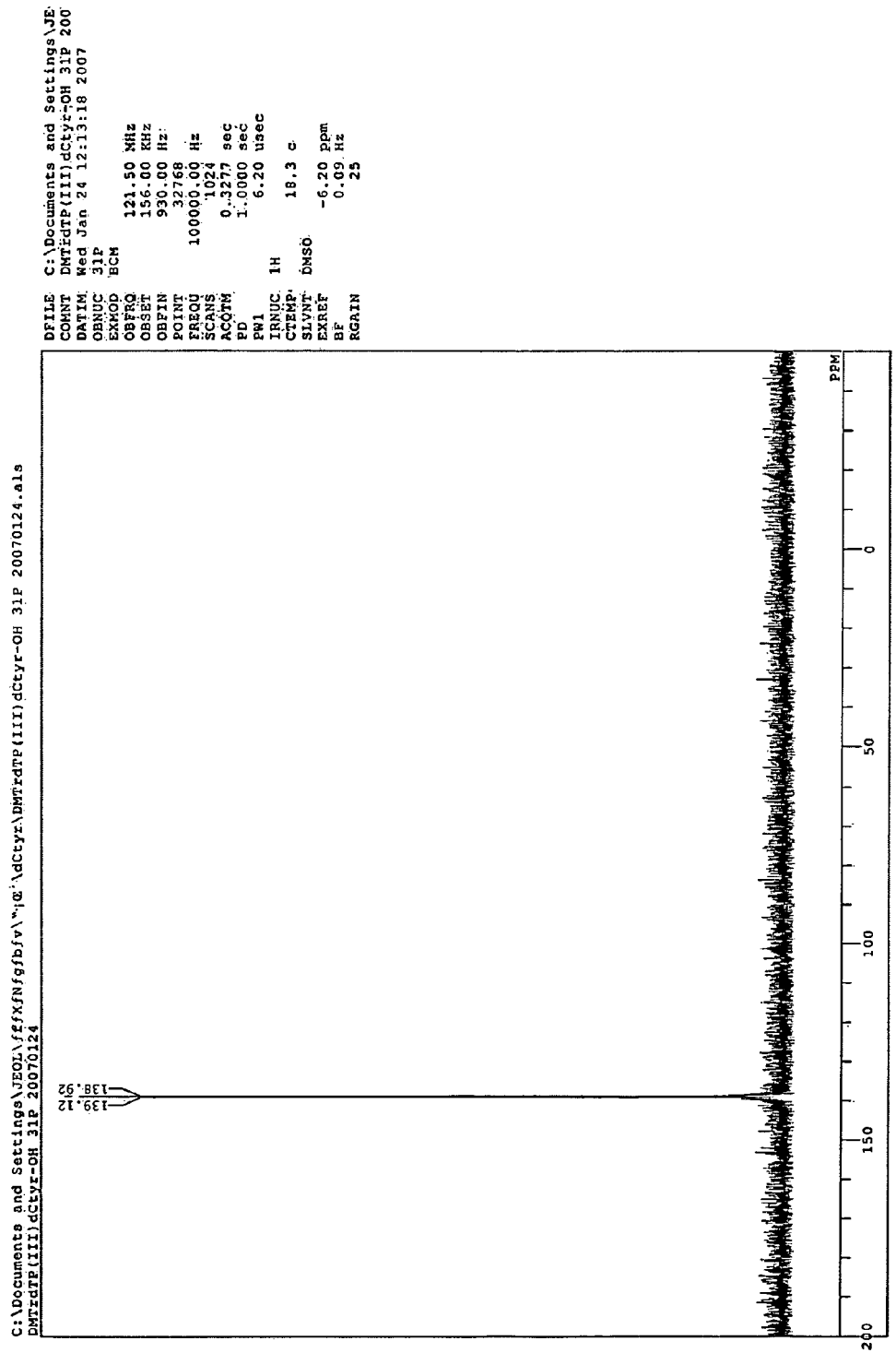
FIG. 10-M

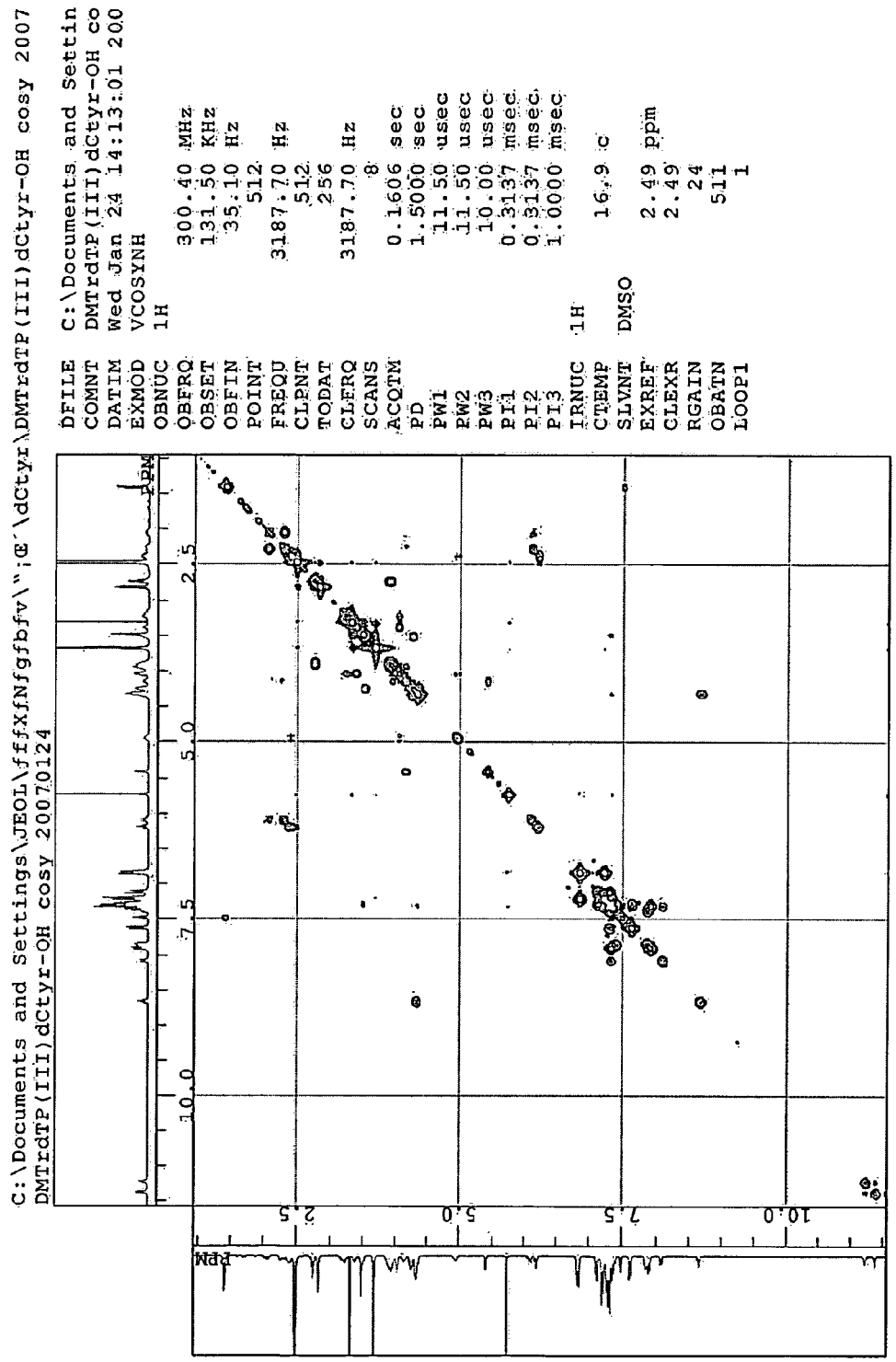
FIG. 10-N

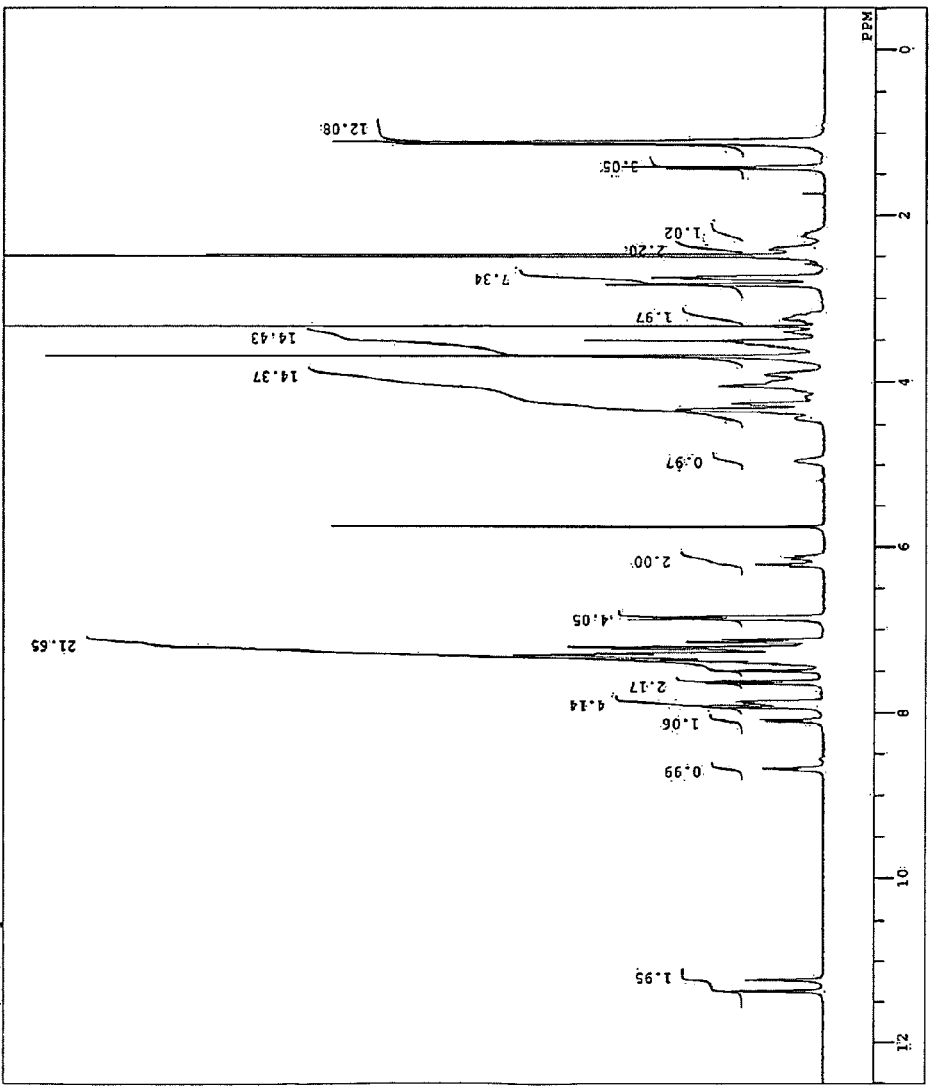
FIG. 10-O

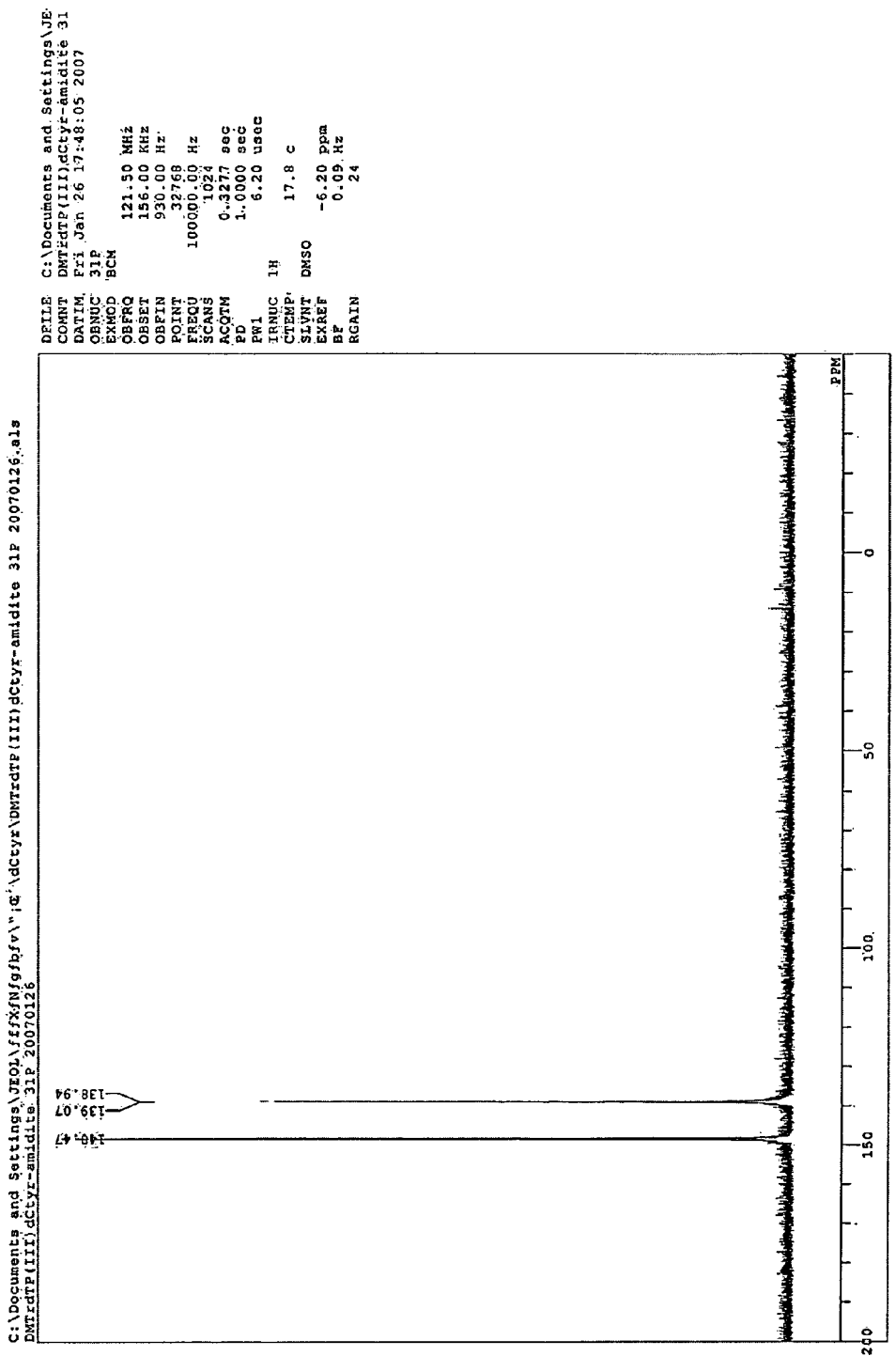
FIG. 10-P

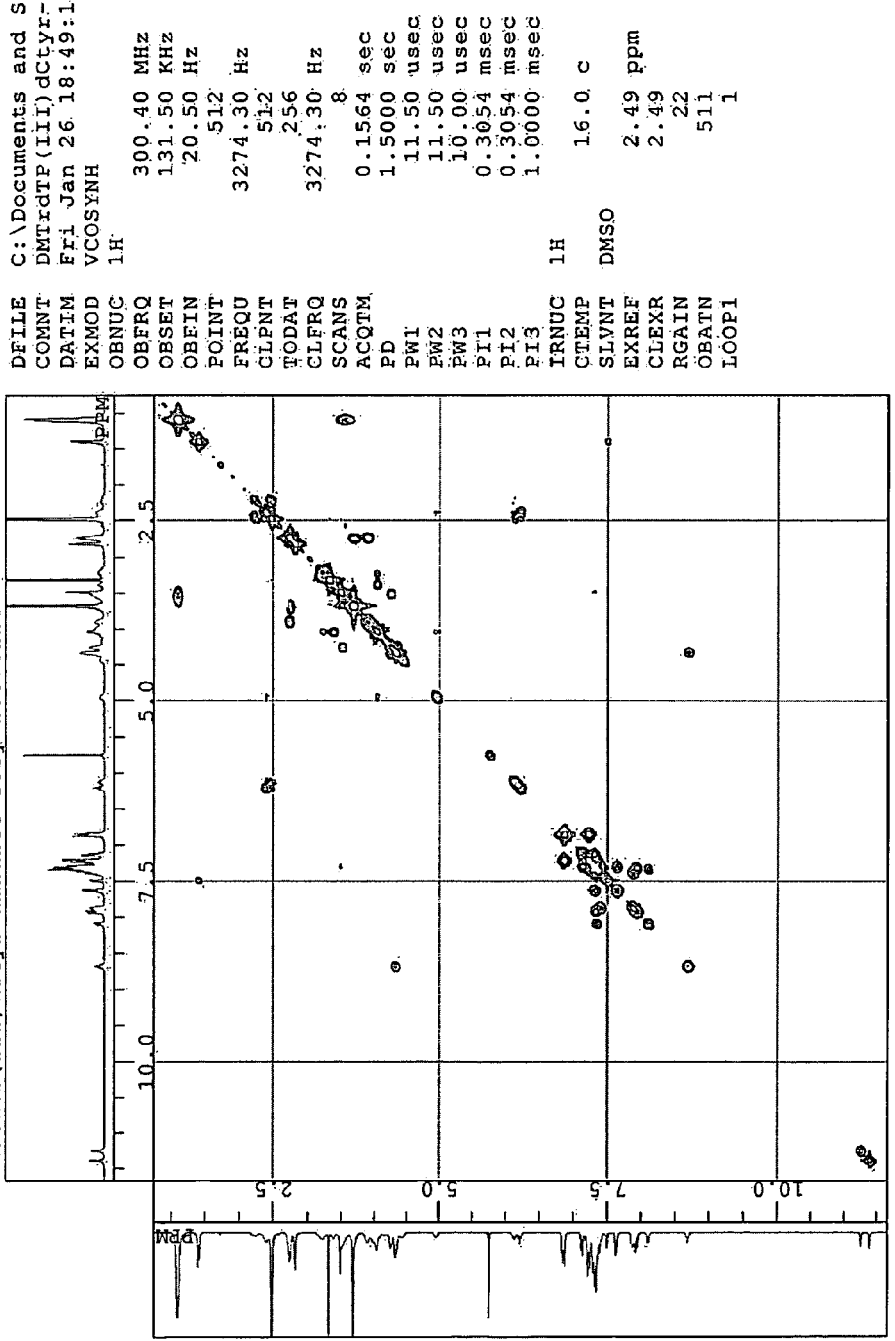
FIG. 10-Q

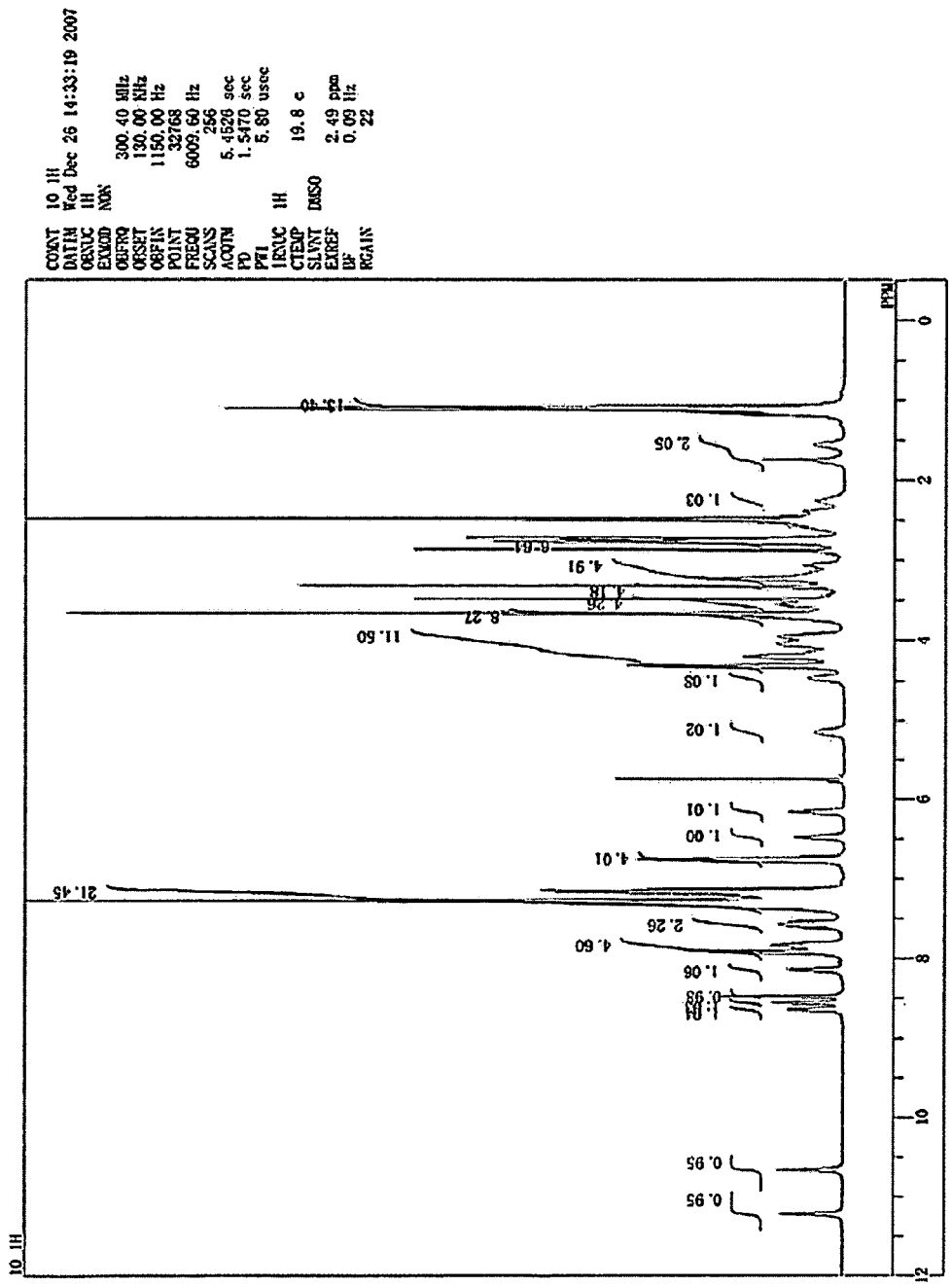
FIG. 11-A

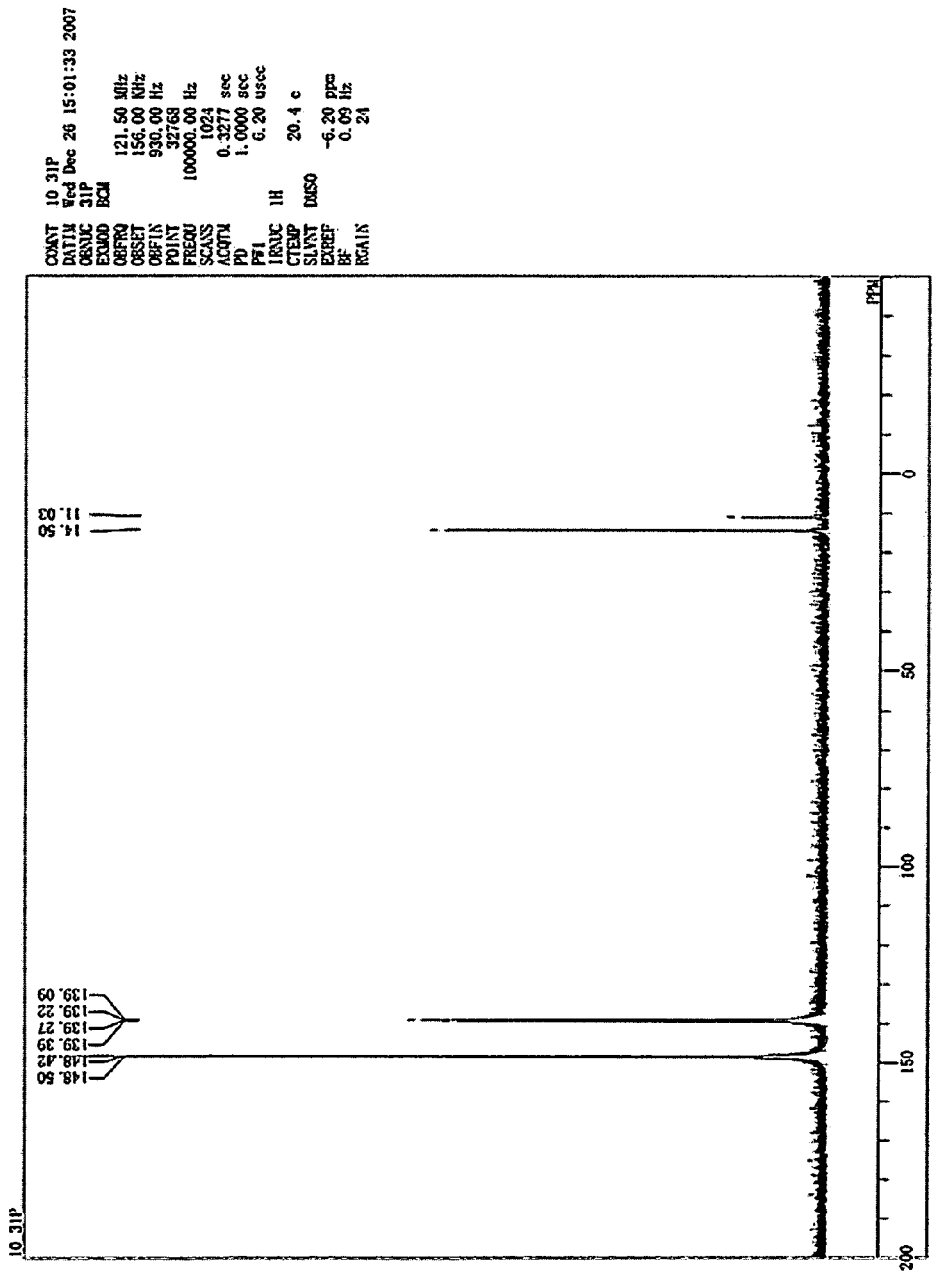
FIG. 11-B

FIG. 11-C
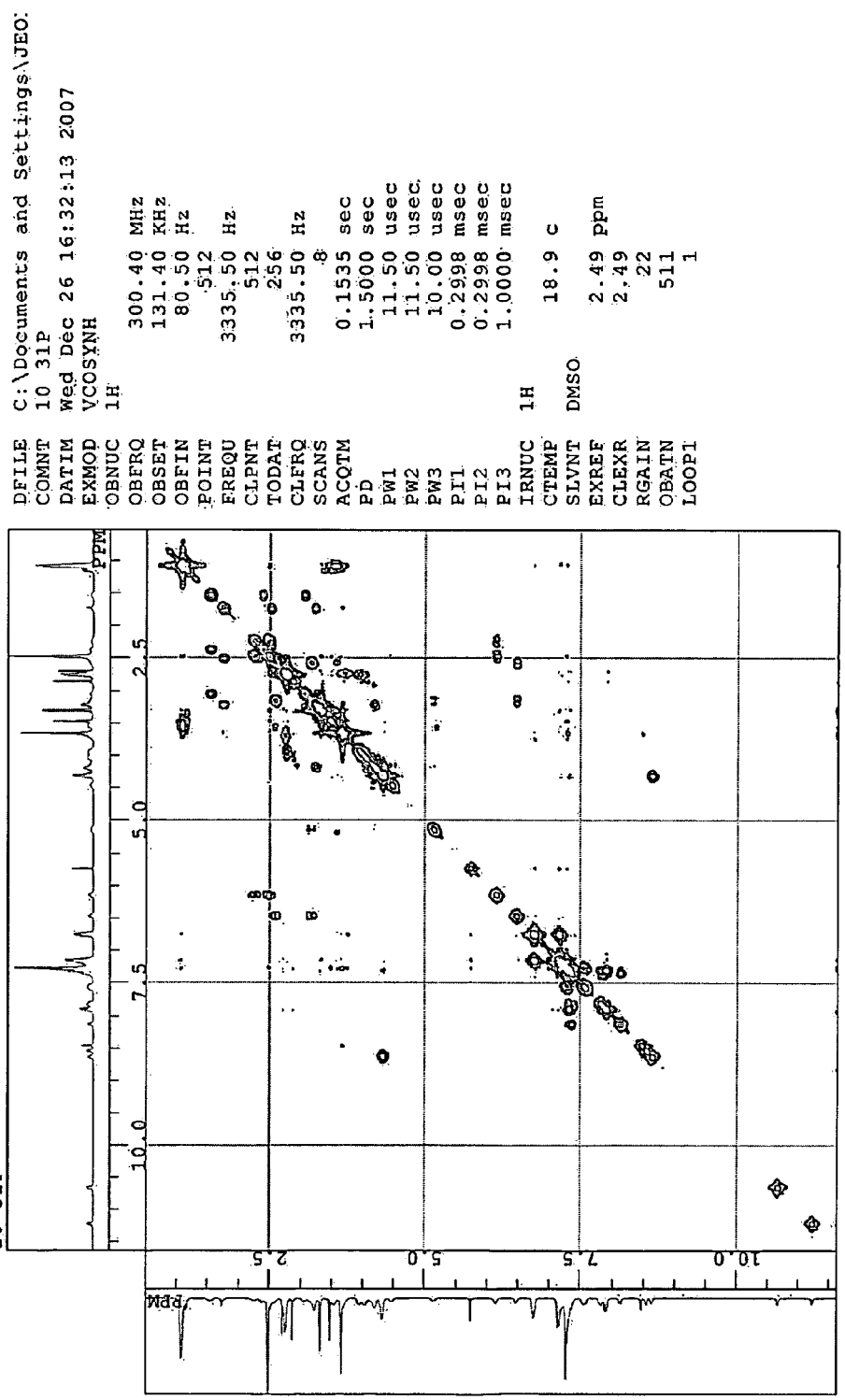

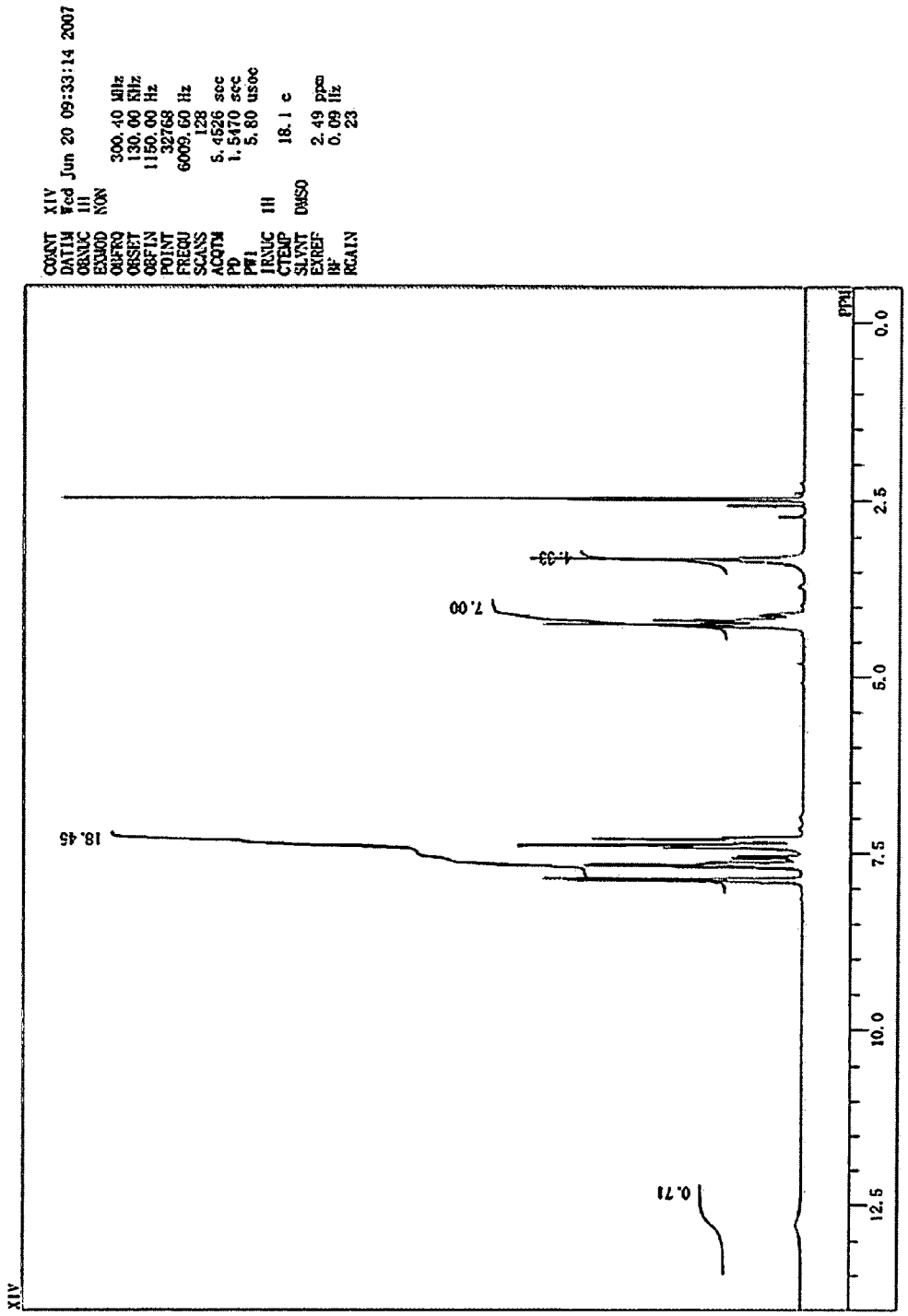
FIG. 12-A

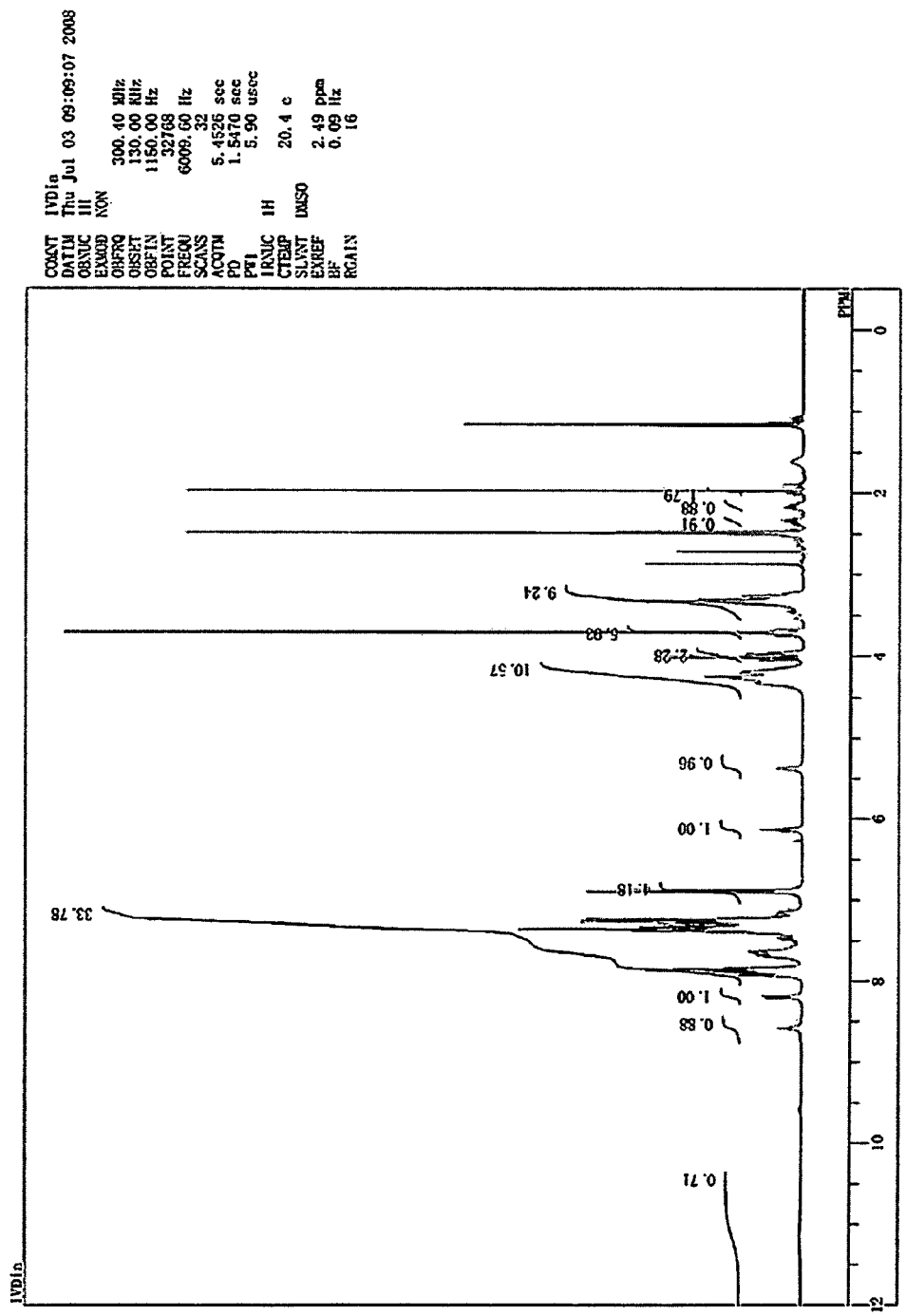
FIG. 12-B

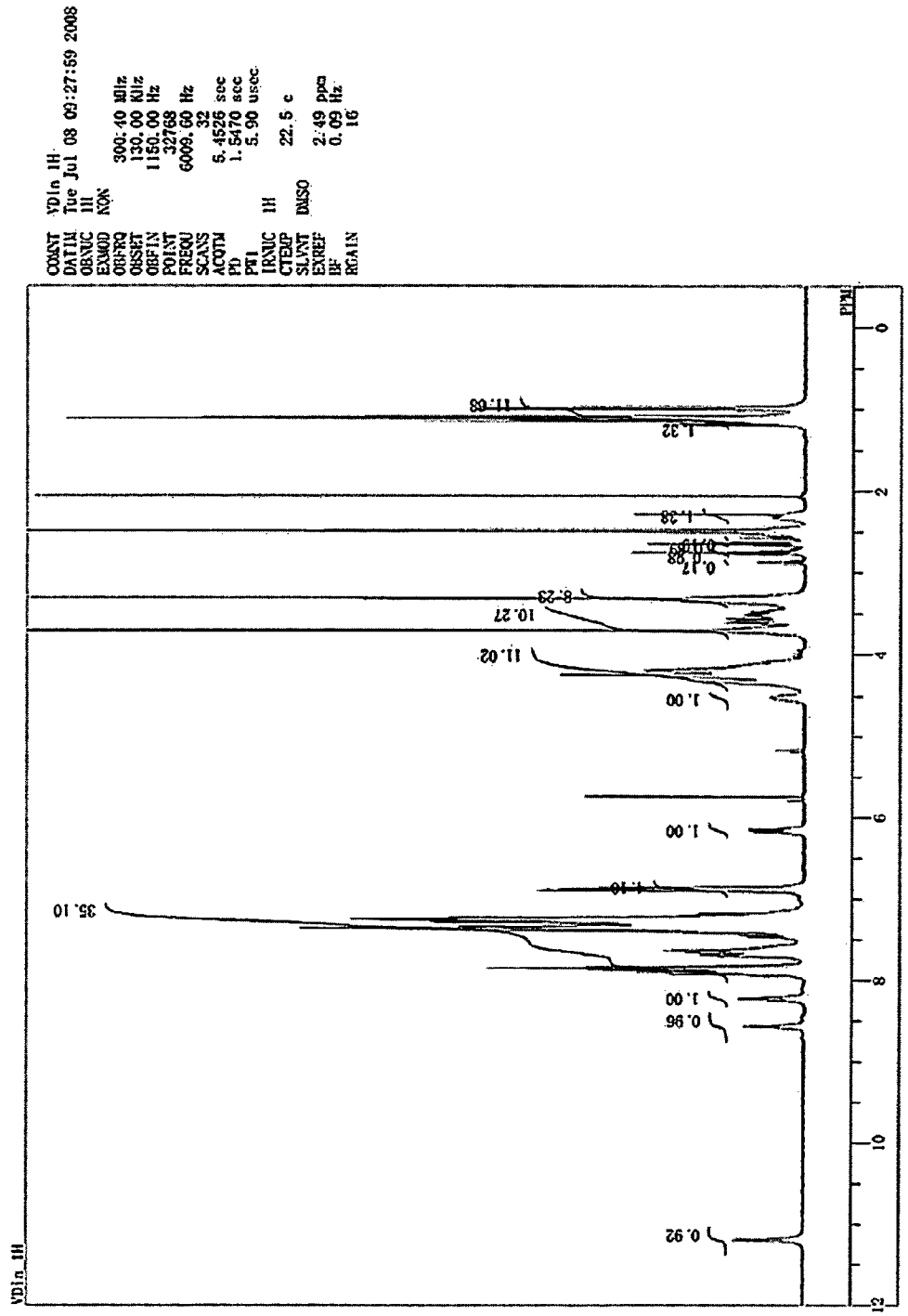
FIG. 12-C

FIG. 12-D
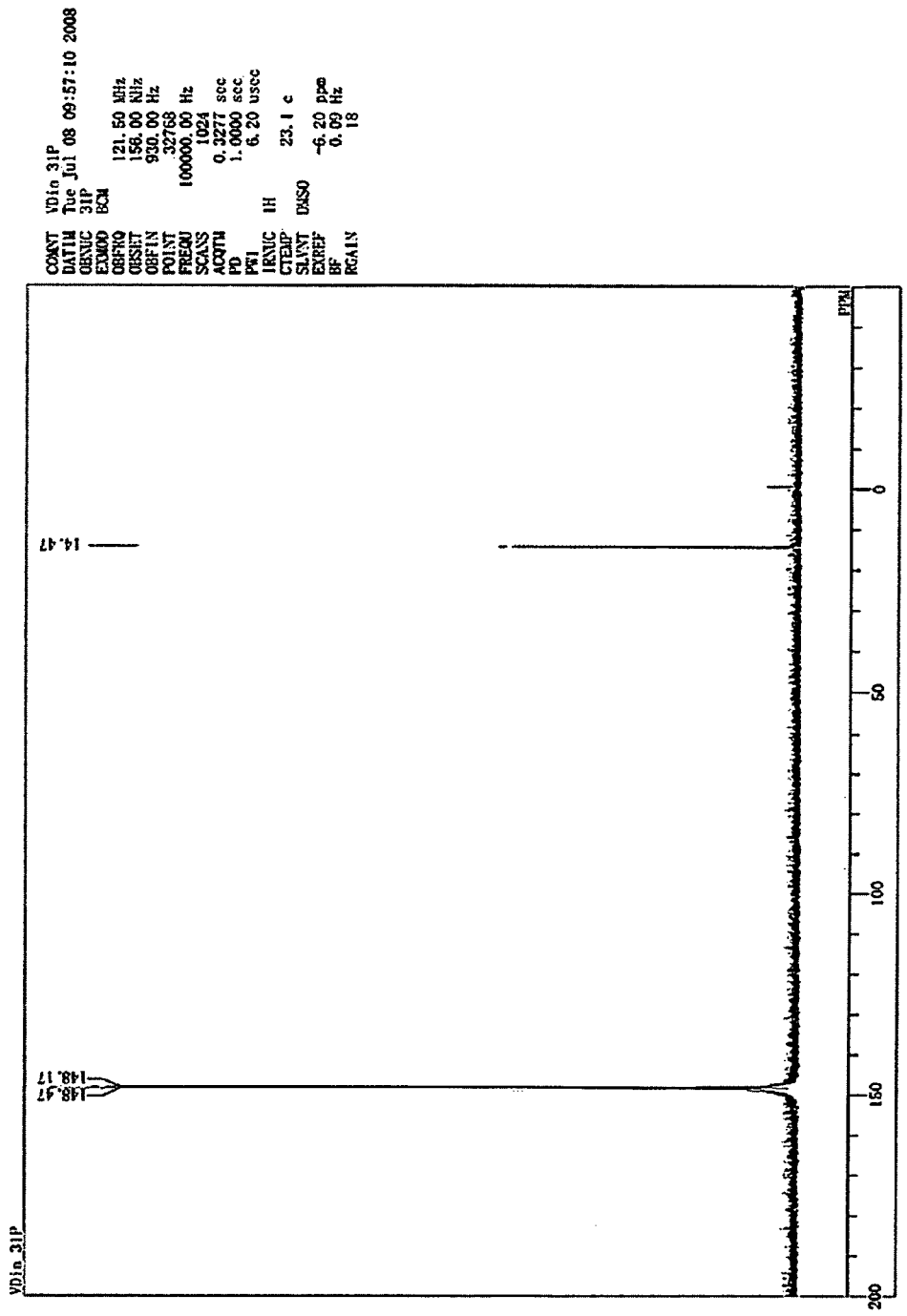

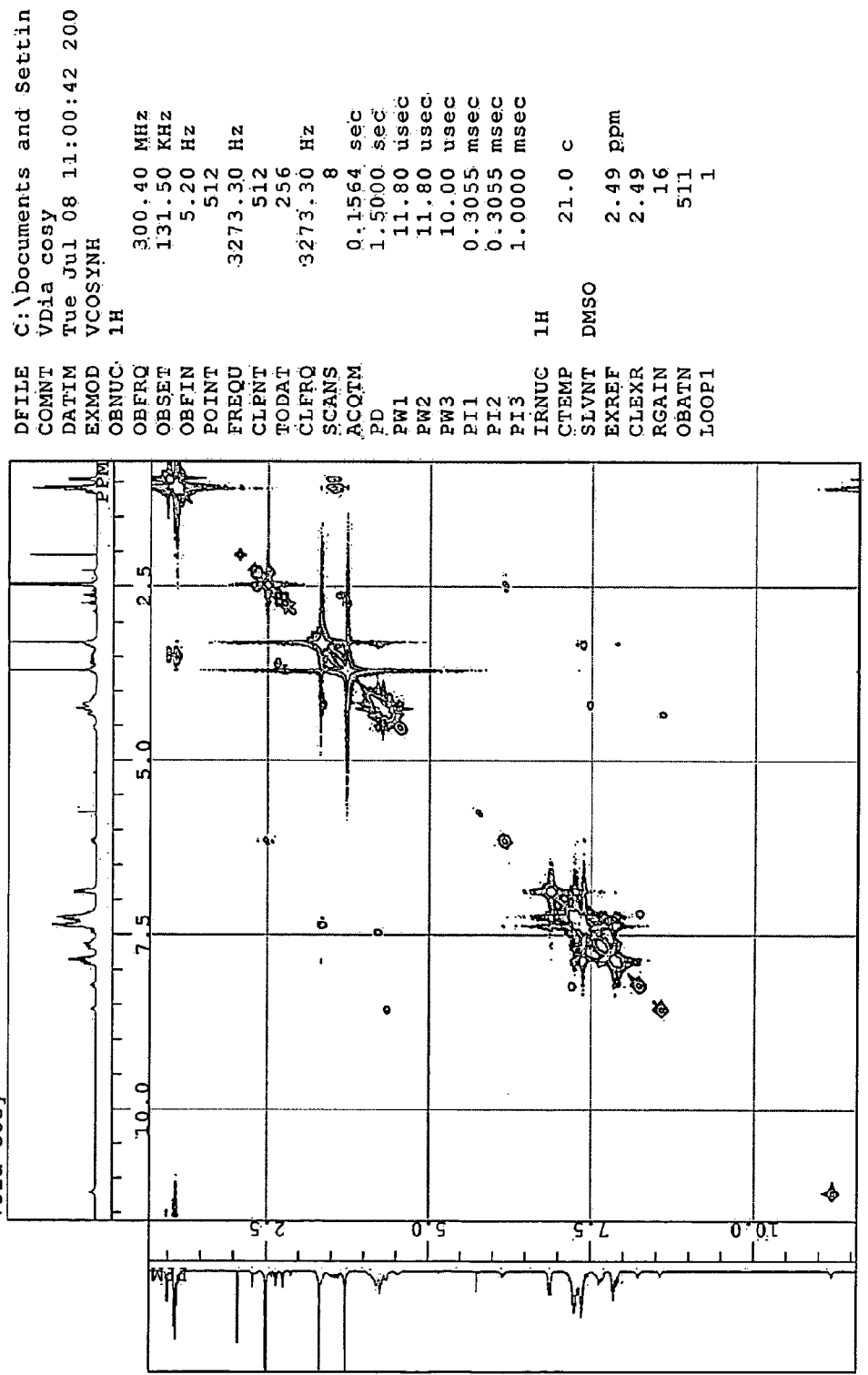
FIG. 12-E

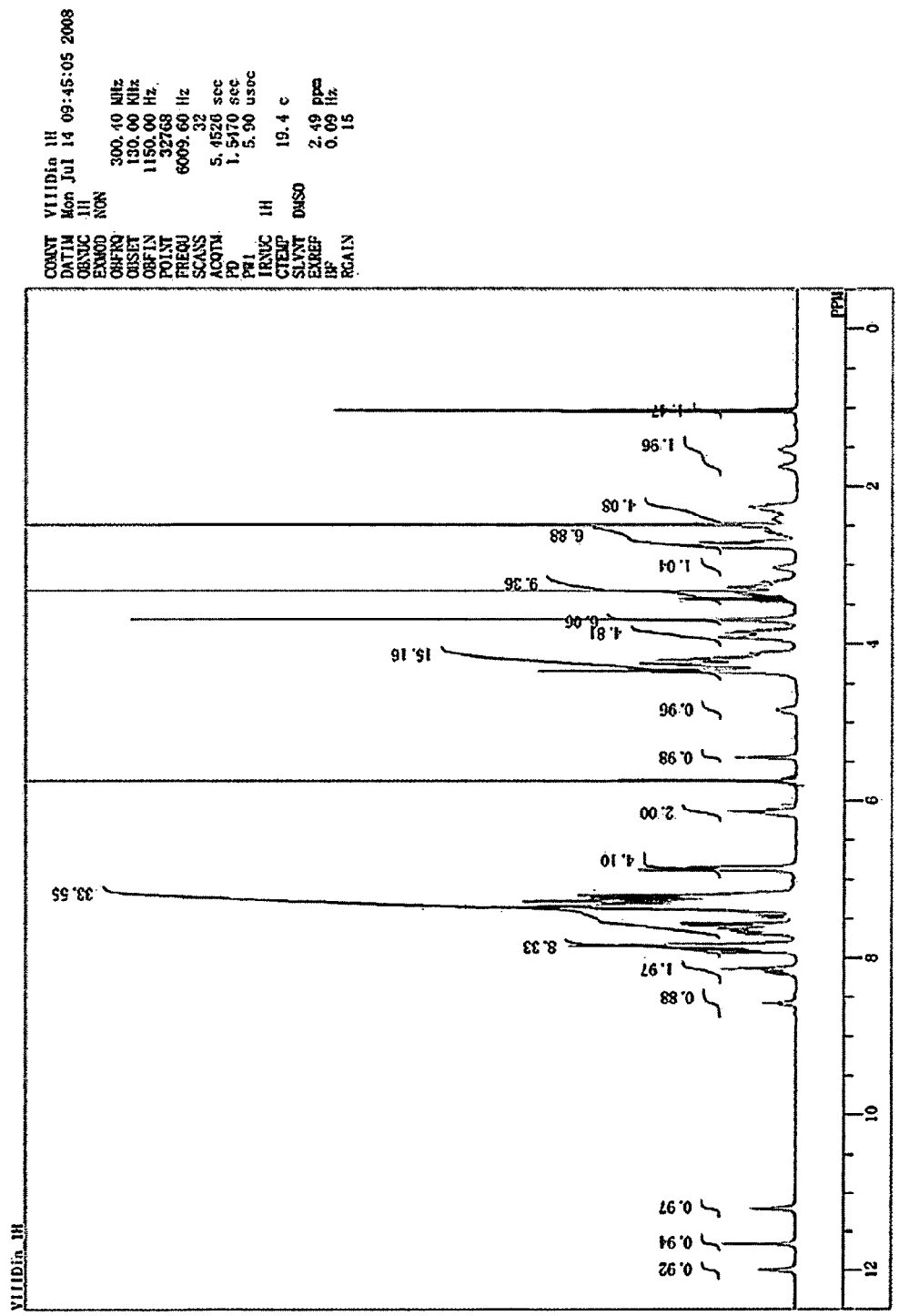
FIG. 12-F

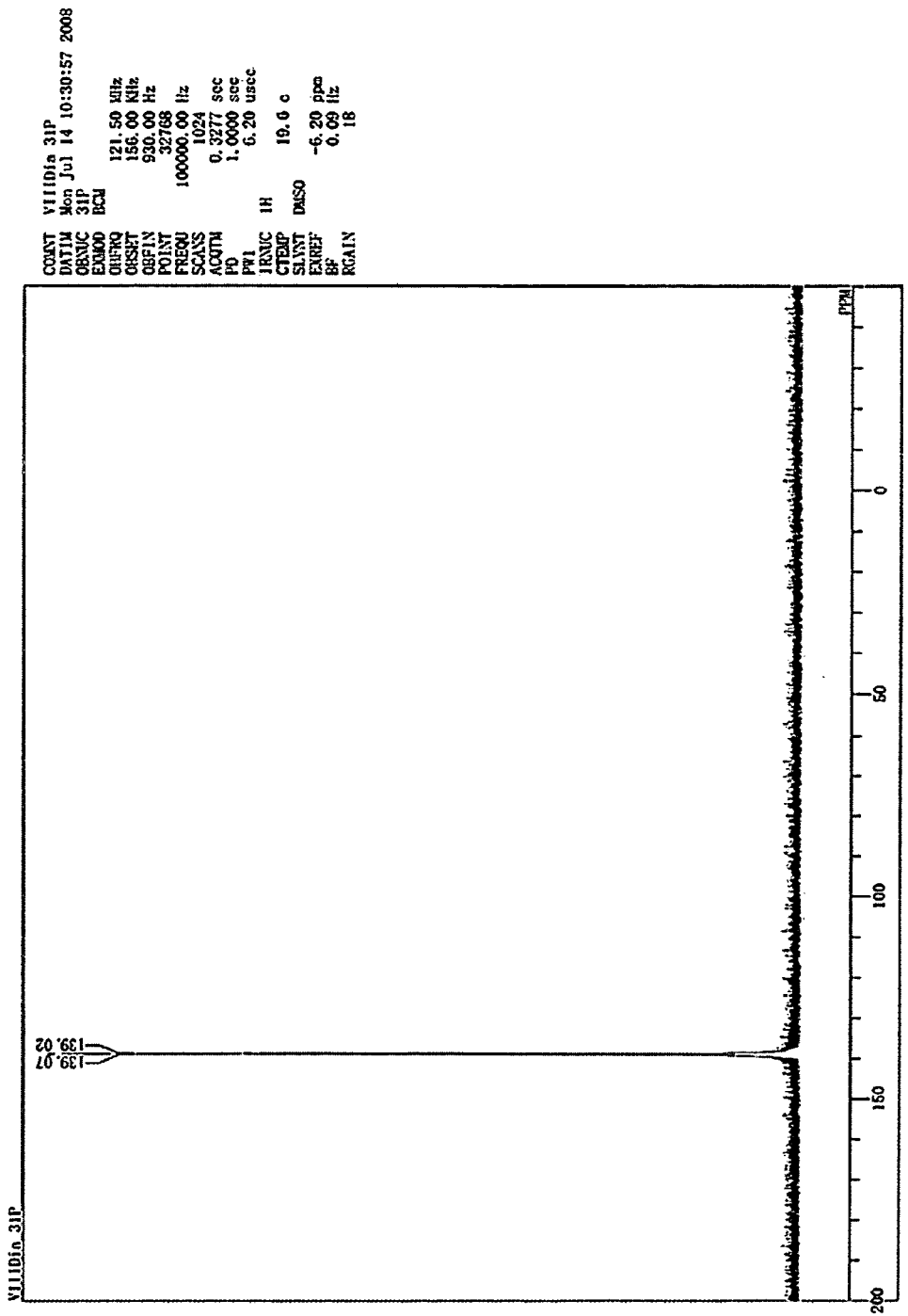
FIG. 12-G

FIG. 12-H
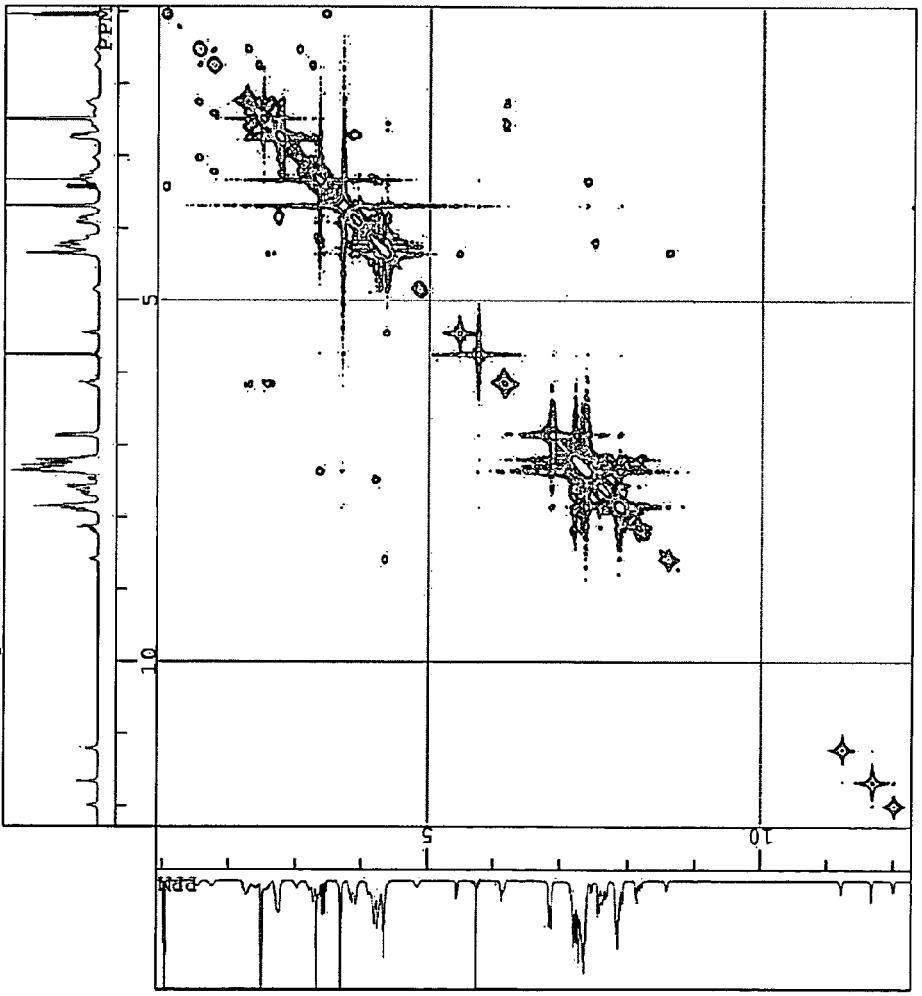

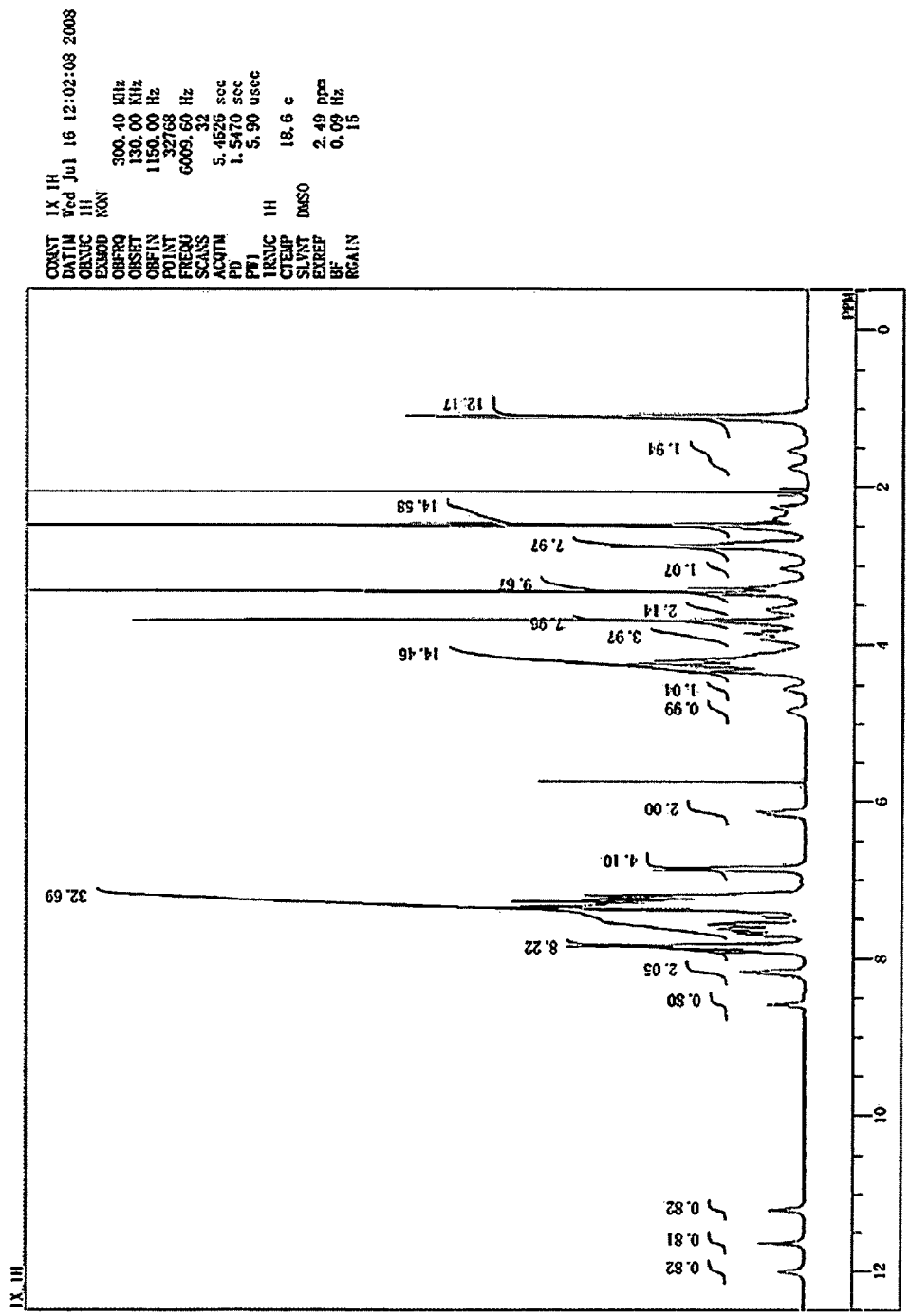
FIG. 12-I

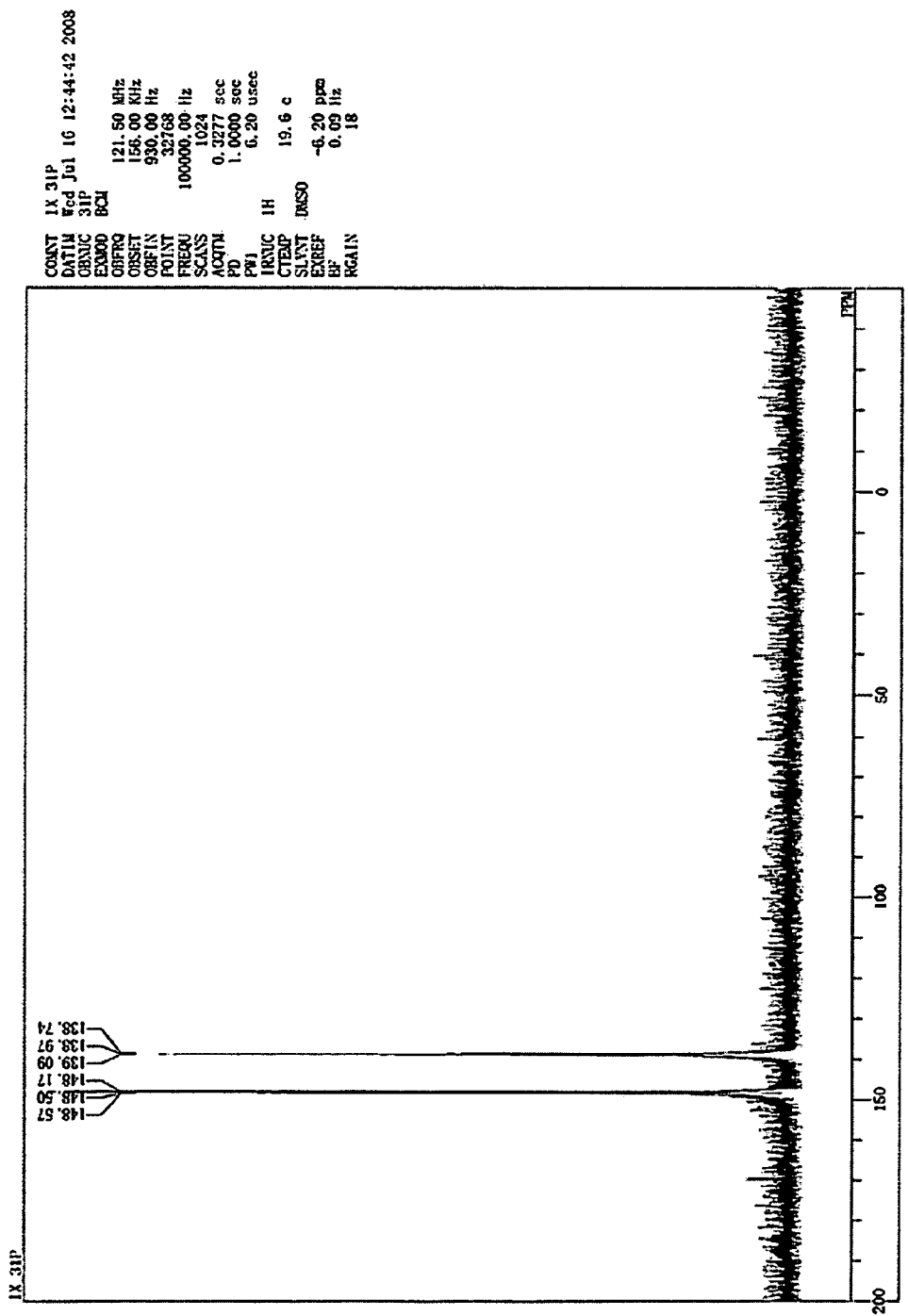
FIG. 12-J

FIG. 12-K
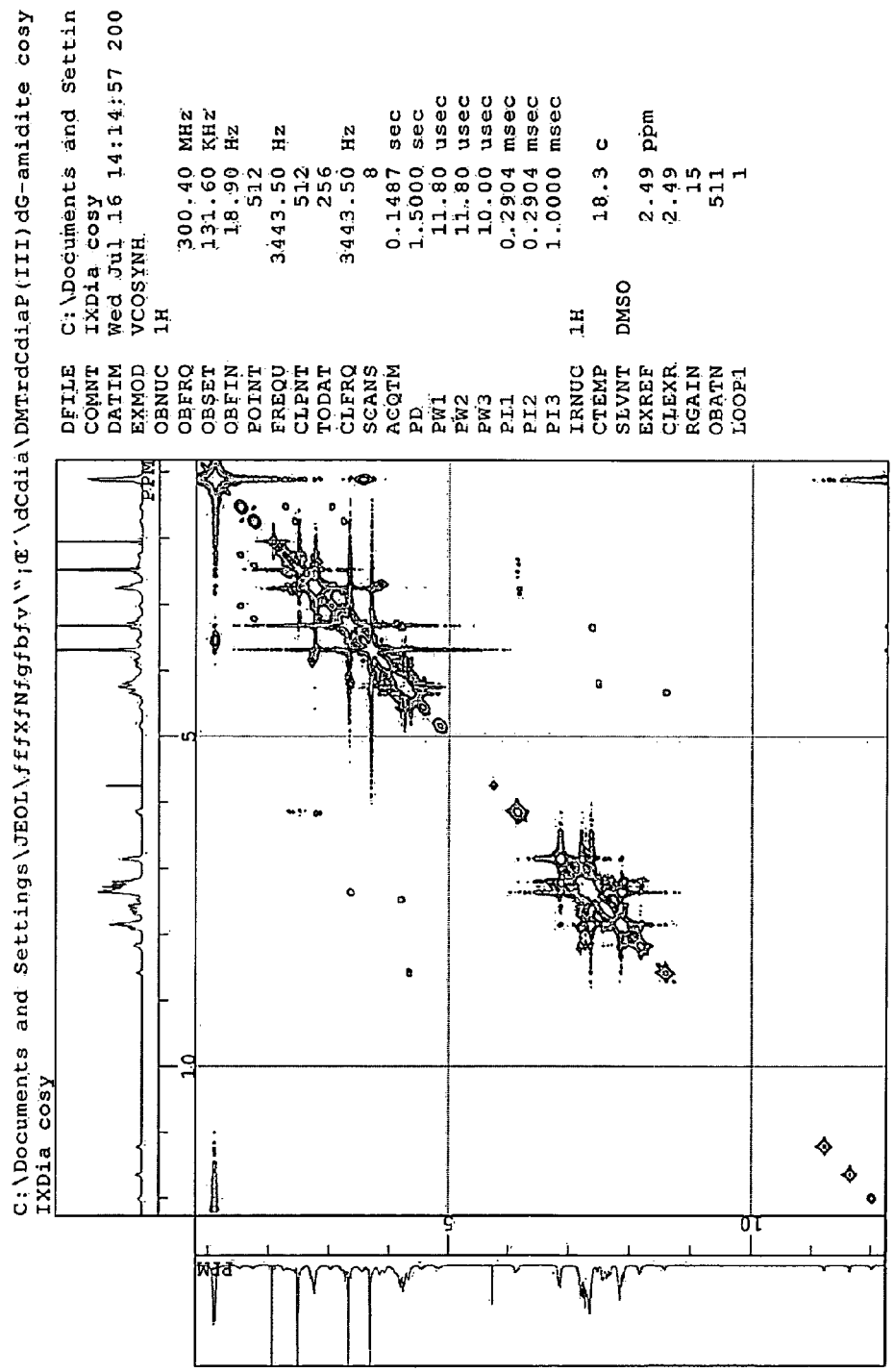

A: 0.1M Aqueous ammonium formate solution

B: Acetonitrile B 50% → 95% (25 min)

NUCLEIC ACID SYNTHESIZING DIMER AMIDITE AND NUCLEIC ACID SYNTHESIZING METHOD

CROSS-REFERENCE TO RELATED APPLICATIONS

This is a continuation application of PCT/JP2008/064701, filed on Aug. 18, 2008. This application is based upon and claims the benefit of priority of the prior Japanese Patent Application No. 2007/225507, filed on Aug. 31, 2007, the entire contents of which are incorporated herein by reference.

FIELD

The embodiments discussed herein relate to a nucleic acid synthesizing dimer amidite and to a nucleic acid synthesizing method.

BACKGROUND

Unraveling of the whole human genome has shifted the focus of interest of scientists and researchers on the analysis of proteins; i.e., gene products. It may not be overstating to say that substantial protein analysis can be made possible only when a molecule that exhibits affinity (binding property) for each protein of interest has been successfully obtained. Cells, however, each contain quite many different types of proteins, and the amino acid sequence and structure of many of which are still unknown.

The most common technique for obtaining a molecule that exhibits affinity for a specific protein is to prepare an affinity antibody by utilizing the immune system of animal. However, this technique uses animals and thus, requires a large quantity of proteins, a large number of steps and large cost. Additionally, no affinity antibody can be obtained for specific substances with this technique.

A technique called the aptamer method (also referred to as the SELEX method) that does not rely on any living organism has been proposed to avoid this problem. However, while a molecule obtained by this technique strongly interacts with a specific protein, this technique is not applicable to all the proteins. In view of such circumstances, the present inventors proposed a modified aptamer method that is established by improving the aptamer method so as to use a modified nucleic acid (see International Publication No. WO2003/078623 pamphlet). However, since the modified aptamer method uses a modified nucleic acid having different types of substituents, the properties of each of the substituents have to be considered when amplifying a modified nucleic acid exhibiting affinity for a target protein. Thus, it has been difficult to find excellent PCR conditions. Additionally, the above method poses a problem that a functional molecule that tends to be strongly bound to a target substance is hard to be amplified by PCR.

In order to solve the above existing problems, the inventors have previously proposed dimer amidites—raw materials for modified nucleic acids to which substituents have been introduced or bound so that they can be removed through a treatment with ammonia, the substituents allowing binding to proteins. Here, the types of the substituents correspond one-to-one to the sequences of the dimer amidites; and the substituents are removed after binding to proteins and then, the resultant modified nucleic acid can be amplified by PCR. However, these dimer amidites each have both a moiety quite labile to an acid and a moiety quite labile to a base and thus, pose a problem in that they are decomposed to a considerable extent by purification. These dimer amidites, therefore, are forced to be used without purification. When certain dimer amidites are used, the synthesis yield of nucleic acid using an automatic nucleic acid synthesizer may be lowered. Thus, further improvement is demanded.

Meanwhile, a solid-phase synthesis of nucleic acid has been performed for 20 years or longer, and an automatic synthesizer employing it was also sold at that time. The solid-phase synthesis of nucleic acid is performed by, for example, condensating nucleic acid raw materials (amidites) with nucleosides bound to a solid-phase support (e.g., CPG). During this condensation reaction, it is necessary that only the phosphoric acid moiety of each amidite is condensated with only the hydroxyl group of another amidite so that the other reactive groups do not participate in the condensation reaction. Thus, protective groups are introduced to the reactive groups (e.g., exocyclic amino groups of bases of amidites used and a phosphoric acid moiety which is not made to participate in the condensation reaction) so that they do not participate in the condensation reaction, and the protective groups are removed (deprotected) after completion of the whole condensation reaction. Conventionally, a benzoyl group, an isobutyryl group, other groups have been used as a protective group which is introduced to the exocyclic amino group of a base, and these protective groups are generally removed by treating the obtained nucleic acid with concentrated aqueous ammonia at 55° C. for 8 hours to 15 hours.

However, in the production of the above-described modified nucleic acids having affinity (binding property) for proteins, under such conventional deprotection conditions, not only the protective groups but also their modified moieties (substituents having binding property for proteins) are removed, resulting in that modified nucleic acids cannot be stably produced. Thus, in the production of such modified nucleic acids, in order to prevent the substituents having binding property for proteins from being removed together with the protective groups, there is a need to use amidites having protective groups which can be removed under milder conditions.

For example, some conventional literatures report nucleic acid amidites having protective groups which can be removed by diazabicycloundecene (DBU) (i.e., a bulky base) (Acta. Chem., Scand., B37, 263 (1983) and J. Org. Chem., 54, 1657 (1989)). But, these nucleic acid synthesizing amidites are not stable in acetonitrile (i.e., an aprotic solvent) (Tetrahedron Letters No. 46, 6729 (1990)) and are not suitable to practical use. Other literatures report nucleic acid synthesizing amidites having protective groups which can be removed in pyridine using 0.5M DBU for 16 hours (Tetrahedron No. 20, 4171 (1992) and Nucleodied & Nuclrotides 13, 2059 (1994)). But, the use of a high concentration of DBU and the deprotection for a long time problematically cause alkylation of the base of nucleic acid. Other literatures report nucleic acid synthesizing amidites having protective groups which can be removed in methanol using $K_2CO_3$ (Tetrahedron Letters No. 46, 6729 (1990) and Nucleic Acids Reserch 21, 3493 (1993)). But, use of $K_2CO_3$ (a base) in methanol (a protic solvent) problematically causes decomposition of the esters, etc.

Under such circumstances, at present, demand has arisen for developments of a nucleic acid synthesizing dimer amidite which can be subjected to purification, preferably, whose protective groups can be removed under mild conditions; and a nucleic acid synthesizing method using the nucleic acid synthesizing dimer amidite.

SUMMARY

According to an aspect of the invention, a nucleic acid synthesizing dimer amidite includes two nucleoside compounds, wherein the two nucleoside compounds are linked with each other via a phosphite triester bond.

According to another aspect of the invention, a nucleic acid synthesizing method includes synthesizing nucleic acid using a nucleic acid synthesizing dimer amidite, wherein the nucleic acid synthesizing dimer amidite includes two nucleoside compounds, and the two nucleoside compounds are linked with each other via a phosphite triester bond.

According to another aspect of the invention, a nucleic acid is obtained by a nucleic acid synthesizing method including synthesizing nucleic acid using a nucleic acid synthesizing dimer amidite, wherein the nucleic acid synthesizing dimer amidite includes two nucleoside compounds, and the two nucleoside compounds are linked with each other via a phosphite triester bond.

The object and advantages of the invention will be realized and attained by means of the elements and combinations particularly pointed out in the claims. It is to be understood that both the foregoing general description and the following detailed description are exemplary and explanatory and are not restrictive of the invention, as claimed.

BRIEF DESCRIPTION OF DRAWINGS

FIG. 2-A is a $^1$H-NMR spectrum of compound II of Example 1 (scheme 1);
FIG. 2-B is a $^1$H-NMR spectrum of compound $IV_{Ser}$ of Example 1 (scheme 1);
FIG. 2-C is a $^1$H-NMR spectrum of compound $V_{Ser}$ of Example 1 (scheme 1);
FIG. 2-D is a $^{31}$P-NMR spectrum of compound $V_{Ser}$ of Example 1 (scheme 1);
FIG. 2-E is a $^1$H-NMR spectrum of compound $VIII_{Ser}$ of Example 1 (scheme 1);
FIG. 2-F is a $^{31}$P-NMR spectrum of compound $VIII_{Ser}$ of Example 1 (scheme 1);
FIG. 2-G is a HHcosy spectrum of compound $VIII_{Ser}$ of Example 1 (scheme 1);
FIG. 2-H is a $^1$H-NMR spectrum of compound $IX_{Ser}$ of Example 1 (scheme 1);
FIG. 2-I is a $^{31}$P-NMR spectrum of compound $IX_{Ser}$ of Example 1 (scheme 1);
FIG. 2-J is a HHcosy spectrum of compound $IX_{Ser}$ of Example 1 (scheme 1);
FIG. 2-K is a $^1$H-NMR spectrum of compound $VII'_{Ser}$ of Example 1 (scheme 1);
FIG. 2-L is a $^1$H-NMR spectrum of compound $VIII'_{Ser}$ of Example 1 (scheme 1);
FIG. 2-M is a $^1$H-NMR spectrum of compound $IX'_{Ser}$ of Example 1 (scheme 1);
FIG. 2-N is a $^{31}$P-NMR spectrum of compound $IX'_{Ser}$ of Example 1 (scheme 1);
FIG. 2-O is a HHcosy spectrum of compound $IX'_{Ser}$ of Example 1 (scheme I);
FIG. 3-A is a $^1$H-NMR spectrum of compound $VIII_{Leu}$ of Example 1 (scheme 2);
FIG. 3-B is a $^{31}$P-NMR spectrum of compound $VIII_{Leu}$ of Example 1 (scheme 2);
FIG. 3-C is a HHcosy spectrum of compound $VIII_{Leu}$ of Example 1 (scheme 2);
FIG. 3-D is a $^1$H-NMR spectrum of compound $IX_{Leu}$ of Example 1 (scheme 2);
FIG. 3-E is a $^{31}$P-NMR spectrum of compound $IX_{Leu}$ of Example 1 (scheme 2);
FIG. 3-F is a HHcosy spectrum of compound $IX_{Leu}$ of Example 1 (scheme 2);
FIG. 4-A is a $^1$H-NMR spectrum of compound $VIII_{Phe}$ of Example 1 (scheme 3);
FIG. 4-B is a $^{31}$P-NMR spectrum of compound $VIII_{Phe}$ of Example 1 (scheme 3);
FIG. 4-C is a HHcosy spectrum of compound $VIII_{Phe}$ of Example 1 (scheme 3);
FIG. 4-D is a $^1$H-NMR spectrum of compound $IX_{Phe}$ of Example 1 (scheme 3);
FIG. 4-E is a HHcosy spectrum of compound $IX_{Phe}$ of Example 1 (scheme 3);
FIG. 5-A is a $^1$H-NMR spectrum of compound $VIII_{Glu}$ of Example 1 (scheme 4);
FIG. 5-B is a $^{31}$P-NMR spectrum of compound $VIII_{Glu}$ of Example 1 (scheme 4);
FIG. 5-C is a HHcosy spectrum of compound $VIII_{Glu}$ of Example 1 (scheme 4);
FIG. 5-D is a $^1$H-NMR spectrum of compound $IX_{Glu}$ of Example 1 (scheme 4);
FIG. 5-E is a $^{31}$P-NMR spectrum of compound $IX_{Glu}$ of Example 1 (scheme 4);
FIG. 5-F is a HHcosy spectrum of compound $IX_{Glu}$ of Example 1 (scheme 4);
FIG. 6-A is a $^1$H-NMR spectrum of compound $VIII_{A-Lys}$ of Example 1 (scheme 5);
FIG. 6-B is a $^{31}$P-NMR spectrum of compound $VIII_{A-Lys}$ of Example 1 (scheme 5);
FIG. 6-C is a HHcosy spectrum of compound $VIII_{A-Lys}$ of Example 1 (scheme 5);
FIG. 6-D is a $^1$H-NMR spectrum of compound $IX_{A-Lys}$ of Example 1 (scheme 5);
FIG. 6-E is a $^{31}$P-NMR spectrum of compound $IX_{A-Lys}$ of Example 1 (scheme 5);
FIG. 6-F is a HHcosy spectrum of compound $IX_{A-Lys}$ of Example 1 (scheme 5);
FIG. 7-A is a $^1$H-NMR spectrum of compound $VIII_{G-Lys}$ of Example 1 (scheme 6);
FIG. 7-B is a $^{31}$P-NMR spectrum of compound $VIII_{G-Lys}$ of Example 1 (scheme 6);
FIG. 7-C is a HHcosy spectrum of compound $VIII_{G-Lys}$ of Example 1 (scheme 6);
FIG. 7-D is a $^1$H-NMR spectrum of compound $IX_{G-Lys}$ of Example 1 (scheme 6);
FIG. 7-E is a $^{31}$P-NMR spectrum of compound $IX_{G-Lys}$ of Example 1 (scheme 6);
FIG. 7-F is a HHcosy spectrum of compound $IX_{G-Lys}$ of Example 1 (scheme 6);
FIG. 8-A is a $^1$H-NMR spectrum of compound $IV_{The}$ of Example 1 (scheme 7);
FIG. 8-B is a $^1$H-NMR spectrum of compound $V_{The}$ of Example 1 (scheme 7);
FIG. 8-C is a $^{31}$P-NMR spectrum of compound $V_{The}$ of Example 1 (scheme 7);
FIG. 8-D is a HHcosy spectrum of compound $V_{The}$ of Example 1 (scheme 7);
FIG. 8-E is a $^1$H-NMR spectrum of compound $VIII_{The}$ of Example 1 (scheme 7);
FIG. 8-F is a $^{31}$P-NMR spectrum of compound $VIII_{The}$ of Example 1 (scheme 7);
FIG. 8-G is a HHcosy spectrum of compound $VIII_{The}$ of Example 1 (scheme 7);
FIG. 8-H is a $^1$H-NMR spectrum of compound $IX_{The}$ of Example 1 (scheme 7);
FIG. 8-I is a $^{31}$P-NMR spectrum of compound $IX_{The}$ of Example 1 (scheme 7);
FIG. 8-J is a HHcosy spectrum of compound $IX_{The}$ of Example 1 (scheme 7);
FIG. 9-A is a $^1$H-NMR spectrum of compound $IV_{Met}$ of Example 1 (scheme 8);

FIG. 9-B is a $^1$H-NMR spectrum of compound $V_{Met}$ of Example 1 (scheme 8);

FIG. 9-C is a $^{31}$P-NMR spectrum of compound $V_{Met}$ of Example 1 (scheme 8);

FIG. 9-D is a $^1$H-NMR spectrum of compound $VI_{Met}$ of Example 1 (scheme 8);

FIG. 9-E is a $^1$H-NMR spectrum of compound $VIII_{Met}$ of Example 1 (scheme 8);

FIG. 9-F is a $^{31}$P-NMR spectrum of compound $VIII_{Met}$ of Example 1 (scheme 8);

FIG. 9-G is a HHcosy spectrum of compound $VIII_{Met}$ of Example 1 (scheme 8);

FIG. 9-H is a $^1$H-NMR spectrum of compound $IX_{Met}$ of Example 1 (scheme 8);

FIG. 9-I is a $^{31}$P-NMR spectrum of compound $IX_{Met}$ of Example 1 (scheme 8);

FIG. 9-J is a HHcosy spectrum of compound $IX_{Met}$ of Example 1 (scheme 8);

FIG. 10-A is a $^1$H-NMR spectrum of compound X of Example 1 (scheme 9);

FIG. 10-B is a $^1$H-NMR spectrum of compound $III_c$ of Example 1 (scheme 9);

FIG. 10-C is a $^1$H-NMR spectrum of compound XI of Example 1 (scheme 9);

FIG. 10-D is a $^1$H-NMR spectrum of compound $XII_{Tyr}$ of Example 1 (scheme 9);

FIG. 10-E is a $^1$H-NMR spectrum of compound XIII of Example 1 (scheme 9);

FIG. 10-F is a $^1$H-NMR spectrum of compound $XIV_{Tyr}$ of Example 1 (scheme 9);

FIG. 10-G is a $^1$H-NMR spectrum of compound $IV_{Tyr}$ of Example 1 (scheme 9);

FIG. 10-H is a $^1$H-NMR spectrum of compound $V_{Tyr}$ of Example 1 (scheme 9);

FIG. 10-I is a $^{31}$P-NMR spectrum of compound $V_{Tyr}$ of Example 1 (scheme 9);

FIG. 10-J is a HHcosy spectrum of compound $V_{Tyr}$ of Example 1 (scheme 9);

FIG. 10-K is a $^1$H-NMR spectrum of compound $VI_{Tyr}$ of Example 1 (scheme 9);

FIG. 10-L is a $^1$H-NMR spectrum of compound $VIII_{Tyr}$ of Example 1 (scheme 9);

FIG. 10-M is a $^{31}$P-NMR spectrum of compound $VIII_{Tyr}$ of Example 1 (scheme 9);

FIG. 10-N is a HHcosy spectrum of compound $VIII_{Tyr}$ of Example 1 (scheme 9);

FIG. 10-O is a $^1$H-NMR spectrum of compound $IX_{Tyr}$ of Example 1 (scheme 9);

FIG. 10-P is a $^{31}$P-NMR spectrum of compound $IX_{Tyr}$ of Example 1 (scheme 9);

FIG. 10-Q is a HHcosy spectrum of compound $IX_{Tyr}$ of Example 1 (scheme 9);

FIG. 11-A is a $^1$H-NMR spectrum of compound $IX'_{Phe}$ of Example 1 (scheme 10);

FIG. 11-B is a $^{31}$P-NMR spectrum of compound $IX'_{Phe}$ of Example 1 (scheme 10);

FIG. 11-C is a HHcosy spectrum of compound $IX'_{Phe}$ of Example 1 (scheme 10);

FIG. 12-A is a $^1$H-NMR spectrum of compound XIV of Example 1 (scheme 11);

FIG. 12-B is a $^1$H-NMR spectrum of compound $IV_{Dia}$ of Example 1 (scheme 11);

FIG. 12-C is a $^1$H-NMR spectrum of compound $V_{Dia}$ of Example 1 (scheme 11);

FIG. 12-D is a $^{31}$P-NMR spectrum of compound $V_{Dia}$ of Example 1 (scheme 11);

FIG. 12-E is a HHcosy spectrum of compound $V_{Dia}$ of Example 1 (scheme 11);

FIG. 12-F is a $^1$H-NMR spectrum of compound $M_{Dia}$ of Example 1 (scheme 11);

FIG. 12-G is a $^{31}$P-NMR spectrum of compound $VIII_{Dia}$ of Example 1 (scheme 11);

FIG. 12-H is a HHcosy spectrum of compound $VIII_{Dia}$ of Example 1 (scheme 11);

FIG. 12-I is a $^1$H-NMR spectrum of compound $IX_{Dia}$ of Example 1 (scheme 11);

FIG. 12-J is a $^{31}$P-NMR spectrum of compound $IX_{Dia}$ of Example 1 (scheme 11);

FIG. 12-K is a HHcosy spectrum of compound $IX_{Dia}$ of Example 1 (scheme 11);

Figure 1:
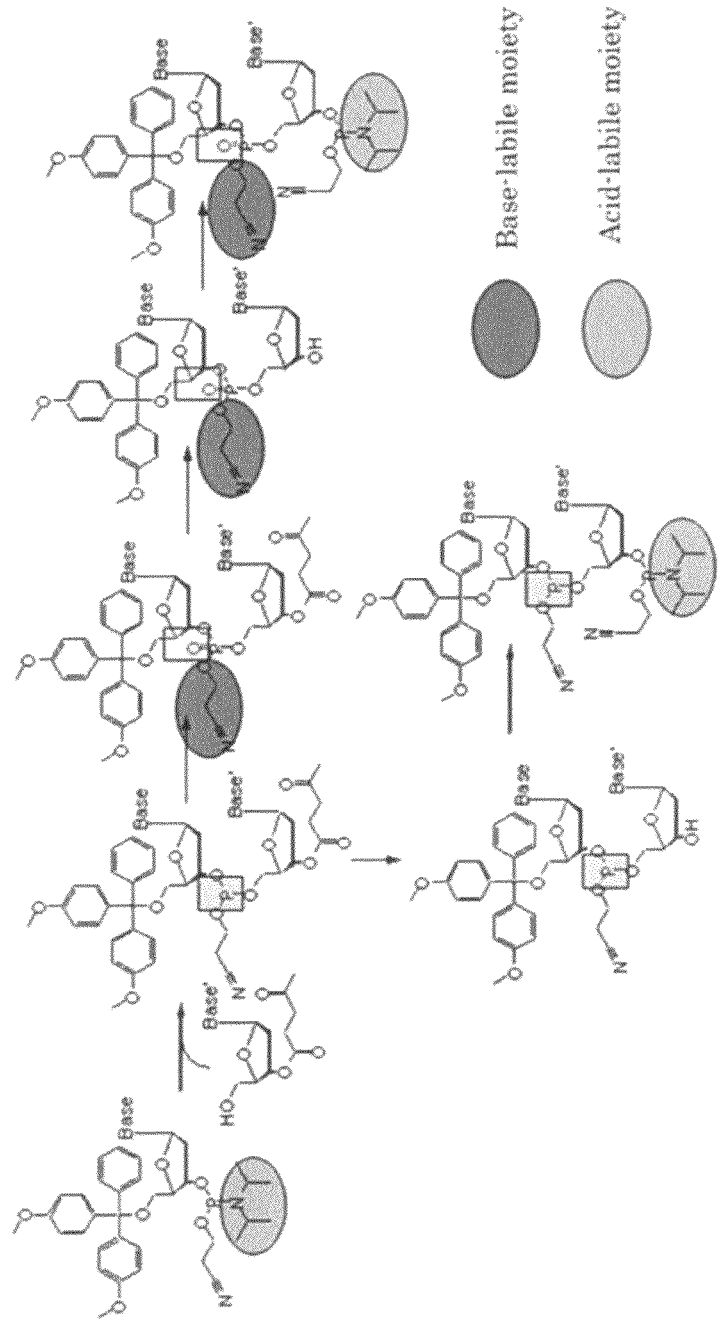
FIG. 1 illustrates the differences between a nucleic acid synthesizing dimer amidite containing a phosphite triester bond as a linking moiety and a comparative control dimer amidite containing a phosphate triester bond as a linking moiety.

DESCRIPTION OF EMBODIMENTS (Nucleic acid synthesizing dimer amidite) The nucleic acid synthesizing dimer amidite includes two nucleoside compounds, wherein the two nucleoside compounds are linked with each other via a phosphite triester bond. Preferably, the protective groups of its phosphoric acid group and base can be removed in an aprotic solvent.

<Nucleoside compound> The "nucleoside compound" refers to a monomer of nucleoside or a nucleoside derivative used for the synthesis of nucleic acid. The nucleoside derivative encompasses a "nucleic acid synthesizing amidite" whose end has been modified so as to serve as an amidite. Next will be described the "nucleoside compound" taking the "nucleic acid synthesizing amidite" as an example.

—Nucleic acid synthesizing amidite— The "nucleic acid synthesizing amidite" is a monomer of a nucleoside derivative whose end has been modified so as to serve as an amidite and which is used for the synthesis of nucleic acid. The type of it is not particularly limited, and examples thereof include those having the following Formulas (I) to (III).

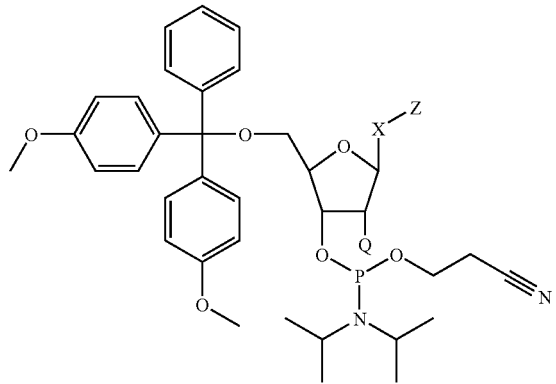

Formula (I)

-continued

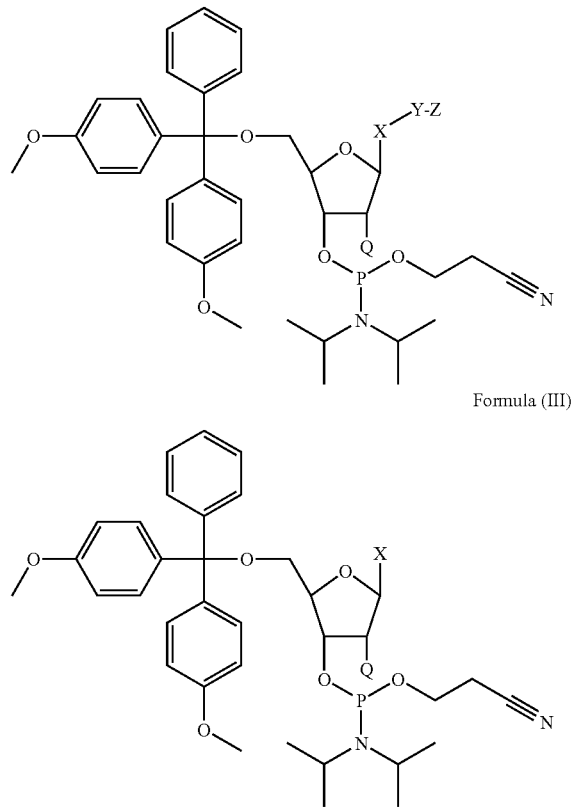

Formula (II)

Formula (III)

In Formulas (I) to (III), X represents a base, Y represents a substituent, Z represents a protective group which is introduced directly to the base (in Formula (I)) or which is introduced via a substituent (in Formula (II)) (in this specification, the protective group in this case may be referred to simply as a "protective group of a base"), and Q represents a hydrogen atom or a hydroxyl group.

For example, the nucleic acid synthesizing amidite represented by Formula (I) is that in which the exocyclic amino group of the base X is protected by the protective group Z. When the amidite has a base containing an exocyclic amino group (e.g., adenine, cytosine and guanine), preferably, a protective group is introduced to the exocyclic amino group in order to prevent unnecessary reactions of the exocyclic amino group during the synthesis of nucleic acid. Thus, in such a case, the nucleic acid synthesizing amidite represented by Formula (I) can be used.

The nucleic acid synthesizing amidite represented by Formula (II) is that in which the substituent Y is introduced to the exocyclic amino group of the base X and is protected by the protective group Z. For example, for producing a modified nucleic acid capable of binding to a target substance (e.g., proteins), a substituent capable of binding to the target substance (e.g., proteins) can be introduced to the exocyclic amino group of the base. In this case, a protective group is preferably introduced to the substituent in order to prevent unnecessary reactions during the synthesis of nucleic acid. Thus, in such a case, the nucleic acid synthesizing amidite represented by Formula (II) can be used.

The nucleic acid synthesizing amidite represented by Formula (III) is that having neither the protective group Z nor the substituent Y. When the amidite has a base containing no exocyclic amino group (e.g., thymidine), it is not necessary that a protective group is not introduced to the base in order to prevent unnecessary reactions of the exocyclic amino group during the synthesis of nucleic acid. Thus, the nucleic acid synthesizing amidite represented by General Fromula (III) can be used.

—Base— The base represented by X in Formulas (I) to (III) is not particularly limited and may be appropriately selected depending on the purpose. Examples thereof include adenine (A), guanine (G), cytosine (C), thymine (T) and uracil (U). The position at which a protective group or substituent is introduced to the base is not particularly limited and may be appropriately selected depending on the purpose. The position is preferably the 6-position of the adenine base, the 6-position of the cytosine base and the 2-position of the guanine base.

—Protective group for base— In Formulas (I) and (II), the protective group Z for the base is preferably a protective group which can be removed in an aprotic solvent; i.e., which can be removed under mild conditions.

Here, the "protective group which can be removed under mild conditions" refers to a protective group which can be removed in an aprotic solvent by a bulky base. The aprotic solvent is not particularly limited and may be appropriately selected depending on the purpose. Examples thereof include acetonitrile, dichloromethane, N,N-dimethylformamide (DMF) and N-methylpyrrolidone. The bulky base is not particularly limited and may be appropriately selected depending on the purpose. Examples thereof include (1,8-diazabicyclo[5.4.0]-7-undecene) (DBU), (1,5-diazabicyclo[4.3.0]-5-nonene) (DBN) and tetramethylguanidine. In particular, the protective group is preferably removed in acetonitrile by DBU. In this case, the concentration of DBU for removing the protective group is preferably 0.5M or lower, more preferably 0.1M or lower, particularly preferably 0.01M or lower. The time for the removal of the protective group is preferably 8 hours or shorter, more preferably 1 hour or shorter, particularly preferably 15 minutes or shorter.

In particular, the protective group for the base is preferably any one of a 3-aminopropionic acid derivative, a 4-aminobutyric acid derivative, a 5-aminovaleric acid derivative, an aminomethylcarbonic acid deribative, an aminoethylcarbonic acid derivative, an aminobenzoic acid derivative, an aminomethylbenzoic acid derivative, an aminophenylacetic acid derivative, an aminomethylphenylacetic acid derivative, an aminophenylpropionic acid derivative and an aminomethylphenylpropionic acid derivative.

—Substituent— The structure of the substituent Y in Formula (II) is not particularly limited and may be appropriately selected depending on the purpose. Examples of the substituent include a naturally occurring amino acid or non-naturally occurring amino acid, a metal complex, a fluorescent dye, an oxidation-reduction dye, a spin-labeling body, a hydrogen atom, an alkyl group having 1 to 10 carbon atoms and a group having any of the following formulas (1) to (10). Here, the substituent is preferably introduced to the base so that it is not removed when the protective group of the base is removed under mild conditions.

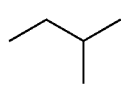

(1)

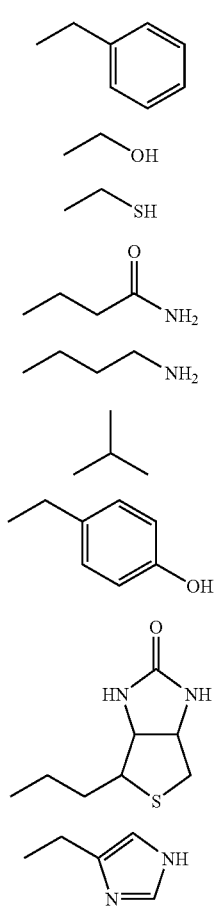

The naturally occurring or non-naturally occurring amino acid is not particularly limited and may be appropriately selected depending on the purpose. Examples thereof include valine, leucine, isoleucine, alanine, arginine, glutamine, lysine, asparagic acid, glutamic acid, proline, cysteine, threonine, methionine, histidine, phenylalanine, tyrosine, tryptophan, asparagine, glycine and serine.

The metal complex is not particularly limited, so long as it is a compound in which ligands are coordinated to a metal ion, and may be appropriately selected depending on the purpose. Examples thereof include Ru bipyridyl complexes, ferrocene complexes and nickel imidazole complexes.

The fluorescent dye is not particularly limited and may be appropriately selected depending on the purpose. Examples thereof include fluoroscein dyes, rhodamine dyes, eosin dyes and NBD dyes.

The oxidation-reduction dye is not particularly limited and may be appropriately selected depending on the purpose. Examples thereof include leuco dyes such as leucoaniline and leucoanthocyanin.

The spin labeling body is not particularly limited and may be appropriately selected depending on the purpose. Examples thereof include iron N-(dithiocarboxy)sarcosine and tetramethylpiperidine (TEMPO) derivatives.

The alkyl groups having 1 to 10 carbon atoms are not particularly limited and may be appropriately selected depending on the purpose. Examples thereof include methyl, ethyl, propyl, isopropyl, butyl, isobutyl, tert-butyl, pentyl, neopentyl, hexyl, cyclohexyl, octyl, nonyl and decyl.

Any of the above listed substituents may be further substituted.

—Protective group for phosphoric acid group— In the nucleic acid synthesizing amidite, in order to prevent unnecessary reactions during the synthesis of nucleic acid, a protective group is preferably introduced to a reactive group of the phosphoric acid moiey which is not made to participate in condensation reaction during the synthesis of nucleic acid (in this specification, the protective group may be referred to simply as a "protective group for a phosphoric acid group"). The protective group for a phosphoric acid group is preferably a protective group which can be removed in an aprotic solvent; i.e., which can be removed under mild conditions. Here, the "protective group which can be removed under mild conditions" is similar to the above-described protective group for the base. After the phosphite triester bond of the nucleic acid synthesizing amidite had been oxidized to be a phosphate triester bond during the synthesis of nucleic acid, the protective group on the phosphoric acid group in the phosphate triester bond is preferably removed under the above-described mild conditions.

Notably, in each of the nucleic acid synthesizing amidites represented by Formulas (I) to (III), a cyanoethyl group is exemplarily used as the protective group for the phorophoric acid group. But, the protective group for the phorphoric acid group is not limited thereto and may be appropriately selected depending on the purpose. Preferably, this protective group is selected from the group consisting of a cyanoethyl group and derivatives thereof a fluorenylmethyl group and derivatives thereof; a phenethyl group and derivatives thereof and a nitro-ethyl group and derivatives thereof.

The nucleoside compound typlified by the above-described nucleic acid synthesizing amidite can be synthesized by, for example, a method described in Examples given below.

<Linking of two nucleoside compounds> Two of the above-described nucleoside compound are linked each other via a phosphite triester bond (P(OR)$_3$), and an end of the resultant dimer is modified so as to serve as an amidite, whereby the nucleic acid synthesizing dimer amidite can be obtained.

A method for linking two nucleoside compounds via a phosphite triester bond (P(OR)$_3$) is not particularly limited, and phosphorous acid chloride and phosphorous acid dichloride may be used. In the viewpoint of suppressing side reactions, a method described in the below-given Examples is thought to be preferred.

The two nucleoside compounds used may be different from or identical to each other. Here, at least one of the two nucleoside compounds preferably has, on the exocyclic amino group of its base, the above-described protective group which can be removed in an aprotic solvent. Also, both of the nucleoside compounds may have, on the exocyclic amino groups of their bases, the protective group which can be removed in an aprotic solvent. The protective group for a base may be bound directly to the base as illustrated in Formula (I), or may be bound to the base via a substituent as illustrated in Formula (II). Notably, the protective group which can be removed in an aprotic solvent; i.e., which can be removed under mild conditions is previously described in detail.

Specific Examples

Specific examples of the nucleic acid synthesizing dimer amidite include those having the following Structural Formulas (1) to (11). The nucleic acid synthesizing dimer amidite should not be construed as being limited thereto.

Structural Formula (1)
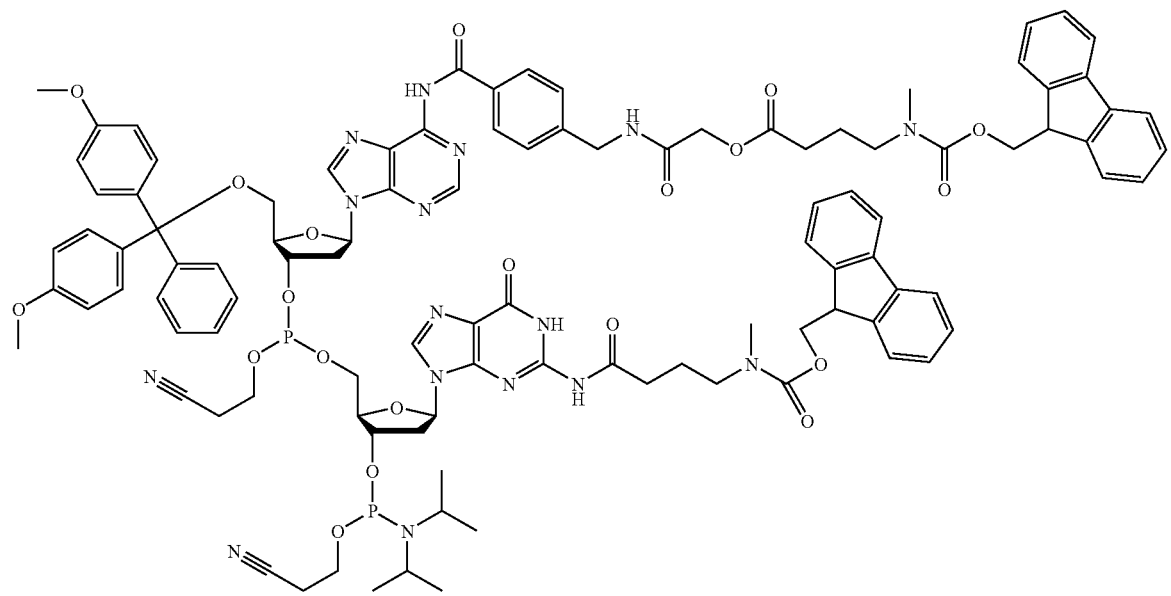
Structural Formula (2)
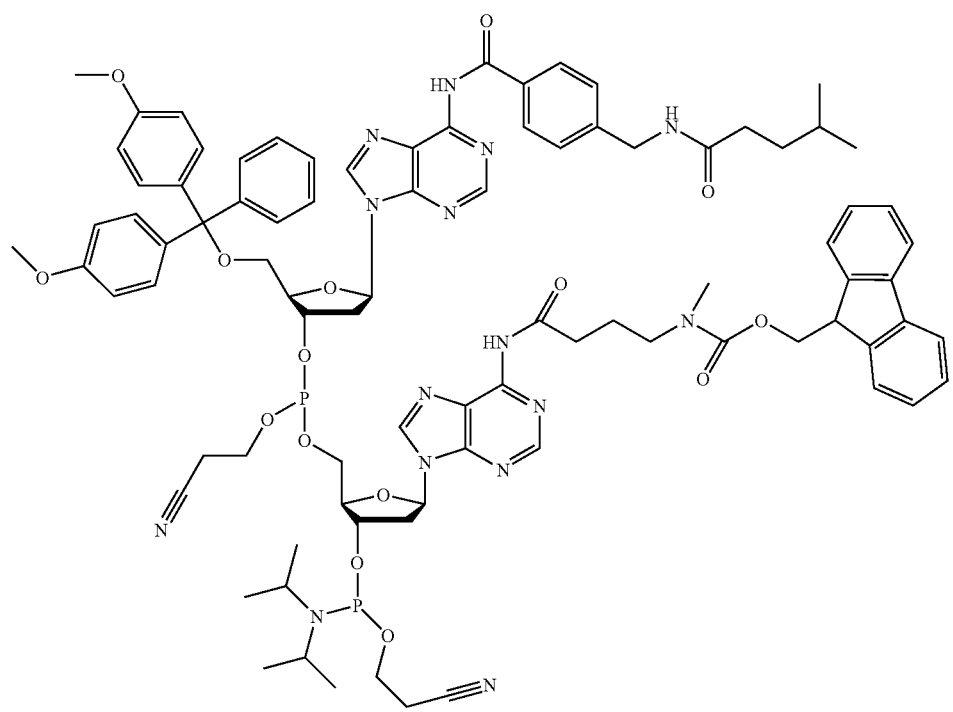

Structural Formula (3)
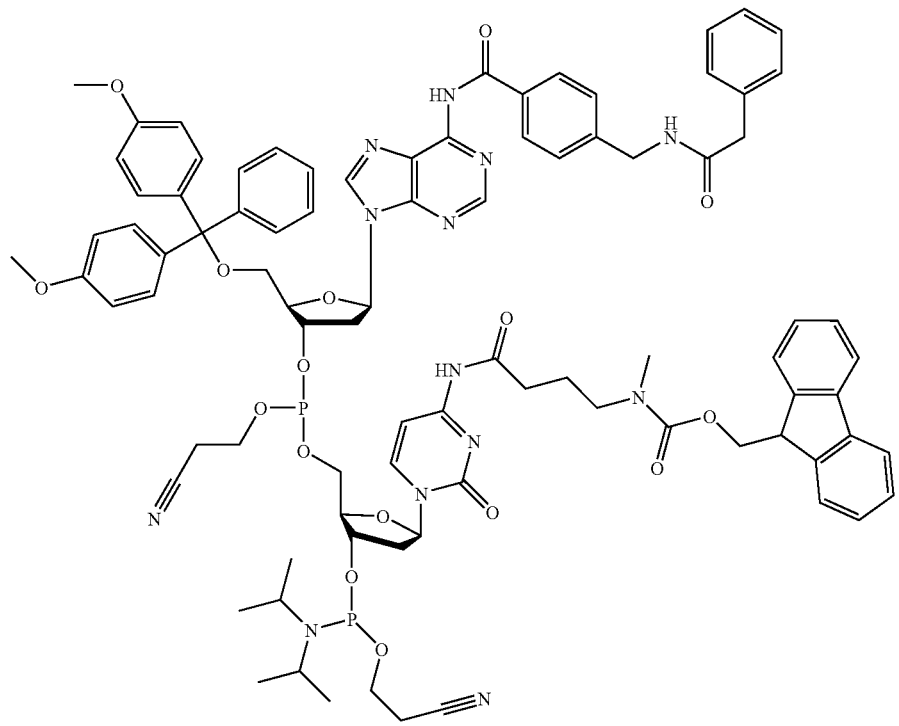
Structural Formula (4)
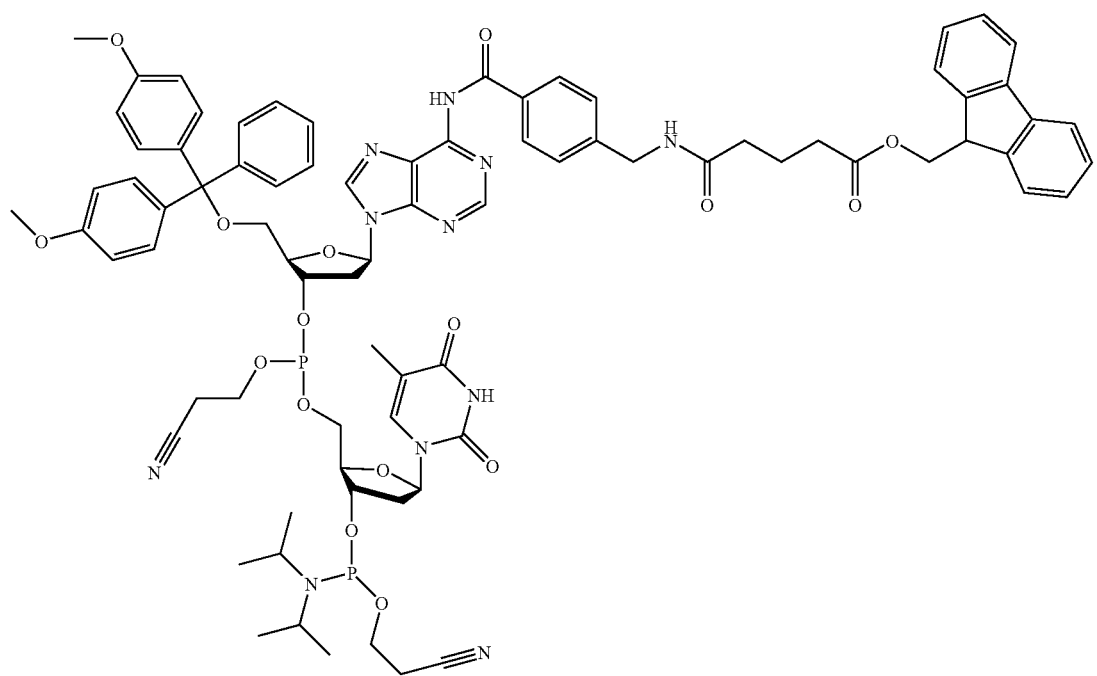

Structural Formula (5)
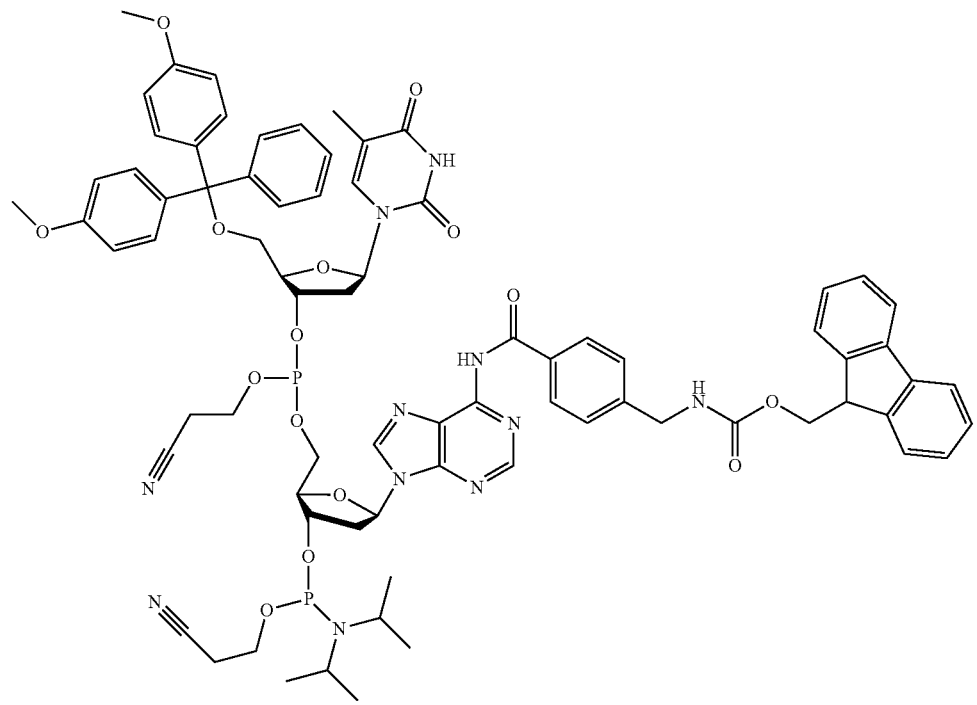
Structural Formula (6)
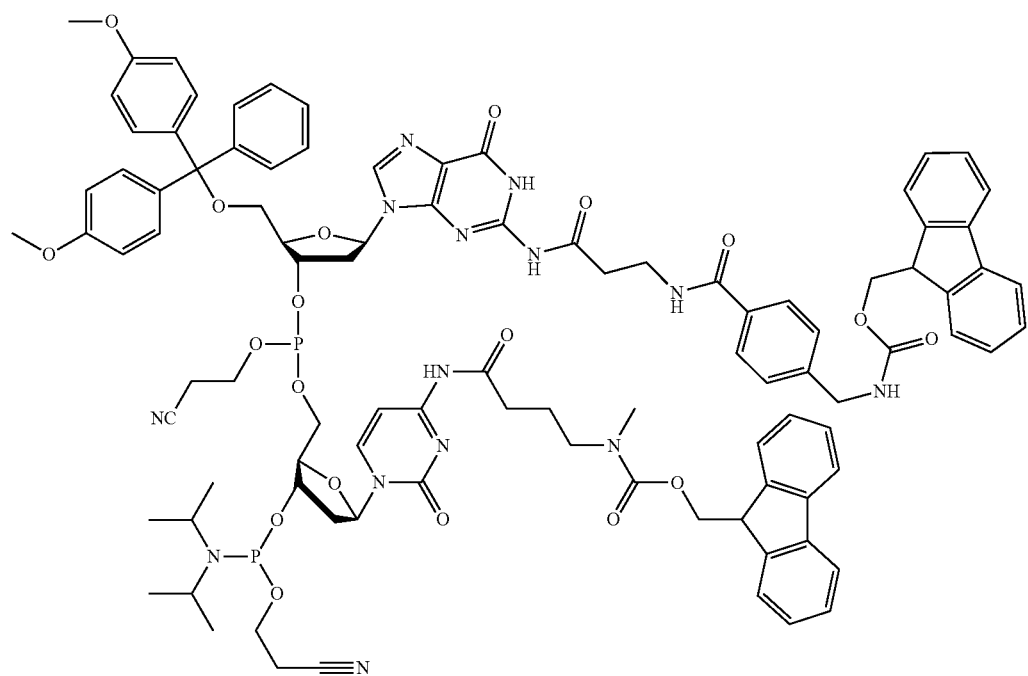

Structural Formula (7)
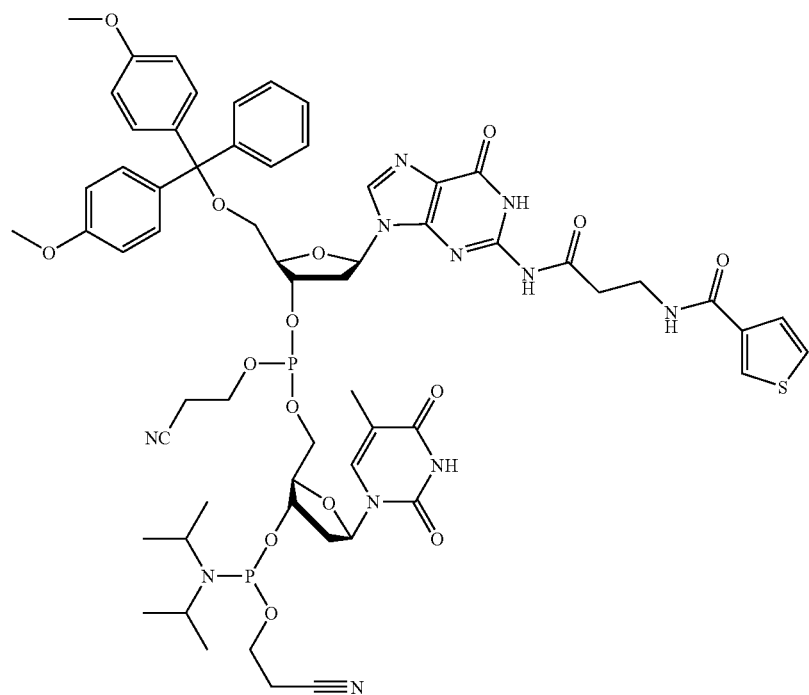
Structural Formula (8)
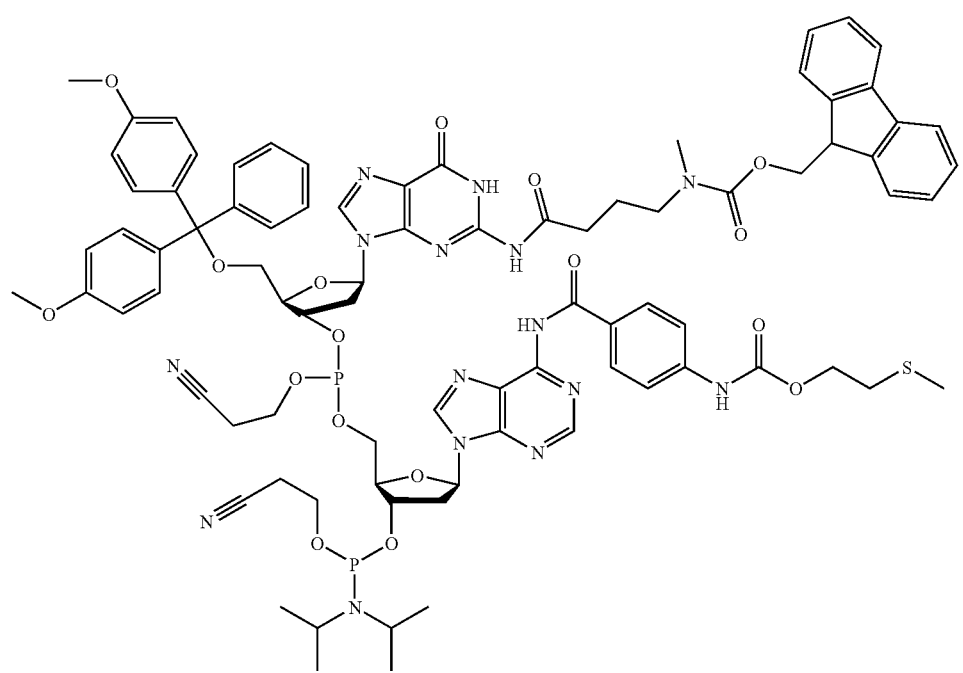

Structural Formula (9)
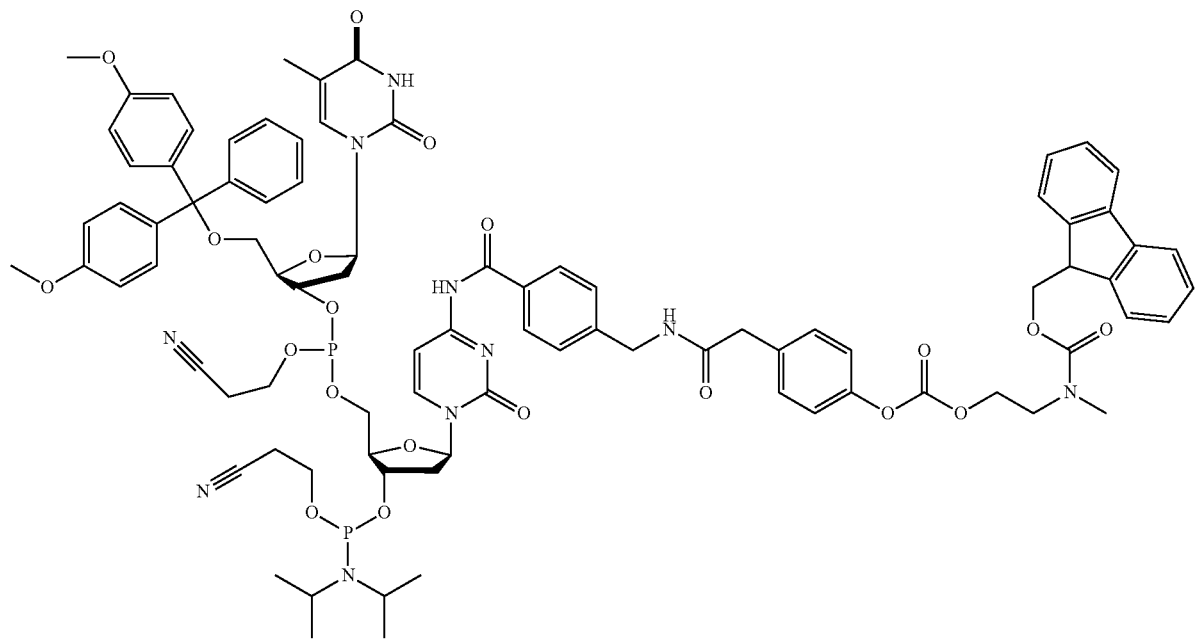
Structural Formula (10)
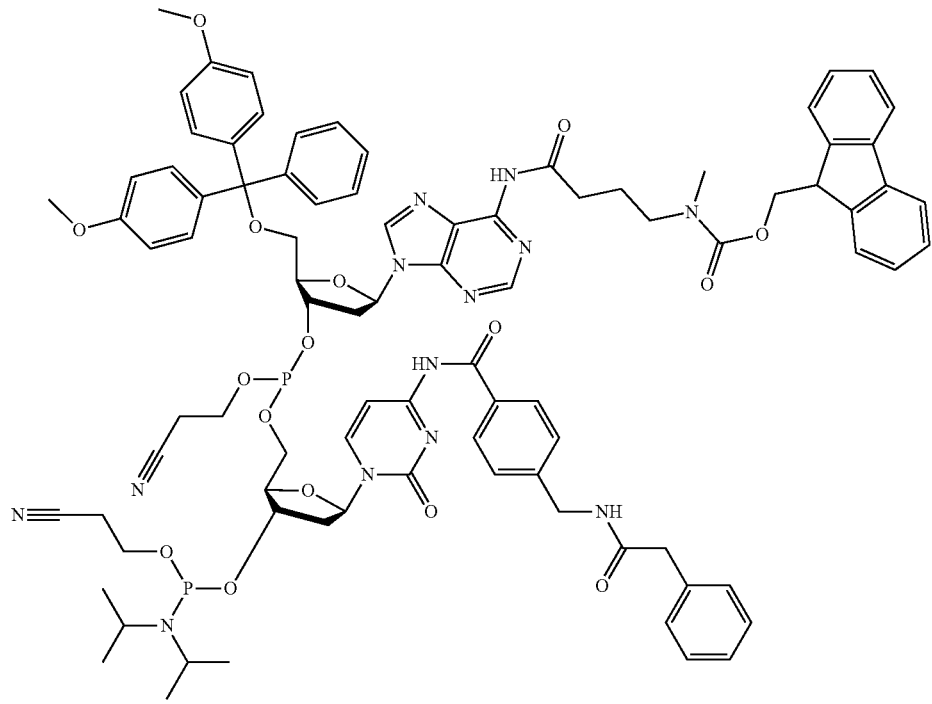

Structural Formula (11)

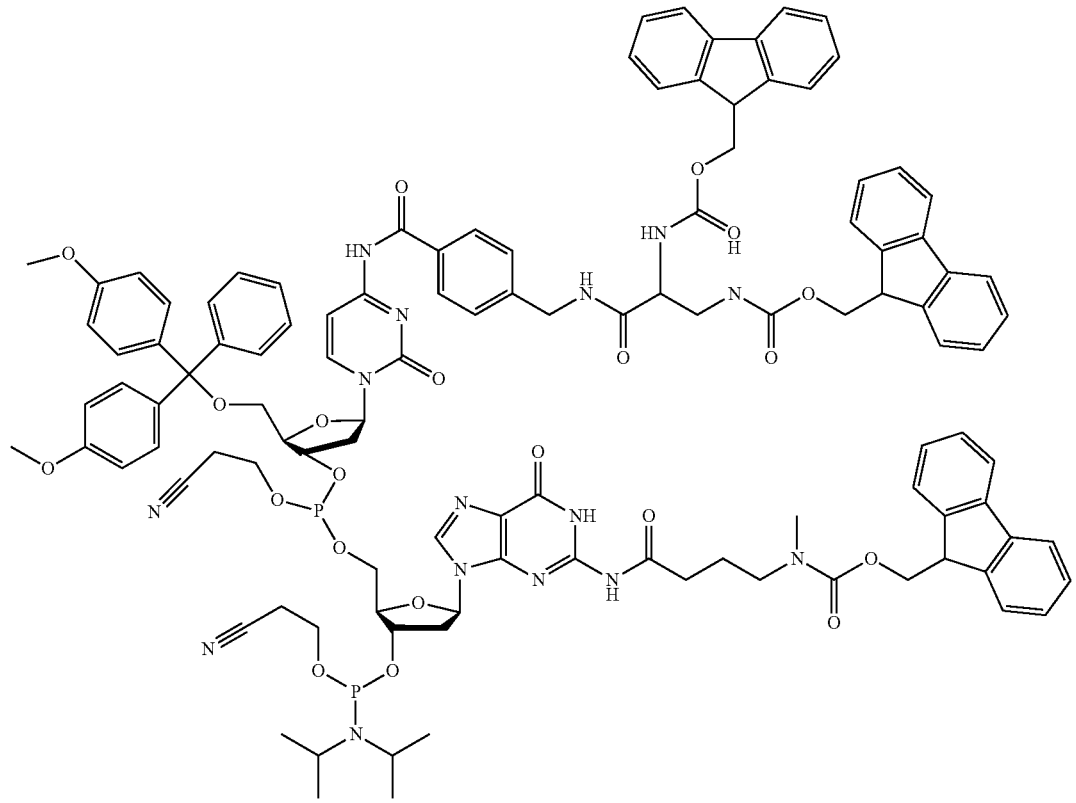

-continued

The nucleic acid synthesizing dimer amidite contains a phosphite triester bond as a linking moiety and thus can be subjected to purification. Therefore, the nucleic acid synthesizing dimer amidite can be obtained in high purity.

FIG. 1 illustrates the comparison of a comparative control dimer amidite containing a phosphate triester bond as a linking moiety with the nucleic acid synthesizing dimer amidite containing a phosphite triester bond as a linking moiety. The comparative control dimer amidite (the phosphoric acid (P(V)) method; the upper scheme of FIG. 1), which contains a phosphate triester bond (P(=O)(OR)$_3$) as a linking moiety, has both a moiety quite labile to an acid and a moiety quite labile to a base; and thus, poses a problem in that it is decomposed to a considerable extent by purification.

In contrast, the nucleic acid synthesizing dimer amidite (the phosphorous acid (P(III)) method; the lower scheme of FIG. 1), which contains a phosphite triester bond (P(OR)$_3$) as a linking moiety, has no moiety quite labile to a base; and thus can be subjected to purification. As a result, the nucleic acid synthesizing dimer amidite can be obtained in high purity.

Since it is composed of two nucleoside compounds which are linked with each other via a phosphite triester bond, the nucleic acid synthesizing dimer amidite is highly stable under basic conditions as compared to a dimer amidite having a phosphate triester bond as a linking moiety and thus, can be subjected to purification. Thus, unlike the dimer amidite that has a phosphate triester bond as a linking moiety and is difficult to purify, the nucleic acid synthesizing dimer amidite can be obtained in high purity. Further, preferably, the nucleic acid synthesizing dimer amidite has protective groups which protect a phosphoric acid group and bases and which can be removed in an aprotic solvent; i.e., under mild conditions. Thus, for example, a desired substituent may be stably introduced between each base and the protective group therefor.

(Nucleic acid synthesizing method) The nucleic acid synthesizing method includes synthesizing nucleic acid using the above-described nucleic acid synthesizing dimer amidite. The nucleic acid synthesizing method can be performed by, for example, a conventional automatic nucleic acid synthesizer.

In the nucleic acid synthesizing method, one type of nucleic acid synthesizing dimer amidite may be used, or two or more types of nucleic acid synthesizing dimer amidite may be used. Also, the nucleic acid synthesizing method may use other dimer amidites in combination with the nucleic acid synthesizing dimer amidite disclosed herein. In this case, the other dimer amidites preferably contain the above-described protective groups which can be removed under mild conditions. Such dimer amidites may be, for example, those described in Japanese Patent Application No. 2007-069378.

In the nucleic acid synthesizing method, after the condensation reaction of the nucleic acid synthesizing dimer amidites (and the other dimer amidites), the protective groups for the phosphoric acid groups and bases of the nucleic acid synthesizing dimer amidites (and the other dimer amidites) are removed. The conditions under which the protective groups are removed are not particularly limited and may be appropriately selected depending on the purpose. The removal of the protective groups is preferably performed under the above-described mild conditions; e.g., it is preferably performed in an aprotic solvent by a bulky base. The aprotic solvent and bulky base used are similar to the above. Further, the concentration of the base and the time for the removal are similar to the above.

The nucleic acid synthesizing method may use the nucleic acid synthesizing dimer amidite; i.e., a high purity of nucleic acid synthesizing dimer amidite having undergone purification. Thus, the synthesis yield of nucleic acid can be increased. Also, in the nucleic acid synthesizing method using the nucleic acid synthesizing dimer amidite, preferably, the removal of the protective groups can be performed under mild conditions. Therefore, even when the nucleic acid synthesizing dimer amidites have substituents, only the protective groups can be readily removed without removing the substituents. The nucleic acid synthesizing method can stably produce nucleic acid having a desired substituent.

(Nucleic acid) The nucleic acid is obtained by the nucleic acid synthesizing method.

The number of nucleotide units constituting the nucleic acid is not particularly limited and may be appropriately selected depending on the purpose. For example, it is preferably 10 to 200, more preferably 20 to 100, particularly preferably 30 to 80. Notably, among the nucleotide units constituting the nucleic acid, the rate of the nucleotide units derived from the nucleic acid synthesizing dimer amidites is not particularly limited and may be appropriately selected depending on the purpose. The nucleic acid may be a DNA or RNA sequence, and the DNA or RNA sequence may be a single- or double-strand.

The nucleic acid is obtained by the nucleic acid synthesizing method and thus, may be a modified nucleic acid having a desired substituent stably. The modified nucleic acid can bind via the substituent to a target substance (e.g., proteins). Thus, such modified nucleic acid is suitably used for the analysis of a target substance (e.g., proteins).

Specifically, for example, the type of a substituent introduced to each of the nucleic acid synthesizing dimer amidites is defined in advance based on a dimer code correspondence table which shows the correspondence of the base sequence of the nucleic acid synthesizing dimer amidite and the type of the substituent. Thereafter, several types of modified nucleic acid obtained using the nucleic acid synthesizing dimer amidites are reacted with a desired target substance. Next, the several types of modified nucleic acid are screened for a modified nucleic acid that exhibits high binding property for the target substance. Then, the substituents are removed from the modified nucleic acid, followed by PCR amplification and sequencing (for determining the base sequence). Finally, the type of the substituent introduced to the modified nucleic acid can be confirmed based on the dimer code correspondence table. Using the thus-obtained information, for example, such a modified nucleic acid that exhibits high binding property for the target substance can be replicated in a large amount and thus, can be utilized for the analysis of the target substance.

According to the above-described embodiments, there can be provided a nucleic acid synthesizing dimer amidite which can be subjected to purification, preferably, whose protective groups can be removed under mild conditions; and a nucleic acid synthesizing method using the nucleic acid synthesizing dimer amidite.

EXAMPLES

Hereinafter, the examples of the present invention will be specifically explained, but these examples shall not be construed as to limit the scope of the present invention. In the following EXAMPLES, unless otherwise specified, "%" means "mol %."

Example 1

Synthesis of Nucleic Acid Synthesizing Dimer Amidite

Nucleic acid synthesizing dimer amidites $IX_{Ser}$, $IX_{Leu}$, $IX_{Phe}$, $IX_{Glu}$, $IX_{A-Lys}$, $IX_{G-Lys}$, $IX_{The}$, $IX_{Met}$, $IX_{Tyr}$, $IX'_{Phe}$ and $IX_{Dia}$ were synthesized as follows. Notably, nucleic acid synthesizing dimer amidites $IX_{Ser}$, $IX_{Leu}$, $IX_{Phe}$, $IX_{Glu}$, $IX_{A-Lys}$, $IX_{G-Lys}$, $IX_{The}$, $IX_{Met}$, $IX_{Tyr}$, $IX'_{Phe}$ and $IX_{Dia}$ have Structural Formulas (1) to (11), respectively.

Notably, the below-given compounds I, $III_A$, $VI_G$, $V_{Leu}$, $VI_A$, $V_{Phe}$, $VI_C$, $V_{Glu}$, $VI_T$, $VI_{A-Lys}$, $V_T$, $V_{G-Lys}$, $III_G$ and $V_G$ were synthesized according to the synthesizing methods described in Japanese Patent Application No. 2007-069378.

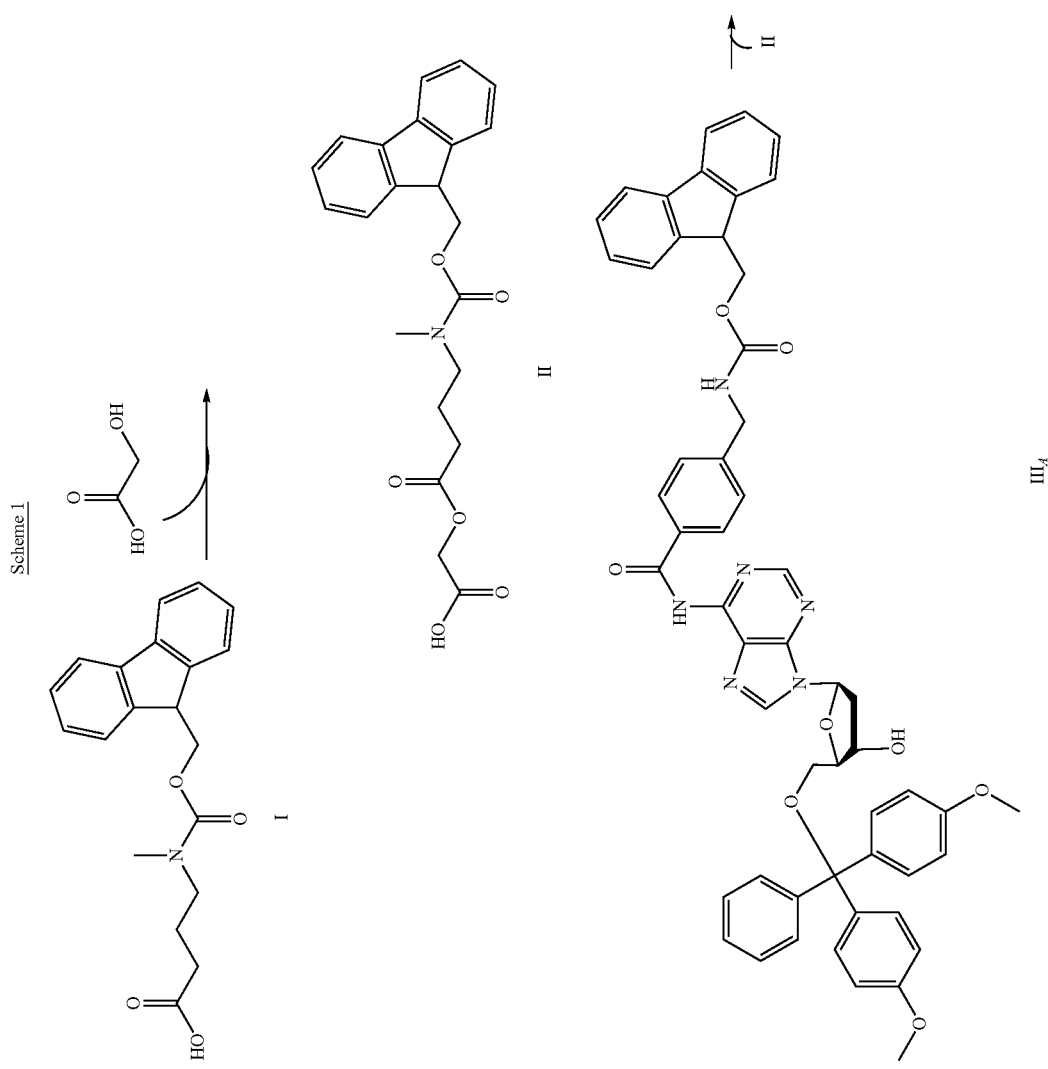
Scheme 1

-continued
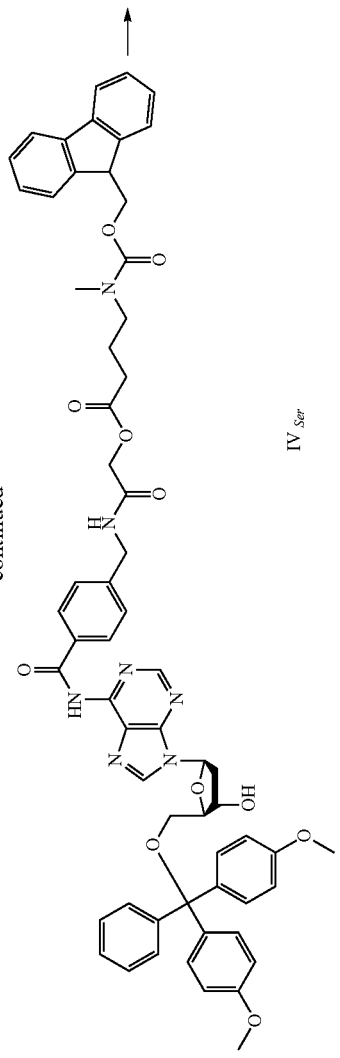
IV Ser
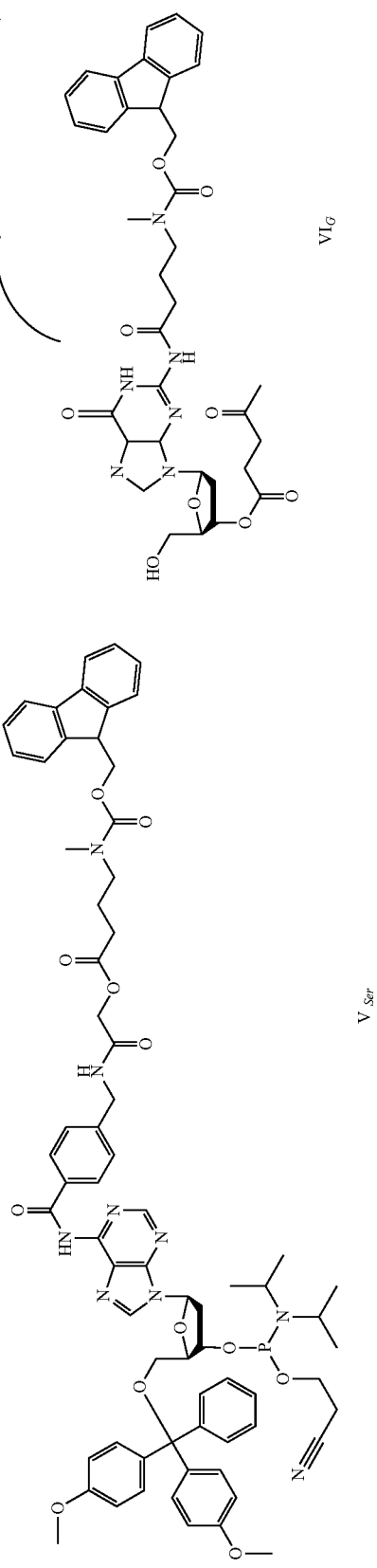
V Ser
VI G

-continued
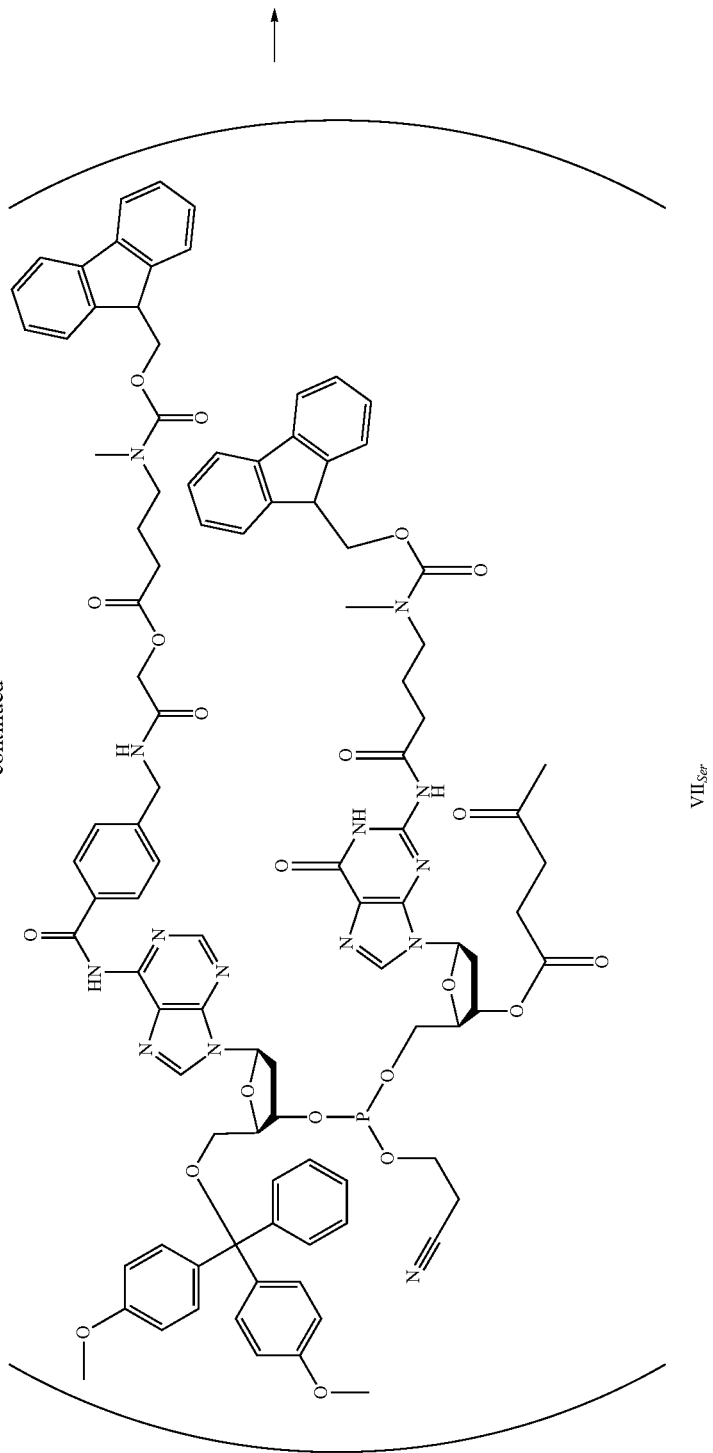
VII_Ser

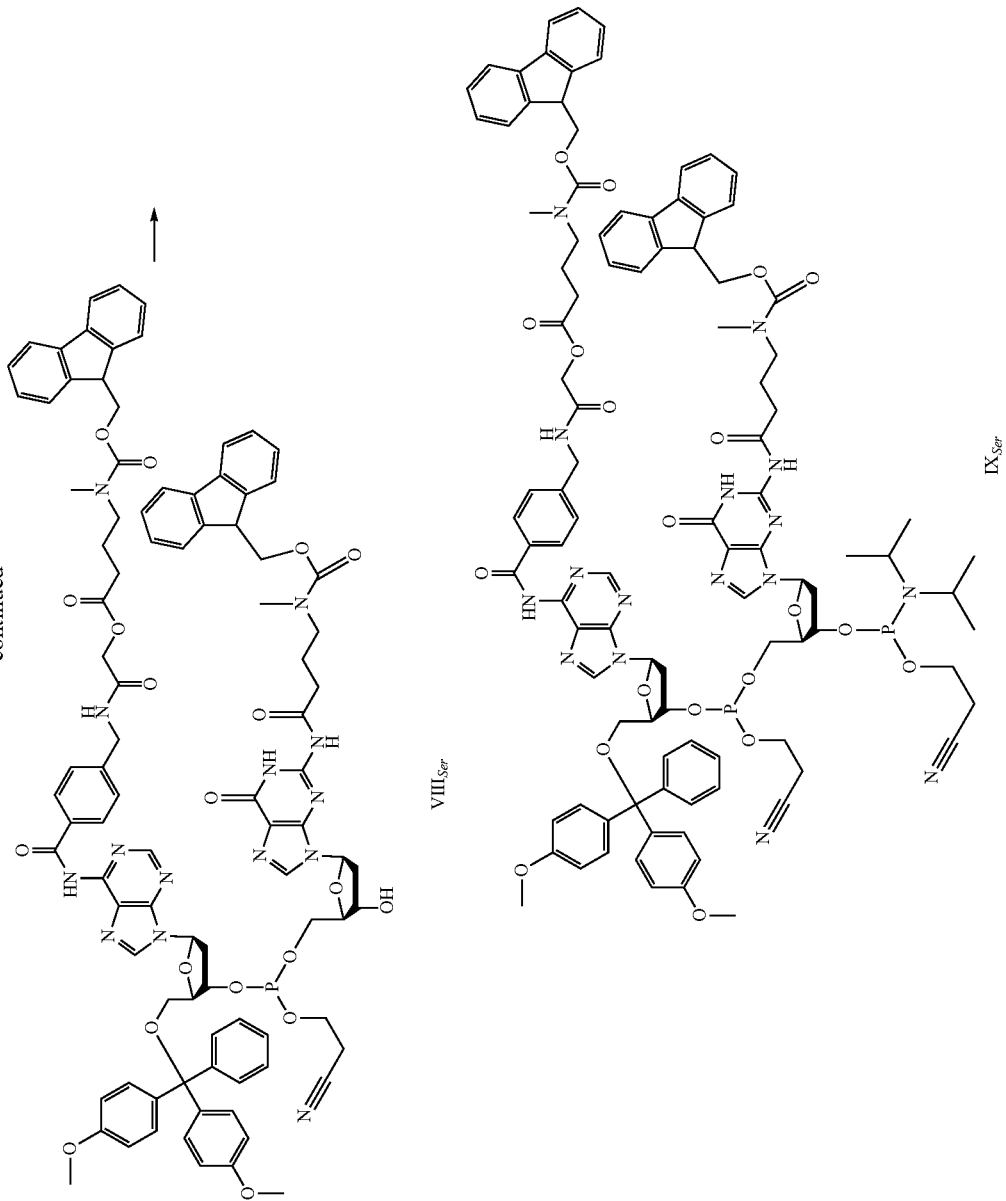

-continued
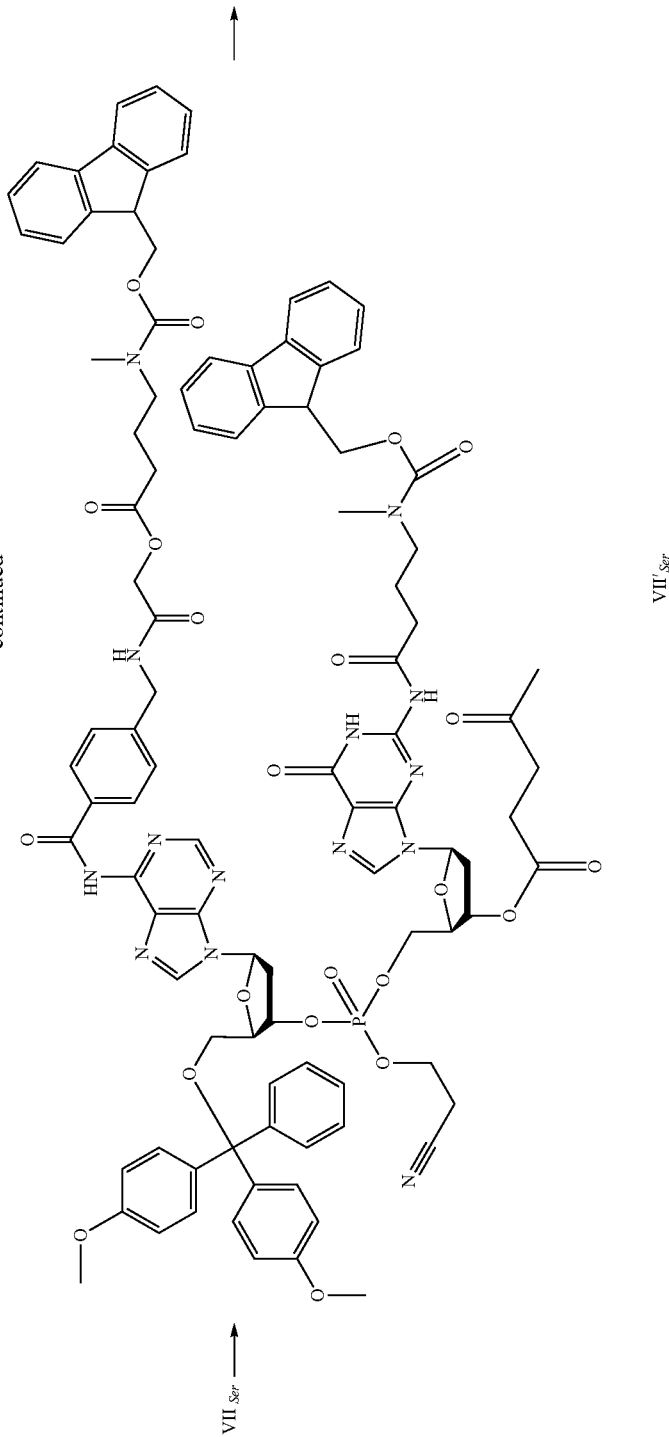
VII'Ser
VIISer

-continued
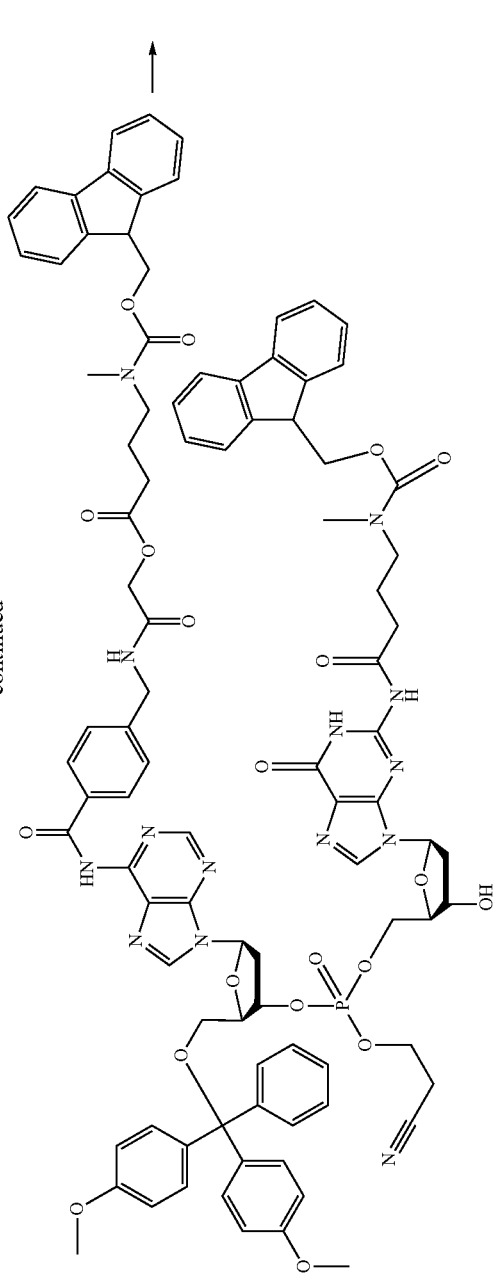
VIII'<sub>Ser</sub>
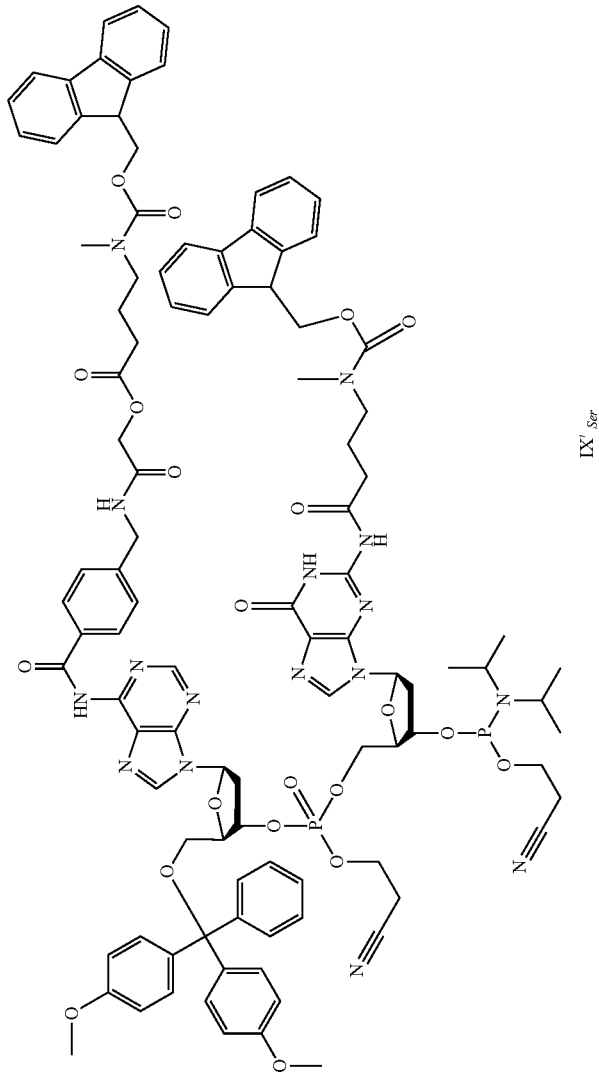
IX'<sub>Ser</sub>

<Synthesis of II> 13.58 g (40 mmol) of I was dissolved in dehydrated acetonitrile, and the solution was concentrated under reduced pressure three times. The residue was dissolved in 200 mL of dehydrated acetonitrile, and 3.88 mL (48 mmol) of pyridine and 6.79 g (40 mmol) of silver nitrate were added to the solution. 4.93 mL (40 mmol) of pivaloyl chloride was further added to the solution while being cooled with ice, followed by agitating at 0° C. for 15 minutes. Subsequently, 4.56 g (60 mmol) of glycolic acid was added to the solution, followed by agitating at room temperature for 4 hours. The reaction solution was diluted with dichloromethane and washed with water. The dichloromethane solution was concentrated under reduced pressure. The residue was purified by medium pressure chromatography (1% acetic acid (constant), dichloromethane:ethanol=100:0→19:1), to thereby obtain 13.03 g (82%) of target product II.

<Synthesis of $IV_{Ser}$> 10.58 g (10 mmol) of $III_A$ was dissolved in 20 mL of dehydrated dichloromethane, and 2.40 mL (15 mmol) of triethylsilane and 2.24 mL (15 mmol) of diazabicycloundecene were added to the solution, followed by agitating at room temperature for 10 minutes. A mixed solution containing 1.27 mL (16.5 mmol) of trifluoroacetic acid, 1.45 mL (18 mmol) of pyridine and 10 mL of dichloromethane was added to the reaction mixture to prepare reaction mixture A.

4.97 g (12.5 mmol) of II was dissolved in dehydrated toluene, and the solution was concentrated under reduced pressure three times. The residue was dissolved in 30 mL of dehydrated dichloromethane, and 1.58 g (13.8 mmol) of N-hydroxysuccinimide was added to the solution. 2.71 g (13.1 mmol) of dicyclohexylcarbodiimide was further added to the solution while being cooled with ice, followed by agitating at room temperature for 1 hour. The insoluble matter was removed by filtration, and the filtrate was added to reaction mixture A. The reaction mixture was agitated at room temperature for 1 hour. Subsequently, 5 mL of methanol was added thereto, followed by agitating for 30 minutes. The reaction solution was diluted with dichloromethane and washed with water. The dichloromethane solution was concentrated under reduced pressure, and the residue was purifed by medium pressure chromatography (dichloromethane:ethanol=97:3→47:3), to thereby obtain 10.11 g (95%) of target product $IV_{Ser}$.

<Synthesis of $V_{Ser}$> 10.11 g (9.48 mmol) of $IV_{Ser}$ was dissolved in a mixed solution of dehydrated acetonitrile and dehydrated dichloromethane, and the solution was concentrated under reduced pressure three times. The residue was dissolved in 38 mL of dehydrated dichloromethane. Under cooling with ice, 57.9 mg (0.47 mmol) of dimethylaminopyridine and 1.87 mL (11.4 mmol) of diisopropylethylamine were added to the solution, and a solution of 2-cyanoethyldiisopropylchlorophosphoroamidite (2.33 mL (10.4 mmol)) in dichloromethane (9.5 mL) was added dropwise thereto over 5 minutes or longer. The mixed solution was agitated at 0° C. for 1 hour. Subsequently, 9.5 mL of methanol was added thereto, followed by agitating for 30 minutes. The reaction solution was diluted with dichloromethane and washed with water. The dichloromethane solution was concentrated under reduced pressure, and the residue was purified by medium pressure chromatography (2% pyridine in ethyl acetate and hexane (2:1):2% pyridine and 3% ethanol in ethyl acetate=1:0→0:1), to thereby obtain 10.31 g (86%) of target product $V_{Ser}$.

<Synthesis of $VIII_{Ser}$> 10.31 g (8.14 mmol) of $V_{Ser}$ and 5.87 g (8.55 mmol) of $VI_G$ were dissolved in dehydrated acetonitrile, and the solution was concentrated under reduced pressure three times. The residue was dissolved in 41 mL of dehydrated acetonitrile, and 2.85 g (40.7 mmol) of tetrazole was added to the solution while being cooled with ice, followed by agitating at room temperature for 30 minutes. Subsequently, 3.3 mL of methanol was added thereto, followed by agitating for 30 minutes. The solution was diluted with dichloromethane and washed with water. The dichloromethane solution was concentrated under reduced pressure. The residue was dissolved in 43 mL of pyridine, and a solution (12.8 mL) of 1M hydrazine monohydrate in a solvent mixture containing pyridine and acetic acid in the ratio of 5:2 was added to the solution while being cooled with ice, followed by agitating at 0° C. for 1 hour. Until the disappearance of $VII_{Ser}$ was confirmed, 4.3 mL of the solution of 1M hydrazine monohydrate in a solvent mixture containing pyridine and acetic acid in the ratio of 5:2 was added to the solution every 30 minutes. Under cooling with ice, 30 mL of acetone was added thereto, followed by agitating at 0° C. for 10 minutes. Thereafter, the mixture was diluted with dichloromethane and washed with water. The dichloromethane solution was concentrated under reduced pressure. The residue was purified by medium pressure chromatography (dichloromethane:ethanol=97:3→9:1), to thereby obtain 11.07 g (78%) of target product $VIII_{Ser}$.

<Synthesis of $IX_{Ser}$> 10.03 g (6.29 mmol) of $VIII_{Ser}$ was dissolved in a mixed solution of dehydrated acetonitrile and dehydrated dichloromethane, and the solution was concentrated under reduced pressure three times. The residue was dissolved in 25 mL of dehydrated dichloromethane. Under cooling with ice, 38 mg (0.3 mmol) of dimethylaminopyridine and 1.25 mL (7.55 mmol) of diisopropylethylamine were added to the solution, and then a diluted solution of 2-cyanoethyldiisopropylchlorophosphoroamidite (1.54 mL (6.92 mmol)) in dichloromethane (6.3 mL) was further added thereto. The mixed solution was agitated at 0° C. for 12 hours and then agitated at room temperature for 2 hours. Subsequently, 2.5 mL of methanol was added thereto, followed by agitating for 30 minutes. The reaction solution was diluted with dichloromethane and washed with water. The dichloromethane solution was concentrated under reduced pressure, and the residue was purified (2% pyridine in dichloromethane and hexane (2:1):2% pyridine in dichloromethane=100:0→0:100, then 2% pyridine:20% ethanol and 2% pyridine in dichloromethane=1:0→3:1), to thereby obtain 8.83 g (71%) of target product $IX_{Ser}$.

<Synthesis of $VII_{Ser}$> 4.14 g (3.27 mmol) of $V_{Ser}$ and 2.25 g (3.27 mmol) of $VI_G$ were dissolved in dehydrated acetonitrile, and the solution was concentrated under reduced pressure three times. The residue was dissolved in 32 mL of dehydrated acetonitrile, and 1.16 g (16.34 mmol) of tetrazole was added to the solution while being cooled with ice, followed by agitating at room temperature for 1 hour. Subsequently, 1.0 mL of water was added thereto, followed by agitating for 15 minutes. The solution was diluted with dichloromethane and washed with water. The dichloromethane solution was concentrated under reduced pressure. The residue was dissolved in 114 mL of a solution containing 0.1M iodine in THF, water and pyridine in the proportion of 7:2:1, followed by agitating at room temperature for 30 minutes. 290 mL of dichloromethane was added to the reaction mixture, and 7.2 g of sodium sulfite was added thereto, followed by agitating at room temperature for 15 minutes. About 25 g of sodium sulfate was added to the reaction mixture, and the mixture was thoroughly agitated. Thereafter, the insoluble matter was filtrated, and the filtrate was concentrated under reduced pressure. The residue was purified by medium pressure chromatography (dichloromethane:ethanol=49:1→8:1), to thereby obtain 4.86 g (80%) of target product VII'$_{Ser}$.

<Synthesis of VIII'$_{Ser}$> 4.74 g (2.60 mmol) of VII'$_{Ser}$ was dissolved in 26 mL of pyridine, and a diluted solution (26 mL (pyridine:acetic acid=3:2)) of hydrazine monohydrate (1.26 mL (26.0 mmol)) was added to the solution, followed by agitating at room temperature for 5 minutes. Under cooling with ice, 26 mL of acetone was added thereto, followed by agitating at 0° C. for 10 minutes. Thereafter, the mixture was diluted with dichloromethane and washed with water. The dichloromethane solution was concentrated under reduced pressure. The residue was purified by medium pressure chromatography (dichloromethane:ethanol=49:1→17:3), to thereby obtain 3.59 g (78%) of target product VIII'$_{Ser}$.

<Synthesis of IX'$_{Ser}$> 3.14 g (1.77 mmol) of VIII'$_{Ser}$ was dissolved in dehydrated acetonitrile, and the solution was concentrated under reduced pressure three times. The residue was dissolved in 18 mL of dehydrated dichloromethane. Under cooling with ice, 12.7 mg (0.089 mmol) of dimethylaminopyridine and 401 µL (2.30 mmol) of diisopropylethylamine were added to the solution, and 471 µl (2.12 mmol) of 2-cyanoethyldiisopropylchlorophosphoroamidite was added thereto. The mixed solution was agitated at 0° C. for 1 hour and then agitated at room temperature for 2 hours. Subsequently, 1.8 mL of methanol was added thereto, followed by agitating for 30 minutes. The reaction solution was diluted with dichloromethane and washed with water. The dichloromethane solution was concentrated under reduced pressure, and the residue was dissolved in 25 mL of ethyl acetate and 10 mL of dichloromethane. The solution was added dropwise to 177 mL of hexane at −60° C. The insoluble matter was removed through filtration, followed by washing with cold hexane. The solvent of the filtrated product was removed under reduced pressure, to thereby obtain 2.98 g (86%) of target product IX'$_{Ser}$.

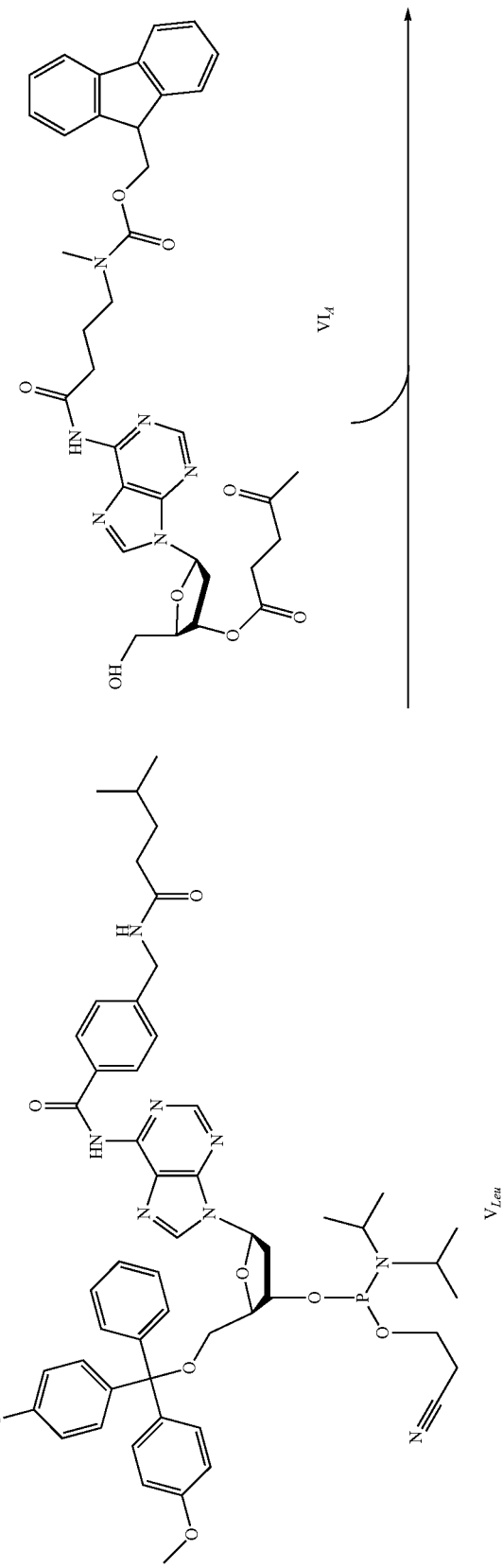
Scheme 2

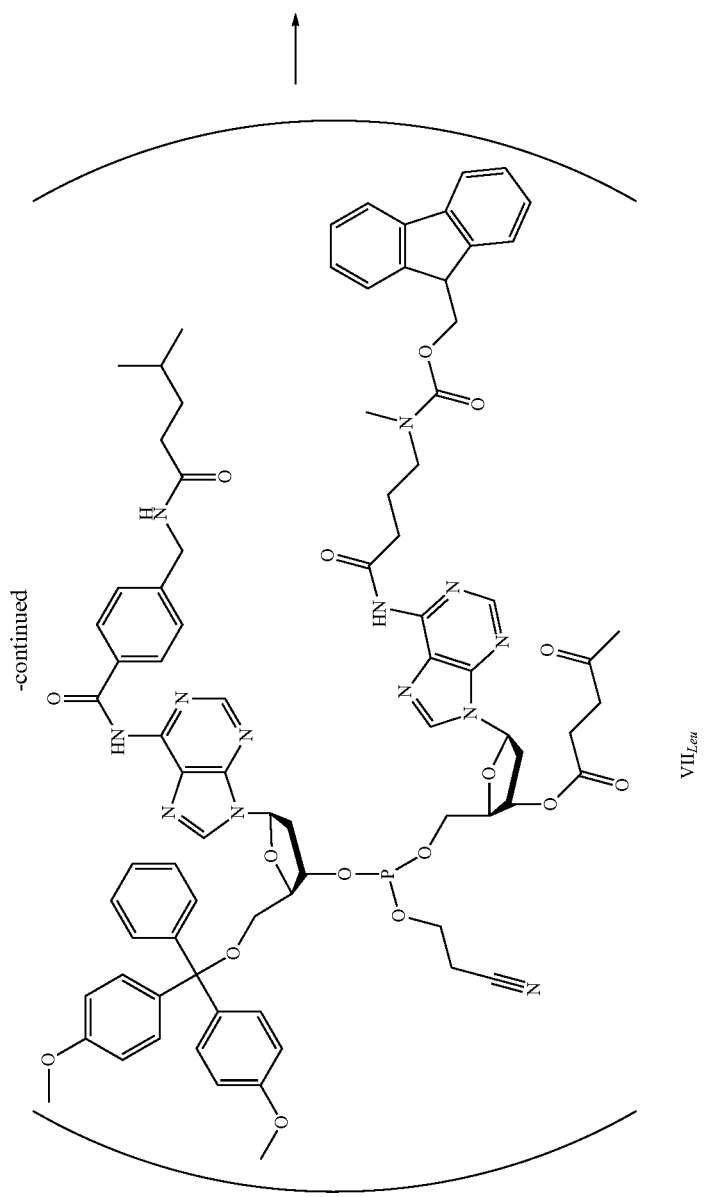

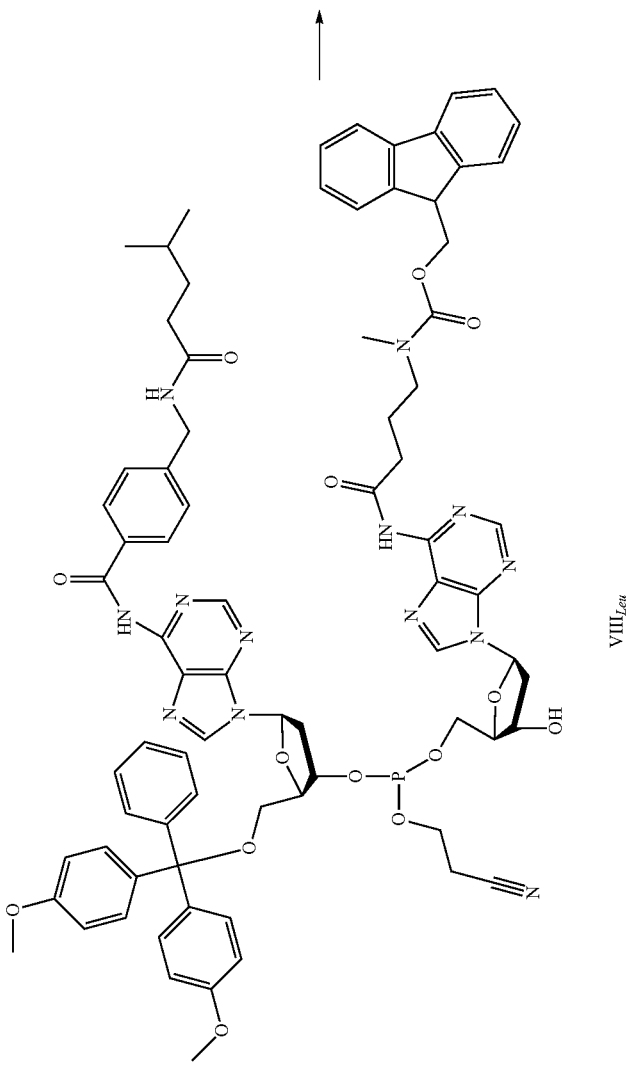

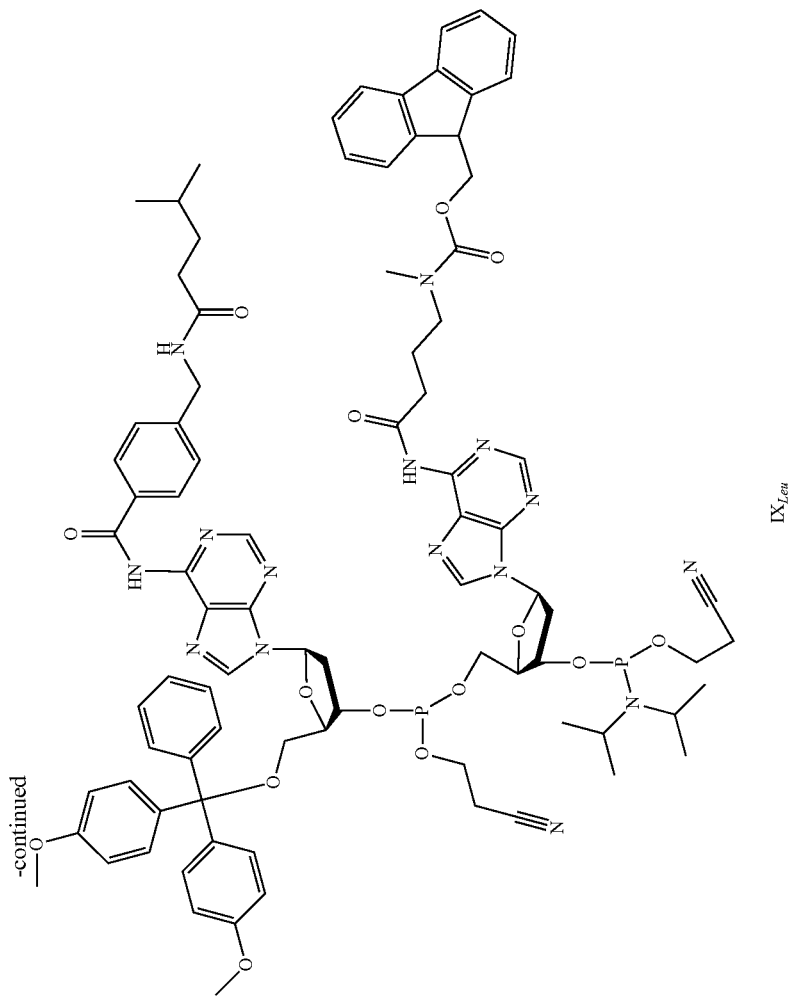
IX$_{Leu}$

<Synthesis of VIII$_{Leu}$> 7.39 g (7.51 mmol) of V$_{Leu}$ and 5.79 g (8.63 mmol) of VI$_A$ were dissolved in dehydrated acetonitrile, and the solution was concentrated under reduced pressure three times. The residue was dissolved in 38 mL of dehydrated acetonitrile, and 2.65 g (37.5 mmol) of tetrazole was added to the solution while being cooled with ice, followed by agitating at room temperature for 2 hours. Subsequently, 1.7 mL of methanol thereto, followed by agitating for 30 minutes. The solution was diluted with dichloromethane and washed with water. The dichloromethane solution was concentrated under reduced pressure. The residue was dissolved in 43 mL of pyridine, and a solution (12.9 mL) of 1M hydrazine monohydrate in a solvent mixture containing pyridine and acetic acid in the ratio of 5:2 was added to the solution while being cooled with ice, followed by agitating at 0° C. for 1 hour. Until the disappearance of VII$_{Leu}$ was confirmed, 4.3 mL of the solution of 1M hydrazine monohydrate in a solvent mixture containing pyridine and is acetic acid in the ratio of 5:2 was added to the solution every 30 minutes. Under cooling with ice, 30 mL of acetone was added thereto, followed by agitating at 0° C. for 10 minutes. Thereafter, the mixture was diluted with dichloromethane and washed with water. The dichloromethane solution was concentrated under reduced pressure. The residue was purified by medium pressure chromatography (dichloromethane:ethanol=97:3→9:1), to thereby obtain 8.22 g (75%) of target product VIII$_{Leu}$.

<Synthesis of IX$_{Leu}$> 7.08 g (4.86 mmol) of VIII$_{Leu}$ was dissolved in a mixed solution of dehydrated acetonitrile and dehydrated dichloromethane, and the solution was concentrated under reduced pressure three times. The residue was dissolved in 19 mL of dehydrated dichloromethane. Under cooling with ice, 30 mg (0.24 mmol) of dimethylaminopyridine and 964 µL (7.55 mmol) of diisopropylethylamine were added to the solution, and a diluted solution of 2-cyanoethyl-diisopropylchlorophosphoroamidite (1.19 mL (5.35 mmol)) in dichloromethane (4.9 mL) was added thereto. The mixed solution was agitated at 4° C. overnight. Subsequently, 1.9 mL of methanol was added thereto, followed by agitating for 30 minutes. The reaction solution was diluted with dichloromethane and washed with water. The dichloromethane solution was concentrated under reduced pressure, and the residue was purified (2% pyridine in dichloromethane and hexane (2:1):2% pyridine in dichloromethane=100:0→0:100, then 2% pyridine in dichloromethane:2% pyridine, 20% ethanol and 2% pyridine in dichloromethane=1:0→3:1), to thereby obtain 3.86 g (48%) of target product IX$_{Leu}$.

Scheme 3

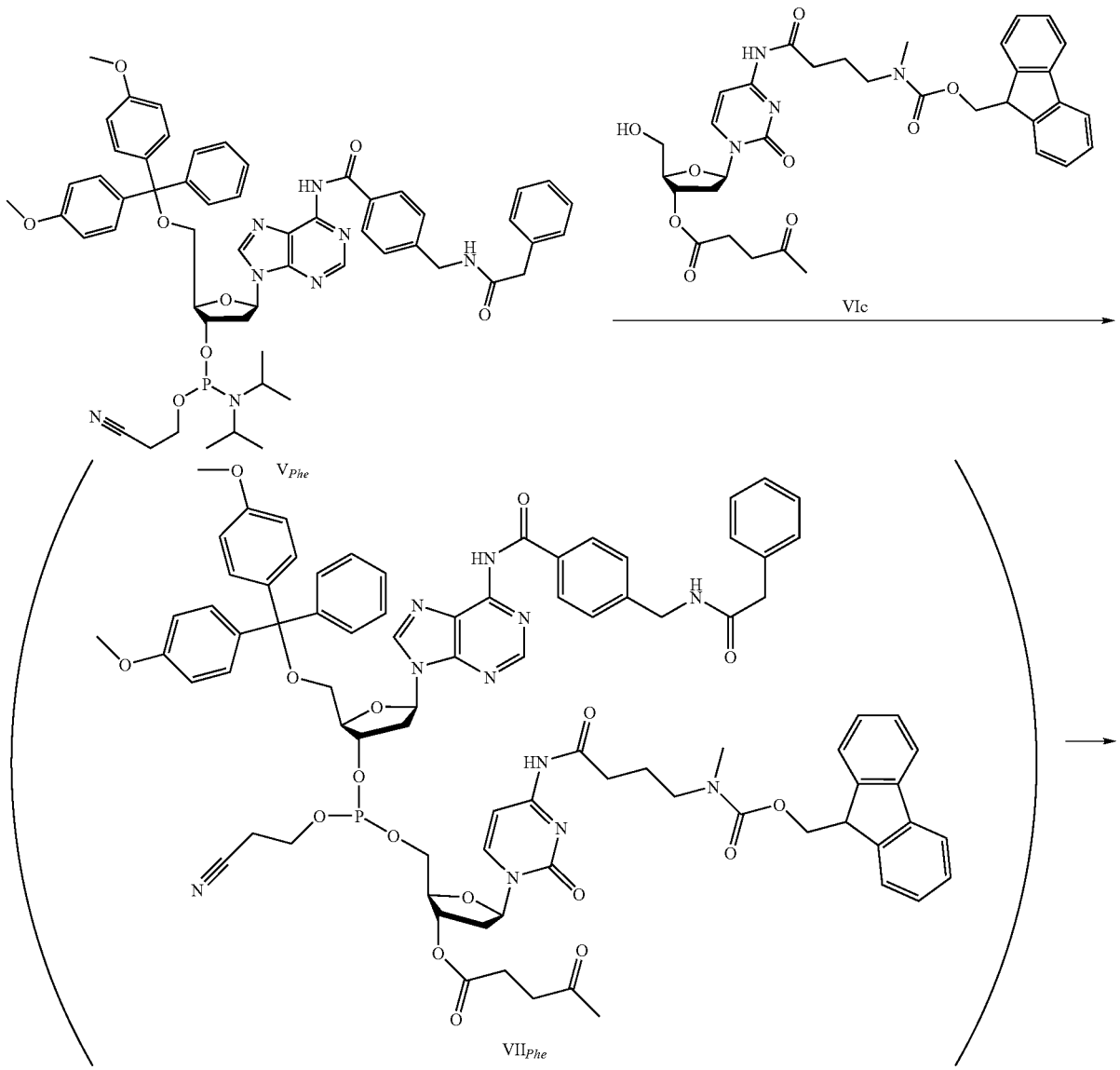

-continued

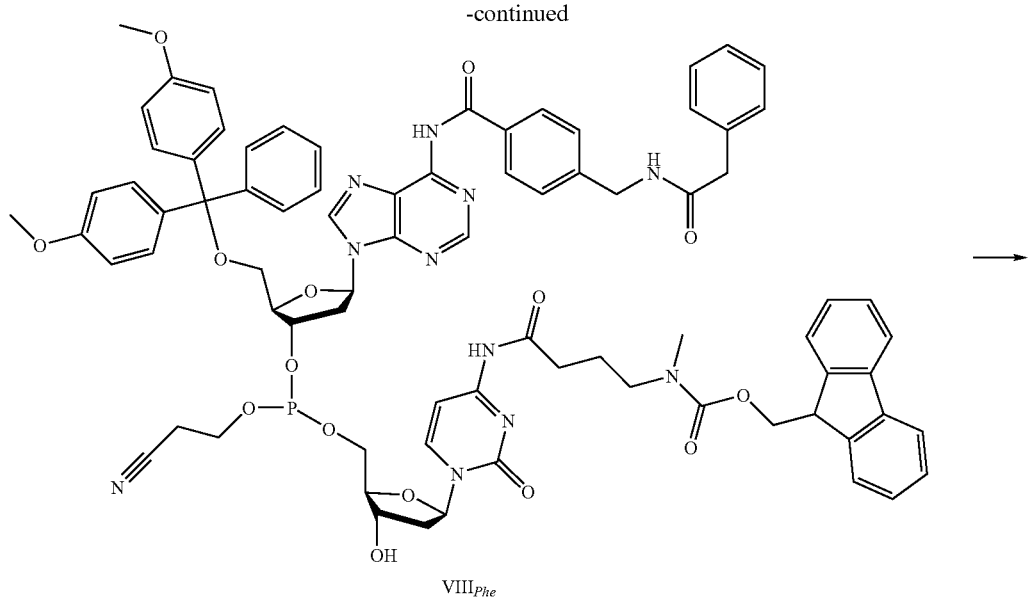

VIII$_{Phe}$

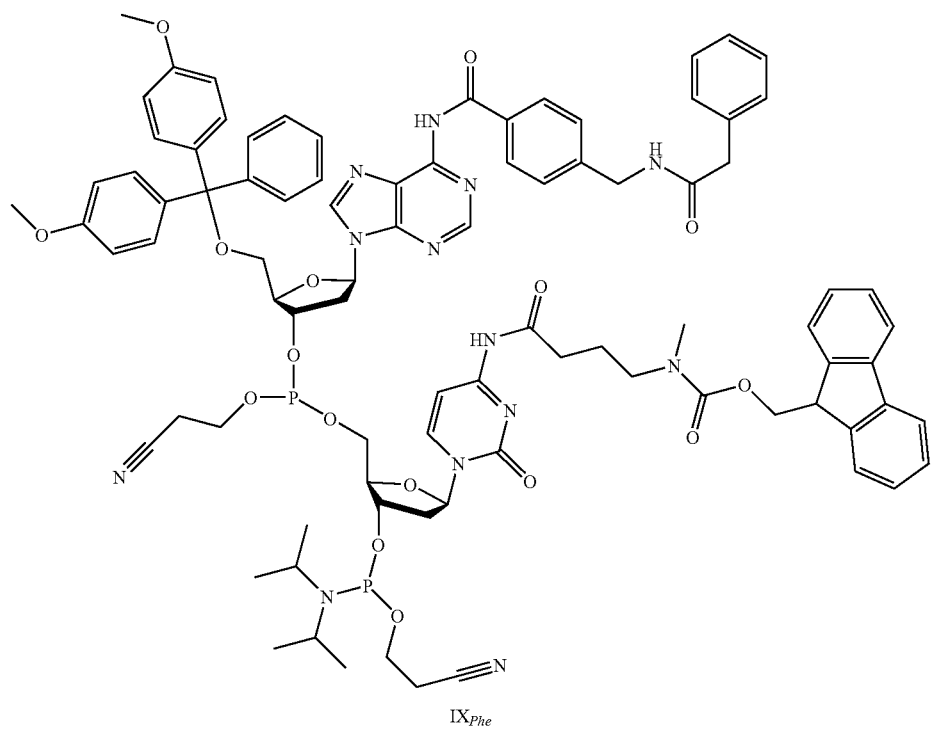

IX$_{Phe}$

<Synthesis of VIII$_{Phe}$> 7.09 g (7.05 mmol) of V$_{Phe}$ and 4.79 g (7.41 mmol) of VI$_C$ were dissolved in dehydrated acetonitrile, and the solution was concentrated under reduced pressure three times. The residue was dissolved in 35 mL of dehydrated acetonitrile, and 2.47 g (35.3 mmol) of tetrazole was added to the solution while being cooled with ice, followed by agitating for 45 minutes under cooling with ice. Subsequently, 1.4 mL of methanol was added thereto, followed by agitating for 15 minutes. The solution was diluted with dichloromethane and washed with water. The dichloromethane solution was concentrated under reduced pressure. The residue was dissolved in 38 mL of pyridine, and a solution (11.1 mL) of 1M hydrazine monohydrate in a solvent mixture containing pyridine and acetic acid in the ratio of 5:2 was added to the solution while being cooled with ice, followed by agitating at 0° C. for 1 hour. Until the disappearance of VII$_{Phe}$ was confirmed, 3.7 mL of the solution of 1M hydrazine monohydrate in a solvent mixture containing pyridine and acetic acid in the ratio of 5:2 was added to the solution every 30 minutes. Under cooling with ice, 30 mL of acetone was added thereto, followed by agitating at 0° C. for 10 minutes. Thereafter, the mixture was diluted with dichloromethane and washed with water. The dichloromethane solution was concentrated under reduced pressure. The residue was purified by medium pressure chromatography (dichloromethane:ethanol=97:3→92:8), to thereby obtain 7.07 g (69%) of target product VIII$_{Phe}$.

<Synthesis of IX$_{Phe}$> 5.17 g (3.56 mmol) of VIII$_{Phe}$ was dissolved in a mixed solution of dehydrated acetonitrile and dehydrated dichloromethane, and the solution was concentrated under reduced pressure three times. The residue was dissolved in 14 mL of dehydrated dichloromethane. Under cooling with ice, 22 mg (0.18 mmol) of dimethylaminopyridine and 706 μL (5.34 mmol) of diisopropylethylamine were added to the solution, and a diluted solution of 2-cyanoethylthisopropylchlorophosphoroamidite (873 μL (3.92 mmol)) in dichloromethane (3.6 mL) was added thereto, followed by agitating at 0° C. for 5 hours. Subsequently, 1.4 mL of methanol was added thereto, followed by agitating for 30 minutes. The reaction solution was diluted with dichloromethane and washed with water. The dichloromethane solution was concentrated under reduced pressure, and the residue was purified (2% pyridine in dichloromethane and hexane (2:1):2% pyridine in dichloromethane=100:0→0:100, then 2% pyridine in dichloromethane:2% pyridine, 20% ethanol and 2% pyridine in dichloromethane=1:0→3:1), to thereby obtain 4.01 g (68%) of target product IX$_{Phe}$.

Scheme 4

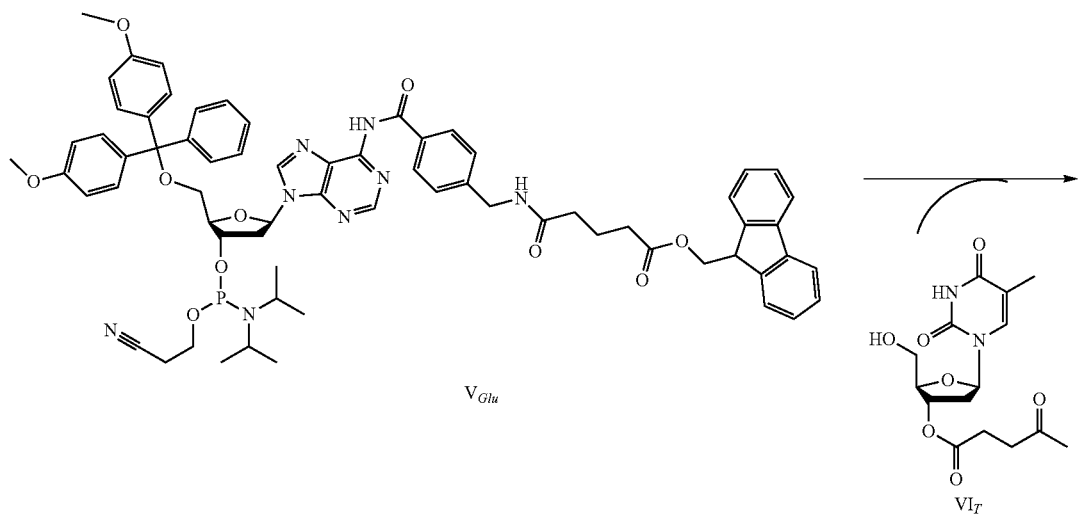

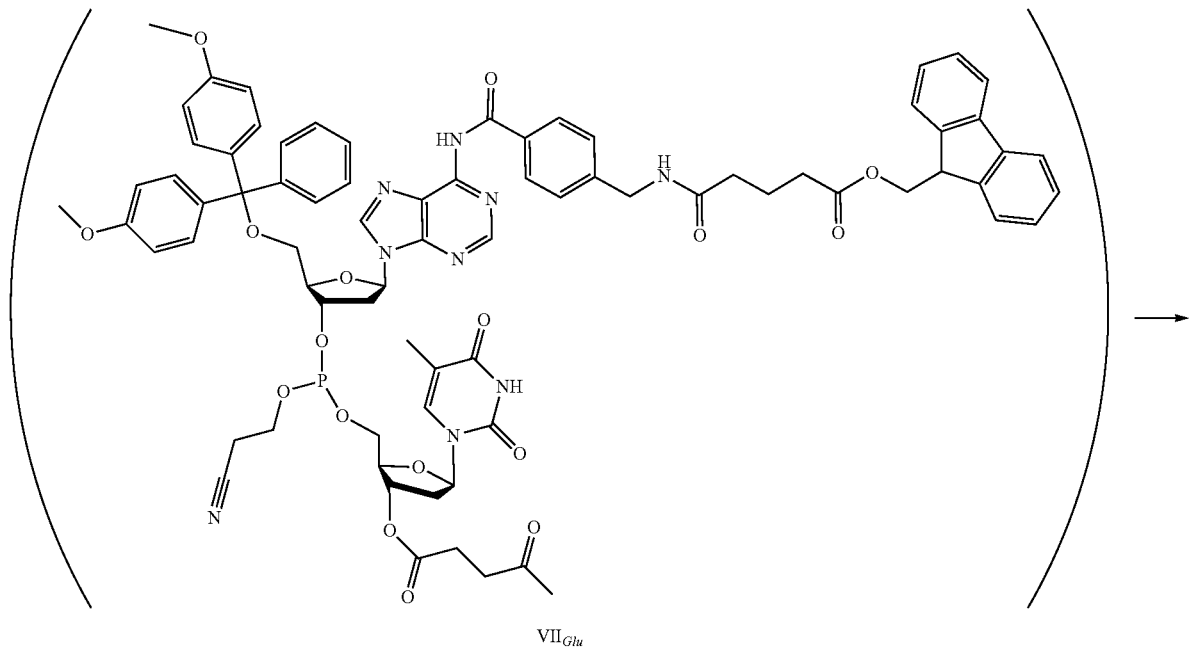

-continued

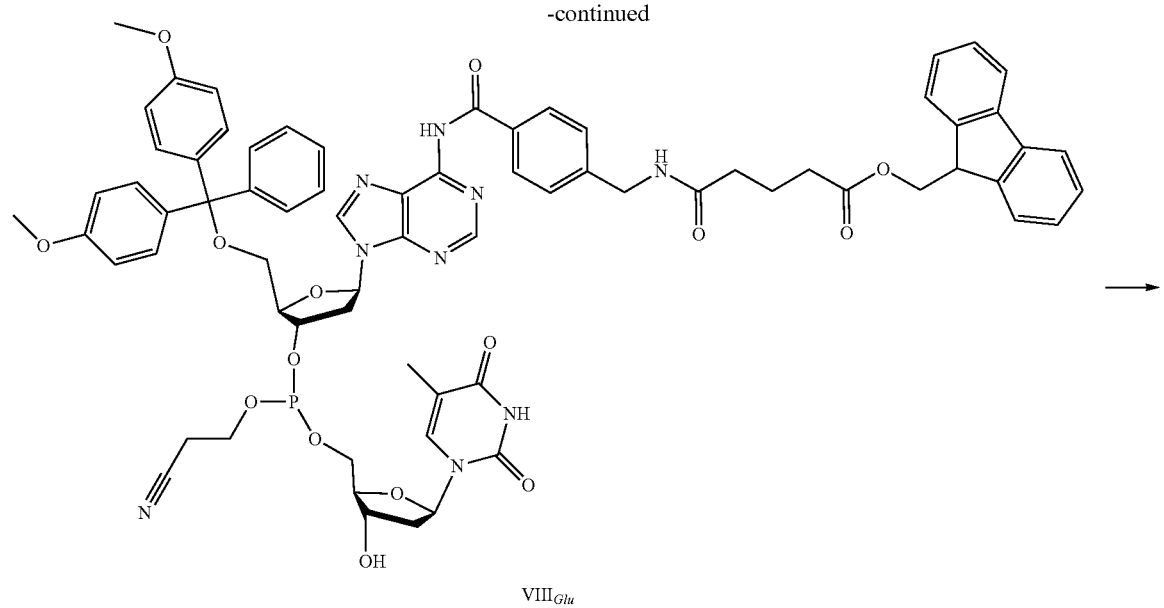
VIII$_{Glu}$

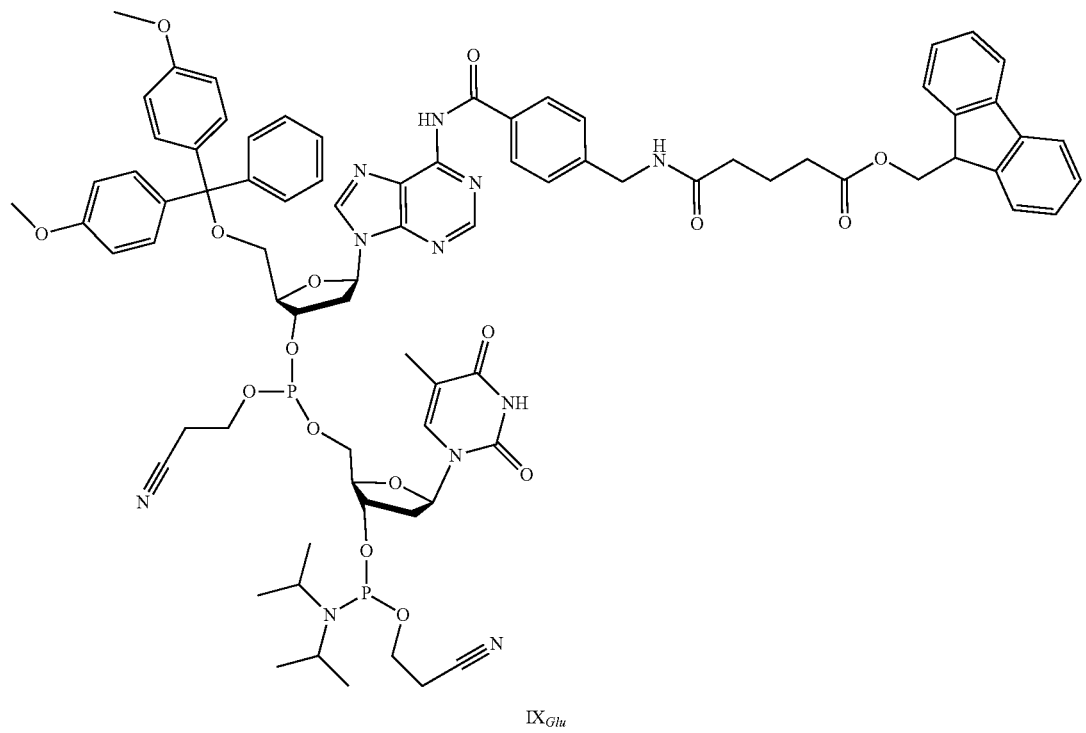
IX$_{Glu}$

<Synthesis of VIII$_{Glu}$> 6.52 g (5.53 mmol) of V$_{Glu}$ and 1.98 g (5.81 mmol) of VI$_T$ were dissolved in dehydrated acetonitrile, and the solution was concentrated under reduced pressure three times. The residue was dissolved in 28 mL of dehydrated acetonitrile, and 1.94 g (27.7 mmol) of tetrazole was added to the solution while being cooled with ice, followed by agitating for 1 hour under cooling with ice. Subsequently, 2.2 mL of methanol was added thereto, followed by agitating for 5 minutes. The solution was diluted with dichloromethane and washed with water. The dichloromethane solution was concentrated under reduced pressure. The residue was dissolved in 29 mL of pyridine, and a solution (8.7 mL) of 1M hydrazine monohydrate in a solvent mixture containing pyridine and acetic acid in the ratio of 5:2 were added to the solution while being cooled with ice, followed by agitating at 0° C. for 1 hour. Until the disappearance of VII$_{Glu}$ was confirmed, 2.9 mL of the solution of 1M hydrazine monohydrate in a solvent mixture containing pyridine and acetic acid in the ratio of 5:2 was added to the solution every 30 minutes. Under cooling with ice, 23 mL of acetone was added thereto, followed by agitating at 0° C. for 10 minutes. Thereafter, the mixture was diluted with dichloromethane and washed with water. The dichloromethane solution was concentrated under reduced pressure. The residue was purified by medium pressure chromatography (dichloromethane:ethanol=97:3→91:9), to thereby obtain 6.17 g (85%) of target product VIII$_{Glu}$.

<Synthesis of IX$_{Glu}$> 6.17 g (4.67 mmol) of VIII$_{Glu}$ was dissolved in a mixed solution of dehydrated acetonitrile and dehydrated dichloromethane, and the solution was concentrated under reduced pressure three times. The residue was dissolved in 19 mL of dehydrated dichloromethane. Under cooling with ice, 29 mg (0.23 mmol) of dimethylaminopyridine and 0.93 mL (5.33 mmol) of diisopropylethylamine were added to the solution, and a diluted solution of 2-cyanoethyldiisopropylchlorophosphoroamidite (1.15 mL (5.14 mmol)) in dichloromethane (4.8 mL) was added thereto, followed by agitating at 0° C. for 2 hours. Subsequently, 1.9 mL of methanol was added thereto, followed by agitating for 30 minutes. The reaction solution was diluted with dichloromethane and washed with water. The dichloromethane solution was concentrated under reduced pressure, and the residue was purified (2% pyridine in dichloromethane and hexane (2:1):2% pyridine in dichloromethane=100:0→0:100, then 2% pyridine in dichloromethane:2% pyridine, 20% ethanol and 2% pyridine in dichloromethane=1:0→3:1), to thereby obtain 4.79 g (67%) of target product IX$_{Glu}$.

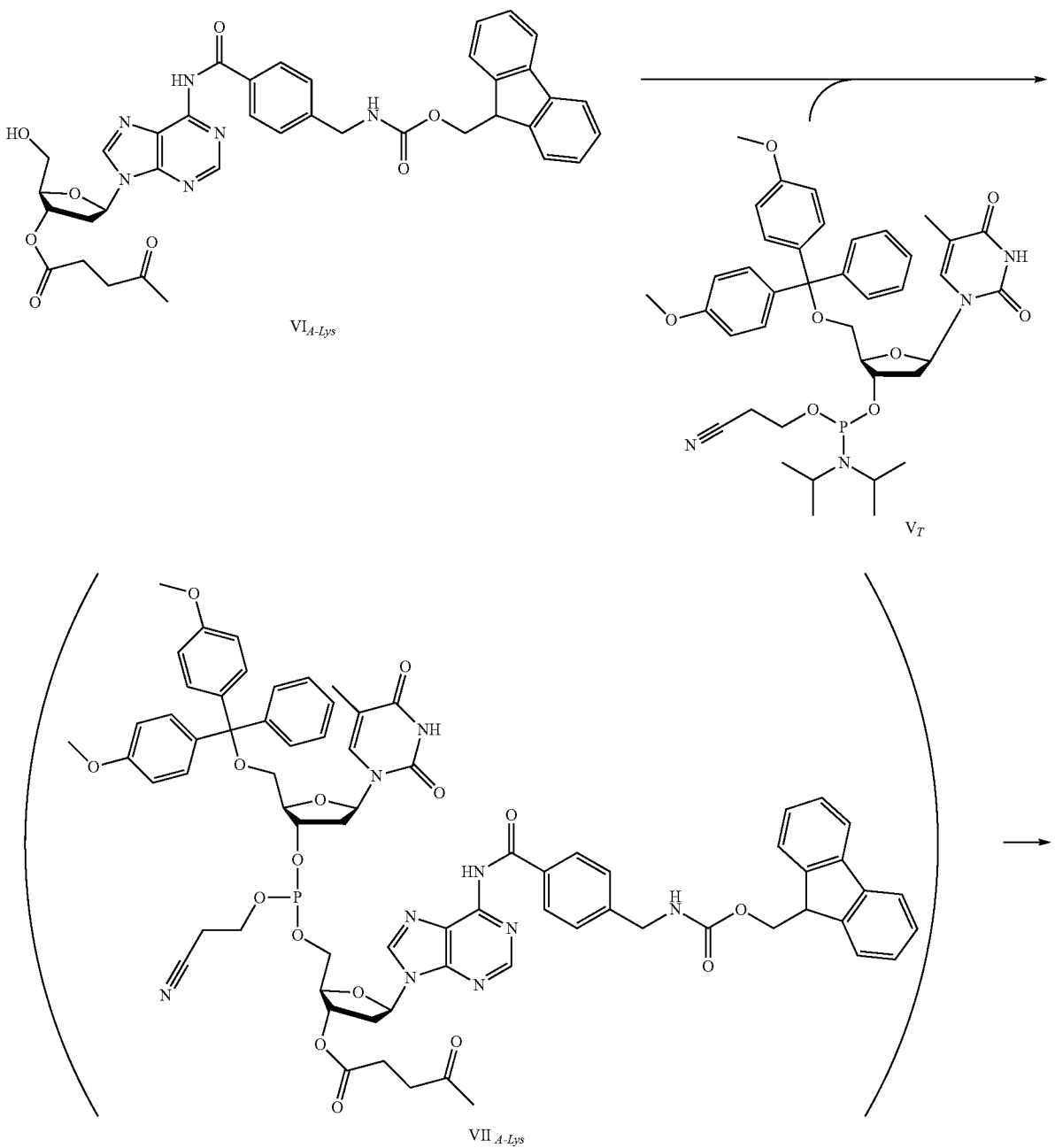

Scheme 5

-continued

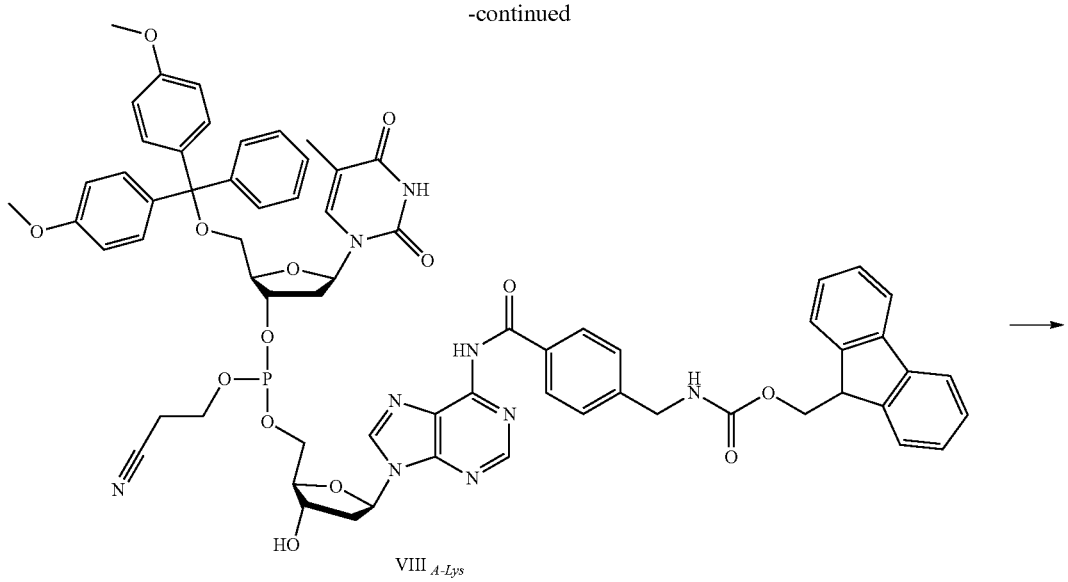

VIII<sub>A-Lys</sub>

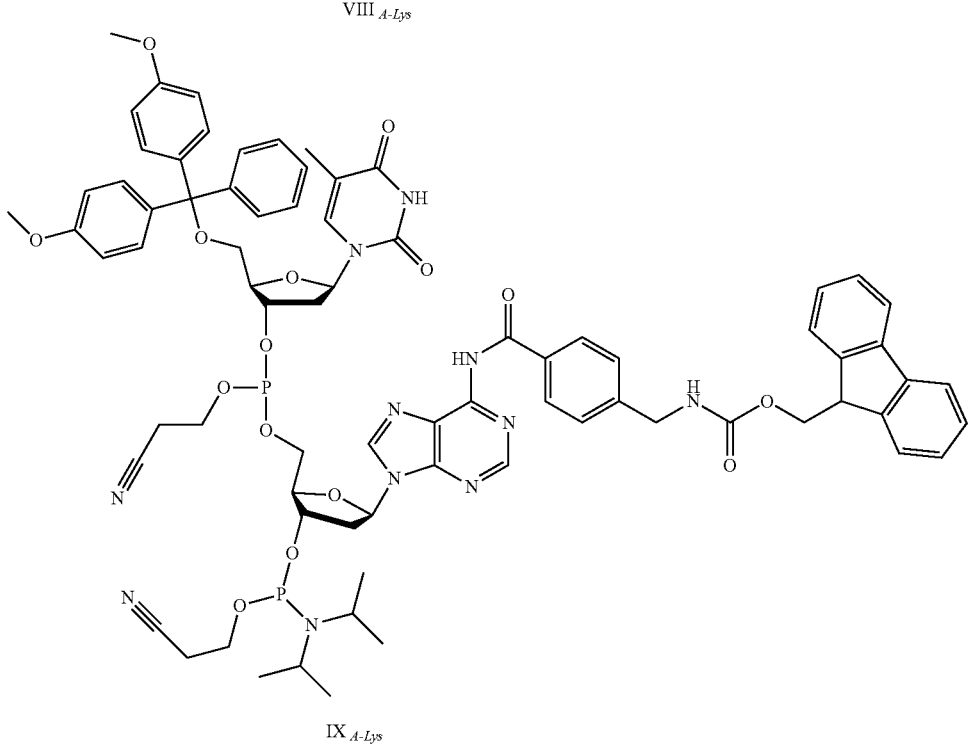

IX<sub>A-Lys</sub>

<Synthesis of VIII$_{A\text{-}Lys}$> 6.89 g (9.77 mmol) of VI$_{A\text{-}Lys}$ and 8.0 g (10.7 mmol) of V$_T$ were dissolved in dehydrated acetonitrile, and the solution was concentrated under reduced pressure three times. The residue was dissolved in 50 mL of dehydrated acetonitrile, and 3.42 g (48.9 mmol) of tetrazole was added to the solution while being cooled with ice, followed by agitating for 1 hour under cooling with ice. Subsequently, 3.9 mL of methanol was added thereto, followed by agitating for 5 minutes. The solution was diluted with dichloromethane and washed with water. The dichloromethane solution was concentrated under reduced pressure. The residue was dissolved in 49 mL of pyridine, and a solution (14.6 mL) of 1M hydrazine monohydrate in a solvent mixture containing pyridine and acetic acid in the ratio of 5:2 was added to the solution while being cooled with ice, followed by agitating at 0° C. for 1 hour. Until the disappearance of VII$_{A\text{-}Lys}$ was confirmed, 4.9 mL of the solution of 1M hydrazine monohydrate in a solvent mixture containing pyridine and acetic acid in the ratio of 5:2 was added to the solution every 30 minutes. Under cooling with ice, 15 mL of acetone was added thereto, followed by agitating at 0° C. for 10 minutes. Thereafter, the mixture was diluted with dichloromethane and washed with water. The dichloromethane solution was concentrated under reduced pressure. The residue was purified by medium pressure chromatography (dichloromethane:ethanol=97:3→9:1), to thereby obtain 9.09 g (74%) of target product $VIII_{A-Lys}$.

<Synthesis of $IX_{A-Lys}$> 9.09 g (7.27 mmol) of $VIII_{A-Lys}$ was dissolved in a mixed solution of dehydrated acetonitrile and dehydrated dichloromethane, and the solution was concentrated under reduced pressure three times. The residue was dissolved in 29 mL of dehydrated dichloromethane. Under cooling with ice, 44 mg (0.36 mmol) of dimethylaminopyridine and 1.44 mL (8.27 mmol) of diisopropylethylamine were added to the solution, and a diluted solution of 2-cyanoethyldiisopropylchlorophosphoroamidite (1.78 mL (7.99 mmol)) in dichloromethane (7.3 mL), followed by agitating at 0° C. for 4 hours. Subsequently, 2.9 mL of methanol was added thereto, followed by agitating for 30 minutes. The reaction solution was diluted with dichloromethane and washed with water. The dichloromethane solution was concentrated under reduced pressure, and the residue was purified (2% pyridine in dichloromethane and hexane (2:1):2% pyridine in dichloromethane=100:0→0:100, then 2% pyridine in dichloromethane:2% pyridine, 20% ethanol and 2% pyridine in dichloromethane=1:0→3:1), to thereby obtain 6.64 g (63%) of target product $IX_{A-Lys}$.

Scheme 6
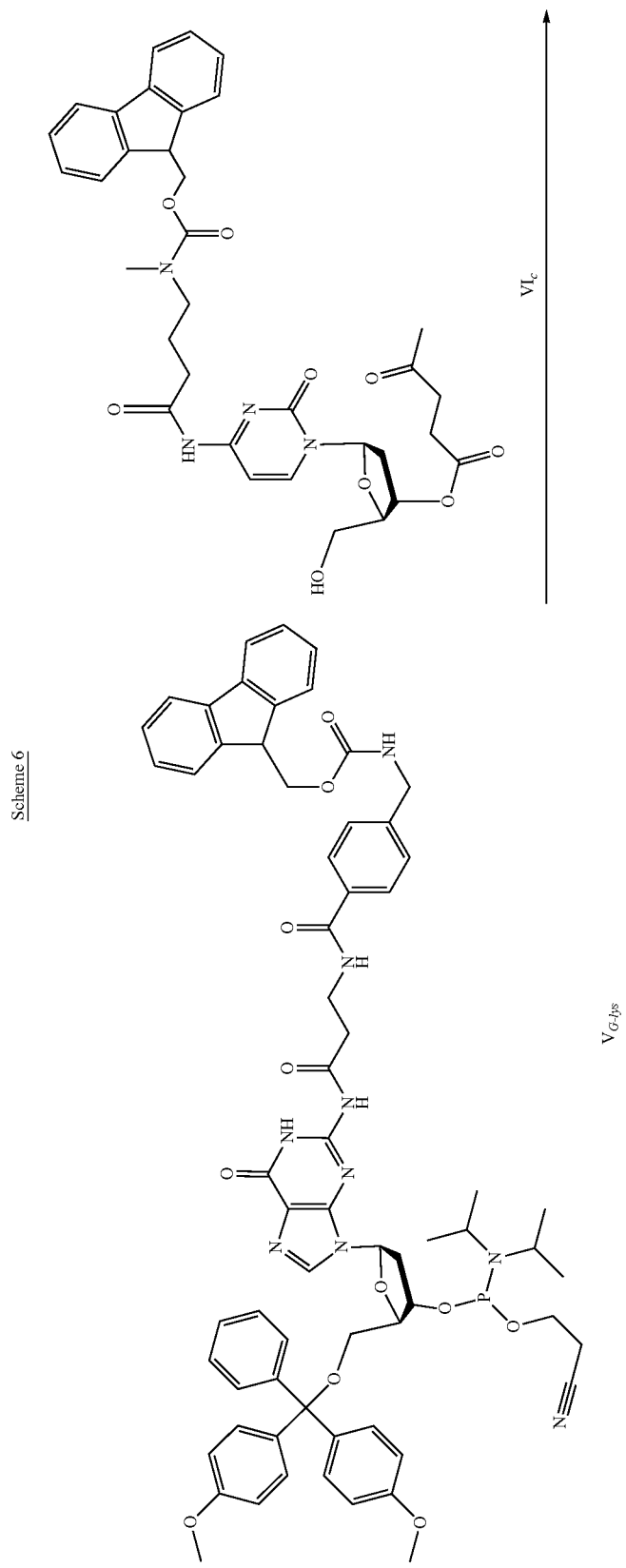

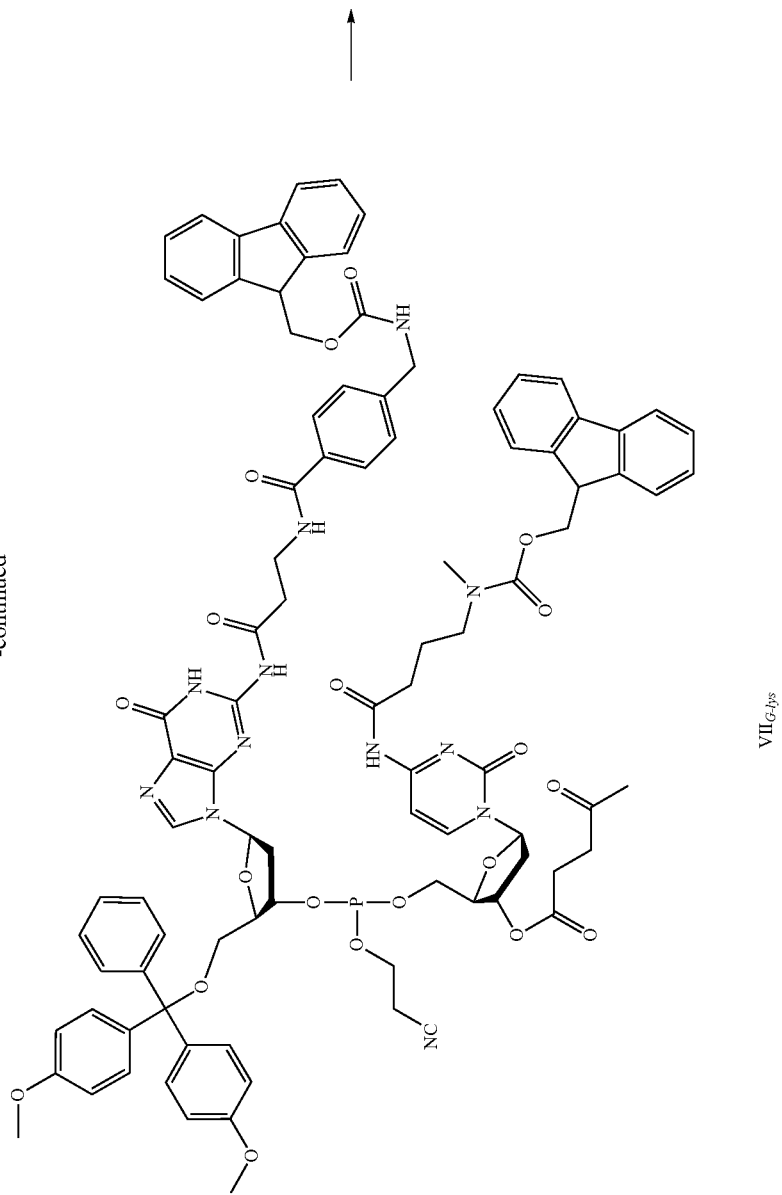
-continued
VII<sub>G-lys</sub>

-continued
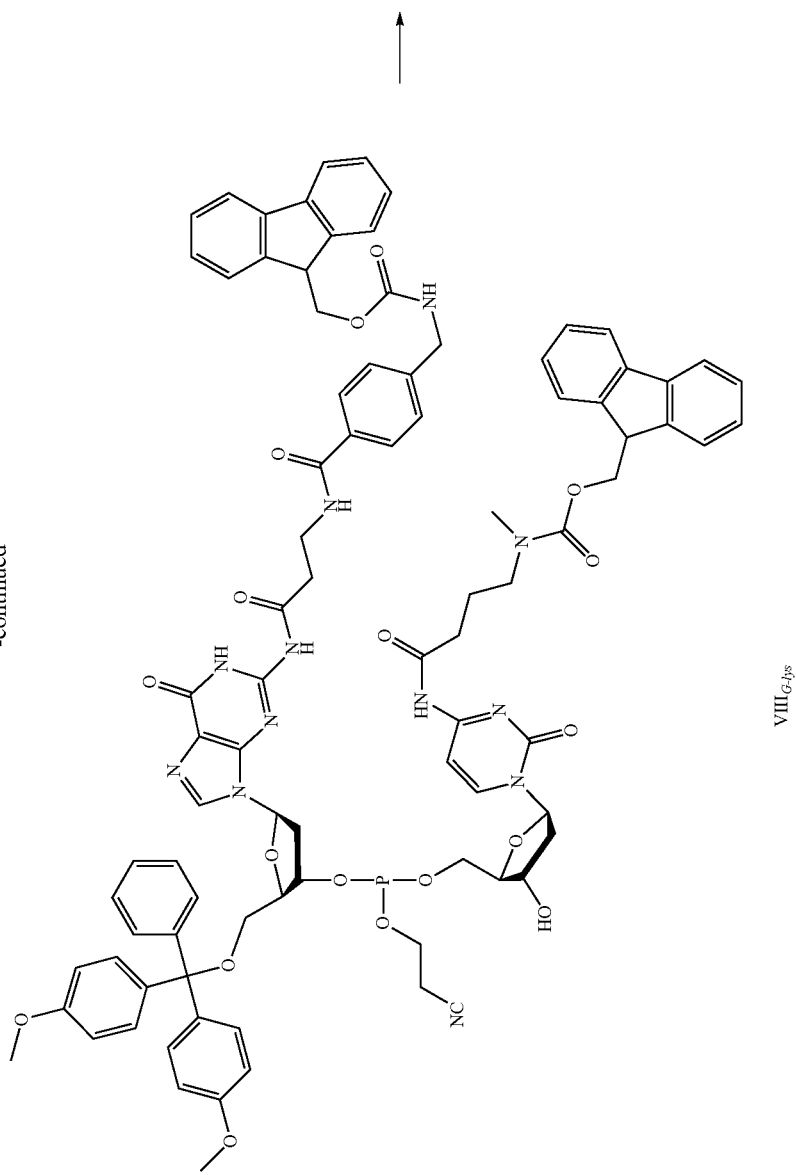
VIII_{G-lys}

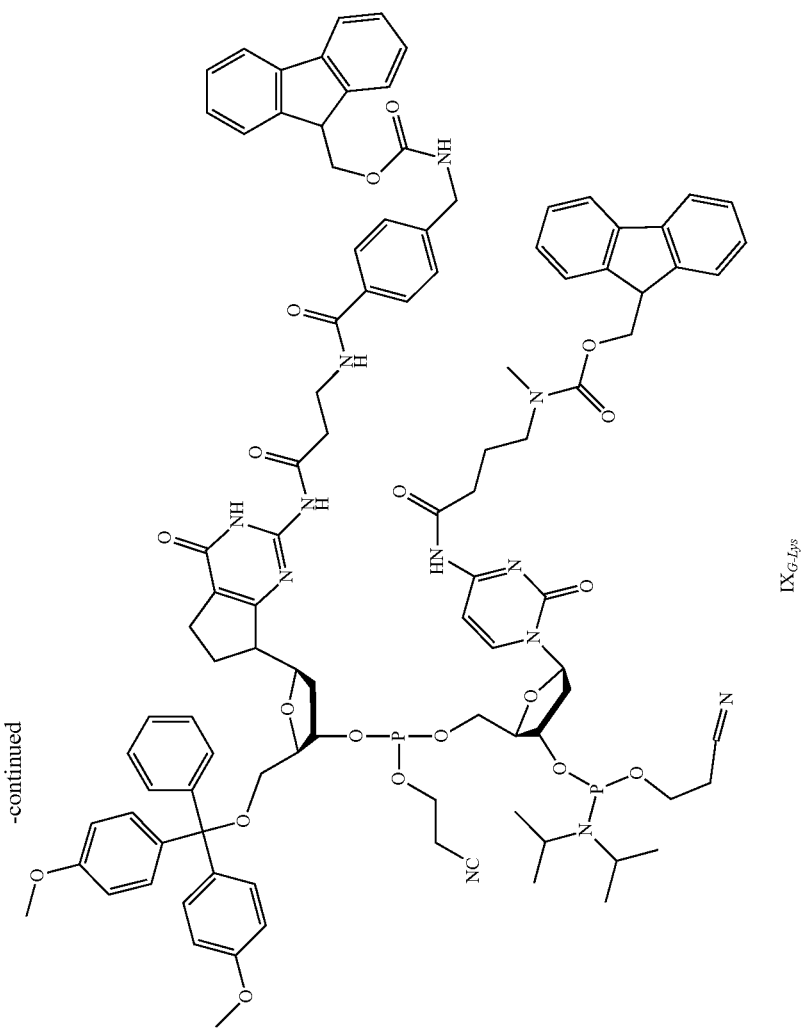
IX$_{G-Lys}$

<Synthesis of VIII$_{G-Lys}$> 9.47 g (7.92 mmol) of V$_{G-Lys}$ and 5.37 g (8.31 mmol) of VI$_C$ were dissolved in a mixed solution of dehydrated acetonitrile and dehydrated dichloromethane, and the solution was concentrated under reduced pressure three times. The residue was dissolved in 50 mL of a solution containing dehydrated acetonitrile and dehydrated dichloromethane in the ratio of 4:1. 2.77 g (39.6 mmol) of tetrazole was added to the solution while being cooled with ice, followed by agitating for 2 hours under cooling with ice. Subsequently, 3.2 mL of methanol was added thereto, followed by agitating for 5 minutes. The solution was diluted with dichloromethane and washed with water. The dichloromethane solution was concentrated under reduced pressure. The residue was dissolved in 41.6 mL of pyridine, and a solution (12.4 mL) of 1M hydrazine monohydrate in a solvent mixture containing pyridine and acetic acid in the ratio of 5:2 was added to the solution while being cooled with ice, followed by agitating at 0° C. for 1 hour. Until the disappearance of VII$_{G-Lys}$ was confirmed, 2.9 mL of the solution of 1M hydrazine monohydrate in a solvent mixture containing pyridine and acetic acid in the ratio of 5:2 was added to the solution every 30 minutes. Under cooling with ice, 25 mL of acetone was added thereto, followed by agitating at 0° C. for 10 minutes. Thereafter, the mixture was diluted with dichloromethane and washed with water. The dichloromethane solution was concentrated under reduced pressure. The residue was purified by medium pressure chromatography (dichloromethane:ethanol=96:4→92:8), to thereby obtain 10.3 g (79%) of target product VIII$_{G-Lys}$.

<Synthesis of IX$_{G-Lys}$> 9.93 g (6.04 mmol) of VIII$_{G-Lys}$ was dissolved in a mixed solution of dehydrated acetonitrile and dehydrated dichloromethane, and the solution was concentrated under reduced pressure three times. The residue was dissolved in 24 mL of dehydrated dichloromethane. Under cooling with ice, 37 mg (0.30 mmol) of dimethylaminopyridine and 1.12 mL (6.88 mmol) of diisopropylethylamine were added to the solution, and a diluted solution of 2-cyanoethyldiisopropylchlorophosphoroamidite (1.48 mL (6.65 mmol)) in dichloromethane (6 mL), followed by agitating at 0° C. for 5 hours. Subsequently, 2.4 mL of methanol was added thereto, followed by agitating for 30 minutes. The reaction solution was diluted with dichloromethane and washed with water. The dichloromethane solution was concentrated under reduced pressure, and the residue was purified (2% pyridine in dichloromethane and hexane (2:1):2% pyridine in dichloromethane=100:0→0:100, then 2% pyridine in dichloromethane:2% pyridine, 20% ethanol and 2% pyridine in dichloromethane=1:0→3:1), to thereby obtain 6.58 g (59%) of target product IX$_{G-Lys}$.

Scheme 7

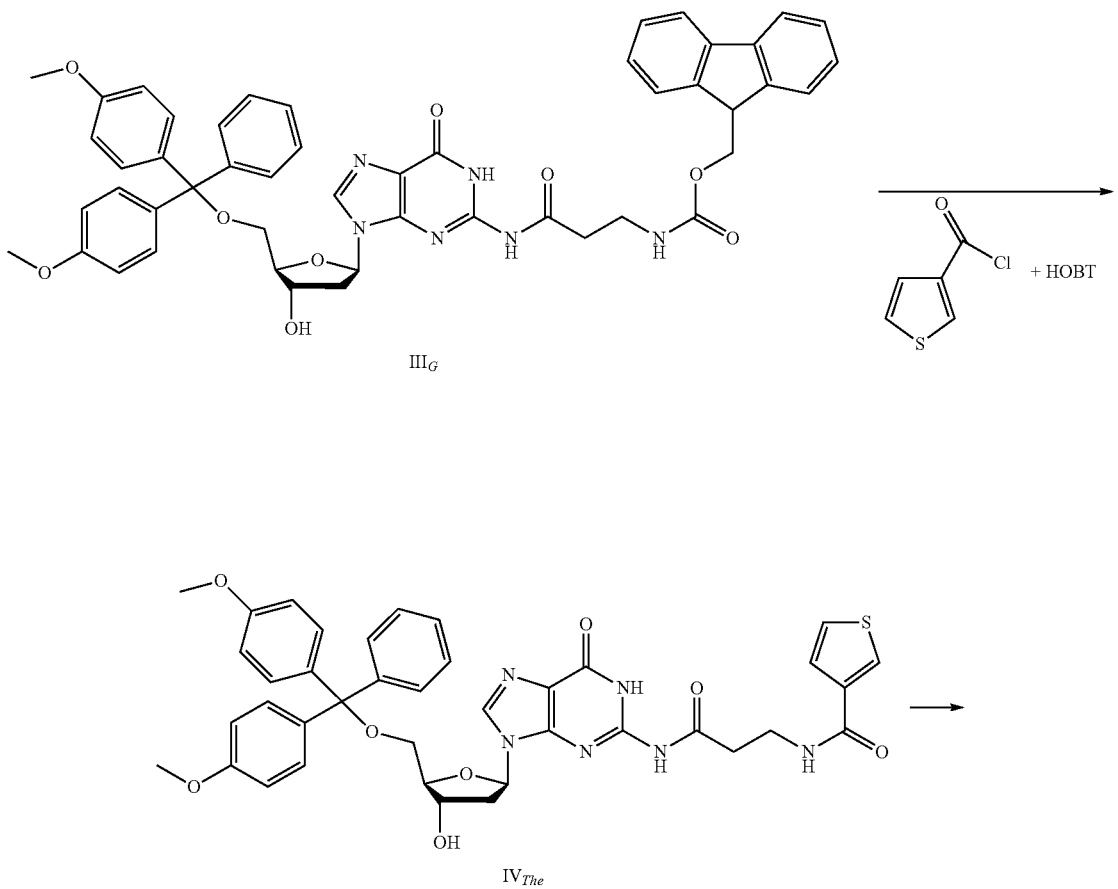

-continued
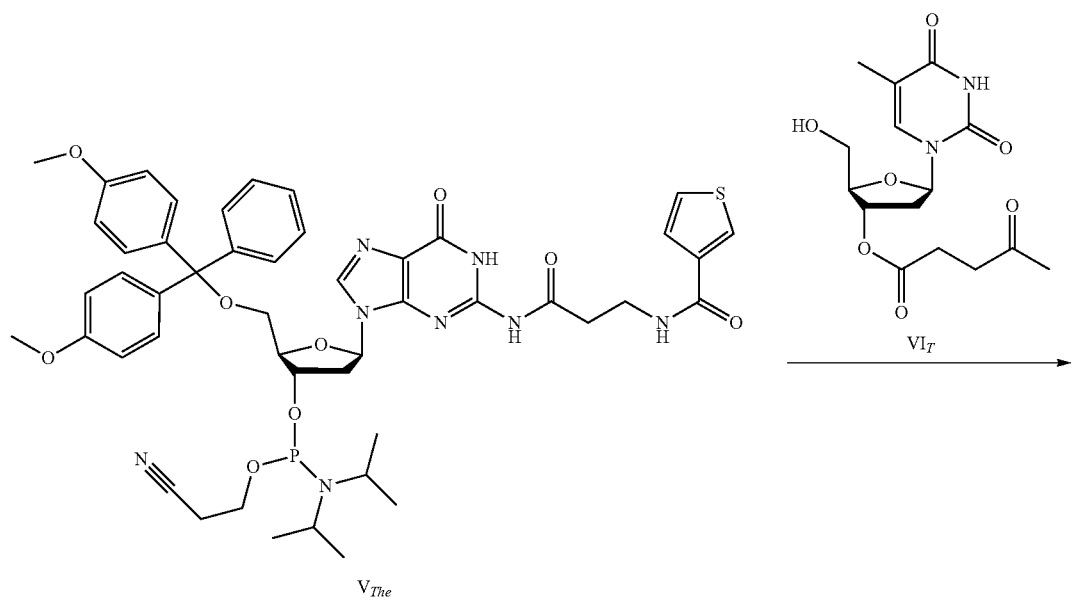
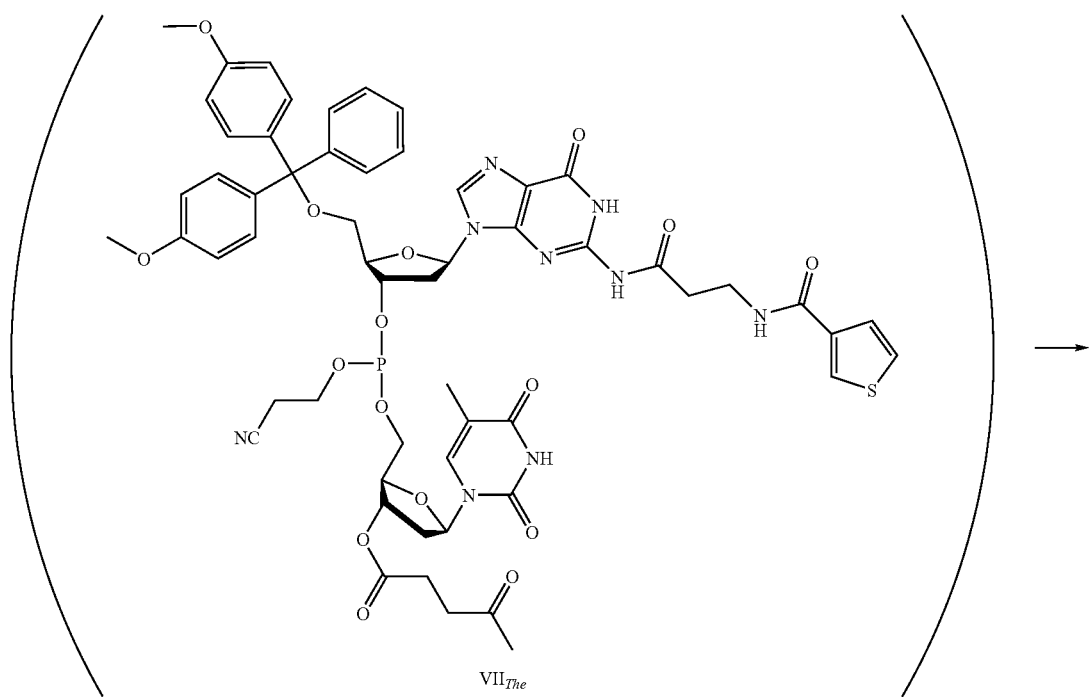

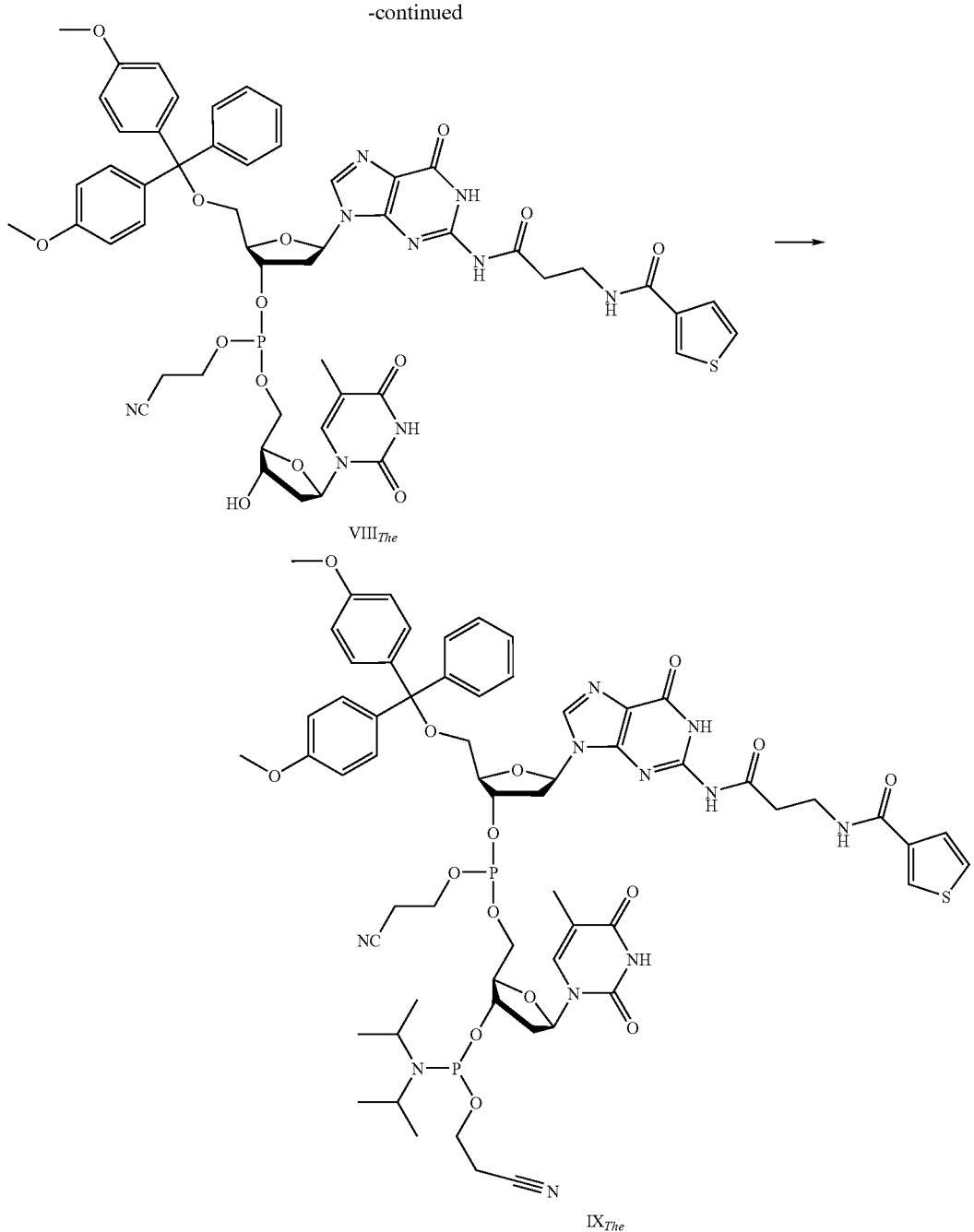

<Synthesis of IV$_{The}$> 10.35 g (12 mmol) of III$_G$ was dissolved in 24 mL of dehydrated dichloromethane, and 2.88 mL (18 mmol) of triethylsilane and 2.69 mL (18 mmol) of diazabicycloundecene were added to the solution, followed by agitating at room temperature for 30 minutes. 3.30 g (24 mmol) of triethylammonium hydrochloride was added to the reaction mixture to prepare reaction mixture A.

2.20 g (15 mmol) of 3-thenoyl chloride was dissolved in 36 mL of dehydrated dichloromethane, and 2.23 g (16.5 mmol) of N-hydroxybenzotriazole was added to the solution. Under cooling with ice, 1.82 g (22.5 mmol) of pyridine was added thereto, followed by agitating at room temperature for 30 minutes. The thus-prepared mixture was added to reaction mixture A. The reaction mixture was agitated at room temperature for 30 minutes. The reaction solution was diluted with dichloromethane and washed with water. The dichloromethane solution was concentrated under reduced pressure, and the residue was purified by medium pressure chromatography (dichloromethane:ethanol=92:8→88:12), to thereby obtain 7.23 g (80%) of target product IV$_{The}$.

<Synthesis of V$_{The}$> 7.26 g (9.66 mmol) of IV$_{The}$ was dissolved in a mixed solution of dehydrated acetonitrile and dehydrated dichloromethane, and the solution was concentrated under reduced pressure three times. The residue was dissolved in 40 mL of dehydrated dichloromethane. Under cooling with ice, 59 mg (0.48 mmol) of dimethlyaminopyridine and 1.92 mL (11.0 mmol) of diisopropylethylamine were added to the solution, and a solution of 2-cyanoethyldiisopropylchlorophosphoroamidite (2.37 mL (10.6 mmol)) in dichloromethane (9.7 mL) was added dropwise thereto over 5 minutes or longer. The mixed solution was agitated at 0° C. overnight. Subsequently, 1.9 mL of methanol was added thereto, followed by agitating for 30 minutes. The reaction solution was diluted with dichloromethane and washed with water. The dichloromethane solution was concentrated under reduced pressure, and the residue was purified by medium pressure chromatography (2% pyridine in ethyl acetate and hexane (2:1):2% pyridine and 5% ethanol in ethyl acetate=1: 0→0:1), to thereby obtain 7.69 g (84%) of target product $V_{The}$.

<Synthesis of $VIII_{The}$> 7.48 g (7.87 mmol) of $V_{The}$ and 2.81 g (8.26 mmol) of $VI_T$ were dissolved in dehydrated acetonitrile, and the solution was concentrated under reduced pressure three times. The residue was dissolved in 39 mL of dehydrated acetonitrile, and 2.75 g (39.3 mmol) of tetrazole was added to the solution while being cooled with ice, followed by agitating at room temperature for 1 hour. Subsequently, 3.1 mL of methanol was added thereto, followed by agitating for 5 minutes. The solution was diluted with dichloromethane and washed with water. The dichloromethane solution was concentrated under reduced pressure. The residue was dissolved in 41 mL of pyridine, and a solution (12.4 mL) of 1M hydrazine monohydrate in a solvent mixture containing pyridine and acetic acid in the ratio of 5:2 was added to the solution while being cooled with ice, followed by agitating at 0° C. for 1 hour. Until the disappearance of $VII_{The}$ was confirmed, 4.1 mL of the solution of 1M hydrazine monohydrate in a solvent mixture containing pyridine and acetic acid in the ratio of 5:2 was added to the solution every 30 minutes. Under cooling with ice, 28 mL of acetone was added thereto, followed by agitating at 0° C. for 10 minutes. Thereafter, the mixture was diluted with dichloromethane and washed with water. The dichloromethane solution was concentrated under reduced pressure. The residue was purified by medium pressure chromatography (dichloromethane: ethanol=95:5→9:1), to thereby obtain 5.44 g (64%) of target product $VIII_{The}$.

<Synthesis of $IX_{The}$> 5.49 g (5.03 mmol) of $VIII_{The}$ was dissolved in a mixed solution of dehydrated acetonitrile and dehydrated dichloromethane, and the solution was concentrated under reduced pressure three times. The residue was dissolved in 20 mL of dehydrated dichloromethane. Under cooling with ice, 31 mg (0.25 mmol) of dimethylaminopyridine and 1.00 mL (5.72 mmol) of diisopropylethylamine were added to the solution, and a diluted solution of 2-cyanoethyldiisopropylchlorophosphoroamidite (1.23 mL (5.53 mmol)) in dichloromethane (5.0 mL) was added thereto. The mixed solution was agitated at 0° C. for 1 day. Subsequently, 1.0 mL of methanol was added thereto, followed by agitating for 30 minutes. The reaction solution was diluted with dichloromethane and washed with water. The dichloromethane solution was concentrated under reduced pressure, and the residue was purified (2% pyridine in dichloromethane and hexane (2:1):2% pyridine in dichloromethane=100:0→0: 100, then 2% pyridine:20% ethanol and 2% pyridine in dichloromethane=1:0→4:1), to thereby obtain 4.30 g (66%) of target product $IX_{The}$.

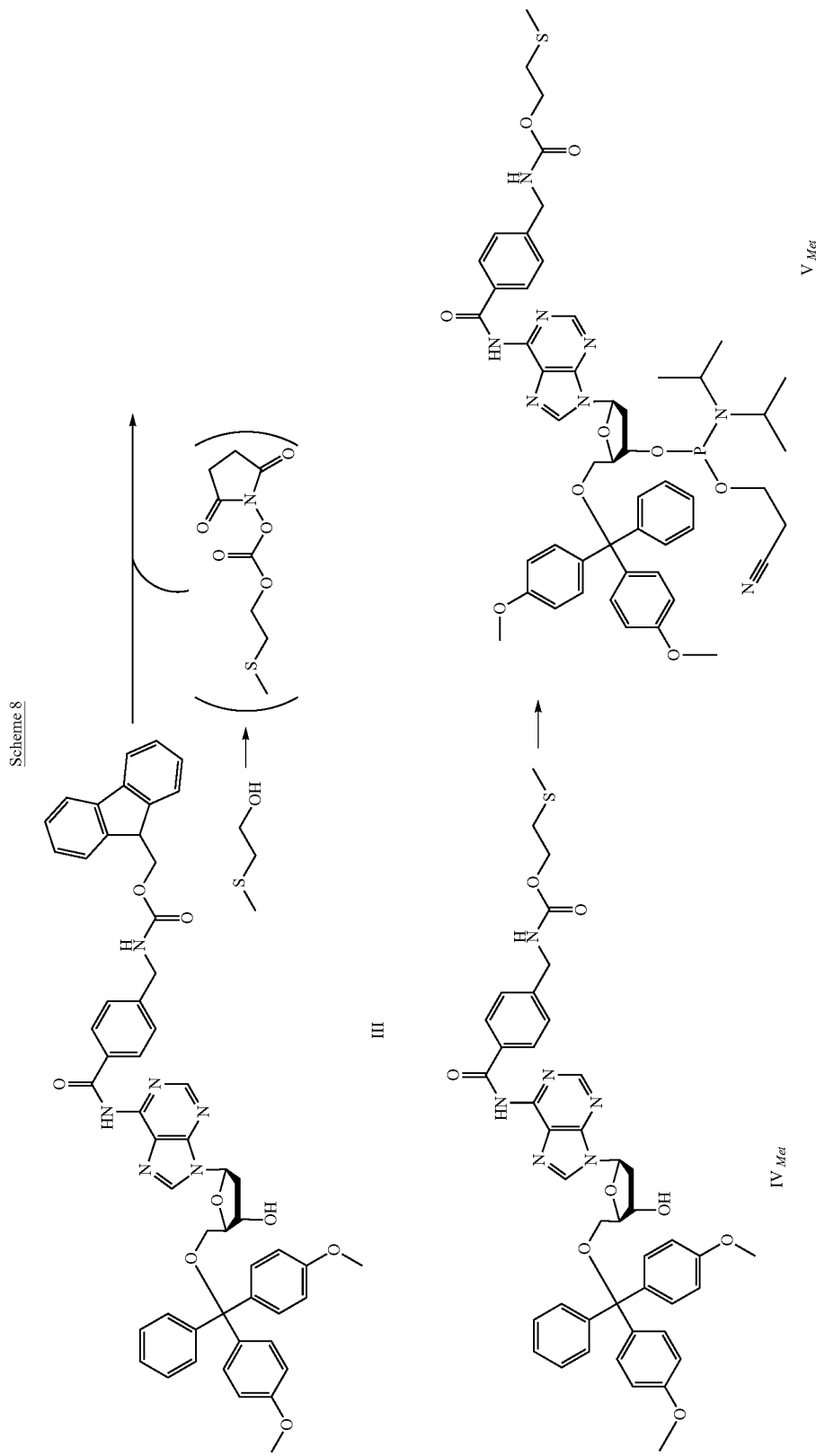

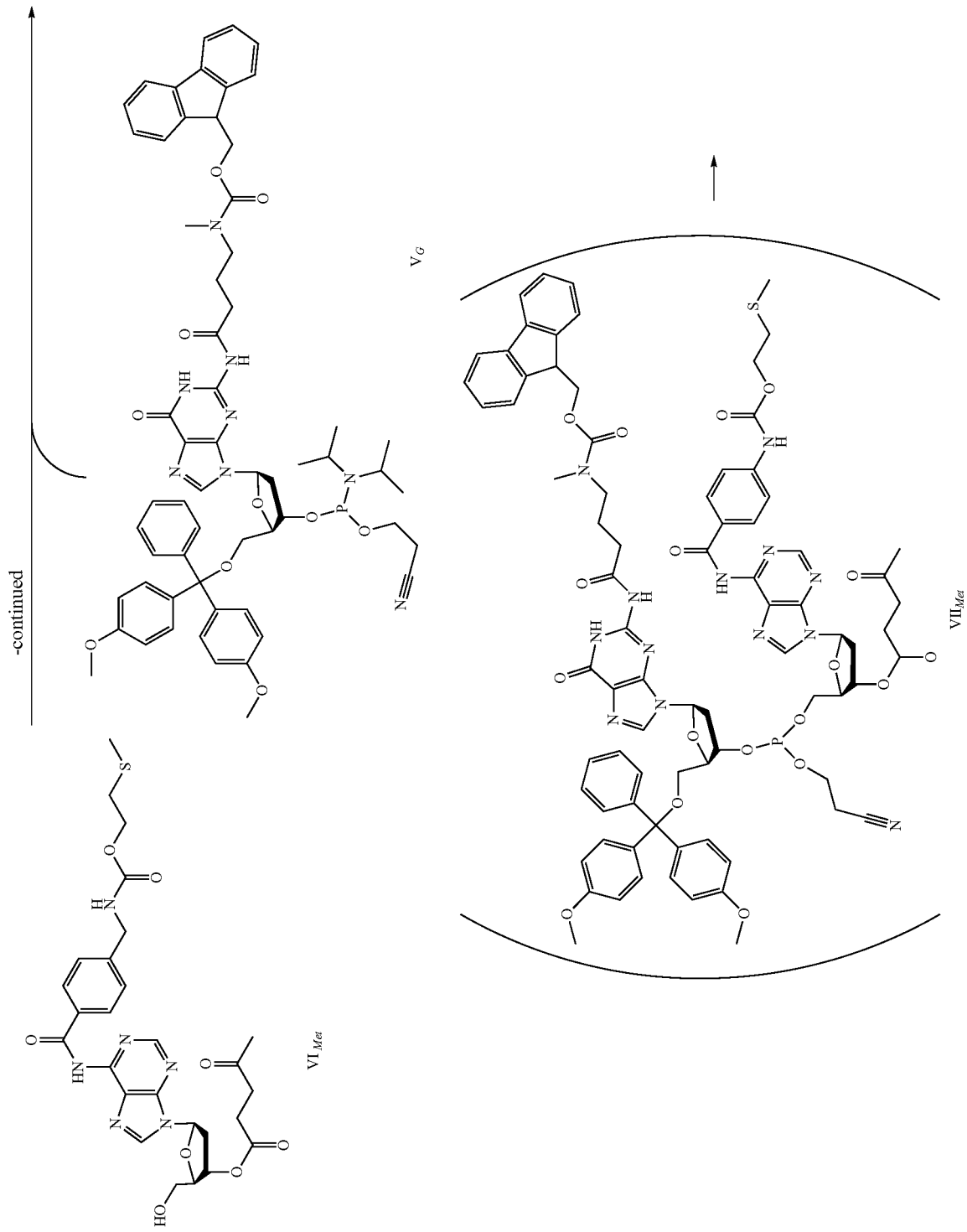

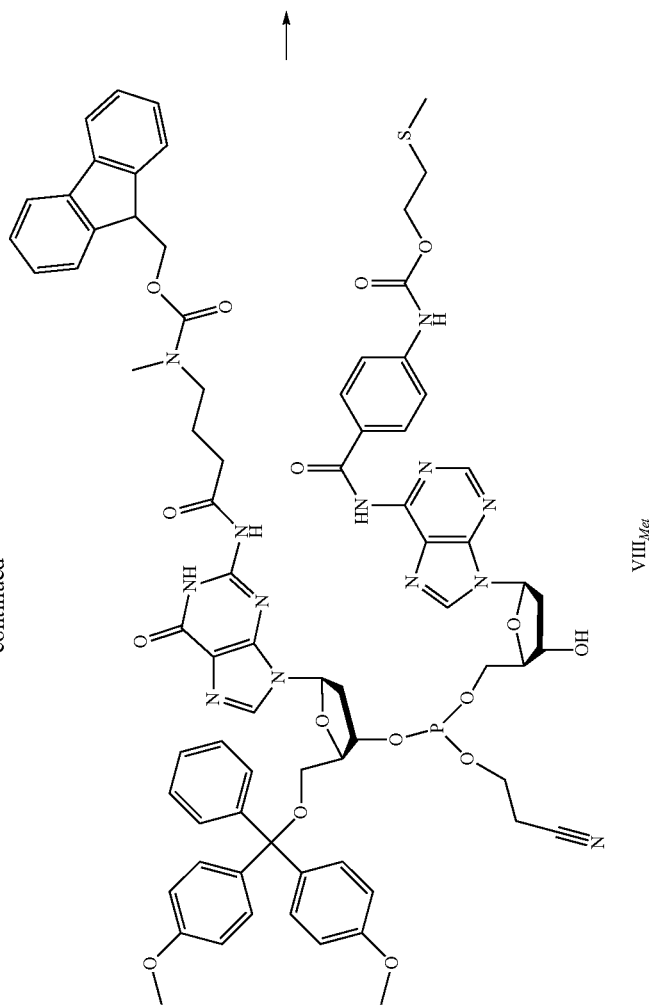

-continued
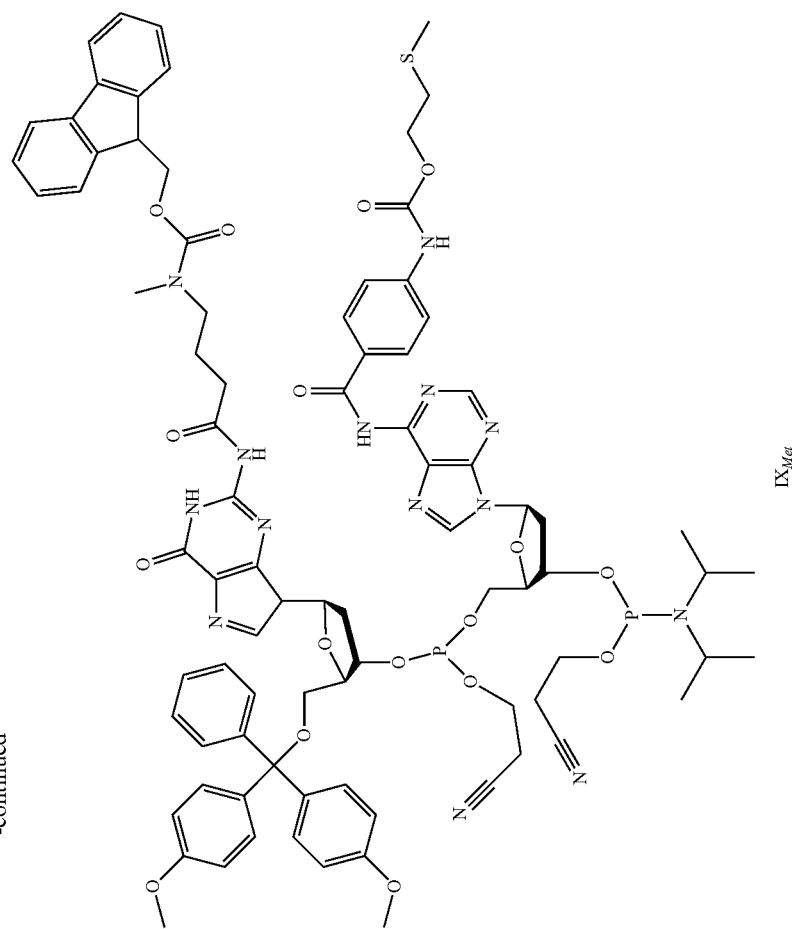
IX_Met

<Synthesis of IV$_{Met}$> 15.78 g (15 mmol) of III$_A$ was dissolved in 30 mL of dehydrated dichloromethane, and 3.59 mL (22.5 mmol) of triethylsilane and 3.37 mL (22.5 mmol) of diazabicycloundecene were added to the solution, followed by agitating at room temperature for 10 minutes. A mixed solution of trifluoroacetic acid (1.27 mL (16.5 mmol)), pyridine (1.45 mL (18 mmol)) and dichloromethane (10 mL) was added to the reaction mixture to prepare reaction mixture A.

2.23 g (7.5 mmol) of triphosgene was dissolved in 33 mL of dehydrated dichloromethane. Under cooling with ice, a solution of pyridine (2.0 mL (24.8 mmol)) and 2-(methylthio)ethanol (1.96 mL (22.5 mmol)) in dichloromethane (15 mL) was added dropwise to the solution. The reaction mixture was agitated at room temperature for 15 minutes. 3.11 g (27.0 mmol) of N-hydroxysuccinimide and 2.0 mL (24.8 mmol) of pyridine were added thereto, followed by agitating at room temperature for 15 minutes. The resultant mixture was added to reaction mixture A. The reaction mixture was agitated at room temperature for 8 hours. The reaction solution was diluted with dichloromethane and washed with water. The dichloromethane solution was concentrated under reduced pressure, and the residue was purified by medium pressure chromatography (dichloromethane:ethanol=98:2→93:7), to thereby obtain 8.37 g (69%) of target product IV$_{Met}$.

Synthesis of V$_{met}$> 8.25 g (10.25 mmol) of IV$_{Met}$ was dissolved in dehydrated acetonitrile, and the solution was concentrated under reduced pressure three times. The residue was dissolved in 41 mL of dehydrated dichloromethane. Under cooling with ice, 63 mg (0.51 mmol) of dimethylaminopyridine and 2.03 mL (11.7 mmol) of diisopropylethylamine were added to the solution, and a solution of 2-cyanoethyldiisopropylchlorophosphoroamidite (2.51 mL (11.3 mmol)) in dichloromethane (10 mL) was added dropwise thereto over 5 minutes or longer. The mixed solution was agitated at 0° C. for 45 minutes. Subsequently, 2.0 mL of methanol was added thereto, followed by agitating for 30 minutes. The reaction solution was diluted with dichloromethane and washed with water. The dichloromethane solution was concentrated under reduced pressure, and the residue was purified by medium pressure chromatography (2% pyridine in ethyl acetate and hexane (2:1):2% pyridine in ethyl acetate=1:0→0:1), to thereby obtain 8.10 g (79%) of target product V$_{Met}$.

<Synthesis of VI$_{Met}$> 15.3 g (19.3 mmol) of IV$_{Met}$ was dissolved in dehydrated dioxane, and the solution was concentrated under reduced pressure three times. The residue was dissolved in 96 mL of dehydrated dichloromethane. Then, 189 mg (1.55 mmol) of dimethylaminopyridine, 7.96 g (35.6 mmol) of dicyclohexylcarbodiimide and 3.96 mL (35.6 mmol) of levulinic acid were added to the solution. The mixed solution was agitated at room temperature for 1 hour. Subsequently, 3.9 mL of methanol was added thereto, followed by agitating for 15 minutes. The insoluble matter was removed by filtration, and the filtrate was concentrated under reduced pressure. The residue was dissolved in ethyl acetate, followed by washing with water. The ethyl acetate solution was concentrated under reduced pressure, and the residue was dissolved in 180 mL of dichloromethane. 9.65 mL of trifluoroacetic acid was added to the solution while being cooled with ice, followed by agitating at 0° C. for 30 minutes. Subsequently, 77 mL of methanol and 21 mL of pyridine were added thereto, followed by agitating at room temperature overnight. The reaction solution was washed with water, and the dichloromethane solution was concentrated under reduced pressure. The residue was purified by medium pressure chromatography (dichloromethane:ethanol=98:2→95:5), to thereby obtain 10.0 g (86.3%) of target product VI$_{Met}$.

<Synthesis of VIII$_{Met}$> 6.01 g (10 mmol) of VI$_{Met}$ and 11.46 g (10.5 mmol) of V$_G$ were dissolved in dehydrated acetonitrile, and the solution was concentrated under reduced pressure three times. The residue was dissolved in 50 mL of dehydrated acetonitrile, and 3.50 g (50 mmol) of tetrazole was added to the solution while being cooled with ice, followed by agitating at room temperature for 4 hours. Subsequently, 2.0 mL of methanol was added thereto, followed by agitating for 15 minutes. The solution was diluted with dichloromethane and washed with water. The dichloromethane solution was concentrated under reduced pressure. The residue was dissolved in 50 mL of pyridine, and a solution (15 mL) of 1M hydrazine monohydrate in a solvent mixture containing pyridine and acetic acid in the ratio of 5:2 was added to the solution while being cooled with ice, followed by agitating at 0° C. for 1 hour. Until the disappearance of VII$_{met}$ was confirmed, 5.0 mL of the solution of 1M hydrazine monohydrate in a solvent mixture containing pyridine and acetic acid in the ratio of 5:2 was added to the solution every 30 minutes. Under cooling with ice, 30 mL of acetone was added thereto, followed by agitating at 0° C. for 10 minutes. Thereafter, the mixture was diluted with dichloromethane and washed with water. The dichloromethane solution was concentrated under reduced pressure. The residue was purified by medium pressure chromatography (dichloromethane:ethanol=97:3→9:1), to thereby obtain 8.09 g (54%) of target product VIII$_{Met}$.

<Synthesis of IX$_{Met}$> 7.94 g (5.32 mmol) of VIII$_{Met}$ was dissolved in a mixed solution of dehydrated acetonitrile and dehydrated dichloromethane, and the solution was concentrated under reduced pressure three times. The residue was dissolved in 21 mL of dehydrated dichloromethane. Under cooling with ice, 32 mg (0.27 mmol) of dimethylaminopyridine and 1.06 mL (6.06 mmol) of diisopropylethylamine were added to the solution, and a diluted solution of 2-cyanoethyldiisopropylchlorophosphoroamidite (1.31 mL (5.85 mmol)) in dichloromethane (5.3 mL) was added thereto. The mixed solution was agitated at 0° C. for 2 days. Subsequently, 1.1 mL of methanol was added thereto, followed by agitating for 30 minutes. The reaction solution was diluted with dichloromethane and washed with water. The dichloromethane solution was concentrated under reduced pressure, and the residue was purified (2% pyridine in dichloromethane and hexane (2:1):2% pyridine in dichloromethane=100:0→0:100, then 2% pyridine:20% ethanol and 2% pyridine in dichloromethane=1:0→85:15), to thereby obtain 5.64 g (63%) of target product IX$_{Met}$.

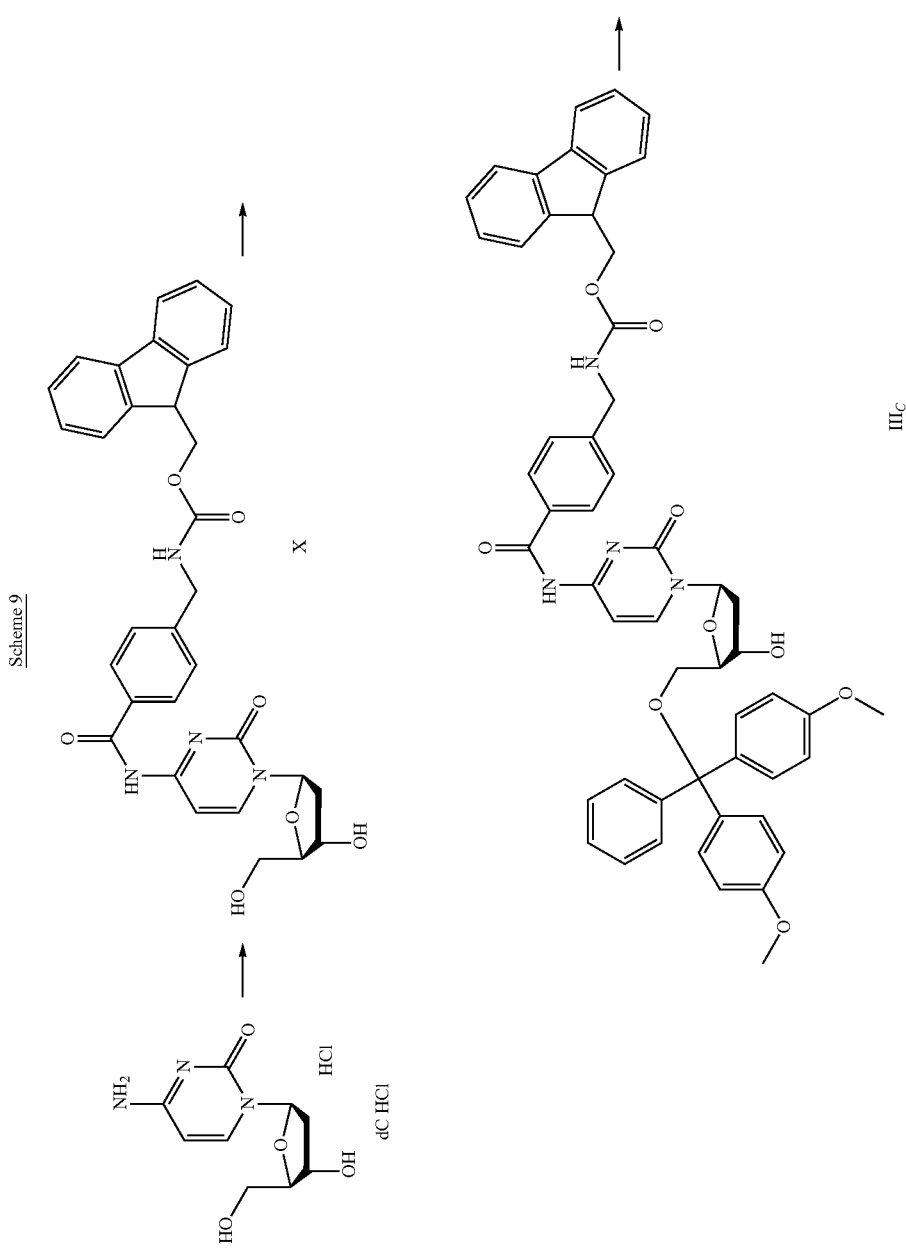

-continued
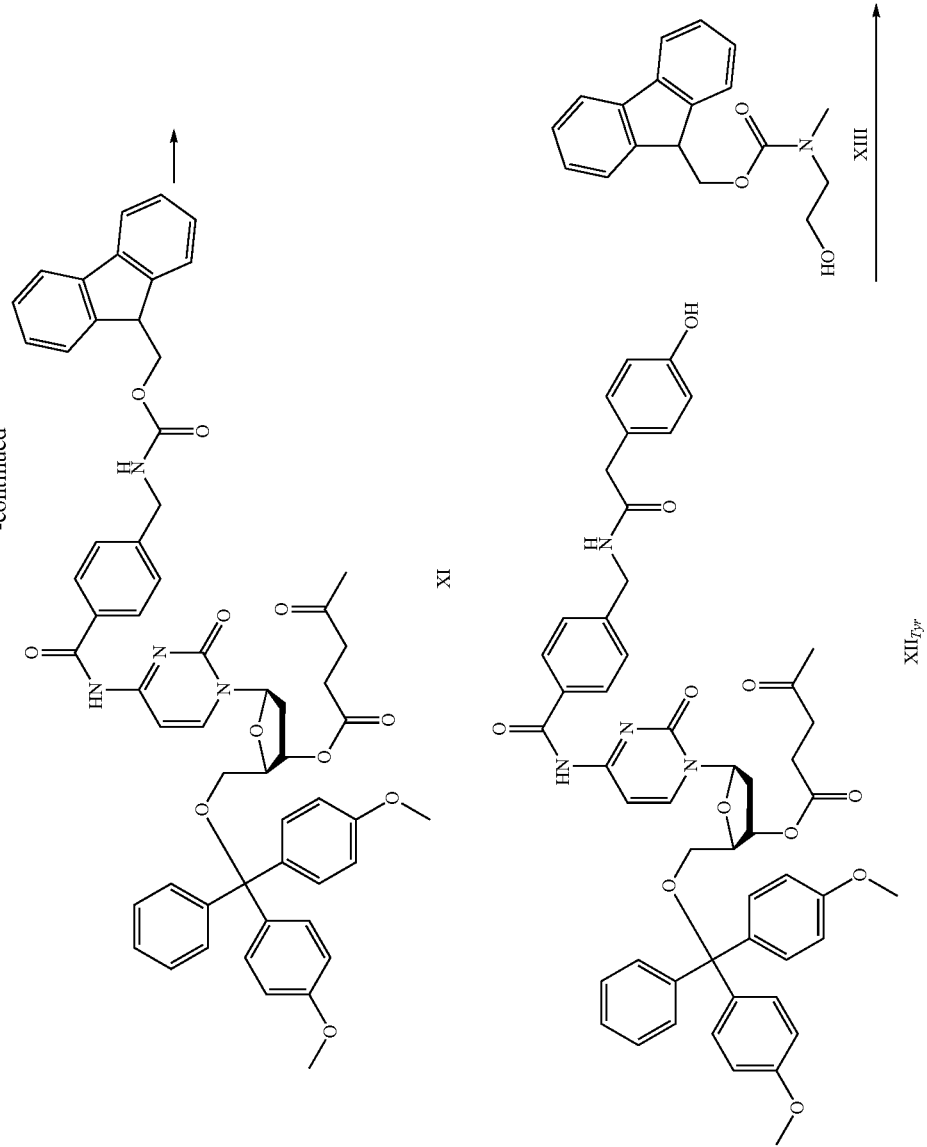

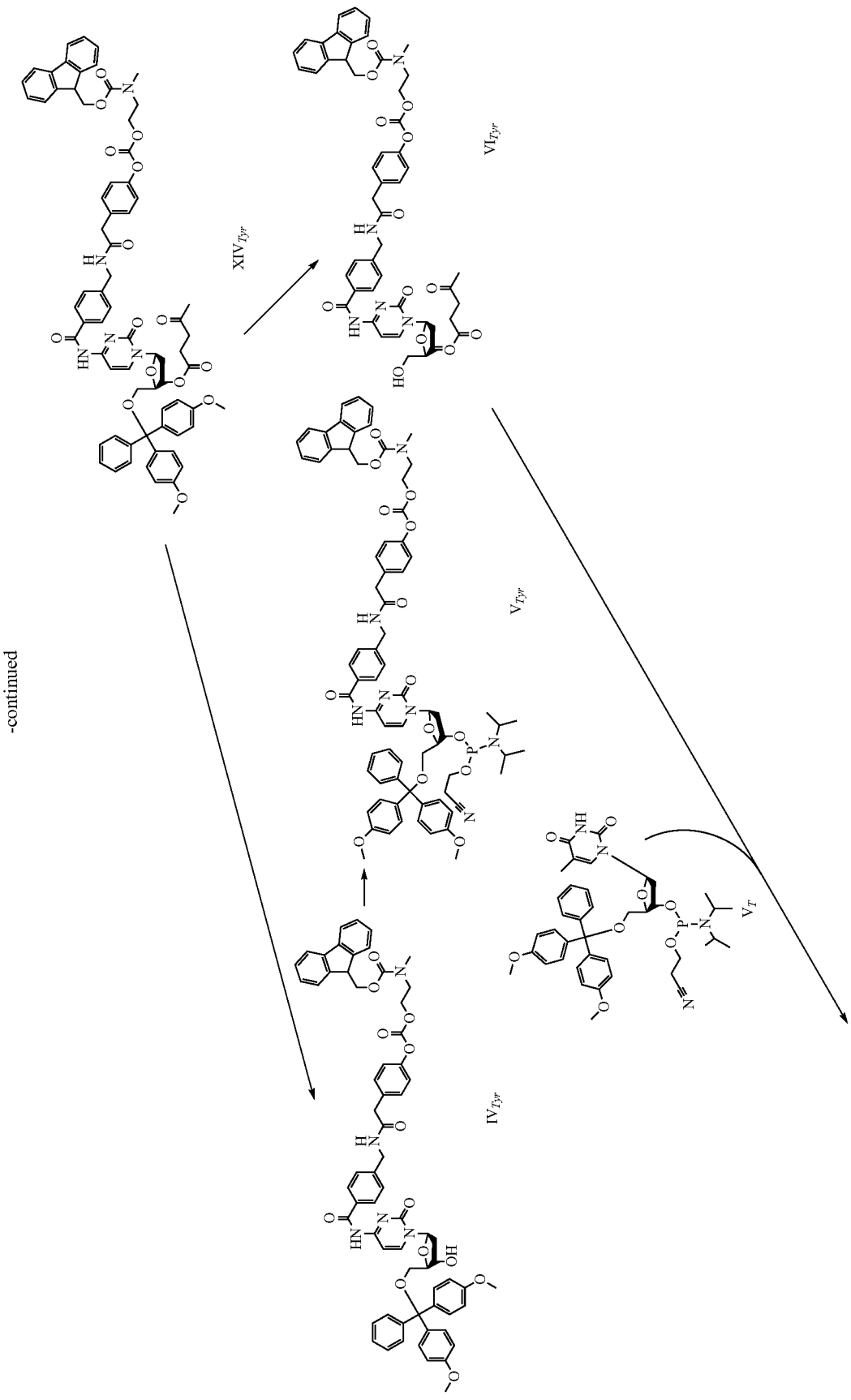

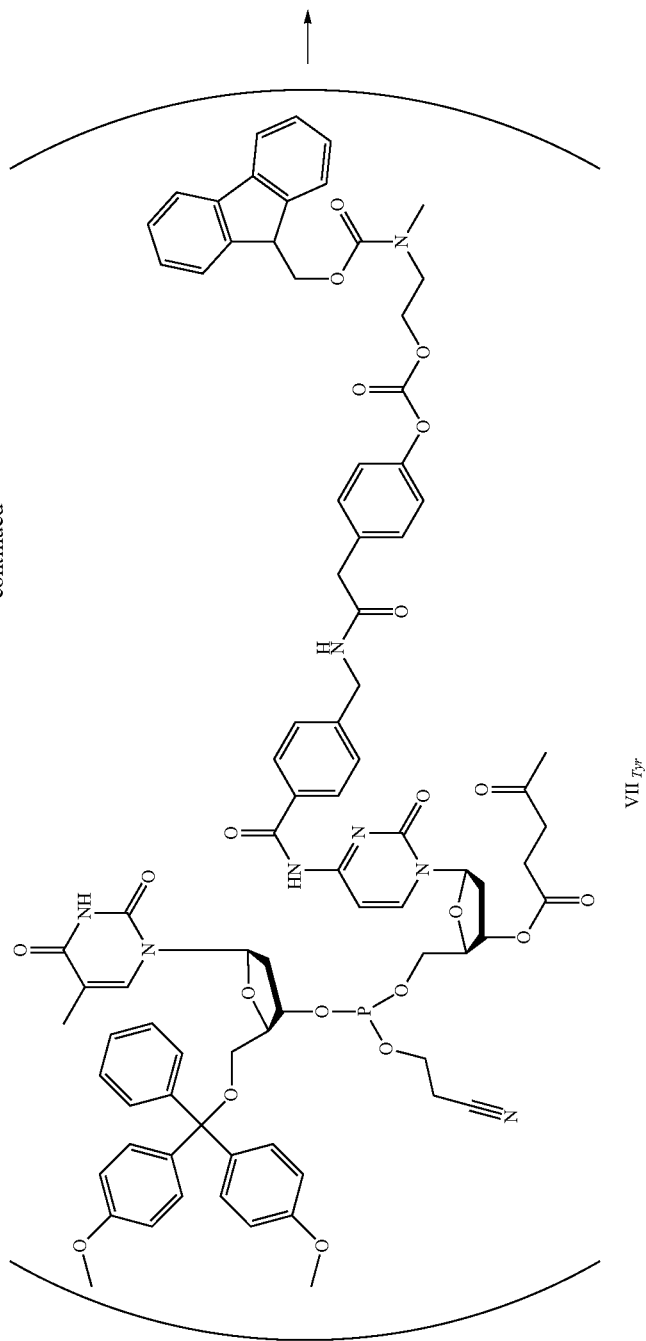

-continued
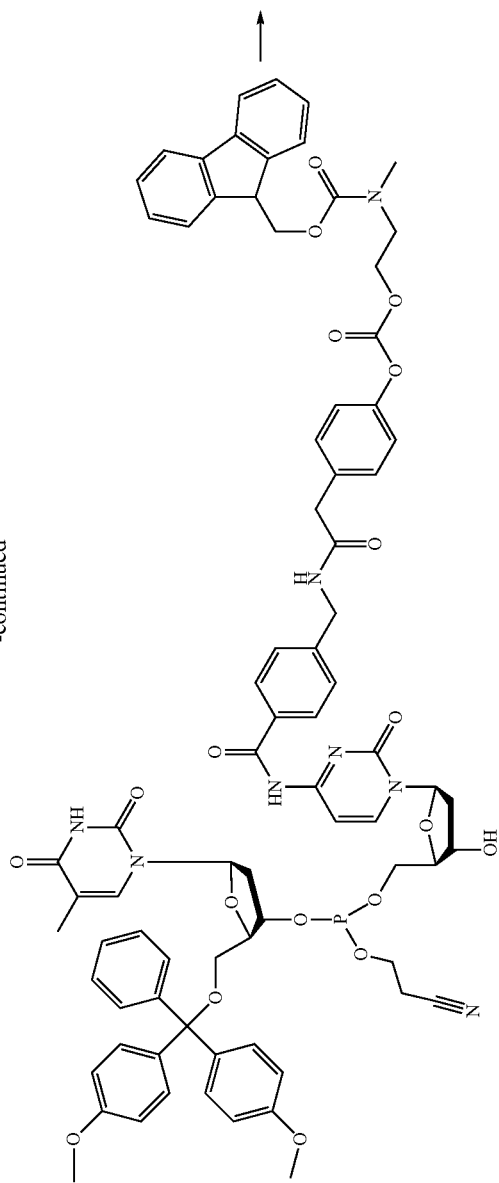
VIII_Tyr
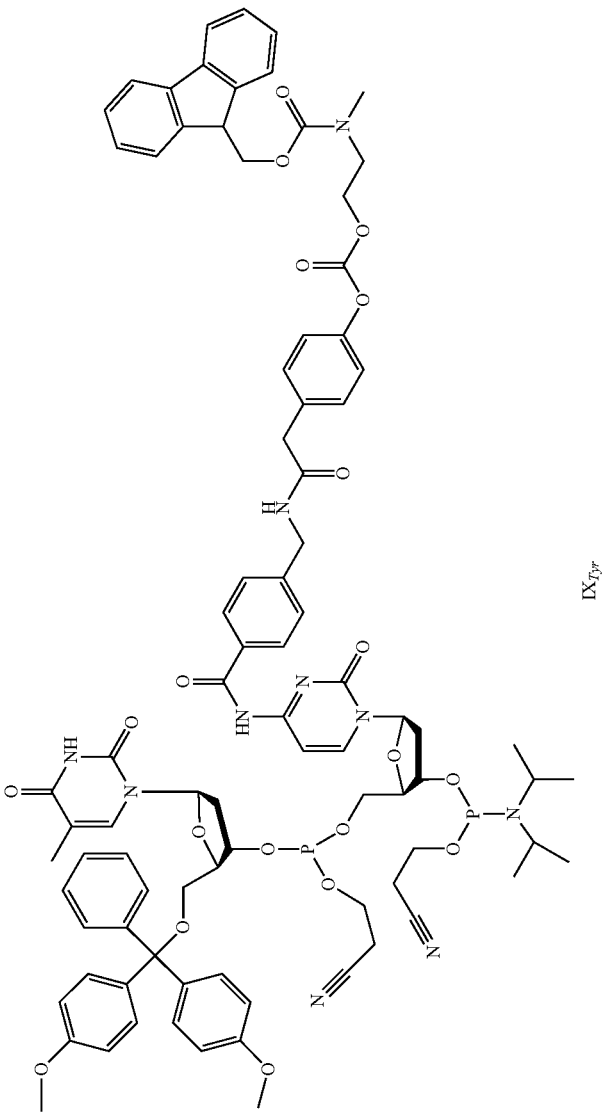
IX_Tyr

<Synthesis of X> 37.3 g (100 mmol) of 4-(FMOC-aminomethyl)benzoic acid was suspended in 400 mL of dehydrated dichloromethane, and 12.9 mL (150 mmol) of oxalyl chloride and 0.15 mL (1.9 mmol) of dimethylformamide were added to the suspension in an argon atmosphere, followed by agitating at room temperature for 7 hours. The reaction solution was concentrated under reduced pressure, and dehydrated toluene was added to the residue. Then, the mixture was concentrated under reduced pressure, and dissolved in 400 mL of dehydrated dichloromethane, to thereby obtain solution A.

29.0 g (110 mmol) of deoxycytidine hydrochloride was suspended in dehydrated pyridine, and an operation of concentrating the suspension under reduced pressure was repeated three times. The residue was suspended in 375 mL of dehydrated pyridine, and 46.4 mL (396 mmol) of trimethylchlorosilane was added to the suspension at 0° C., followed by agitating at room temperature for 1 hour. After cooled again to 0° C., the resultant solution was introduced into solution A under cooling with ice. The reaction mixture was agitated at room temperature for 1 hour. Under cooling with ice, 100 mL of water was added thereto, followed by agitating at room temperature for 8 hours. The resultant solution was concentrated under reduced pressure. 500 mL of ethyl acetate and 500 mL of water were added to the residue, followed by thoroughly agitating. The resultant mixture was filtrated to obtain 61.6 g of crude target product X.

<Synthesis of $III_C$> 61.6 g of the crude X was dissolved in dehydrated pyridine, and the solution was concentrated under reduced pressure three times. The residue was dissolved in 500 mL of dehydrated pyridine. Under cooling with ice, 33.92 g (100 mmol) of 4,4'-dimethoxytrityl chloride was added to the solution, followed by agitating at 0° C. for 8 hours. Subsequently, 20 mL of methanol was added thereto, followed by agitating for 30 minutes. The solution was concentrated under reduced pressure, diluted with ethyl acetate and washed with water. The ethyl acetate solution was concentrated under reduced pressure, and the residue was purified by medium pressure chromatography (ethyl acetate:ethanol=1:0→19:1), to thereby obtain 76.2 g (90%, 2 steps) of target product $III_C$.

<Synthesis of XI> 23.11 g (26.1 mmol) of $III_C$ was dissolved in dehydrated dioxane, and the solution was concentrated under reduced pressure three times. The residue was dissolved in 130 mL of dehydrated dioxane. Then, 226 mg (0.21 mmol) of dimethylaminopyridine, 10.78 g (52.2 mmol) of dicyclohexylcarbodiimide and 5.36 mL (52.2 mmol) of levulinic acid were added to the solution, followed by agitating at room temperature for 2 hours. 5 mL of methanol was added to the reaction solution, followed by agitating for 30 minutes. The insoluble matter was filtrated, and the filtrate was concentrated under reduced pressure, diluted with dichloromethane and washed with water. The dichloromethane solution was concentrated under reduced pressure, and the residue was purified by medium pressure chromatography (ethyl acetate:ethanol=1:0→19:1), to thereby obtain 25.2 g (98%) of target product XI.

<Synthesis of $XII_{Tyr}$> 17.86 g (15 mmol) of XI was dissolved in 38 mL of dehydrated dichloromethane, and 4.53 mL (28.3 mmol) of triethylsilane and 4.23 mL (28.3 mmol) of diazabicycloundecene were added to the solution, followed by agitating at room temperature for 10 minutes. A mixed solution of trifluoroacetic acid (2.39 mL (31.1 mmol)), pyridine (2.74 mL (34.0 mmol)) and dichloromethane (19 mL) was added to the reaction mixture to prepare reaction mixture A.

Separately, 5.74 g (37.7 mmol) of p-hydroxyphenylacetic acid and 5.21 g (45.3 mmol) of N-hydroxysuccinimide were dissolved in acetonitrile. 8.17 g (39.6 mmol) of dicyclohexylcarbodiimide was added to the solution while being cooled with ice, followed by agitating at 0° C. for 1 hour. The insoluble matter was removed by filtration and the filtrate was added to reaction mixture A. The reaction mixture was agitated at room temperature for 1 hour. Subsequently, 3.7 mL of piperidine was added thereto, followed by agitating for 30 minutes. The reaction solution is diluted with dichloromethane and washed with water. The dichloromethane solution was concentrated under reduced pressure, and the residue was purified by medium pressure chromatography (ethyl acetate:ethanol=19:1→9:1), to thereby obtain 5.03 g (64%) of target product $XII_{Tyr}$.

<Synthesis of XIII> 33.74 g (100 mmol) of FMOC-Suc was dissolved in 100 mL of dichloromethane, and 8.25 mL (105 mmol) of 2-(methylamino)ethanol was added to the solution while being cooled with ice, followed by agitating at room temperature overnight. The reaction solution was washed with water, and the dichloromethane solution was concentrated under reduced pressure. The residue was purified by medium pressure chromatography (ethyl acetate hexane=1:1→1:0), to thereby obtain 28.72 g (97%) of target product XIII.

<Synthesis of $XIV_{Tyr}$> 10.38 g (11.6 mmol) of $XII_{Tyr}$ was dissolved in dehydrated acetonitrile, and the solution was concentrated under reduced pressure three times. The residue was dissolved in 26 mL of dehydrated acetonitrile, and 2.36 mL (29.2 mmol) of pyridine was added to the solution to prepare reaction mixture A.

1.38 g (4.64 mmol) of triphosgene was dissolved in 16 mL of dehydrated dichloromethane, and a solution of pyridine (1.2 mL (14.6 mmol)) and XIII (4.14 g (13.92 mmol)) in dichloromethane (16 mL) was added dropwise to the solution while being cooled with ice. The reaction mixture was agitated at room temperature for 15 minutes. This reaction mixture was added to reaction mixture A at 0° C. The reaction mixture was agitated at room temperature for 15 minutes. The reaction solution was diluted with dichloromethane and washed with water. The dichloromethane solution was concentrated under reduced pressure, and the residue was purified by medium pressure chromatography (ethyl acetate:ethanol=94:6→91:9), to thereby obtain 12.0 g (85%) of target product $XIV_{Tyr}$.

<Synthesis of $IV_{Tyr}$> 9.14 g (7.5 mmol) of $XIV_{Tyr}$ was dissolved in 75 mL of pyridine, and a diluted solution (90 mL (pyridine:acetic acid=2:1) of hydrazine monohydrate (3.11 mL (64.3 mmol)), followed by agitating at room temperature for 5 minutes. 53 mL of acetone was added the mixture while being cooled with ice, followed by agitating at 0° C. for 10 minutes. The resultant mixture was diluted with dichloromethane and washed with water. The dichloromethane solution was concentrated under reduced pressure, and the residue was purified by medium pressure chromatography (dichloromethane:ethanol=1:0→19:1), to thereby obtain 6.26 g (75%) of target product $IV_{Tyr}$.

<Synthesis of $V_{Tyr}$> 5.72 g (5.10 mmol) of $IV_{Tyr}$ was dissolved in a mixed solution of dehydrated acetonitrile and dehydrated dichloromethane, and the solution was concentrated under reduced pressure three times. The residue was dissolved in 20 mL of dehydrated dichloromethane. Under cooling with ice, 31 mg (0.26 mmol) of dimethylaminopyridine and 1.01 mL (5.81 mmol) of diisopropylethylamine were added to the solution, and a solution of 2-cyanoethyldiisopropylchlorophosphoroamidite (1.25 mL (5.61 mmol)) in dichloromethane (5.1 mL) was added dropwise thereto over 5 minutes or longer. The mixed solution was agitated at 0° C. for 90 minutes. Subsequently, 1.0 mL of methanol was added thereto, followed by agitating for 15 minutes. The reaction solution was diluted with dichloromethane and washed with water. The dichloromethane solution was concentrated under reduced pressure, and the residue was purified by medium pressure chromatography (2% pyridine in ethyl acetate and hexane (2:1):2% pyridine in ethyl acetate=100:0→0:100, then 2% pyridine:20% ethanol 2% and pyridine in dichloromethane=1:0→17:3), to thereby obtain 5.72 g (85%) of target product $V_{Tyr}$.

<Synthesis of $VI_{Tyr}$> 12.0 g (9.82 mmol) of $XIV_{Tyr}$ was dissolved in 98 mL of dichloromethane, and 4.91 mL of trifluoroacetic acid was dissolved in the solution while being cooled with ice, followed by agitating at 0° C. for 45 minutes. Subsequently, 49 mL of methanol and 11 mL of pyridine were added thereto, followed by agitating at room temperature overnight. The reaction solution was washed with water, and the dichloromethane solution was concentrated under reduced pressure. The residue was purified by medium pressure chromatography (ethyl acetate:ethanol=93:7→86:14), to thereby obtain 8.24 g (92%) of target product $VI_{Tyr}$.

<Synthesis of $VIII_{Tyr}$> 8.24 g (9.00 mmol) of $VI_{Tyr}$ and 6.75 g (9.06 mmol) of $V_T$ were dissolved in dehydrated acetonitrile, and the solution was concentrated under reduced pressure three times. The residue was dissolved in 45 mL of dehydrated acetonitrile, and 3.15 g (45 mmol) of tetrazole was added to the solution while being cooled with ice, followed by agitating at room temperature for 30 minutes. Subsequently, 1.8 mL of methanol was added thereto, followed by agitating for 15 minutes. The solution was diluted with dichloromethane and washed with water. The dichloromethane solution was concentrated under reduced pressure. The residue was dissolved in 45 mL of pyridine, and a solution (13.5 mL) of 1M hydrazine monohydrate in a solvent mixture containing pyridine and acetic acid in the ratio of 5:2 was added to the solution while being cooled with ice, followed by agitating at 0° C. for 1 hour. Until the disappearance of $VII_{Tyr}$ was confirmed, 4.5 mL of the solution of 1M hydrazine monohydrate in a solvent mixture containing pyridine and acetic acid in the ratio of 5:2 was added to the solution every 30 minutes. Under cooling with ice, 23 mL of acetone was added thereto, followed by agitating at 0° C. for 10 minutes. Thereafter, the mixture was diluted with dichloromethane and washed with water. The dichloromethane solution was concentrated under reduced pressure. The residue was purified by medium pressure chromatography (dichloromethane:ethanol=97:3→9:1), to thereby obtain 11.25 g (85%) of target product $VIII_{Tyr}$.

<Synthesis of $IX_{Tyr}$> 10.72 g (7.34 mmol) of $VIII_{Tyr}$ was dissolved in a mixed solution of dehydrated acetonitrile and dehydrated dichloromethane, and the solution was concentrated under reduced pressure three times. The residue was dissolved in 29 mL of dehydrated dichloromethane. Under cooling with ice, 45 mg (0.40 mmol) of dimethylaminopyridine and 1.46 mL (8.35 mmol) of diisopropylethylamine were added to the solution, and a diluted solution of 2-cyanoethyldiisopropylchlorophosphoroamidite (1.80 mL, (8.07 mmol)) in dichloromethane (7.3 mL) was added thereto, followed by agitating at 0° C. for 2 hours. Subsequently, 1.5 mL of methanol was added thereto, followed by agitating for 30 minutes. The reaction solution was diluted with dichloromethane and washed with water. The dichloromethane solution was concentrated under reduced pressure, and the residue was purified (2% pyridine in dichloromethane and hexane (2:1):2% pyridine in dichloromethane=100:0→0: 100, then 2% pyridine:20% ethanol and 2% pyridine in dichloromethane=1:0→80:20), to thereby obtain 7.36 g (60%) of target product $IX_{Tyr}$.

Scheme 10

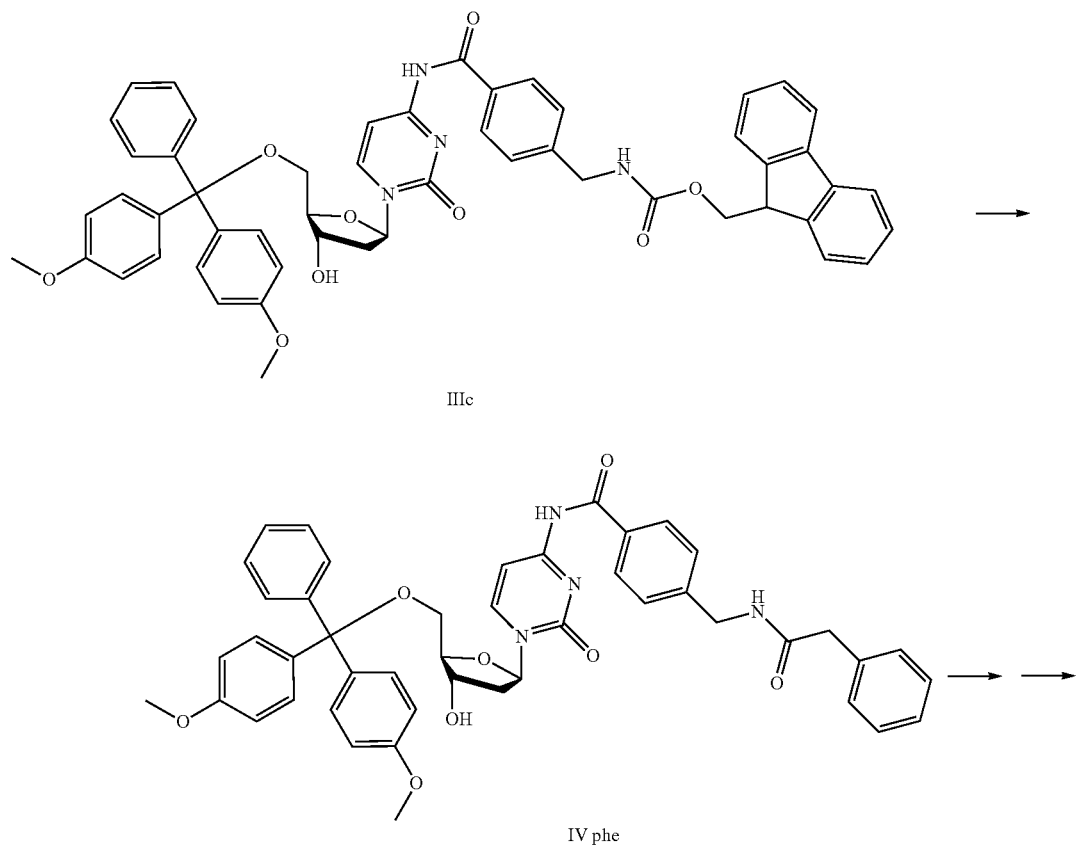

IIIc

IV phe

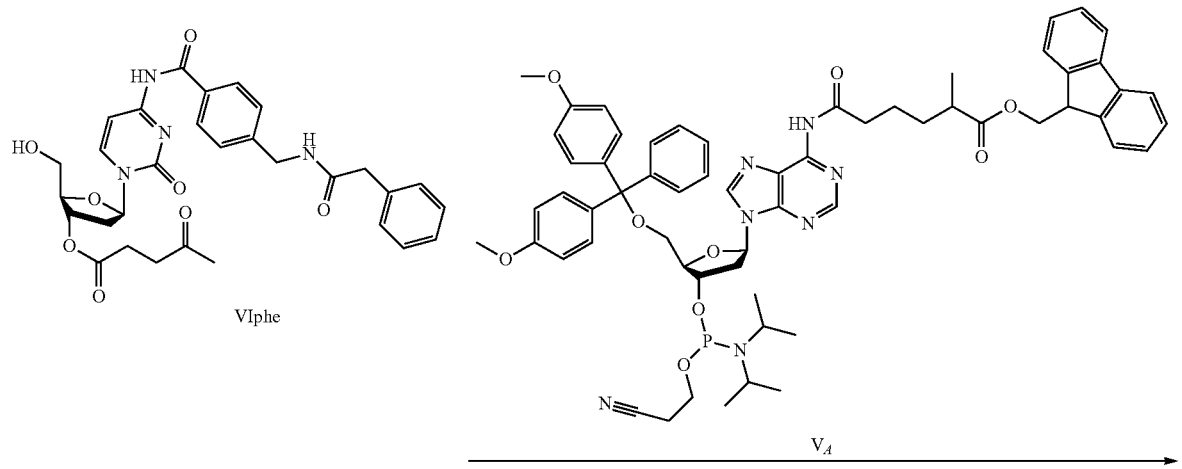
VIphe
$V_A$
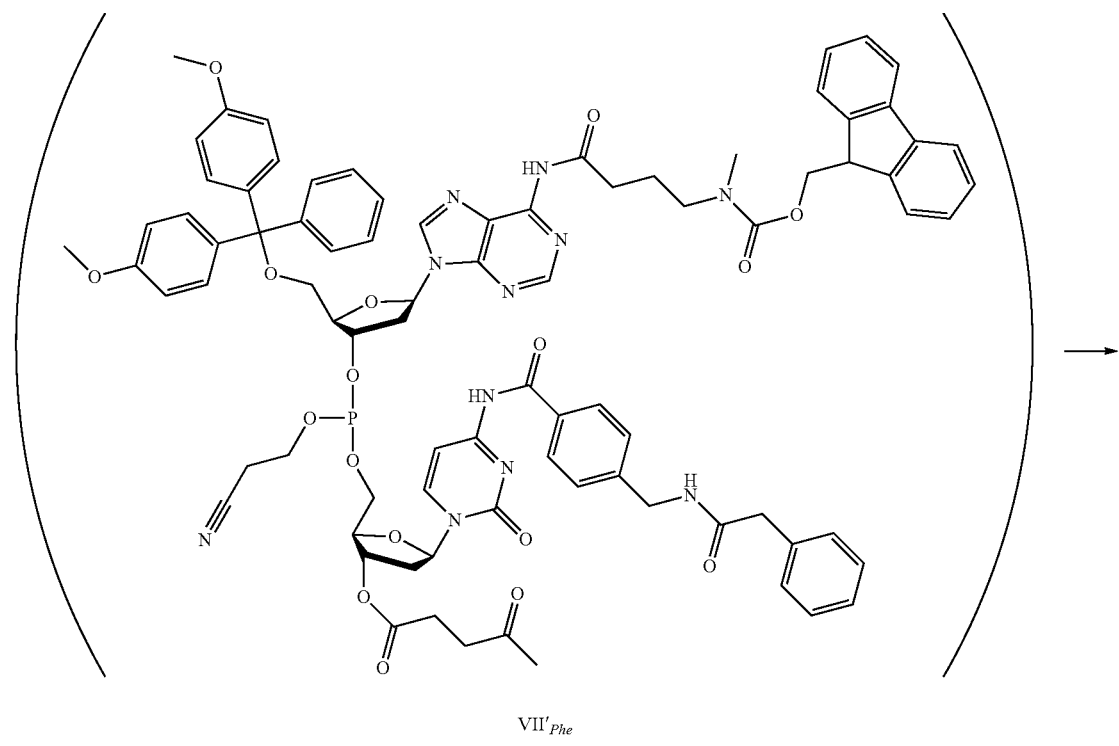
VII'_Phe

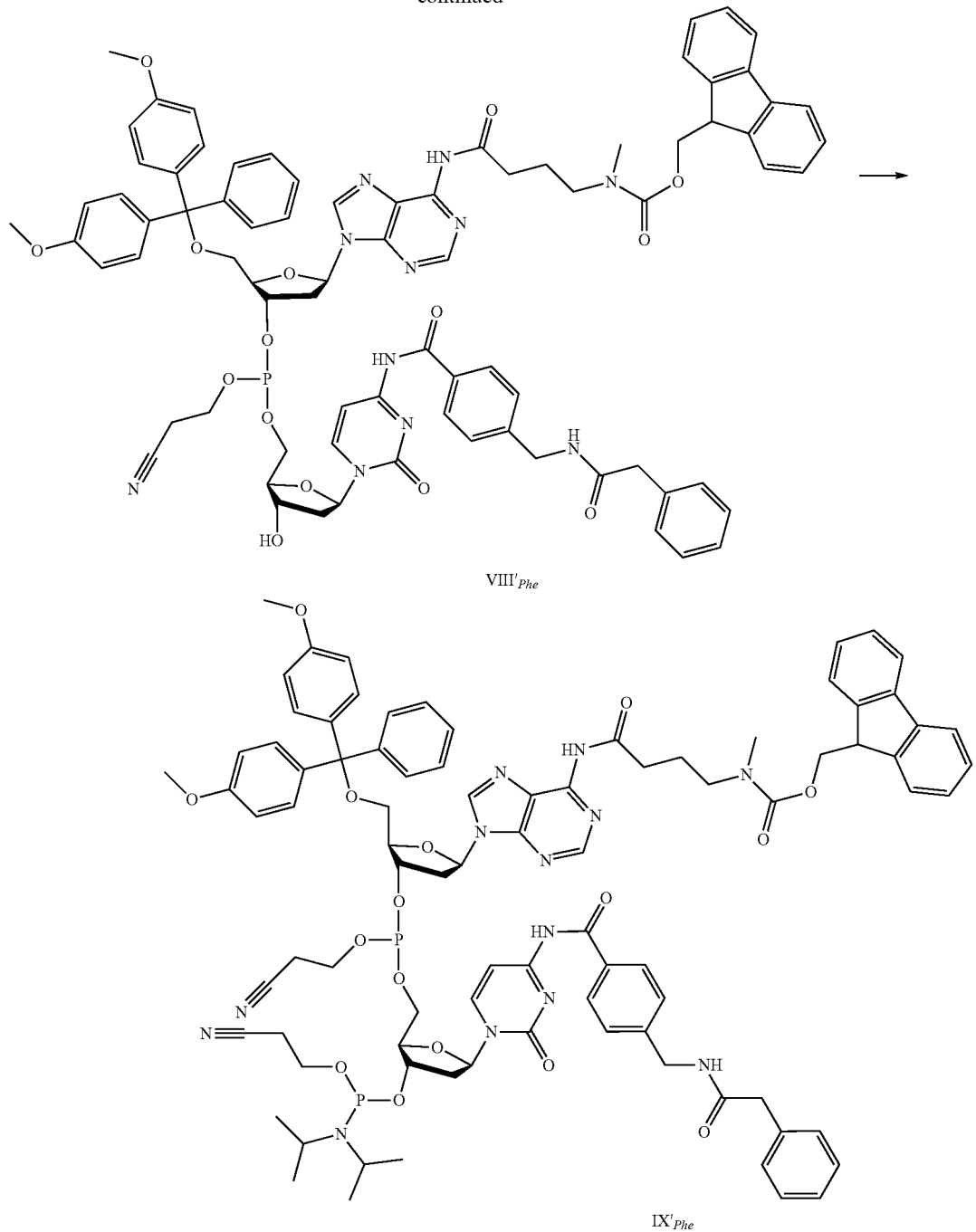

<Synthesis of IV$_{Phe}$> 35.4 g (40 mmol) of III$_C$ was dissolved in 80 mL of dehydrated dichloromethane, and 9.58 mL (60.0 mmol) of triethylsilane and 8.97 mL (60.0 mmol) of diazabicycloundecene were added to the solution, followed by agitating at room temperature for 10 minutes. 4.13 g (30.0 mmol) of triethylaminen hydrochloride was added to the reaction mixture to prepare reaction mixture A.

Separately, 6.33 g (55.0 mmol) of N-hydroxysuccinimide and 9.09 mL (55.0 mL) of diisopropylethylamine were dissolved in acetonitrile, and 6.61 mL (50.0 mmol) of phenylacetyl chloride was added to the solution while being cooled with ice, followed by agitating at room temperature for 15 minutes. The insoluble matter was removed by filtration and the filtrate was added to reaction mixture A. The reaction mixture was agitated at room temperature for 20 minutes. Subsequently, 1.19 mL of piperidine was added thereto, followed by agitating for 10 minutes. The reaction solution was diluted with dichloromethane and washed with water. The dichloromethane solution was concentrated under reduced pressure, and the residue was purified by medium pressure chromatography (dichloromethane:ethanol=49:1→9:1), to thereby obtain 29.44 g (94%) of target product IV$_{Phe}$.

<Synthesis of VI$_{Phc}$> 13.73 g (17.58 mmol) of IV$_{Phc}$ was dissolved in dehydrated dioxane, and the solution was concentrated under reduced pressure three times. The residue was dissolved in 90 mL of dehydrated dioxane, and 172 mg of dimethylaminopyridine, 7.26 g (35.2 mmol) of dicyclohexylcarbodiimide and 3.61 mL (35.2 mmol) of levulinic acid were added to the solution, followed by agitating at room temperature for 1 hour. The reaction solution was added to 3.5 mL of methanol, followed by agitating for 1 hour. The insoluble matter was removed by filtration and the filtrate was concentrated under reduced pressure. The residue was dissolved in 170 mL of dichloromethane, and 8.79 mL of trifluoroacetic acid was added to the solution while being cooled with ice, followed by agitating at 0° C. for 45 minutes. 70 mL of methanol and 38.7 mL of pyridine were added to the reaction mixture, followed by agitating at room temperature for 4 hours. The reaction mixture was washed with water, and the dichloromethane solution was concentrated under reduced pressure. The residue was suspended in 150 mL of ethyl acetate, and the insoluble matter (i.e., $VI_{Phc}$) was obtained by filtration. In this manner, target product $VI_{Phe}$ was obtained in an amount of 8.92 g (85%, containing about 5% (mol/mol) dicyclohexylcarbodiurea (DCU)).

<Synthesis of $VIII'_{Phe}$> 6.24 g (10 mmol) of $VI_{Phe}$ (containing DCU) and 10.75 g (10 mmol) of $V_A$ were dissolved in dehydrated acetonitrile/dehydrated dichloromethane, and the solution was concentrated under reduced pressure three times. The residue was dissolved in a mixture containing 40 mL of dehydrated acetonitrile and 10 mL of dichloromethane, and 3.50 g (50.0 mmol) of tetrazole was added to the solution while being cooled with ice, followed by agitating at room temperature for 1 hour. Subsequently, 2.0 mL of methanol was added thereto, followed by agitating for 15 minutes. The solution was diluted with dichloromethane and washed with water. The dichloromethane solution was concentrated under reduced pressure. The residue was dissolved in 50 mL of pyridine, and a solution (51 mL) of 1M hydrazine monohydrate in a solvent mixture containing pyridine and acetic acid in the ratio of 5:2 was added to the solution while being cooled with ice, followed by agitating at 0° C. for 2 hours. Under cooling with ice, 10 mL of acetone was added thereto, followed by agitating at 0° C. for 10 minutes. Then, the resultant mixture was diluted with dichloromethane and washed with water. The dichloromethane solution was concentrated under reduced pressure. The residue was purified by medium pressure chromatography (dichloromethane:ethanol=95:5→9:1), to thereby obtain 8.99 g (62%) of target product $VIII'_{Phe}$.

<Synthesis of $IX_{Phc}$> 8.61 g (5.93 mmol) of $VIII'_{Phc}$ was dissolved in a mixed solution of dehydrated acetonitrile and dehydrated dichloromethane, and the solution was concentrated under reduced pressure three times. The residue was dissolved in 24 mL of dehydrated dichloromethane. Under cooling with ice, 36 mg (0.30 mmol) of dimethylaminopyridine and 1.24 mL (7.12 mmol) of diisopropylethylamine were added to the solution, and a diluted solution of 2-cyanoethyldiisopropylchlorophosphoroamidite (1.46 mL (6.52 mmol)) in dichloromethane (6.0 mL) was added thereto. The mixed solution was agitated at 0° C. for 2 hours. Subsequently, 1.2 mL of methanol was added thereto, followed by agitating for 30 minutes. The reaction solution was diluted with dichloromethane and washed with water. The dichloromethane solution was concentrated under reduced pressure, and the residue was purified (2% pyridine in dichloromethane and hexane (1:1):2% pyridine in dichloromethane=100:0→0:100, then 2% pyridine:20% ethanol and 2% pyridine in dichloromethane=1:0→80:20), to thereby obtain 7.45 g (76%) of target product $IX'_{Phe}$.

Scheme 11
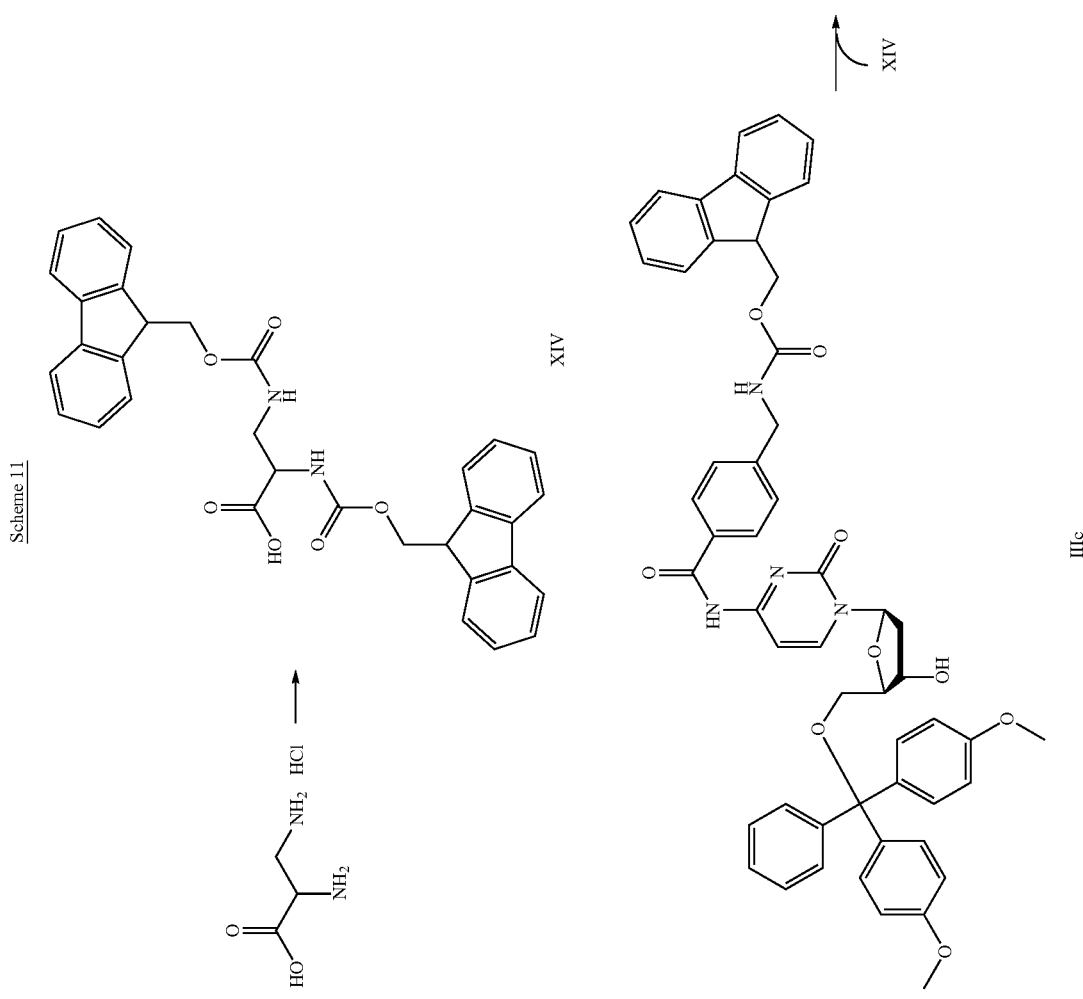

-continued
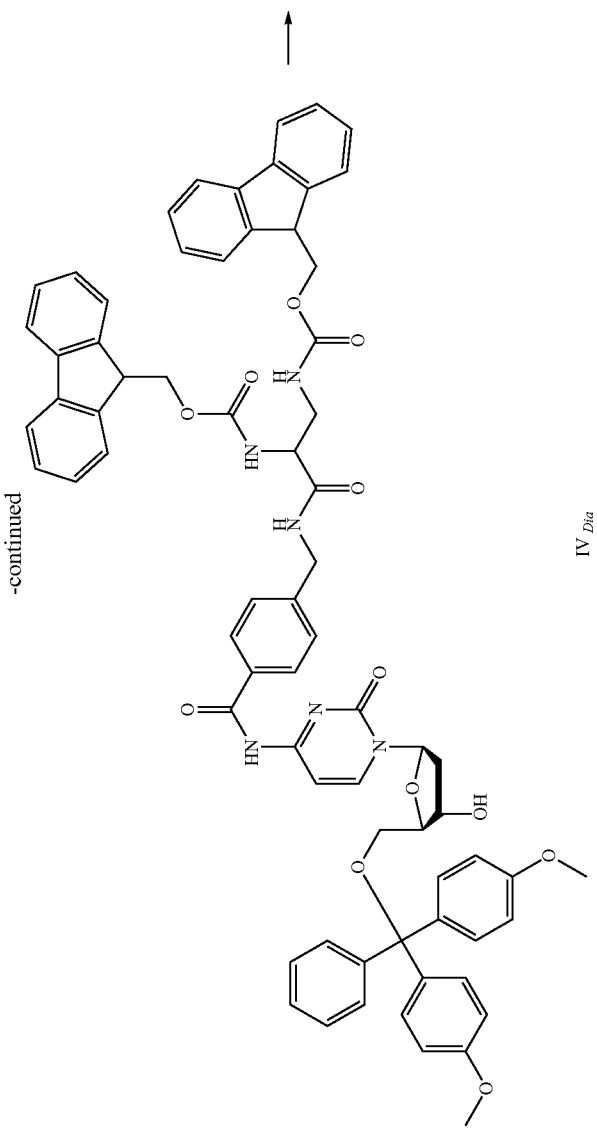
IV $_{Dia}$

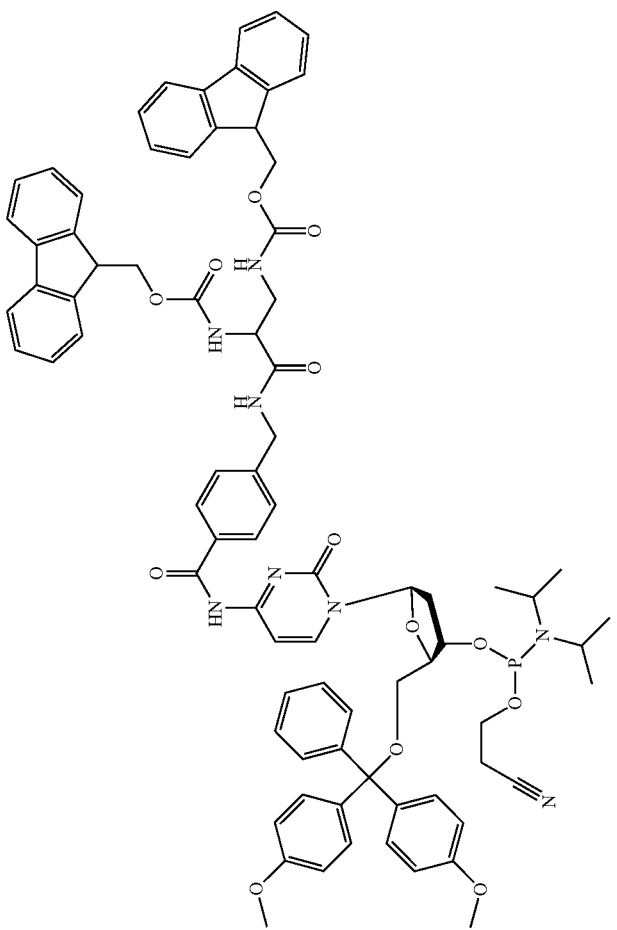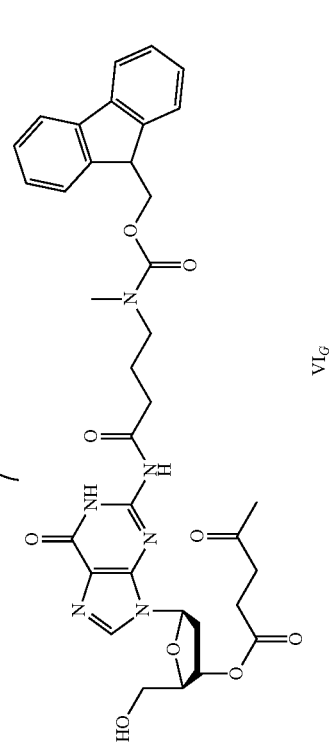

-continued
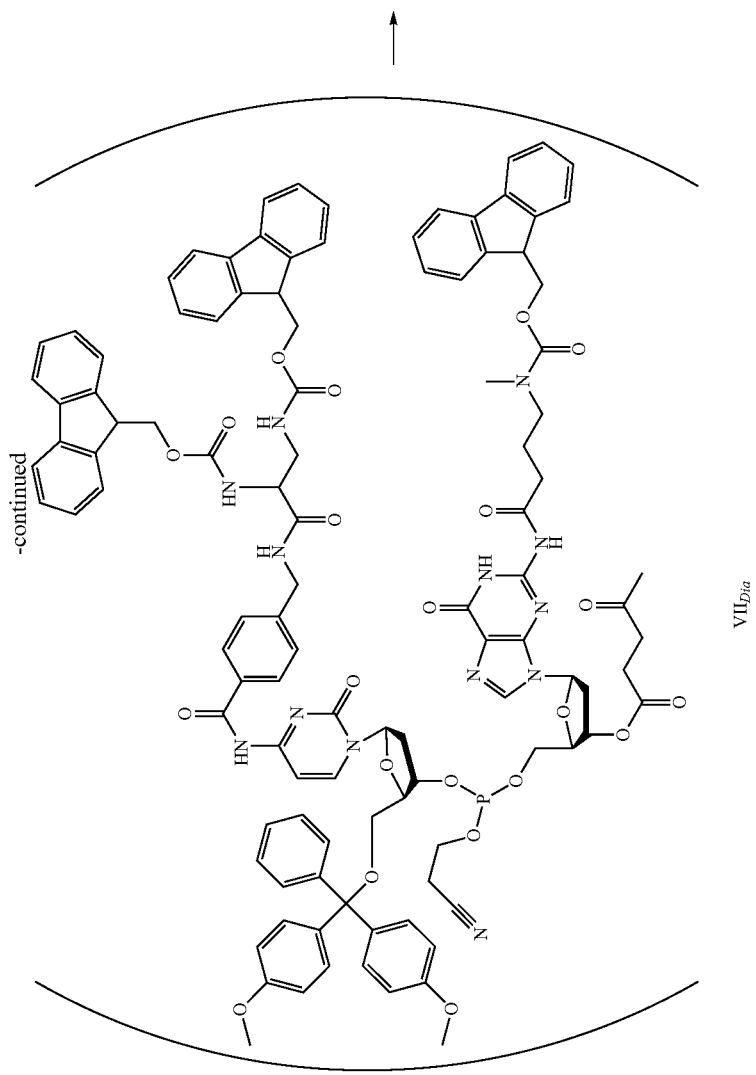
VII_Dia

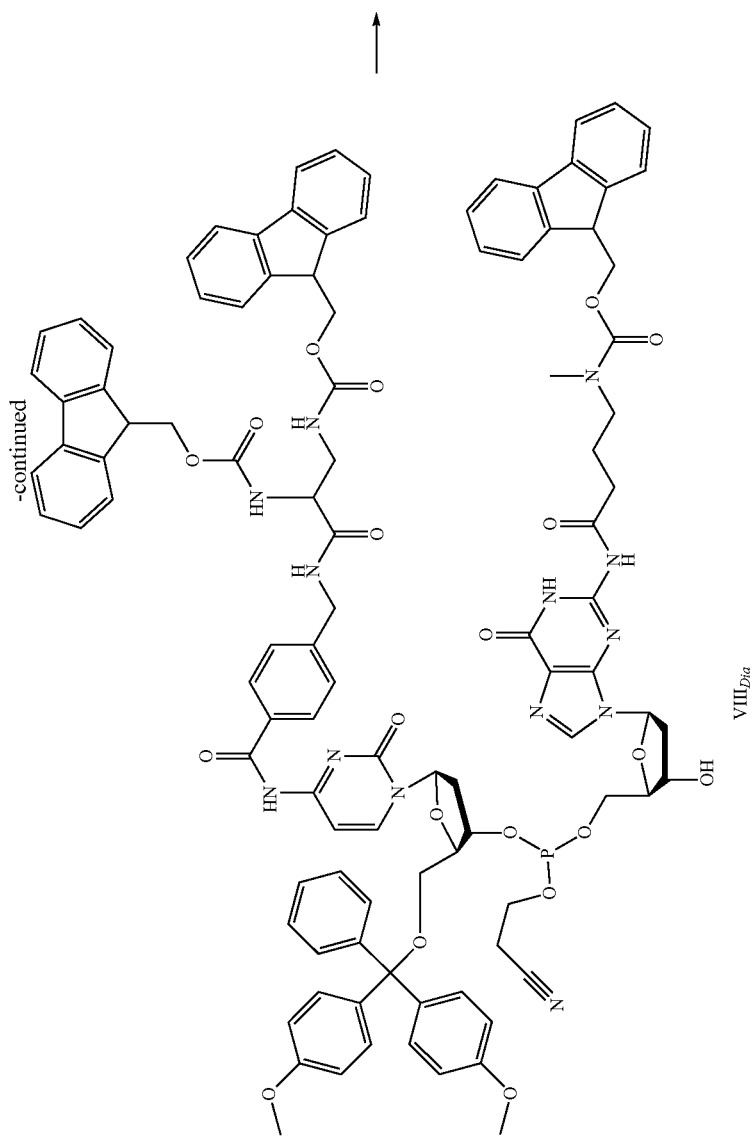

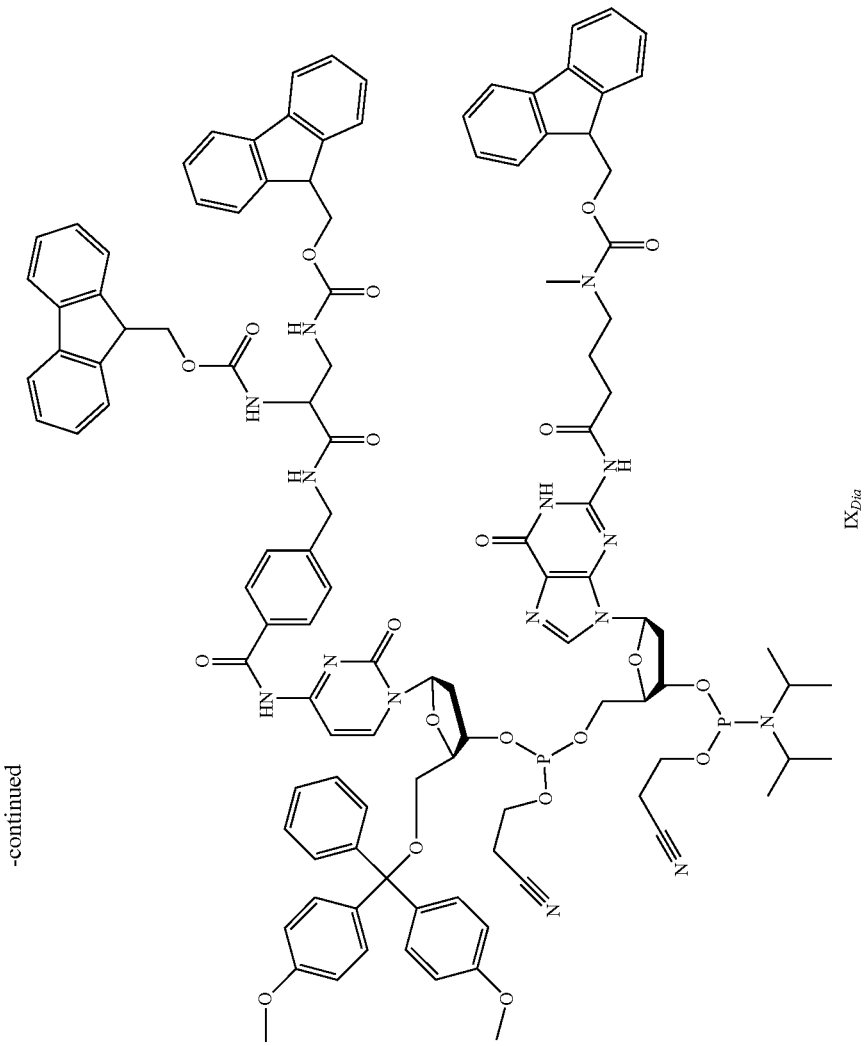

<Synthesis of XIV> 7.03 g (50 mmol) of L-α,β-diaminopropionic acid chloride was dissolved in 150 mL of distilled water, and 4.22 g (52.5 mmol) of sodium hydrogen carbonate was added to the solution, followed by agitating for 5 minutes. Subsequently, 300 mL of dimethoxyethane and 35.4 g (110 mmol) of N-(9-fluorenylmethoxycarbonyl)succinimide were added thereto, followed by agitating at room temperature for 1 week. The reaction mixture was concentrated under reduced pressure. The residue was suspended in 250 mL of distilled water and 250 mL of 36% hydrochloric acid and dichloromethane, and the suspension was filtrated to obtain 24.57 g (90%) of target product XIV.

<Synthesis of $IV_{Dia}$> 22.12 g (25 mmol) of $III_C$ was dissolved in 50 mL of dehydrated dichloromethane, and 4.39 mL (27.5 mmol) of triethylsilane and 5.61 mL (37.5 mmol) of diazabicycloundecene were added to the solution, followed by agitaitng at room temperature for 10 minutes. Subsequently, 6.20 g (45 mmol) of triethylamine hydrochloride was added to the reaction mixture to prepare reaction mixture A.

16.46 g (30.0 mmol) of XIV was dissolved in 50 mL of dehydrated dimethylformamide, and 3.81 g (33.0 mmol) of 1-hydroxybenzotriazole was added to the solution. Then, 6.50 g (31.5 mmol) of dicyclohexylcarbodiimide was added to the resultant solution while being cooled with ice, followed by agitating at room temperature for 1 hour. The insoluble matter was removed by filtration and the filtrate was added to reaction mixture A. The reaction mixture was agitated at room temperature for 1 hour. Subsequently, 0.6 mL of piperidine was added thereto, followed by agitating for 5 minutes. The reaction solution was concentrated under reduced pressure. Then, the residue was suspended in 150 mL of ethyl acetate and 150 mL of distilled water, and the suspension was filtrated to obtain 27.51 g of a solid product containint target product $IV_{Dia}$ (crude $IV_{Dia}$). The subscript "Dia" is named based on the "L-α,β-diaminopropionic acid chloride" used in the Synthesis of XIV.

<Synthesis of $V_{Dia}$> 27.51 g of the crude $IV_{Dia}$ was suspended in dehydrated pyridine, and the suspension was concentrated under reduced pressure three times. The residue was suspended in 90 mL of dehydrated dichloromethane. Under cooling with ice, 131 mg (1.2 mmol) of dimethylaminopyridine and 4.57 mL (27.7 mmol) of diisopropylethylamine were added to the suspension, and a solution of 2-cyanoethyldiisopropylchlorophosphoroamidite (5.89 mL (25.3 mmol)) in dichloromethane (23 mL) was added dropwise thereto over 5 minutes or longer. The mixed solution was agitated at 0° C. for 1 hour. Subsequently, 4.7 mL of methanol was added thereto, followed by agitating for 15 minutes. The reaction solution was diluted with dichloromethane and washed with water. The dichloromethane solution was concentrated under reduced pressure, and the residue was purified by medium pressure chromatography (2% pyridine in ethyl acetate and hexane (1:1):2% pyridine and 2% ethanol in ethyl acetate=1:0→0:1), to thereby obtain 16.11 g (46%, 2 steps) of target product $V_{Dia}$.

<Synthesis of $VIII_{Dia}$> 16.06 g (11.5 mmol) of $V_{Dia}$ and 8.71 g (12.7 mmol) of $VI_S$; were dissolved in a mixed solution of dehydrated dichloromethane and dehydrated acetonitrile, and the solution was concentrated under reduced pressure three times. The residue was dissolved in a mixture containing 35 mL of dehydrated acetonitrile and 35 mL of dehydrated dichloromethane, and 4.04 g (57.6 mmol) of tetrazole was added to the solution while being cooled with ice, followed by agitaing at room temperature overnight. Subsequently, 2.3 mL of methanol was added thereto, followed by agitaing for 30 minutes. The solution was diluted with dichloromethane and washed with water. The dichloromethane solution was concentrated under reduced pressure. The residue was dissolved in 58 mL of pyridine, and a solution (34.6 mL) of 1M hydrazine monohydrate in a solvent mixture containing pyridine and acetic acid in the ratio of 3:2 was added to the solution while being cooled with ice, followed by agitating at 0° C. for 1.5 hours. 6 mL of acetone was added to the mixture while being cooled with ice, followed by agitating at 0° C. for 10 minutes. Then, the resultant mixture was diluted with dichloromethane and washed with water. The dichloromethane solution was concentrated under reduced pressure. The residue was purified by medium pressure chromatography (dichloromethane:ethanol=97:3→9:1), to thereby obtain 13.46 g (62%) of target product $VIII_{Dia}$.

<Synthesis of $IX_{Dia}$> 12.98 g (6.90 mmol) of $VIII_{Dia}$ was dissolved in a mixed solution of dehydrated acetonitrile and dehydrated dichloromethane, and the solution was concentrated under reduced pressure three times. The residue was dissolved in 44 mL of dehydrated dichloromethane. Under cooling with ice, 42 mg (0.34 mmol) of dimethylaminopyridine and 2.18 mL (13.2 mmol) of diisopropylethylamine were added to the solution, and a diluted solution of 2-cyanoethyldiisopropylchlorophosphoroamidite (2.70 mL (12.1 mmol)) in dichloromethane (11 mL) was added thereto. The mixed solution was agitated at 0° C. for 12 hours, followed by agitating at room temperature for 2 hours. Subsequently, 2.2 mL of methanol was added thereto, followed by agitating for 30 minutes. The reaction solution was diluted with dichloromethane and washed with water. The dichloromethane solution was concentrated under reduced pressure, and the residue was purified (2% pyridine in ethyl acetate and hexane (2:1):2% pyridine in ethyl acetate=100:0→0:100, then 2% pyridine:20% ethanol and 2% pyridine in ethyl acetate=1:0→1:1), to thereby obtain 10.52 g (73%) of target product $IX_{Dia}$.

<Confirmation of Structure of Compound> The structure of each of the compounds obtained following Schemes 1 to 11 (containing nucleic acid synthesizing dimer amidites $IX_{Ser}$, $IX_{Leu}$, $IX_{Phe}$, $IX_{A-Lys}$, $IX_{G-Lys}$, $IX_{The}$, $IX_{Met}$, $IX_{Tyr}$, $IX'_{Phe}$ and $IX_{Dia}$) was confirmed as follows. The results are given in FIGS. 2-A to 12-K.

[$^1$H-NMR] About 5 mg of each sample was dissolved in a deuterated solvent and subjected to measurement. The peak of the heavy solvent was used as internal standard.

[$^{31}$H-NMR] $PPh_3$ was used as external standard and −6.2 ppm was used as reference for observation. Measurements were conducted by BCM.

Example 2

Confirmation of Purity

Nucleic acid synthesizing dimer amidite $IX_{Ser}$ obtained in Example 1 was purified. The thus-purified $IX_{Ser}$ was compared in terms of purity with unpurified comparative control dimer amidite $IX'_{Ser}$.

Figure 13A:
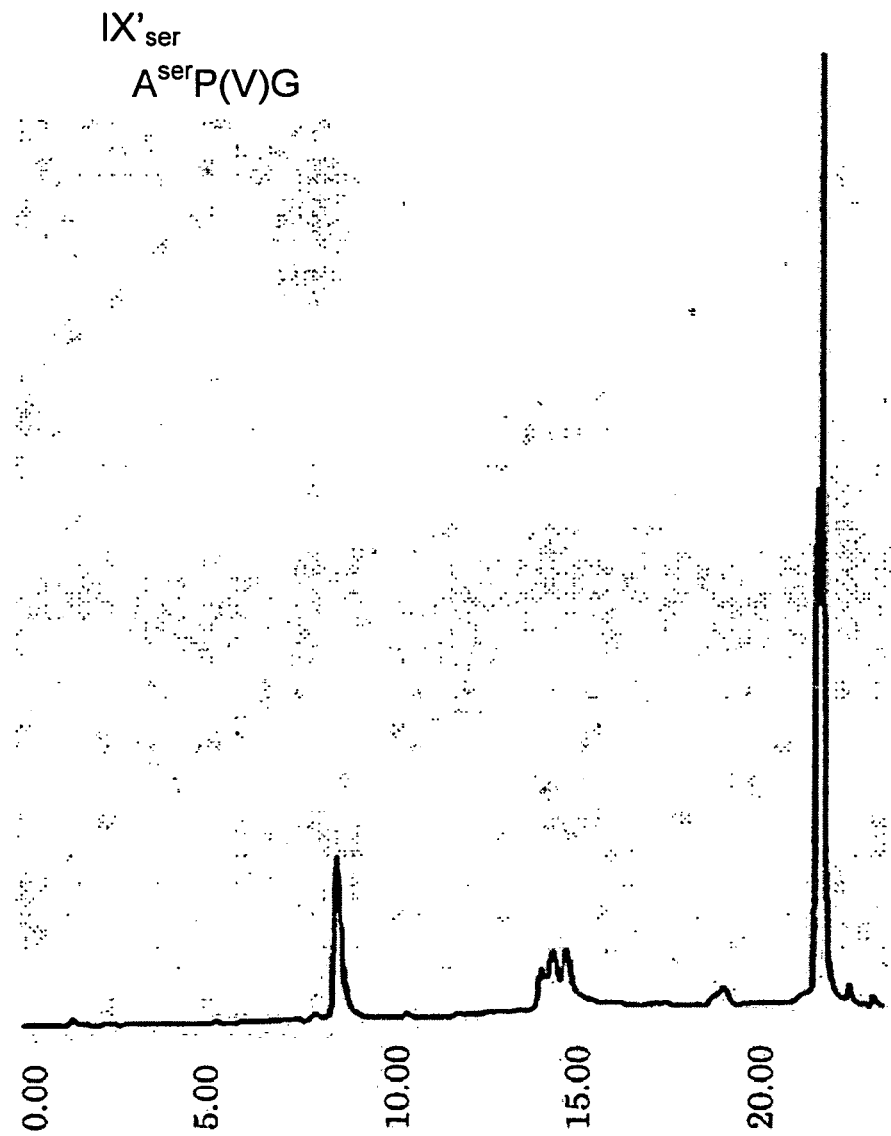
FIG. 13A is an HPLC chart (HPLC chart a) of comparative control dimer amidite $IX'_{Ser}$ in Example 2.
Figure 13B:
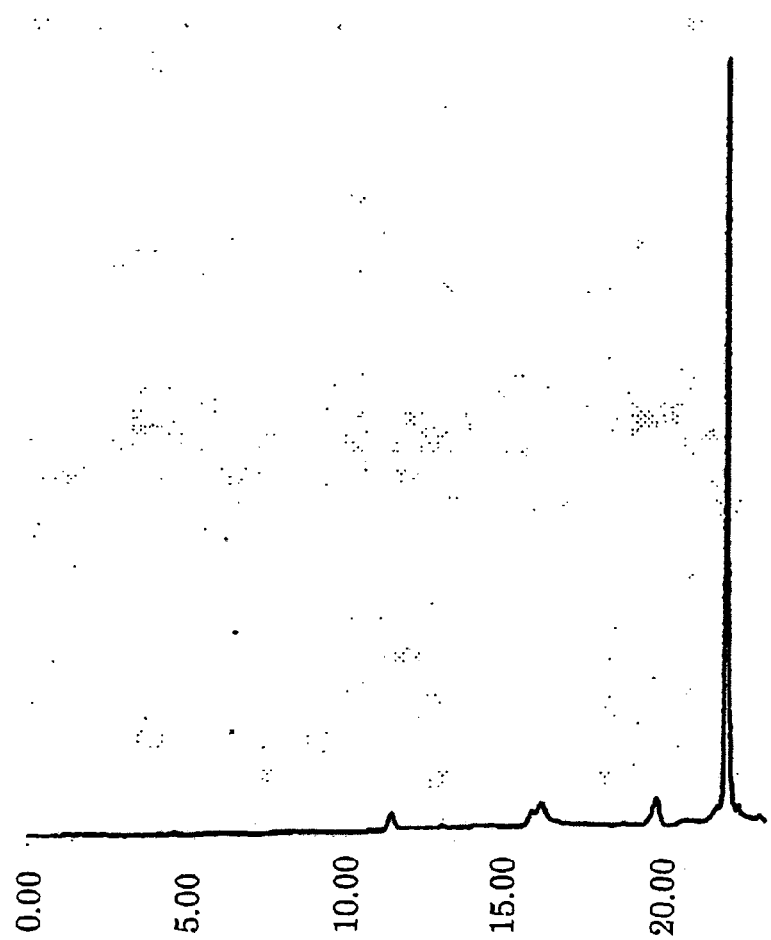
FIG. 13B is an HPLC chart (HPLC chart b) of nucleic acid synthesizing dimer amidite $IX_{Ser}$ in Example 2.

As a result, as given in FIGS. 13A and 13B, the purified nucleic acid synthesizing dimer amidite $IX_{Ser}$ (HPLC Chart b, FIG. 13B) is higher in purity than the unpurified comparative control dimer amidite $IX'_{Ser}$ (HPLC Chart a, FIG. 13A), indicating that the $IX_{Ser}$ is suitable for synthesis of nucleic acid.

Notably, when comparative control dimer amidite $IX'_{Ser}$ was purified by silica gel chlomatography under the same conditions (containing pyridine) under which the $IX_{Ser}$ was purified, the comparative control dimer amidite $IX'_{Ser}$ was decomposed to a considerable extent and the recovery rate was found to be 3% or lower. Notably, the recovery rate by reverse-phase HPLC was found to be about 40%, but there was almost no improvement in synthesis yield of nucleic acid.

Example 3

Confirmation of Yield of Nucleic Acid Synthesis

The DNA synthesis yield attained using nucleic acid synthesizing dimer amidite $IX_{Ser}$ (purified) was compared with that attained using comparative control dimer amidite $IX'_{Ser}$ (unpurified). The DNA synthesis was performed using H-8

Figure 14:
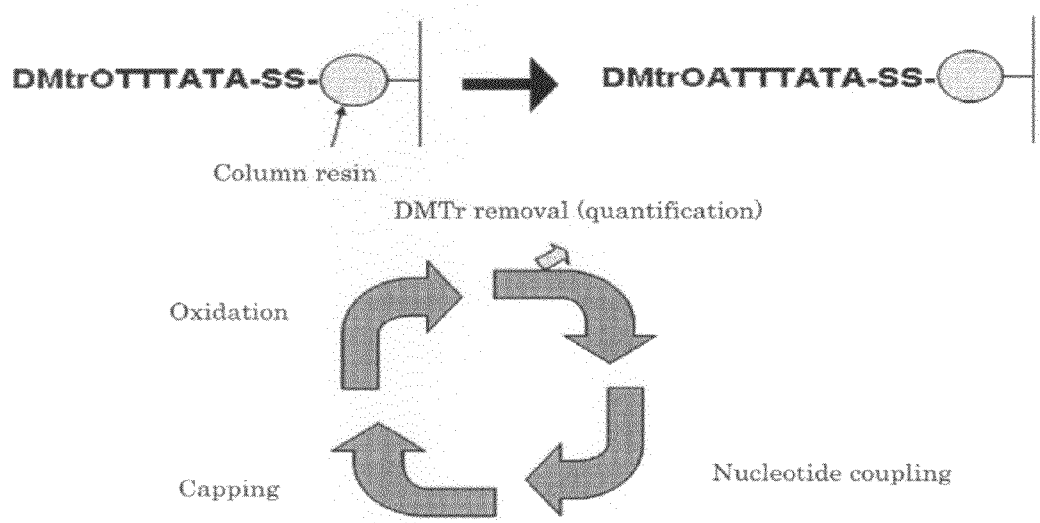
FIG. 14 illustrates a method for confirming the yield of DNA synthesis in Example 3.

DNA synthesizer (product of GeneWorld Co., Ltd.), and coupling and the trityl group-removing program (confirmation of synthesis yield) were utilized without modification (FIG. 14).

Figure 15A:
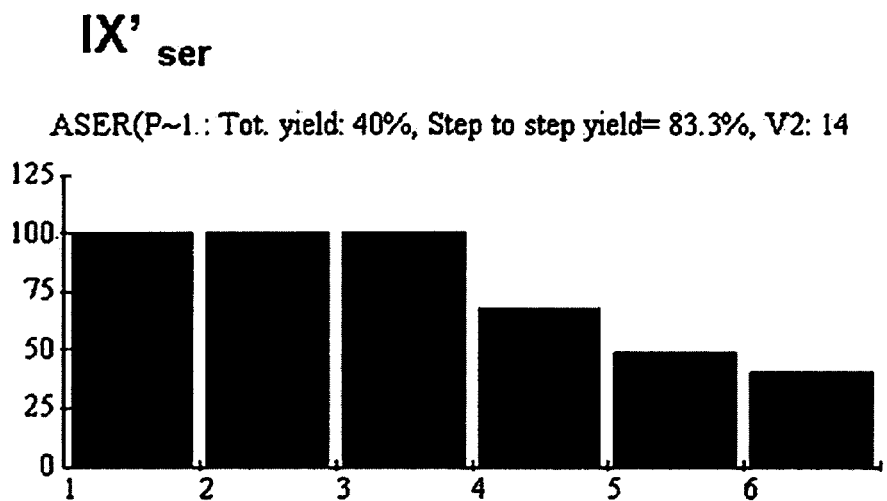
FIG. 15A is a graph of the DNA synthesis yield attained using comparative control dimer amidite $IX'_{Ser}$ in Example 3.
Figure 15B:
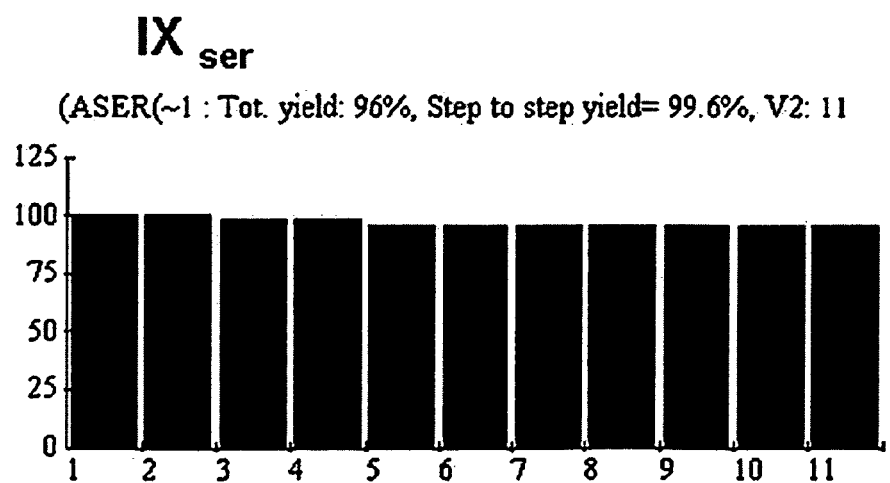
FIG. 15B is a graph of the DNA synthesis yield attained using nucleic acid synthesizing dimer amidite $IX_{Ser}$ in Example 3.

As a result, as given in FIGS. 15A and 15B, when comparative control dimer amidite (unpurified) was used for DNA synthesis, the total yield was found to be about 40% and the step to step yield about 83.3% (FIG. 15A). Meanwhile, when nucleic acid synthesizing dimer amidite $IX_{Ser}$ (purified) was used for DNA synthesis, the total yield was found to be about 96%, and the step to step yield about 99.6% (FIG. 15B).

As a result, use of the nucleic acid synthesizing dimer amidite having a phosphite triester bond as a linking moiety (which can be subjected to purification) was found to attain higher synthesis yield of nucleic acid than use of the nucleic acid synthesizing dimer amidite having a phosphate triester bond as a linking moiety (which cannot be subjected to purification).

The nucleic acid synthesizing dimer amidite of the invention and the nucleic acid synthesizing method of the invention can efficiently and stably produce, for example, a modified nucleic acid having a substituent (one embodiment of the invention). The obtained modified nucleic acid can bind via the substituent to a target substance (e.g., proteins) and thus, for example, the modified nucleic acid can be suitably used for the analysis of a target substance (e.g., proteins).

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification related to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A dimer amidite having a structure represented by the following General Formula (1):

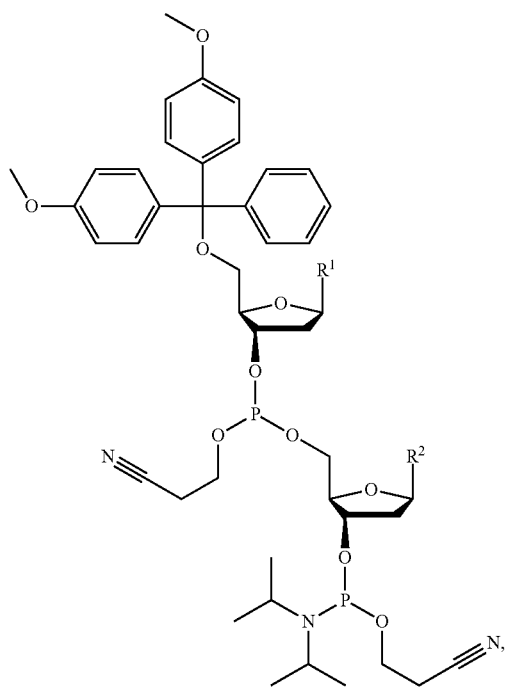

General Formula (1)

wherein in General Formula (1), $R_1$ and $R_2$ each independently represent any one of groups selected from General Formulas (2) to (4) and Structural Formulas (12) to (15) with the proviso that all compounds wherein the substituents $R_1$ and $R_2$ are each selected to represent Structural Formula (12) are excluded:

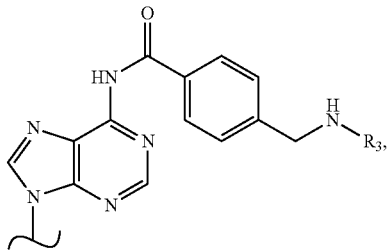

General Formula (2)

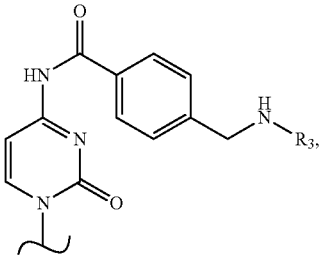

General Formula (3)

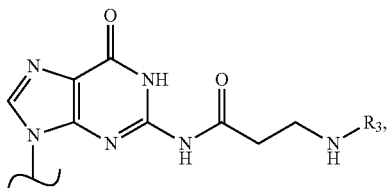

General Formula (4)

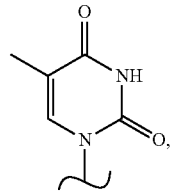

Structural Formula (12)

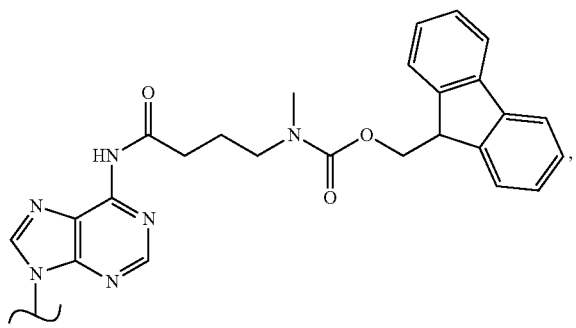

Structural Formula (13)

and
wherein in the General Formulas (2) to (4), R₃ represents any one group represented by the following Structural Formulas (16) to (25):

2. The dimer amidite according to claim 1, wherein the dimer amidite has a structure selected from the following Structural Formulas (1) to (11):

Structural Formula (1)
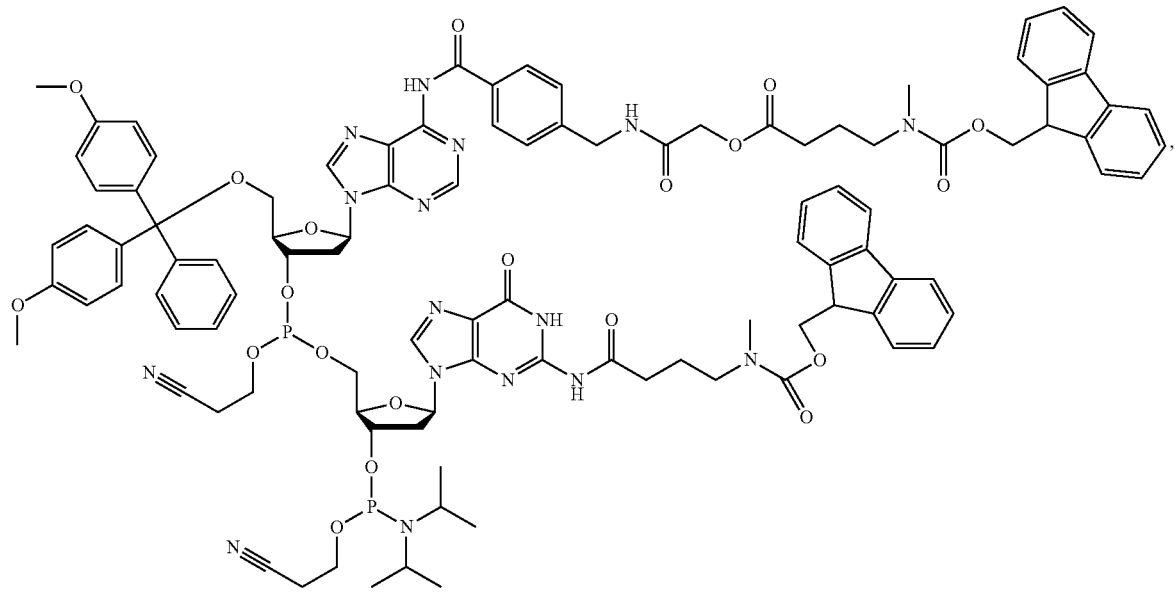
Structural Formula (2)
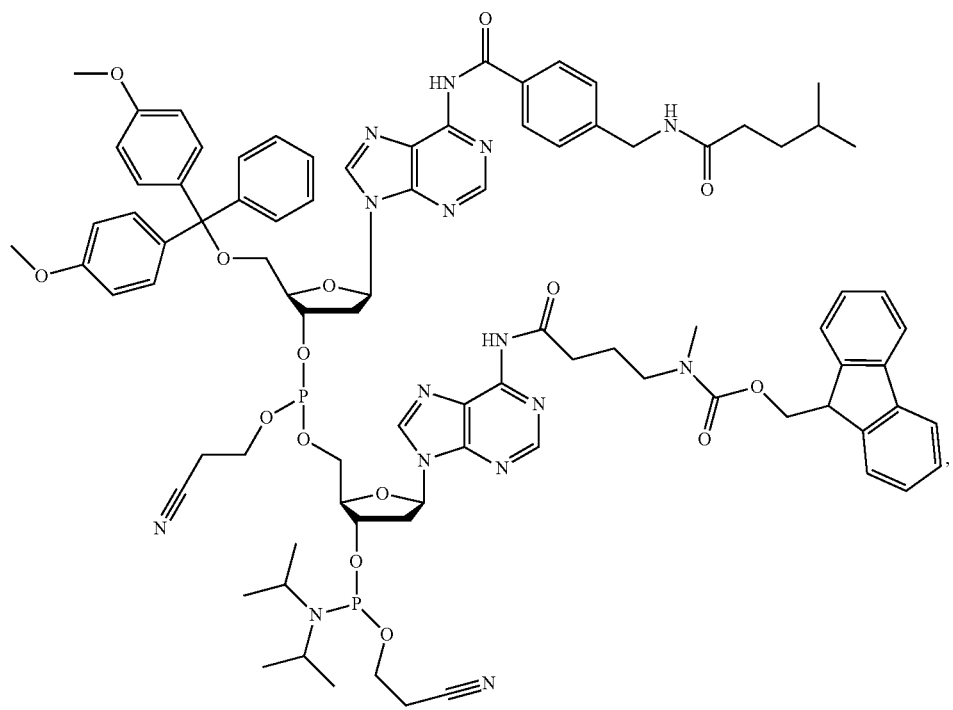

Structural Formula (3)
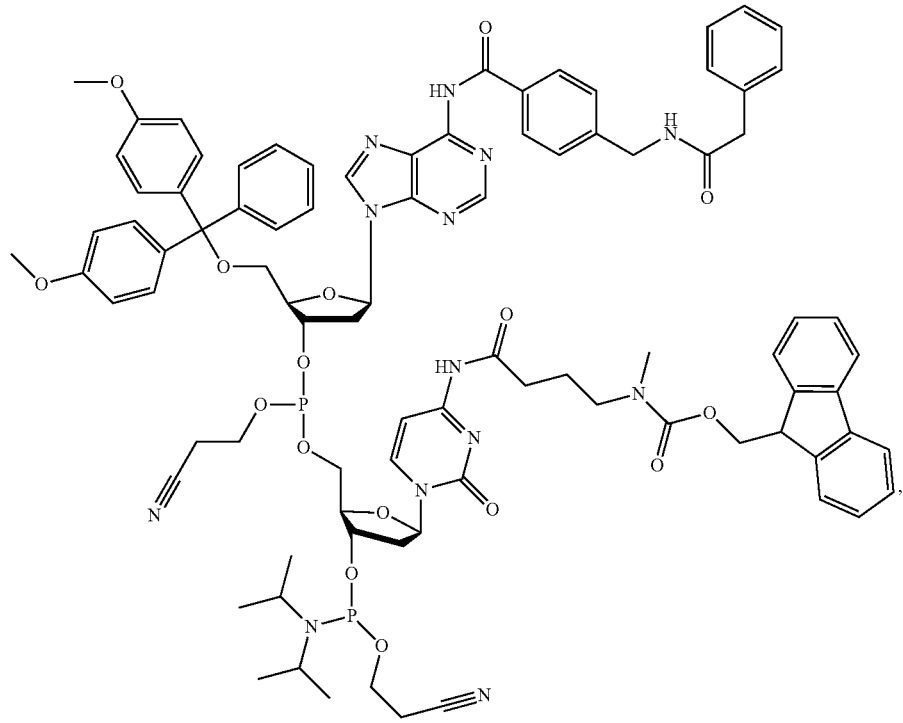
Structural Formula (4)
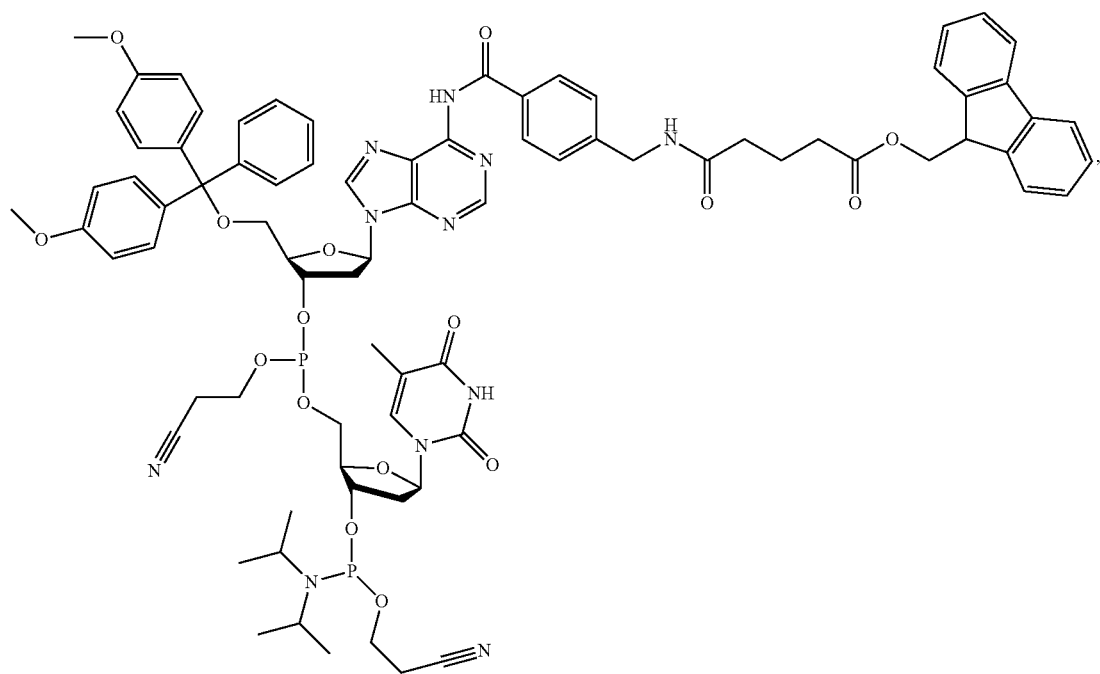

Structural Formula (5)
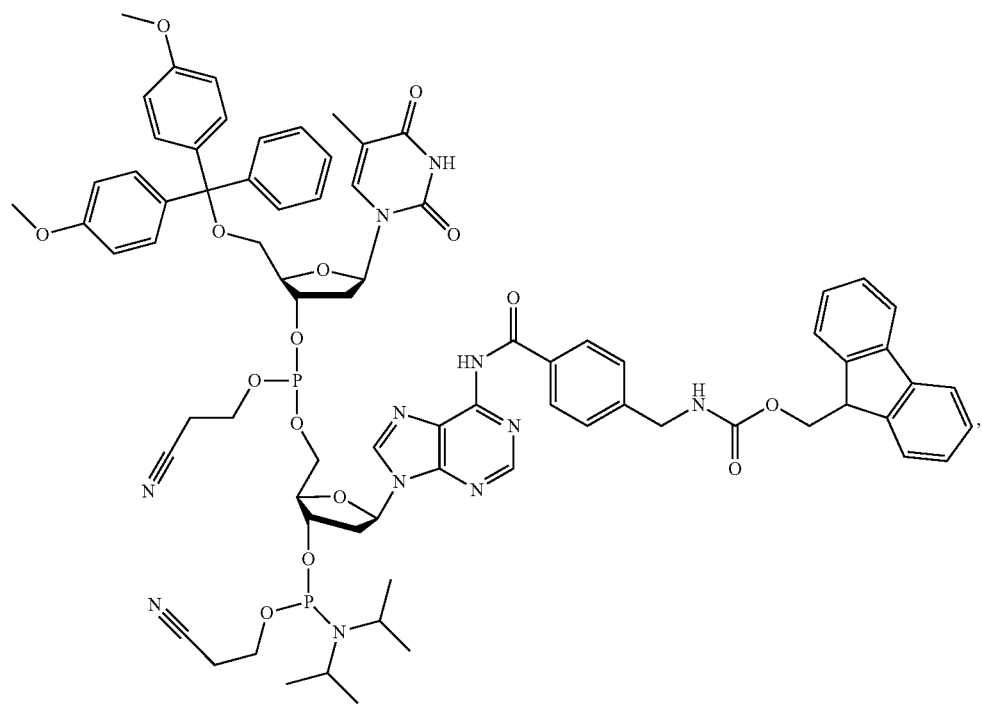
Structural Formula (6)
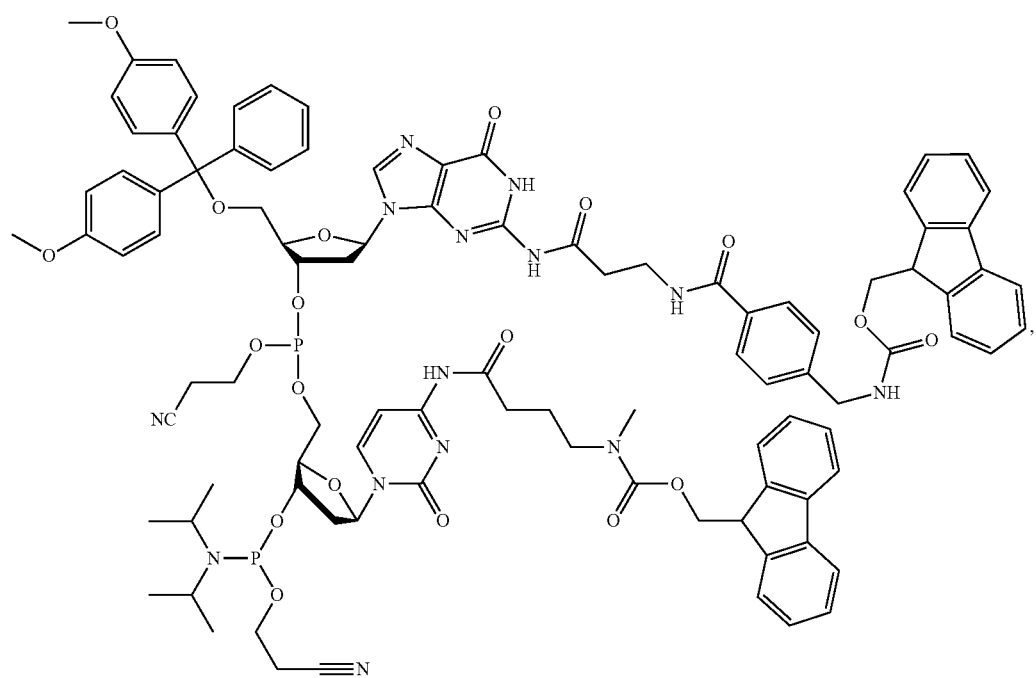

-continued
Structural Formula (7)
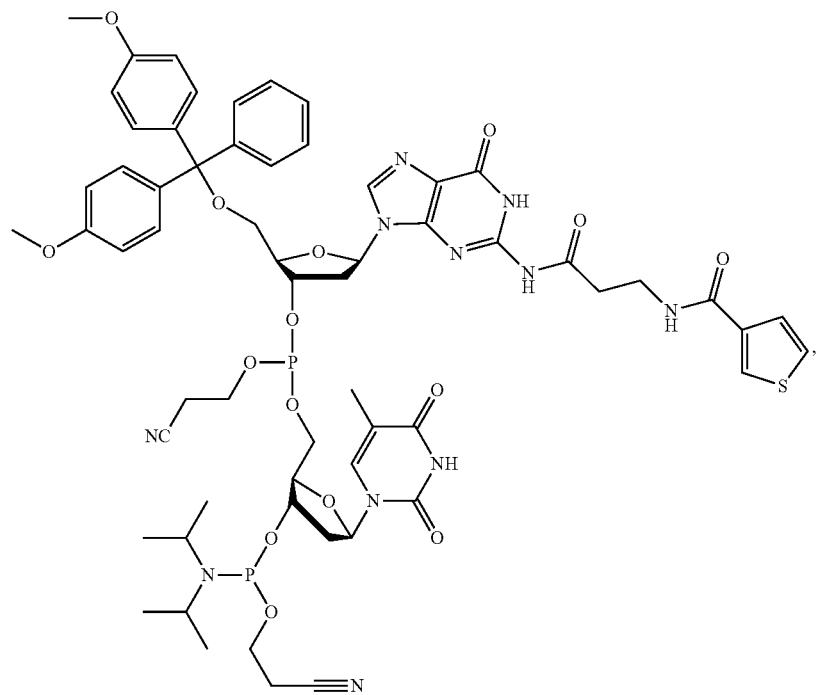
Structural Formula (8)
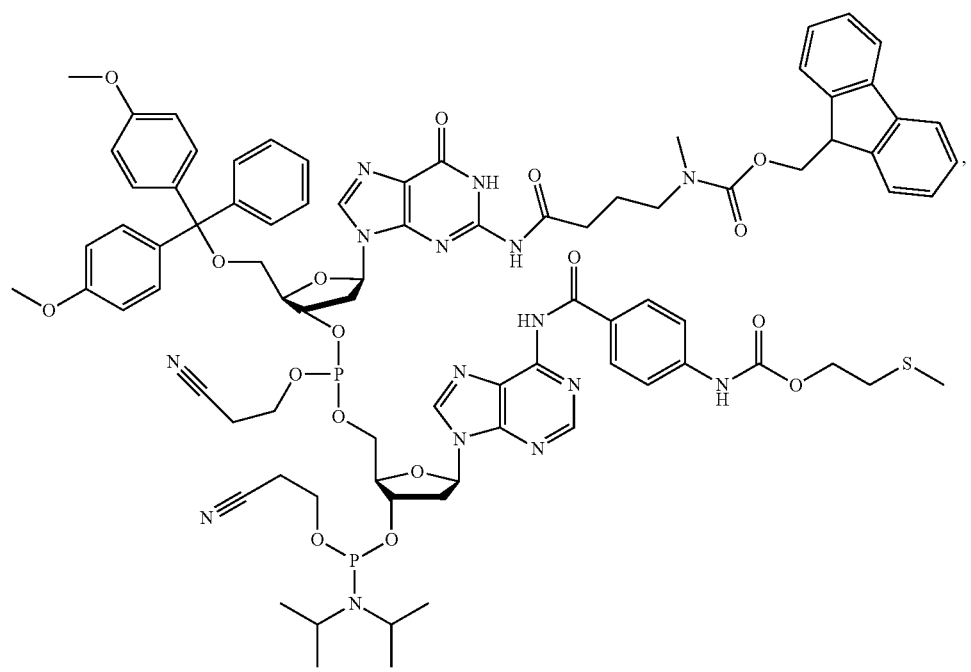

Structural Formula (9)
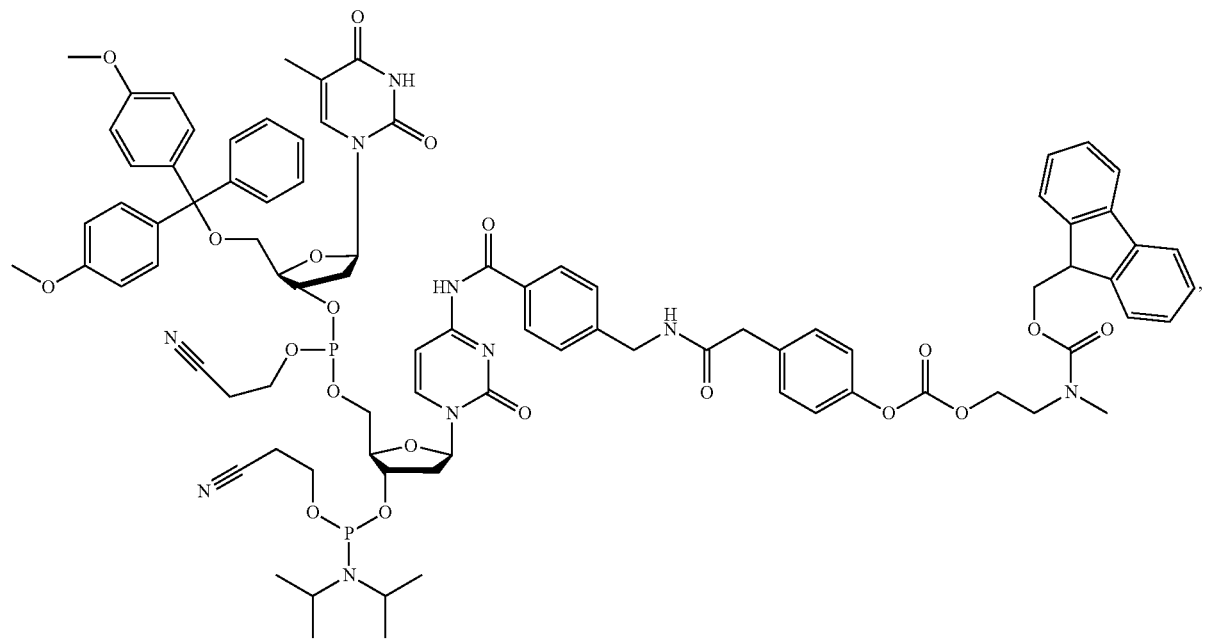
Structural Formula (10)
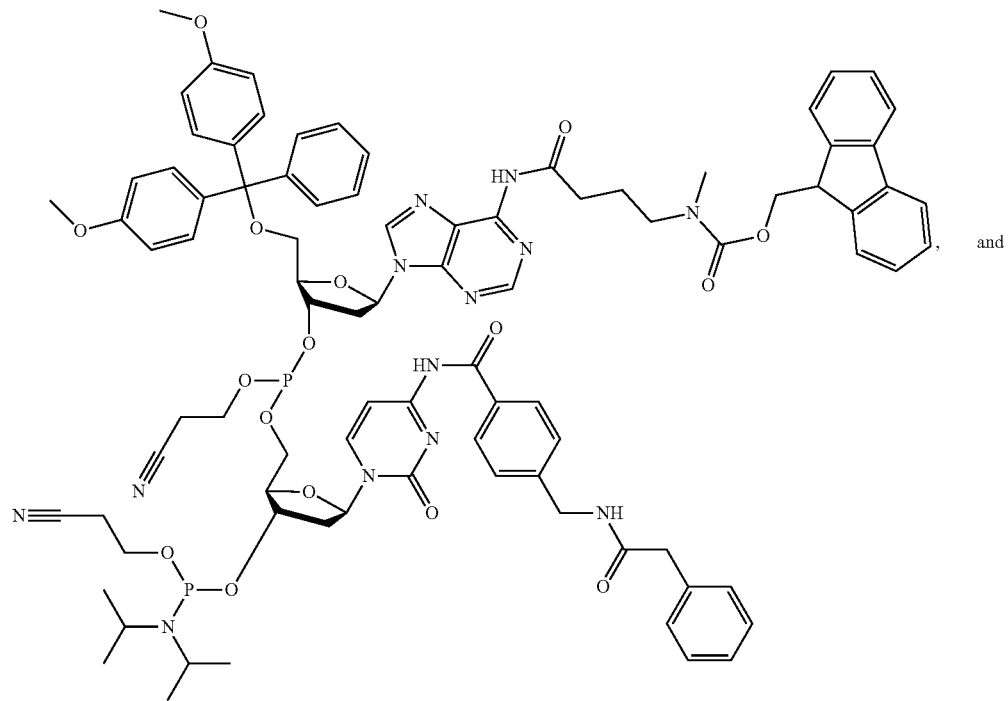
, and

-continued

Structural Formula (11)

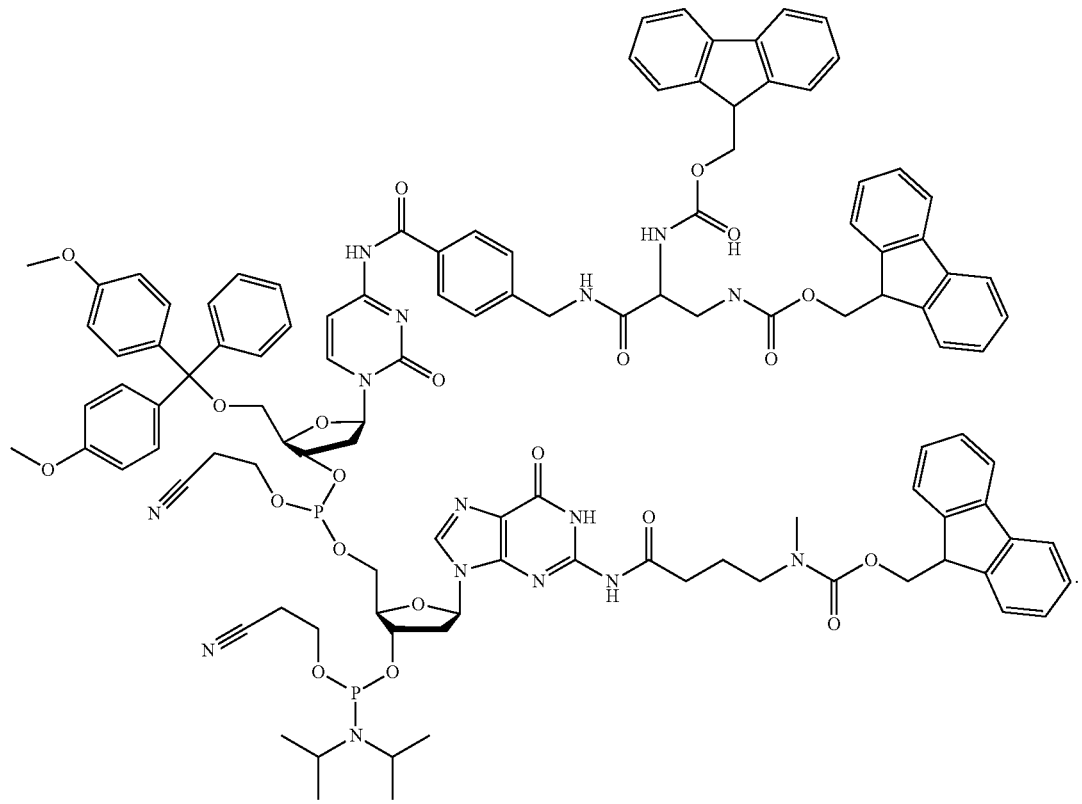

3. A nucleic acid synthesizing method comprising:

removing 4,4'-dimethoxyltrityl group from 5'-terminus of an oligonucleotide, coupling a dimer amidite to the 5'-terminus of the oligonucleotide, capping non-reacted 5'-terminus of the 5'-terminus of the oligonucleotide, and oxidizing the P(III) esters in the dimer amidite to P(V) esters, wherein the dimer amidite has a structure represented by the following General Formula (1):

General Formula (1)

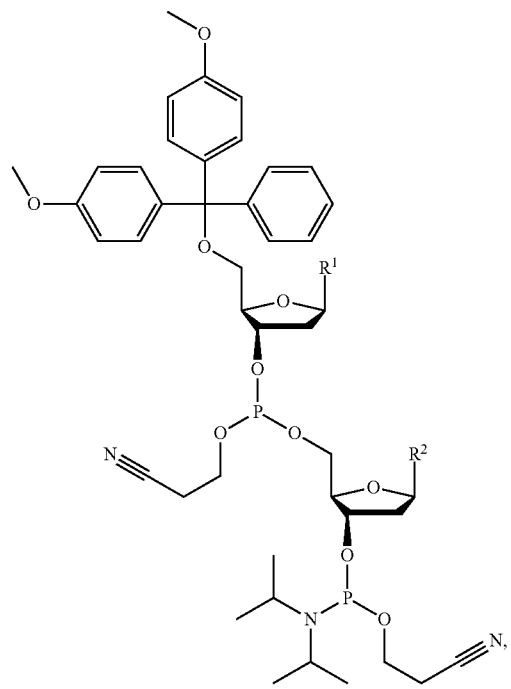

wherein in General Formula (1), $R_1$ and $R_2$ each independently represent any one of groups selected from General Formulas (2) to (4) and Structural Formulas (12) to (15) with the proviso that all compounds wherein the substituents $R_1$ and $R_2$ are each selected to represent Structural Formula (12) are excluded:

General Formula (2)

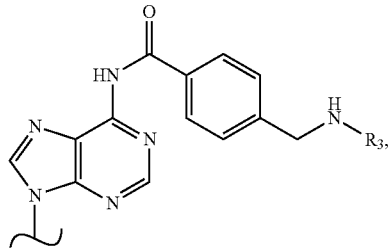

General Formula (3)

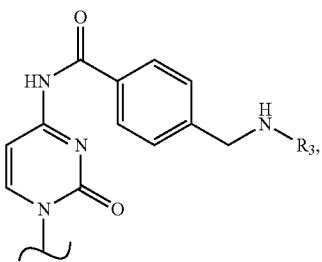

General Formula (4)

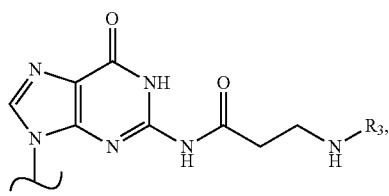

Structural Formula (12)

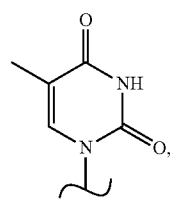

Structural Formula (13)

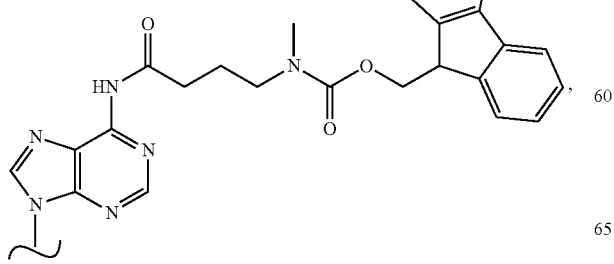

Structural Formula (14)

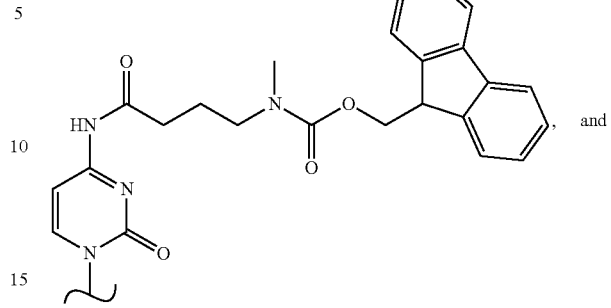
, and

Structural Formula (15)

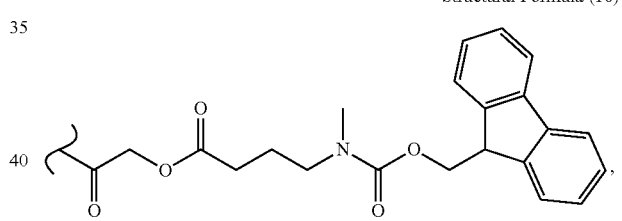
, wherein in the General Formulas (2) to (4), $R_3$ represents any one group represented by the following Structural Formulas (16) to (25):

Structural Formula (16)

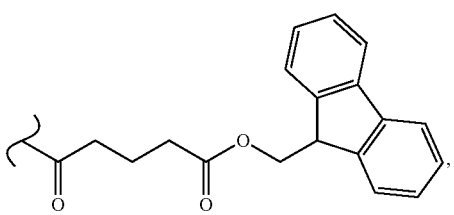
,

Structural Formula (17)

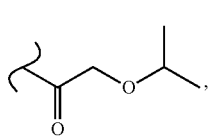
,

Structural Formula (18)

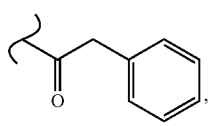
,

Structural Formula (19)

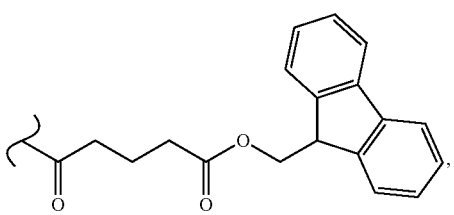
,

-continued

Structural Formula (20)
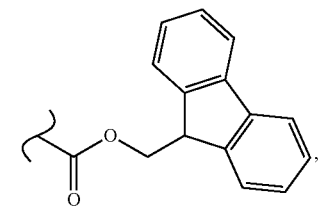

Structural Formula (21)
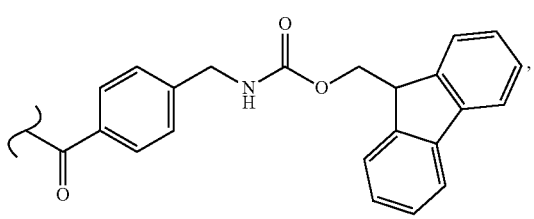

Structural Formula (22)
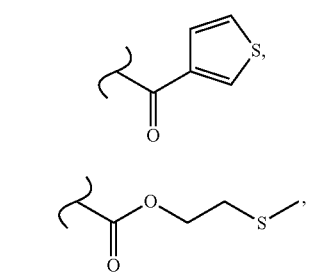

Structural Formula (23)
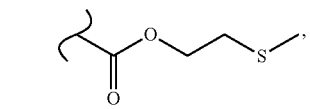

Structural Formula (24)
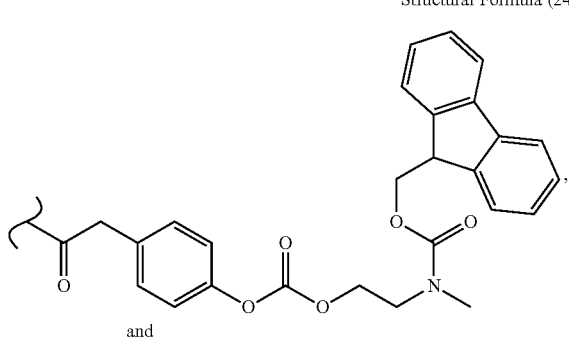

and

Structural Formula (25)
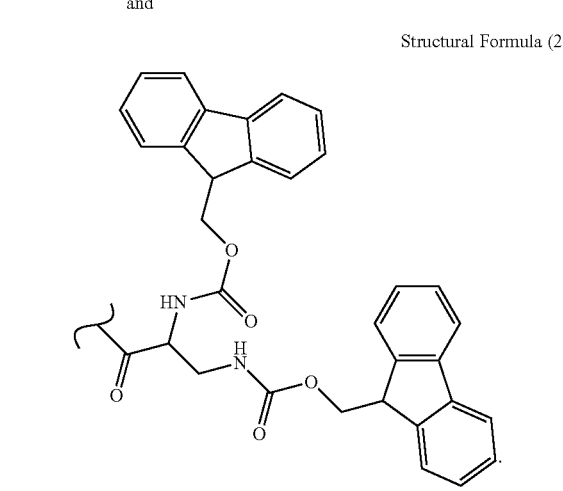

4. The nucleic acid synthesizing method according to claim 3, further comprising removing a protective group of the dimer amidite,
wherein the removing the protective group is performed after the condensation reaction, wherein in Structural Formulas (13) to (16), the protective group is represented by the following Structural Formula (26):

Structural Formula (26)
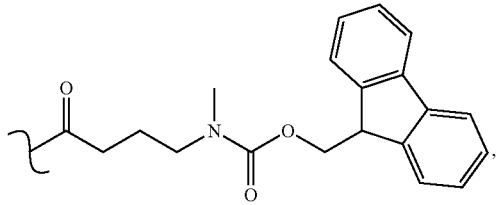

wherein in Structural Formula (19), the protective group is represented by the following Structural Formula (27):

Structural Formula (27)
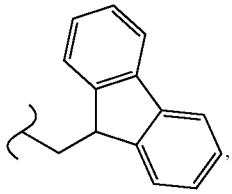

wherein in Structural Formulas (20), (21) and (25) the protective group is represented by the Structural Formula (20), and
wherein in Structural Formulas (24), the protective group is represented by the following Structural Formula (28):

Structural Formula (28)
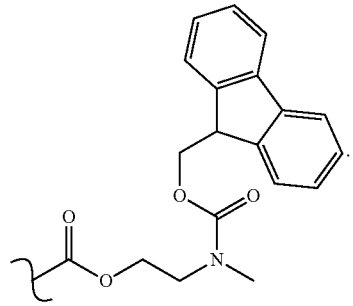

5. The nucleic acid synthesizing method according to claim 4, wherein the removing the protective group is performed in an aprotic solvent.

6. The nucleic acid synthesizing method according to claim 4, wherein the removing the protective group is performed by a bulky base.

7. The nucleic acid synthesizing method according to claim 4, wherein the removing the protective group is performed by 1,8-diazabicyclo[5.4.0]-7-undecene at a concentration of 0.01M or lower.

8. The nucleic acid synthesizing method according to claim 4, wherein the removing the protective group is completed within 15 minutes.

9. The nucleic acid synthesizing method according to claim 3, wherein the nucleic acid synthesizing method is performed by an automatic nucleic acid synthesizer.

10. The nucleic acid synthesizing method according to claim 3, wherein the dimer amidite has a phosphite protective group, and the protective group is removed in an aprotic solvent after the phosphite triester bond is oxidized to be a phosphate triester bond in the course of synthesis of nucleic acid.

11. The nucleic acid synthesizing method according to claim 10, wherein the aprotic solvent is at least one selected from the group consisting of acetonitrile, dichloromethane, N,N-dimethylformamide and N-methylpyrrolidone.

12. The nucleic acid synthesizing method according to claim 3, wherein the dimer amidite has a phosphite protective group, and the protective group is removed by a bulky base after the phosphite triester bond is oxidized to be a phosphate triester bond in the course of synthesis of nucleic acid.

13. The nucleic acid synthesizing method according to claim 12, wherein the bulky base is at least one selected from the group consisting of 1,8-diazabicyclo[5.4.0]-7-undecene, 1,5-diazabicyclo[4.3.0]-5-nonene and tetramethylguanidine.

14. The nucleic acid synthesizing method according to claim 3,
wherein at least one of the two nucleosides has a protective group bound to an exocyclic amino group of a base thereof, and the protective group is removed in an aprotic solvent,
wherein in Structural Formulas (13) to (16), the protective group is represented by the following Structural Formula (26):

Structural Formula (26)

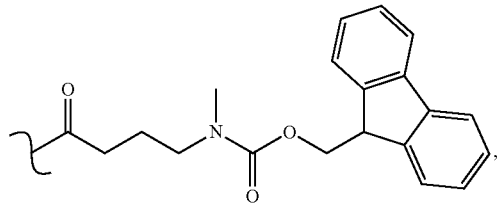

wherein in Structural Formula (19), the protective group is represented by the following Structural Formula (27):

Structural Formula (27)

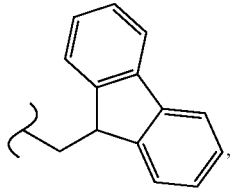

wherein in Structural Formulas (20), (21) and (25) the protective group is represented by the Structural Formula (20), and wherein in Structural Formulas (24), the protective group is represented by the following Structural Formula (28):

Structural Formual (28)

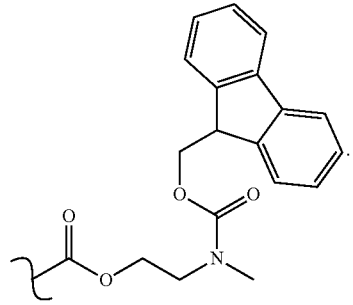

* * * * *